(12) United States Patent
Wang et al.

(10) Patent No.: US 12,428,638 B2
(45) Date of Patent: Sep. 30, 2025

(54) THREE-COMPONENT CRISPR/Cas COMPLEX SYSTEM AND USES THEREOF

(71) Applicant: The Jackson Laboratory, Bar Harbor, ME (US)

(72) Inventors: Haoyi Wang, Beijing (CN); Albert Cheng, Bar Harbor, ME (US); Nathaniel Jillette, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 678 days.

(21) Appl. No.: 17/815,621

(22) Filed: Jul. 28, 2022

(65) Prior Publication Data

US 2023/0071712 A1    Mar. 9, 2023

Related U.S. Application Data

(60) Division of application No. 15/702,944, filed on Sep. 13, 2017, now Pat. No. 11,434,484, which is a continuation of application No. PCT/US2016/021491, filed on Mar. 9, 2016.

(60) Provisional application No. 62/221,249, filed on Sep. 21, 2015, provisional application No. 62/132,644, filed on Mar. 13, 2015.

(51) Int. Cl.
| C12N 15/11 | (2006.01) |
| C12N 9/22 | (2006.01) |
| C12N 15/90 | (2006.01) |

(52) U.S. Cl.
CPC ............ *C12N 15/11* (2013.01); *C12N 9/22* (2013.01); *C12N 15/111* (2013.01); *C12N 15/907* (2013.01); *C12N 2310/20* (2017.05); *C12N 2310/531* (2013.01); *C12N 2800/80* (2013.01)

(58) Field of Classification Search
CPC .................................................. C12N 2310/20
See application file for complete search history.

(56) References Cited

U.S. PATENT DOCUMENTS

| 2010/0204259 A1 | 8/2010 | Tygesen et al. |
| 2013/0129701 A1 | 5/2013 | Wang et al. |
| 2014/0010873 A1 | 1/2014 | Tygesen et al. |
| 2018/0094257 A1 | 4/2018 | Wang et al. |
| 2019/0218261 A1 | 7/2019 | Cheng et al. |

(Continued)

FOREIGN PATENT DOCUMENTS

| WO | WO 2011/160052 A2 | 12/2011 |
| WO | WO 2012/068627 A1 | 5/2012 |
| WO | WO 2013/176772 A1 | 11/2013 |

(Continued)

OTHER PUBLICATIONS

Extended European Search Report, mailed Jun. 28, 2021 for European Application No. 21157844.8.

(Continued)

*Primary Examiner* — Richard A Schnizer
*Assistant Examiner* — Africa M McLeod
(74) *Attorney, Agent, or Firm* — Wolf, Greenfield & Sacks, P.C.

(57) ABSTRACT

The invention described herein provides compositions and reagents for assembling a tripartite complex at a specific location of a target DNA. The invention also provides methods for using the complex to, for example, label a specific genomic locus, to regulate the expression of a target gene, or to create a gene regulatory network.

20 Claims, 22 Drawing Sheets
Specification includes a Sequence Listing.

(56) References Cited

U.S. PATENT DOCUMENTS

| | | |
|---|---|---|
| 2020/0071369 A1 | 3/2020 | Cheng |
| 2021/0062250 A1 | 3/2021 | Yi et al. |

FOREIGN PATENT DOCUMENTS

| | | |
|---|---|---|
| WO | WO 2016/148994 A1 | 9/2016 |
| WO | WO 2017/074943 A1 | 5/2017 |

OTHER PUBLICATIONS

International Search Report and Written Opinion, mailed Jun. 17, 2016 for International Application No. PCT/US2016/021491.
International Preliminary Report on Patentability, mailed Sep. 19, 2017 for International Application No. PCT/US2016/021491.
Invitation to Pay Additional Fees, mailed Nov. 10, 2020 for International Application No. PCT/US2020/046076.
International Search Report and Written Opinion, mailed Feb. 1, 2021 for International Application No. PCT/US2020/046076.
International Preliminary Report on Patentability, mailed Mar. 3, 2022 for International Application No. PCT/US2020/046076.
[No Author Listed], Gene Characterization Kits. Stratagene. La Jolla, California. 1988. 2 pages.
Anton et al., Visualization of specific DNA sequences in living mouse embryonic stem cells with a programmable fluorescent CRISPR/Cas system. Nucleus. Mar.-Apr. 2014;5(2):163-72. doi: 10.4161/nucl.28488. Epub Mar. 12, 2014.
Chen et al., Dynamic imaging of genomic loci in living human cells by an optimized CRISPR/Cas system. Cell. Dec. 19, 2013;155(7):1479-91. doi: 10.1016/j.cell.2013.12.001. Erratum in: Cell. Jan. 16, 2014;156(1-2):373.
Chen et al., Imaging Specific Genomic DNA in Living Cells. Annu Rev Biophys. Jul. 5, 2016;45:1-23. doi: 10.1146/annurev-biophys-062215-010830. Epub Apr. 27, 2016.
Cheng et al., Casilio: a versatile CRISPR-Cas9-Pumilio hybrid for gene regulation and genomic labeling. Cell Res. Feb. 2016;26(2):254-7. doi: 10.1038/cr.2016.3. Epub Jan. 15, 2016.
Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.
Clow et al., CRISPR-mediated multiplexed live cell imaging of nonrepetitive genomic loci with one guide RNA per locus. Nat Commun. Apr. 6, 2022;13(1):1871. doi: 10.1038/s41467-022-29343-z.
Filipovska et al., A universal code for RNA recognition by PUF proteins. Nat Chem Biol. May 15, 2011;7(7):425-7. doi: 10.1038/nchembio.577.
Hong et al., Comparison and optimization of CRISPR/dCas9/gRNA genome-labeling systems for live cell imaging. Genome Biol. Mar. 22, 2018;19(1):39. doi: 10.1186/s13059-018-1413-5.
Knight et al., Genomes in Focus: Development and Applications of CRISPR-Cas9 Imaging Technologies. Angew Chem Int Ed Engl. Apr. 9, 2018;57(16):4329-4337. doi: 10.1002/anie.201709201. Epub Feb. 28, 2018.
Knott et al., CRISPR-Cas guides the future of genetic engineering. Science. Aug. 31, 2018;361(6405):866-869. doi: 10.1126/science.aat5011.
Ma et al., CRISPR-Sirius: RNA scaffolds for signal amplification in genome imaging. Nat Methods. Nov. 2018;15(11):928-931. doi: 10.1038/s41592-018-0174-0. Epub Oct. 30, 2018.
Ma et al., Multiplexed labeling of genomic loci with dCas9 and engineered sgRNAs using CRISPRainbow. Nat Biotechnol. May 2016;34(5):528-30. doi: 10.1038/nbt.3526. Epub Apr. 18, 2016.
Ma et al., Visualization of repetitive DNA sequences in human chromosomes with transcription activator-like effectors. Proc Natl Acad Sci U S A. Dec. 24, 2013;110(52):21048-53. doi: 10.1073/pnas.1319097110. Epub Dec. 9, 2013. Erratum in: Proc Natl Acad Sci U S A. Jan. 21, 2014;111(3):1222.
Maass et al., Spatiotemporal allele organization by allele-specific CRISPR live-cell imaging (SNP-CLING). Nat Struct Mol Biol. Feb. 2018;25(2):176-184. doi: 10.1038/s41594-017-0015-3. Epub Jan. 8, 2018.
Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.
Morisaki et al., Single molecule analysis of transcription factor binding at transcription sites in live cells. Nat Commun. Jul. 18, 2014;5:4456. doi: 10.1038/ncomms5456.
Qi et al., Repurposing CRISPR as an RNA-guided platform for sequence-specific control of gene expression. Cell. Feb. 28, 2013;152(5):1173-83. doi: 10.1016/j.cell.2013.02.022. Erratum in: Cell. Feb. 4, 2021;184(3):844.
Qin et al., Live cell imaging of low- and non-repetitive chromosome loci using CRISPR-Cas9. Nat Commun. Mar. 14, 2017;8:14725. doi: 10.1038/ncomms14725.
Ren et al., Visualization of aging-associated chromatin alterations with an engineered TALE system. Cell Res. Apr. 2017;27(4):483-504. doi: 10.1038/cr.2017.18. Epub Jan. 31, 2017.
Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.
Zalatan et al., Engineering complex synthetic transcriptional programs with CRISPR RNA scaffolds. Cell. Jan. 15, 2015;160(1-2):339-50. doi: 10.1016/j.cell.2014.11.052. Epub Dec. 18, 2014.

Multiplexing

Multimerization

Complex formation

SEQUENCE LISTING

```
Sequence total quantity: 173
SEQ ID NO: 1                 moltype = DNA  length = 37
FEATURE                      Location/Qualifiers
misc_feature                 1..37
                             note = source = /note="Description of Artificial Sequence:
                             Syntheticoligonucleotide"
source                       1..37
                             mol_type = other DNA
                             organism = synthetic construct
SEQUENCE: 1
gttttagagc tagaaatagc aagttaaaat aaggcta                                          37

SEQ ID NO: 2                 moltype = DNA  length = 47
FEATURE                      Location/Qualifiers
misc_feature                 1..47
                             note = source = /note="Description of Artificial Sequence:
                             Syntheticoligonucleotide"
source                       1..47
                             mol_type = other DNA
                             organism = synthetic construct
SEQUENCE: 2
gtttaagagc tatgctggaa acagcatagc aagtttaaat aaggcta                               47

SEQ ID NO: 3                 moltype = AA  length = 349
FEATURE                      Location/Qualifiers
REGION                       1..349
                             note = source = /note="Description of Artificial Sequence:
                             Syntheticpolypeptide"
source                       1..349
                             mol_type = protein
                             organism = synthetic construct
SEQUENCE: 3
GRSRLLEDFR NNRYPNLQLR EIAGHIMEFS QDQHGCRFIQ LKLERATPAE RQLVFNEILQ     60
AAYQLMVDVF GNYVIQKFFE FGSLEQKLAL AERIRGHVLS LALQMYGSRV IEKALEFIPS    120
DQQNEMVREL DGHVLKCVKD QNGNHVVQKC IECVQPQSLQ FIIDAFKGQV FALSTHPYGC    180
RVIQRILEHC LPDQTLPILE ELHQHTEQLV QDQYGSYVIE HVLEHGRPED KSIVAEIRG     240
NVLVLSQHKF ANNVVQKCVT HASRTERAVL IDEVCTMNDG PHSALYTMMK DQYANYVVQK    300
MIDVAEPGQR KIVMHKIRPH IATLRKYTYG KHILAKLEKY YMKNGVDLG                349

SEQ ID NO: 4                 moltype = AA  length = 349
FEATURE                      Location/Qualifiers
source                       1..349
                             mol_type = protein
                             organism = Homo sapiens
SEQUENCE: 4
GRSRLLEDFR NNRYPNLQLR EIAGHIMEFS QDQHGSRFIQ LKLERATPAE RQLVFNEILQ     60
AAYQLMVDVF GNYVIQKFFE FGSLEQKLAL AERIRGHVLS LALQMYGCRV IQKALEFIPS    120
DQQNEMVREL DGHVLKCVKD QNGNHVVQKC IECVQPQSLQ FIIDAFKGQV FALSTHPYGC    180
RVIQRILEHC LPDQTLPILE ELHQHTEQLV QDQYGNYVIQ HVLEHGRPED KSIVAEIRG     240
NVLVLSQHKF ASNVVEKCVT HASRTERAVL IDEVCTMNDG PHSALYTMMK DQYANYVVQK    300
MIDVAEPGQR KIVMHKIRPH IATLRKYTYG KHILAKLEKY YMKNGVDLG                349

SEQ ID NO: 5                 moltype = AA  length = 349
FEATURE                      Location/Qualifiers
VARIANT                      36
                             note = /replace="Ser" or "Gly" or "Ala" or "Thr" or "Asn"
VARIANT                      40
                             note = /replace="Arg" or "Glu"
VARIANT                      72
                             note = /replace="Ser" or "Gly" or "Ala" or "Thr" or "Asn"
VARIANT                      73
                             note = /replace="Tyr"
VARIANT                      76
```

| | | |
|---|---|---|
| | | note = /replace="Arg" or "Glu" |
| VARIANT | 108 | |
| | | note = /replace="Ser" or "Gly" or "Ala" or "Thr" or "Asn" |
| VARIANT | 112 | |
| | | note = /replace="Arg" or "Glu" |
| VARIANT | 144 | |
| | | note = /replace="Ser" or "Gly" or "Ala" or "Thr" or "Asn" |
| VARIANT | 145 | |
| | | note = /replace="His" |
| VARIANT | 148 | |
| | | note = /replace="Arg" or "Glu" |
| VARIANT | 180 | |
| | | note = /replace="Ser" or "Gly" or "Ala" or "Thr" or "Asn" |
| VARIANT | 184 | |
| | | note = /replace="Arg" or "Glu" |
| VARIANT | 216 | |
| | | note = /replace="Ser" or "Gly" or "Ala" or "Thr" or "Asn" |
| VARIANT | 217 | |
| | | note = /replace="Tyr" |
| VARIANT | 220 | |
| | | note = /replace="Arg" or "Glu" |
| VARIANT | 252 | |
| | | note = /replace="Ser" or "Gly" or "Ala" or "Thr" or "Asn" |
| VARIANT | 253 | |
| | | note = /replace="Asn" |
| VARIANT | 256 | |
| | | note = /replace="Arg" or "Glu" |
| VARIANT | 295 | |
| | | note = /replace="Ser" or "Gly" or "Ala" or "Thr" or "Asn" |
| VARIANT | 296 | |
| | | note = /replace="Tyr" |
| VARIANT | 299 | |
| | | note = /replace="Arg" or "Glu" |
| REGION | 1..349 | |
| | | note = MISC_FEATURE - /note="Variant residues given in the sequence have nopreference with respect to those in the annotationsfor variant positions" |
| REGION | 1..349 | |
| | | note = source = /note="Description of Artificial Sequence: Syntheticpolypeptide" |
| REGION | 1..349 | |
| | | note = source = /note="See specification as filed for detailed description ofsubstitutions and preferred embodiments" |
| source | 1..349 | |
| | | mol_type = protein |
| | | organism = synthetic construct |

SEQUENCE: 5
```
GRSRLLEDFR NNRYPNLQLR EIAGHIMEFS QDQHGCRFIQ LKLERATPAE RQLVFNEILQ    60
AAYQLMVDVF GCRVIQKFFE FGSLEQKLAL AERIRGHVLS LALQMYGCRV IQKALEFIPS   120
DQQNEMVREL DGHVLKCVKD QNGCRVVQKC IECVQPQSLQ FIIDAFKGQV FALSTHPYGC   180
RVIQRILEHC LPDQTLPILE ELHQHTEQLV QDQYGCRVIQ HVLEHGRPED KSKIVAEIRG   240
NVLVLSQHKF ACRVVQKCVT HASRTERAVL IDEVCTMNDG PHSALYTMMK DQYACRVVQK   300
MIDVAEPGQR KIVMHKIRPH IATLRKYTYG KHILAKLEKY YMKNGVDLG              349
```

| | | |
|---|---|---|
| SEQ ID NO: 6 | moltype = AA length = 14 | |
| FEATURE | Location/Qualifiers | |
| REGION | 1..14 | |
| | | note = source = /note="Description of Artificial Sequence: Syntheticpeptide" |
| source | 1..14 | |
| | | mol_type = protein |
| | | organism = synthetic construct |

SEQUENCE: 6
QHGCRFIQLK LERA    14

| | | |
|---|---|---|
| SEQ ID NO: 7 | moltype = AA length = 14 | |
| FEATURE | Location/Qualifiers | |
| REGION | 1..14 | |
| | | note = source = /note="Description of Artificial Sequence: Syntheticpeptide" |
| source | 1..14 | |
| | | mol_type = protein |
| | | organism = synthetic construct |

SEQUENCE: 7
QHGSRFIQLK LERA    14

| | | |
|---|---|---|
| SEQ ID NO: 8 | moltype = AA length = 14 | |
| FEATURE | Location/Qualifiers | |

```
                          -continued

REGION                    1..14
                          note = source = /note="Description of Artificial Sequence:
                           Syntheticpeptide"
source                    1..14
                          mol_type = protein
                          organism = synthetic construct
SEQUENCE: 8
QHGSRFIRLK LERA                                                             14

SEQ ID NO: 9              moltype = AA   length = 14
FEATURE                   Location/Qualifiers
REGION                    1..14
                          note = source = /note="Description of Artificial Sequence:
                           Syntheticpeptide"
source                    1..14
                          mol_type = protein
                          organism = synthetic construct
SEQUENCE: 9
QHGGRFIRLK LERA                                                             14

SEQ ID NO: 10             moltype = AA   length = 14
FEATURE                   Location/Qualifiers
REGION                    1..14
                          note = source = /note="Description of Artificial Sequence:
                           Syntheticpeptide"
source                    1..14
                          mol_type = protein
                          organism = synthetic construct
SEQUENCE: 10
QHGARFIRLK LERA                                                             14

SEQ ID NO: 11             moltype = AA   length = 14
FEATURE                   Location/Qualifiers
REGION                    1..14
                          note = source = /note="Description of Artificial Sequence:
                           Syntheticpeptide"
source                    1..14
                          mol_type = protein
                          organism = synthetic construct
SEQUENCE: 11
QHGTRFIRLK LERA                                                             14

SEQ ID NO: 12             moltype = AA   length = 14
FEATURE                   Location/Qualifiers
REGION                    1..14
                          note = source = /note="Description of Artificial Sequence:
                           Syntheticpeptide"
source                    1..14
                          mol_type = protein
                          organism = synthetic construct
SEQUENCE: 12
QHGCRFIRLK LERA                                                             14

SEQ ID NO: 13             moltype = AA   length = 14
FEATURE                   Location/Qualifiers
REGION                    1..14
                          note = source = /note="Description of Artificial Sequence:
                           Syntheticpeptide"
source                    1..14
                          mol_type = protein
                          organism = synthetic construct
SEQUENCE: 13
QHGSRFIELK LERA                                                             14

SEQ ID NO: 14             moltype = AA   length = 14
FEATURE                   Location/Qualifiers
REGION                    1..14
                          note = source = /note="Description of Artificial Sequence:
                           Syntheticpeptide"
source                    1..14
                          mol_type = protein
                          organism = synthetic construct
SEQUENCE: 14
QHGNRFIQLK LERA                                                             14

SEQ ID NO: 15             moltype = AA   length = 14
FEATURE                   Location/Qualifiers
REGION                    1..14
                          note = source = /note="Description of Artificial Sequence:
```

```
                    Syntheticpeptide"
source              1..14
                    mol_type = protein
                    organism = synthetic construct
SEQUENCE: 15
VFGCRVIQKF FEFG                                                              14

SEQ ID NO: 16       moltype = AA  length = 14
FEATURE             Location/Qualifiers
REGION              1..14
                    note = source = /note="Description of Artificial Sequence:
                    Syntheticpeptide"
source              1..14
                    mol_type = protein
                    organism = synthetic construct
SEQUENCE: 16
VFGSRVIQKF FEFG                                                              14

SEQ ID NO: 17       moltype = AA  length = 14
FEATURE             Location/Qualifiers
REGION              1..14
                    note = source = /note="Description of Artificial Sequence:
                    Syntheticpeptide"
source              1..14
                    mol_type = protein
                    organism = synthetic construct
SEQUENCE: 17
VFGCYVIQKF FEFG                                                              14

SEQ ID NO: 18       moltype = AA  length = 14
FEATURE             Location/Qualifiers
REGION              1..14
                    note = source = /note="Description of Artificial Sequence:
                    Syntheticpeptide"
source              1..14
                    mol_type = protein
                    organism = synthetic construct
SEQUENCE: 18
VFGSYVIQKF FEFG                                                              14

SEQ ID NO: 19       moltype = AA  length = 14
FEATURE             Location/Qualifiers
REGION              1..14
                    note = source = /note="Description of Artificial Sequence:
                    Syntheticpeptide"
source              1..14
                    mol_type = protein
                    organism = synthetic construct
SEQUENCE: 19
VFGSYVIRKF FEFG                                                              14

SEQ ID NO: 20       moltype = AA  length = 14
FEATURE             Location/Qualifiers
REGION              1..14
                    note = source = /note="Description of Artificial Sequence:
                    Syntheticpeptide"
source              1..14
                    mol_type = protein
                    organism = synthetic construct
SEQUENCE: 20
VFGGYVIRKF FEFG                                                              14

SEQ ID NO: 21       moltype = AA  length = 14
FEATURE             Location/Qualifiers
REGION              1..14
                    note = source = /note="Description of Artificial Sequence:
                    Syntheticpeptide"
source              1..14
                    mol_type = protein
                    organism = synthetic construct
SEQUENCE: 21
VFGAYVIRKF FEFG                                                              14

SEQ ID NO: 22       moltype = AA  length = 14
FEATURE             Location/Qualifiers
REGION              1..14
                    note = source = /note="Description of Artificial Sequence:
                    Syntheticpeptide"
source              1..14
```

```
                            mol_type = protein
                            organism = synthetic construct
SEQUENCE: 22
VFGTYVIRKF FEFG                                                         14

SEQ ID NO: 23               moltype = AA   length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 23
VFGCYVIRKF FEFG                                                         14

SEQ ID NO: 24               moltype = AA   length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 24
VFGSYVIEKF FEFG                                                         14

SEQ ID NO: 25               moltype = AA   length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 25
VFGNYVIQKF FEFG                                                         14

SEQ ID NO: 26               moltype = AA   length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 26
MYGCRVIQKA LEFI                                                         14

SEQ ID NO: 27               moltype = AA   length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 27
MYGSRVIQKA LEFI                                                         14

SEQ ID NO: 28               moltype = AA   length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 28
MYGSRVIRKA LEFI                                                         14

SEQ ID NO: 29               moltype = AA   length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
```

```
SEQUENCE: 29
MYGGRVIRKA LEFI                                                                 14

SEQ ID NO: 30           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 30
MYGARVIRKA LEFI                                                                 14

SEQ ID NO: 31           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 31
MYGTRVIRKA LEFI                                                                 14

SEQ ID NO: 32           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 32
MYGCRVIRKA LEFI                                                                 14

SEQ ID NO: 33           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 33
MYGSRVIEKA LEFI                                                                 14

SEQ ID NO: 34           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 34
MYGNRVIQKA LEFI                                                                 14

SEQ ID NO: 35           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 35
QNGCRVVQKC IECV                                                                 14

SEQ ID NO: 36           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 36
QNGSRVVQKC IECV                                                                 14
```

```
SEQ ID NO: 37              moltype = AA   length = 14
FEATURE                    Location/Qualifiers
REGION                     1..14
                           note = source = /note="Description of Artificial Sequence:
                            Syntheticpeptide"
source                     1..14
                           mol_type = protein
                           organism = synthetic construct
SEQUENCE: 37
QNGCHVVQKC IECV                                                              14

SEQ ID NO: 38              moltype = AA   length = 14
FEATURE                    Location/Qualifiers
REGION                     1..14
                           note = source = /note="Description of Artificial Sequence:
                            Syntheticpeptide"
source                     1..14
                           mol_type = protein
                           organism = synthetic construct
SEQUENCE: 38
QNGSHVVQKC IECV                                                              14

SEQ ID NO: 39              moltype = AA   length = 14
FEATURE                    Location/Qualifiers
REGION                     1..14
                           note = source = /note="Description of Artificial Sequence:
                            Syntheticpeptide"
source                     1..14
                           mol_type = protein
                           organism = synthetic construct
SEQUENCE: 39
QNGSHVVRKC IECV                                                              14

SEQ ID NO: 40              moltype = AA   length = 14
FEATURE                    Location/Qualifiers
REGION                     1..14
                           note = source = /note="Description of Artificial Sequence:
                            Syntheticpeptide"
source                     1..14
                           mol_type = protein
                           organism = synthetic construct
SEQUENCE: 40
QNGGHVVRKC IECV                                                              14

SEQ ID NO: 41              moltype = AA   length = 14
FEATURE                    Location/Qualifiers
REGION                     1..14
                           note = source = /note="Description of Artificial Sequence:
                            Syntheticpeptide"
source                     1..14
                           mol_type = protein
                           organism = synthetic construct
SEQUENCE: 41
QNGAHVVRKC IECV                                                              14

SEQ ID NO: 42              moltype = AA   length = 14
FEATURE                    Location/Qualifiers
REGION                     1..14
                           note = source = /note="Description of Artificial Sequence:
                            Syntheticpeptide"
source                     1..14
                           mol_type = protein
                           organism = synthetic construct
SEQUENCE: 42
QNGTHVVRKC IECV                                                              14

SEQ ID NO: 43              moltype = AA   length = 14
FEATURE                    Location/Qualifiers
REGION                     1..14
                           note = source = /note="Description of Artificial Sequence:
                            Syntheticpeptide"
source                     1..14
                           mol_type = protein
                           organism = synthetic construct
SEQUENCE: 43
QNGCHVVRKC IECV                                                              14

SEQ ID NO: 44              moltype = AA   length = 14
```

```
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 44
QNGSHVVEKC IECV                                                              14

SEQ ID NO: 45               moltype = AA  length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 45
QNGNHVVQKC IECV                                                              14

SEQ ID NO: 46               moltype = AA  length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 46
PYGCRVIQRI LEHC                                                              14

SEQ ID NO: 47               moltype = AA  length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 47
PYGSRVIQRI LEHC                                                              14

SEQ ID NO: 48               moltype = AA  length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 48
PYGSRVIRRI LEHC                                                              14

SEQ ID NO: 49               moltype = AA  length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 49
PYGGRVIRRI LEHC                                                              14

SEQ ID NO: 50               moltype = AA  length = 14
FEATURE                     Location/Qualifiers
REGION                      1..14
                            note = source = /note="Description of Artificial Sequence:
                             Syntheticpeptide"
source                      1..14
                            mol_type = protein
                            organism = synthetic construct
SEQUENCE: 50
PYGARVIRRI LEHC                                                              14

SEQ ID NO: 51               moltype = AA  length = 14
FEATURE                     Location/Qualifiers
REGION                      1..14
```

```
                        note = source = /note="Description of Artificial Sequence:
                            Syntheticpeptide"
source                  1..14
                        mol_type = protein
                        organism = synthetic construct
SEQUENCE: 51
PYGTRVIRRI LEHC                                                              14

SEQ ID NO: 52           moltype = AA  length = 14
FEATURE                 Location/Qualifiers
REGION                  1..14
                        note = source = /note="Description of Artificial Sequence:
                            Syntheticpeptide"
source                  1..14
                        mol_type = protein
                        organism = synthetic construct
SEQUENCE: 52
PYGCRVIRRI LEHC                                                              14

SEQ ID NO: 53           moltype = AA  length = 14
FEATURE                 Location/Qualifiers
REGION                  1..14
                        note = source = /note="Description of Artificial Sequence:
                            Syntheticpeptide"
source                  1..14
                        mol_type = protein
                        organism = synthetic construct
SEQUENCE: 53
PYGSRVIERI LEHC                                                              14

SEQ ID NO: 54           moltype = AA  length = 14
FEATURE                 Location/Qualifiers
REGION                  1..14
                        note = source = /note="Description of Artificial Sequence:
                            Syntheticpeptide"
source                  1..14
                        mol_type = protein
                        organism = synthetic construct
SEQUENCE: 54
PYGNRVIQRI LEHC                                                              14

SEQ ID NO: 55           moltype = AA  length = 14
FEATURE                 Location/Qualifiers
REGION                  1..14
                        note = source = /note="Description of Artificial Sequence:
                            Syntheticpeptide"
source                  1..14
                        mol_type = protein
                        organism = synthetic construct
SEQUENCE: 55
QYGCRVIQHV LEHG                                                              14

SEQ ID NO: 56           moltype = AA  length = 14
FEATURE                 Location/Qualifiers
REGION                  1..14
                        note = source = /note="Description of Artificial Sequence:
                            Syntheticpeptide"
source                  1..14
                        mol_type = protein
                        organism = synthetic construct
SEQUENCE: 56
QYGSRVIQHV LEHG                                                              14

SEQ ID NO: 57           moltype = AA  length = 14
FEATURE                 Location/Qualifiers
REGION                  1..14
                        note = source = /note="Description of Artificial Sequence:
                            Syntheticpeptide"
source                  1..14
                        mol_type = protein
                        organism = synthetic construct
SEQUENCE: 57
QYGCYVIQHV LEHG                                                              14

SEQ ID NO: 58           moltype = AA  length = 14
FEATURE                 Location/Qualifiers
REGION                  1..14
                        note = source = /note="Description of Artificial Sequence:
                            Syntheticpeptide"
```

| | | |
|---|---|---|
| source | 1..14<br>mol_type = protein<br>organism = synthetic construct | |
| SEQUENCE: 58<br>QYGSYVIQHV LEHG | | 14 |
| SEQ ID NO: 59<br>FEATURE<br>REGION | moltype = AA  length = 14<br>Location/Qualifiers<br>1..14<br>note = source = /note="Description of Artificial Sequence:<br>Syntheticpeptide" | |
| source | 1..14<br>mol_type = protein<br>organism = synthetic construct | |
| SEQUENCE: 59<br>QYGSYVIRHV LEHG | | 14 |
| SEQ ID NO: 60<br>FEATURE<br>REGION | moltype = AA  length = 14<br>Location/Qualifiers<br>1..14<br>note = source = /note="Description of Artificial Sequence:<br>Syntheticpeptide" | |
| source | 1..14<br>mol_type = protein<br>organism = synthetic construct | |
| SEQUENCE: 60<br>QYGGYVIRHV LEHG | | 14 |
| SEQ ID NO: 61<br>FEATURE<br>REGION | moltype = AA  length = 14<br>Location/Qualifiers<br>1..14<br>note = source = /note="Description of Artificial Sequence:<br>Syntheticpeptide" | |
| source | 1..14<br>mol_type = protein<br>organism = synthetic construct | |
| SEQUENCE: 61<br>QYGAYVIRHV LEHG | | 14 |
| SEQ ID NO: 62<br>FEATURE<br>REGION | moltype = AA  length = 14<br>Location/Qualifiers<br>1..14<br>note = source = /note="Description of Artificial Sequence:<br>Syntheticpeptide" | |
| source | 1..14<br>mol_type = protein<br>organism = synthetic construct | |
| SEQUENCE: 62<br>QYGTYVIRHV LEHG | | 14 |
| SEQ ID NO: 63<br>FEATURE<br>REGION | moltype = AA  length = 14<br>Location/Qualifiers<br>1..14<br>note = source = /note="Description of Artificial Sequence:<br>Syntheticpeptide" | |
| source | 1..14<br>mol_type = protein<br>organism = synthetic construct | |
| SEQUENCE: 63<br>QYGCYVIRHV LEHG | | 14 |
| SEQ ID NO: 64<br>FEATURE<br>REGION | moltype = AA  length = 14<br>Location/Qualifiers<br>1..14<br>note = source = /note="Description of Artificial Sequence:<br>Syntheticpeptide" | |
| source | 1..14<br>mol_type = protein<br>organism = synthetic construct | |
| SEQUENCE: 64<br>QYGSYVIEHV LEHG | | 14 |
| SEQ ID NO: 65<br>FEATURE<br>REGION | moltype = AA  length = 14<br>Location/Qualifiers<br>1..14<br>note = source = /note="Description of Artificial Sequence:<br>Syntheticpeptide" | |
| source | 1..14<br>mol_type = protein | |

```
                        -continued

SEQUENCE: 65
QYGNYVIQHV LEHG                                                         14

SEQ ID NO: 66           moltype = AA  length = 14
FEATURE                 Location/Qualifiers
REGION                  1..14
                        note = source = /note="Description of Artificial Sequence:
                         Syntheticpeptide"
source                  1..14
                        mol_type = protein
                        organism = synthetic construct
SEQUENCE: 66
KFACRVVQKC VTHA                                                         14

SEQ ID NO: 67           moltype = AA  length = 14
FEATURE                 Location/Qualifiers
REGION                  1..14
                        note = source = /note="Description of Artificial Sequence:
                         Syntheticpeptide"
source                  1..14
                        mol_type = protein
                        organism = synthetic construct
SEQUENCE: 67
KFASRVVQKC VTHA                                                         14

SEQ ID NO: 68           moltype = AA  length = 14
FEATURE                 Location/Qualifiers
REGION                  1..14
                        note = source = /note="Description of Artificial Sequence:
                         Syntheticpeptide"
source                  1..14
                        mol_type = protein
                        organism = synthetic construct
SEQUENCE: 68
KFACNVVQKC VTHA                                                         14

SEQ ID NO: 69           moltype = AA  length = 14
FEATURE                 Location/Qualifiers
REGION                  1..14
                        note = source = /note="Description of Artificial Sequence:
                         Syntheticpeptide"
source                  1..14
                        mol_type = protein
                        organism = synthetic construct
SEQUENCE: 69
KFASNVVQKC VTHA                                                         14

SEQ ID NO: 70           moltype = AA  length = 14
FEATURE                 Location/Qualifiers
REGION                  1..14
                        note = source = /note="Description of Artificial Sequence:
                         Syntheticpeptide"
source                  1..14
                        mol_type = protein
                        organism = synthetic construct
SEQUENCE: 70
KFASNVVRKC VTHA                                                         14

SEQ ID NO: 71           moltype = AA  length = 14
FEATURE                 Location/Qualifiers
REGION                  1..14
                        note = source = /note="Description of Artificial Sequence:
                         Syntheticpeptide"
source                  1..14
                        mol_type = protein
                        organism = synthetic construct
SEQUENCE: 71
KFAGNVVRKC VTHA                                                         14

SEQ ID NO: 72           moltype = AA  length = 14
FEATURE                 Location/Qualifiers
REGION                  1..14
                        note = source = /note="Description of Artificial Sequence:
                         Syntheticpeptide"
source                  1..14
                        mol_type = protein
                        organism = synthetic construct
SEQUENCE: 72
```

```
KFAANVVRKC VTHA                                                         14

SEQ ID NO: 73           moltype = AA  length = 14
FEATURE                 Location/Qualifiers
REGION                  1..14
                        note = source = /note="Description of Artificial Sequence:
                          Syntheticpeptide"
source                  1..14
                        mol_type = protein
                        organism = synthetic construct
SEQUENCE: 73
KFATNVVRKC VTHA                                                         14

SEQ ID NO: 74           moltype = AA  length = 14
FEATURE                 Location/Qualifiers
REGION                  1..14
                        note = source = /note="Description of Artificial Sequence:
                          Syntheticpeptide"
source                  1..14
                        mol_type = protein
                        organism = synthetic construct
SEQUENCE: 74
KFACNVVRKC VTHA                                                         14

SEQ ID NO: 75           moltype = AA  length = 14
FEATURE                 Location/Qualifiers
REGION                  1..14
                        note = source = /note="Description of Artificial Sequence:
                          Syntheticpeptide"
source                  1..14
                        mol_type = protein
                        organism = synthetic construct
SEQUENCE: 75
KFASNVVEKC VTHA                                                         14

SEQ ID NO: 76           moltype = AA  length = 14
FEATURE                 Location/Qualifiers
REGION                  1..14
                        note = source = /note="Description of Artificial Sequence:
                          Syntheticpeptide"
source                  1..14
                        mol_type = protein
                        organism = synthetic construct
SEQUENCE: 76
KFANNVVQKC VTHA                                                         14

SEQ ID NO: 77           moltype = AA  length = 14
FEATURE                 Location/Qualifiers
REGION                  1..14
                        note = source = /note="Description of Artificial Sequence:
                          Syntheticpeptide"
source                  1..14
                        mol_type = protein
                        organism = synthetic construct
SEQUENCE: 77
QYACRVVQKM IDVA                                                         14

SEQ ID NO: 78           moltype = AA  length = 14
FEATURE                 Location/Qualifiers
REGION                  1..14
                        note = source = /note="Description of Artificial Sequence:
                          Syntheticpeptide"
source                  1..14
                        mol_type = protein
                        organism = synthetic construct
SEQUENCE: 78
QYASRVVQKM IDVA                                                         14

SEQ ID NO: 79           moltype = AA  length = 14
FEATURE                 Location/Qualifiers
REGION                  1..14
                        note = source = /note="Description of Artificial Sequence:
                          Syntheticpeptide"
source                  1..14
                        mol_type = protein
                        organism = synthetic construct
SEQUENCE: 79
QYACYVVQKM IDVA                                                         14
```

```
SEQ ID NO: 80           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 80
QYASYVVQKM IDVA                                                                  14

SEQ ID NO: 81           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 81
QYASYVVRKM IDVA                                                                  14

SEQ ID NO: 82           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 82
QYAGYVVRKM IDVA                                                                  14

SEQ ID NO: 83           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 83
QYAAYVVRKM IDVA                                                                  14

SEQ ID NO: 84           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 84
QYATYVVRKM IDVA                                                                  14

SEQ ID NO: 85           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 85
QYACYVVRKM IDVA                                                                  14

SEQ ID NO: 86           moltype = AA  length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 86
QYASYVVEKM IDVA                                                                  14

SEQ ID NO: 87           moltype = AA  length = 14
FEATURE                 Location/Qualifiers
```

```
REGION                    1..14
                          note = source = /note="Description of Artificial Sequence:
                            Syntheticpeptide"
source                    1..14
                          mol_type = protein
                          organism = synthetic construct
SEQUENCE: 87
QYANYVVQKM IDVA                                                            14

SEQ ID NO: 88             moltype = AA  length = 349
FEATURE                   Location/Qualifiers
REGION                    1..349
                          note = source = /note="Description of Artificial Sequence:
                            Syntheticpolypeptide"
source                    1..349
                          mol_type = protein
                          organism = synthetic construct
SEQUENCE: 88
GRSRLLEDFR NNRYPNLQLR EIAGHIMEFS QDQHGSRFIQ LKLERATPAE RQLVFNEILQ   60
AAYQLMVDVF GNYVIQKFFE FGSLEQKLAL AERIRGHVLS LALQMYGSRV IEKALEFIPS  120
DQQNEMVREL DGHVLKCVKD QNGNHVVQKC IECVQPQSLQ FIIDAFKGQV FALSTHPYGC  180
RVIQRILEHC LPDQTLPILE ELHQHTEQLV QDQYGNYVIQ HVLEHGRPED KSKIVAEIRG  240
NVLVLSQHKF ASNVVEKCVT HASRTERAVL IDEVCTMNDG PHSALYTMMK DQYANYVVQK  300
MIDVAEPGQR KIVMHKIRPH IATLRKYTYG KHILAKLEKY YMKNGVDLG              349

SEQ ID NO: 89             moltype = AA  length = 349
FEATURE                   Location/Qualifiers
REGION                    1..349
                          note = source = /note="Description of Artificial Sequence:
                            Syntheticpolypeptide"
source                    1..349
                          mol_type = protein
                          organism = synthetic construct
SEQUENCE: 89
GRSRLLEDFR NNRYPNLQLR EIAGHIMEFS QDQHGSRFIQ LKLERATPAE RQLVFNEILQ   60
AAYQLMVDVF GNYVIQKFFE FGSLEQKLAL AERIRGHVLS LALQMYGCRV IQKALEFIPS  120
DQQNEMVREL DGHVLKCVKD QNGNHVVQKC IECVQPQSLQ FIIDAFKGQV FALSTHPYGC  180
RVIQRILEHC LPDQTLPILE ELHQHTEQLV QDQYGSYVIE HVLEHGRPED KSKIVAEIRG  240
NVLVLSQHKF ANNVVQKCVT HASRTERAVL IDEVCTMNDG PHSALYTMMK DQYANYVVQK  300
MIDVAEPGQR KIVMHKIRPH IATLRKYTYG KHILAKLEKY YMKNGVDLG              349

SEQ ID NO: 90             moltype = AA  length = 349
FEATURE                   Location/Qualifiers
REGION                    1..349
                          note = source = /note="Description of Artificial Sequence:
                            Syntheticpolypeptide"
source                    1..349
                          mol_type = protein
                          organism = synthetic construct
SEQUENCE: 90
GRSRLLEDFR NNRYPNLQLR EIAGHIMEFS QDQHGSRFIE LKLERATPAE RQLVFNEILQ   60
AAYQLMVDVF GNYVIQKFFE FGSLEQKLAL AERIRGHVLS LALQMYGSRV IEKALEFIPS  120
DQQNEMVREL DGHVLKCVKD QNGNHVVQKC IECVQPQSLQ FIIDAFKGQV FALSTHPYGS  180
RVIERILEHC LPDQTLPILE ELHQHTEQLV QDQYGNYVIQ HVLEHGRPED KSKIVAEIRG  240
NVLVLSQHKF ASNVVEKCVT HASRTERAVL IDEVCTMNDG PHSALYTMMK DQYANYVVQK  300
MIDVAEPGQR KIVMHKIRPH IATLRKYTYG KHILAKLEKY YMKNGVDLG              349

SEQ ID NO: 91             moltype = AA  length = 341
FEATURE                   Location/Qualifiers
REGION                    1..341
                          note = source = /note="Description of Artificial Sequence:
                            Syntheticpolypeptide"
source                    1..341
                          mol_type = protein
                          organism = synthetic construct
SEQUENCE: 91
GRSRLLEDFR NNRYPNLQLR EIAGHIMEFS QDQHGSRFIE LKLERATPAE RQLVFNEILQ   60
AAYQLMVDVF GCRVIQKFFE FGSLEQKLAL AERIRGHVLS LALQMYGSRV IQKALEFIPS  120
DQQNEMVREL DGHVLKCVKD QNGNHVVQKC IECVQPQSLQ FIIDAFKGQV FALSTHPYGC  180
RVIQRILEHC LPDQTLPILE ELHQHTEQLV QDQYGSYVIE HVLEHGRPED KSKIVAEIRG  240
NVLVLSQHKF ANNVVQKCVT HASRTERAVL IDEVCTMNDG PHSALYTMMK DQYASYVVEK  300
MIDVAEPGQR KIVMHKIRPH IATLRKYTYG KHILAKLEKY Y                     341

SEQ ID NO: 92             moltype = AA  length = 341
FEATURE                   Location/Qualifiers
REGION                    1..341
                          note = source = /note="Description of Artificial Sequence:
                            Syntheticpolypeptide"
source                    1..341
```

```
                              mol_type = protein
                              organism = synthetic construct
SEQUENCE: 92
GRSRLLEDFR  NNRYPNLQLR  EIAGHIMEFS  QDQHGNRFIQ  LKLERATPAE  RQLVFNEILQ   60
AAYQLMVDVF  GSYVIEKFFE  FGSLEQKLAL  AERIRGHVLS  LALQMYGSRV  IEKALEFIPS  120
DQQNEMVREL  DGHVLKCVKD  QNGNHVVQKC  IECVQPQSLQ  FIIDAFKGQV  FALSTHPYGS  180
RVIERILEHC  LPDQTLPILE  ELHQHTEQLV  QDQYGSYVIE  HVLEHGRPED  KSKIVAEIRG  240
NVLVLSQHKF  ACNVVQKCVT  HASRTERAVL  IDECVTMNDG  PHSALYTMMK  DQYASYVVEK  300
MIDVAEPGQR  KIVMHKIRPH  IATLRKYTYG  KHILAKLEKY  Y                       341

SEQ ID NO: 93           moltype = AA   length = 341
FEATURE                 Location/Qualifiers
REGION                  1..341
                        note = source = /note="Description of Artificial Sequence:
                         Syntheticpolypeptide"
source                  1..341
                        mol_type = protein
                        organism = synthetic construct
SEQUENCE: 93
GRSRLLEDFR  NNRYPNLQLR  EIAGHIMEFS  QDQHGCRFIQ  LKLERATPAE  RQLVFNEILQ   60
AAYQLMVDVF  GSYVIEKFFE  FGSLEQKLAL  AERIRGHVLS  LALQMYGNRV  IQKALEFIPS  120
DQQNEMVREL  DGHVLKCVKD  QNGNHVVQKC  IECVQPQSLQ  FIIDAFKGQV  FALSTHPYGC  180
RVIQRILEHC  LPDQTLPILE  ELHQHTEQLV  QDQYGSYVIE  HVLEHGRPED  KSKIVAEIRG  240
NVLVLSQHKF  ACNVVQKCVT  HASRTERAVL  IDECVTMNDG  PHSALYTMMK  DQYACYVVQK  300
MIDVAEPGQR  KIVMHKIRPH  IATLRKYTYG  KHILAKLEKY  Y                       341

SEQ ID NO: 94           moltype = AA   length = 8
FEATURE                 Location/Qualifiers
REGION                  1..8
                        note = source = /note="Description of Artificial Sequence:
                         Syntheticpeptide"
source                  1..8
                        mol_type = protein
                        organism = synthetic construct
SEQUENCE: 94
PPKKKRKV                                                                  8

SEQ ID NO: 95           moltype = AA   length = 6
FEATURE                 Location/Qualifiers
REGION                  1..6
                        note = source = /note="Description of Artificial Sequence:
                         Synthetic6xHis tag"
source                  1..6
                        mol_type = protein
                        organism = synthetic construct
SEQUENCE: 95
HHHHHH                                                                    6

SEQ ID NO: 96           moltype = AA   length = 424
FEATURE                 Location/Qualifiers
REGION                  1..424
                        note = source = /note="Description of Artificial Sequence:
                         Syntheticpolypeptide"
source                  1..424
                        mol_type = protein
                        organism = synthetic construct
SEQUENCE: 96
MGILPPKKKR  KVSRGRSRLL  EDFRNNRYPN  LQLREIAGHI  MEFSQDQHGS  RFIQLKLERA   60
TPAERQLVFN  EILQAAYQLM  VDVFGNYVIQ  KFFEFGSLEQ  KLALAERIRG  HVLSLALQMY  120
GSRVIEKALE  FIPSDQQNEM  VRELDGHVLK  CVKDQNGNHV  VQKCIECVQP  QSLQFIIDAF  180
KGQVFALSTH  PYGCRVIQRI  LEHCLPDQTL  PILEELHQHT  EQLVQDQYGN  YVIQHVLEHG  240
RPEDKSKIVA  EIRGNVLVLS  QHKFASNVVE  KCVTHASRTE  RAVLIDEVCT  MNDGPHSALY  300
TMMKDQYANY  VVQKMIDVAE  PGQRKIVMHK  IRPHIATLRK  YTYGKHILAK  LEKYYMKNGV  360
DLGGPAGSGR  ADALDDFDLD  MLGSDALDDF  DLDMLGSDAL  DDFDLDMLGS  DALDDFDLDM  420
LYID                                                                    424

SEQ ID NO: 97           moltype = AA   length = 424
FEATURE                 Location/Qualifiers
REGION                  1..424
                        note = source = /note="Description of Artificial Sequence:
                         Syntheticpolypeptide"
source                  1..424
                        mol_type = protein
                        organism = synthetic construct
SEQUENCE: 97
MGILPPKKKR  KVSRGRSRLL  EDFRNNRYPN  LQLREIAGHI  MEFSQDQHGS  RFIQLKLERA   60
TPAERQLVFN  EILQAAYQLM  VDVFGNYVIQ  KFFEFGSLEQ  KLALAERIRG  HVLSLALQMY  120
GCRVIQKALE  FIPSDQQNEM  VRELDGHVLK  CVKDQNGNHV  VQKCIECVQP  QSLQFIIDAF  180
KGQVFALSTH  PYGCRVIQRI  LEHCLPDQTL  PILEELHQHT  EQLVQDQYGS  YVIEHVLEHG  240
```

```
RPEDKSKIVA EIRGNVLVLS QHKFANNVVQ KCVTHASRTE RAVLIDEVCT MNDGPHSALY    300
TMMKDQYANY VVQKMIDVAE PGQRKIVMHK IRPHIATLRK YTYGKHILAK LEKYYMKNGV    360
DLGGPAGSGR ADALDDFDLD MLGSDALDDF DLDMLGSDAL DDFDLDMLGS DALDDFDLDM    420
LYID                                                                 424

SEQ ID NO: 98           moltype = AA  length = 424
FEATURE                 Location/Qualifiers
REGION                  1..424
                        note = source = /note="Description of Artificial Sequence:
                          Syntheticpolypeptide"
source                  1..424
                        mol_type = protein
                        organism = synthetic construct
SEQUENCE: 98
MGILPPKKKR KVSRGRSRLL EDFRNNRYPN LQLREIAGHI MEFSQDQHGS RFIQLKLERA     60
TPAERQLVFN EILQAAYQLM VDVFGNYVIQ KFFEFGSLEQ KLALAERIRG HVLSLALQMY    120
GCRVIQKALE FIPSDQQNEM VRELDGHVLK CVKDQNGNHV VQKCIECVQP QSLQFIIDAF    180
KGQVFALSTH PYGCRVIQRI LEHCLPDQTL PILEELHQHT EQLVQDQYGN YVIQHVLEHG    240
RPEDKSKIVA EIRGNVLVLS QHKFASNVVE KCVTHASRTE RAVLIDEVCT MNDGPHSALY    300
TMMKDQYANY VVQKMIDVAE PGQRKIVMHK IRPHIATLRK YTYGKHILAK LEKYYMKNGV    360
DLGGPAGSGR ADALDDFDLD MLGSDALDDF DLDMLGSDAL DDFDLDMLGS DALDDFDLDM    420
LYID                                                                 424

SEQ ID NO: 99           moltype = AA  length = 424
FEATURE                 Location/Qualifiers
REGION                  1..424
                        note = source = /note="Description of Artificial Sequence:
                          Syntheticpolypeptide"
source                  1..424
                        mol_type = protein
                        organism = synthetic construct
SEQUENCE: 99
MGILPPKKKR KVSRGRSRLL EDFRNNRYPN LQLREIAGHI MEFSQDQHGS RFIQLKLERA     60
TPAERQLVFN EILQAAYQLM VDVFGNYVIQ KFFEFGSLEQ KLALAERIRG HVLSLALQMY    120
GSRVIEKALE FIPSDQQNEM VRELDGHVLK CVKDQNGNHV VQKCIECVQP QSLQFIIDAF    180
KGQVFALSTH PYGCRVIQRI LEHCLPDQTL PILEELHQT  EQLVQDQYGS YVIEHVLEHG    240
RPEDKSKIVA EIRGNVLVLS QHKFANNVVQ KCVTHASRTE RAVLIDEVCT MNDGPHSALY    300
TMMKDQYANY VVQKMIDVAE PGQRKIVMHK IRPHIATLRK YTYGKHILAK LEKYYMKNGV    360
DLGGPAGSGR ADALDDFDLD MLGSDALDDF DLDMLGSDAL DDFDLDMLGS DALDDFDLDM    420
LYID                                                                 424

SEQ ID NO: 100          moltype = AA  length = 621
FEATURE                 Location/Qualifiers
REGION                  1..621
                        note = source = /note="Description of Artificial Sequence:
                          Syntheticpolypeptide"
source                  1..621
                        mol_type = protein
                        organism = synthetic construct
SEQUENCE: 100
MVSKGEELFT GVVPILVELD GDVNGHKFSV RGEGEGDATN GKLTLKFICT TGKLPVPWPT     60
LVTTFGYGVA CFSRYPDHMK QHDFFKSAMP EGYVQERTIS FKDDGTYKTR AEVKFEGDTL    120
VNRIELKGID FKEDGNILGH KLEYNFNSHN VYITADKQKN GIKANFKIRH NVEDGSVQLA    180
DHYQQNTPIG DGPVLLPDNH YLSHQSALSK DPNEKRDHMV LLEFVTAAGI THGMDELYKS    240
RGPYSIVSPK CGGGGSGPAG ILPPKKKRKV SRGRSRLLED FRNNRYPNLQ LREIAGHIME    300
FSQDQHGSRF IQLKLERATP AERQLVFNEI LQAAYQLMVD VFGNYVIQKF FEFGSLEQKL    360
ALAERIRGHV LSLALQMYGS RVIEKALEFI PSDQQNEMVR ELDGHVLKCV KDQNGNHVVQ    420
KCIECVQPQS LQFIIDAFKG QVFALSTHPY GCRVIQRILE HCLPDQTLPI LEELHQTEQ     480
LVQDQYGNYV IQHVLEHGRP EDKSKIVAEI RGNVLVLSQH KFASNVVEKC VTHASRTERA    540
VLIDEVCTMN DGPHSALYTM MKDQYANYVV QKMIDVAEPG QRKIVMHKIR PHIATLRKYT    600
YGKHILAKLE KYYMKNGVDL G                                              621

SEQ ID NO: 101          moltype = AA  length = 621
FEATURE                 Location/Qualifiers
REGION                  1..621
                        note = source = /note="Description of Artificial Sequence:
                          Syntheticpolypeptide"
source                  1..621
                        mol_type = protein
                        organism = synthetic construct
SEQUENCE: 101
MVSKGEELFT GVVPILVELD GDVNGHKFSV RGEGEGDATN GKLTLKFICT TGKLPVPWPT     60
LVTTFGYGVA CFSRYPDHMK QHDFFKSAMP EGYVQERTIS FKDDGTYKTR AEVKFEGDTL    120
VNRIELKGID FKEDGNILGH KLEYNFNSHN VYITADKQKN GIKANFKIRH NVEDGSVQLA    180
DHYQQNTPIG DGPVLLPDNH YLSHQSALSK DPNEKRDHMV LLEFVTAAGI THGMDELYKS    240
RGPYSIVSPK CGGGGSGPAG ILPPKKKRKV SRGRSRLLED FRNNRYPNLQ LREIAGHIME    300
FSQDQHGSRF IQLKLERATP AERQLVFNEI LQAAYQLMVD VFGNYVIQKF FEFGSLEQKL    360
ALAERIRGHV LSLALQMYGS RVIEKALEFI PSDQQNEMVR ELDGHVLKCV KDQNGNHVVQ    420
KCIECVQPQS LQFIIDAFKG QVFALSTHPY GCRVIQRILE HCLPDQTLPI LEELHQTEQ     480
```

```
LVQDQYGSYV IEHVLEHGRP EDKSKIVAEI RGNVLVLSQH KFANNVVQKC VTHASRTERA  540
VLIDEVCTMN DGPHSALYTM MKDQYANYVV QKMIDVAEPG QRKIVMHKIR PHIATLRKYT  600
YGKHILAKLE KYYMKNGVDL G                                           621

SEQ ID NO: 102           moltype = AA  length = 641
FEATURE                  Location/Qualifiers
REGION                   1..641
                         note = source = /note="Description of Artificial Sequence:
                         Syntheticpolypeptide"
source                   1..641
                         mol_type = protein
                         organism = synthetic construct
SEQUENCE: 102
MVRGSHHHHH HGMASMTGGQ QMGRDLYDDD DKDPMVSKGE ELIKENMRMK VVMEGSVNGH  60
QFKCTGEGEG NPYMGTQTMR IKVIEGGPLP FAFDILATSF MYGSRTFIKY PKGIPDFFKQ  120
SFPEGFTWER VTRYEDGGVV TVMQDTSLED GCLVYHVQVR GVNFPSNGPV MQKKTKGWEP  180
NTEMMYPADG GLRGYTHMAL KVDGGGHLSC SFVTTYRSKK TVGNIKMPGI HAVDHRLERL  240
EESDNEMFVV QREHAVAKFA GLGGGMDELY KGGGGSGPAG ILPPKKKRKV SRGRSRLLED  300
FRNNRYPNLQ LREIAGHIME FSQDQHGSRF IQLKLERATP AERQLVFNEI LQAAYQLMVD  360
VFGNYVIQKF FEFGSLEQKL ALAERIRGHV LSLALQMYGS RVIEKALEFI PSDQQNEMVR  420
ELDGHVLKCV KDQNGNHVVQ KCIECVQPQS LQFIIDAFKG QVFALSTHPY GCRVIQRILE  480
HCLPDQTLPI LEELHQHTEQ LVQDQYGNYV IQHVLEHGRP EDKSKIVAEI RGNVLVLSQH  540
KFASNVVEKC VTHASRTERA VLIDEVCTMN DGPHSALYTM MKDQYANYVV QKMIDVAEPG  600
QRKIVMHKIR PHIATLRKYT YGKHILAKLE KYYMKNGVDL G                     641

SEQ ID NO: 103           moltype = AA  length = 709
FEATURE                  Location/Qualifiers
REGION                   1..709
                         note = source = /note="Description of Artificial Sequence:
                         Syntheticpolypeptide"
source                   1..709
                         mol_type = protein
                         organism = synthetic construct
SEQUENCE: 103
MGILPPKKKR KVSRGRSRLL EDFRNNRYPN LQLREIAGHI MEFSQDQHGS RFIQLKLERA  60
TPAERQLVFN EILQAAYQLM VDVFGNYVIQ KFFEFGSLEQ KLALAERIRG HVLSLALQMY  120
GSRVIEKALE FIPSDQQNEM VRELDGHVLK CVKDQNGNHV VQKCIECVQP QSLQFIIDAF  180
KGQVFALSTH PYGCRVIQRI LEHCLPDQTL PILEELHQHT EQLVQDQYGN YVIQHVLEHG  240
RPEDKSKIVA EIRGNVLVLS QHKFASNVVE KCVTHASRTE RAVLIDEVCT MNDGPHSALY  300
TMMKDQYANY VVQKMIDVAE PGQRKIVMHK IRPHIATLRK YTYGKHILAK LEKYYMKNGV  360
DLGGPAGGGG SGGGGSGGGG SGPKKKRKVA AAGSPSGQIS NQALALAPSS APVLAQTMVP  420
SSAMVPLAQP PAPAPVLTPG PPQSLSAPVP KSTQAGEGTL SEALLHLQFD ADEDLGALLG  480
NSTDPGVFTD LASVDNSEFQ QLLNQGVSMS HSTAEPMLME YPEAITRLVT GSQRPPDPAP  540
TPLGTSGLPN GLSGDEDFSS IADMDFSALL SQISSSGQGG GGSGFSVDTS ALLDLFSPSV  600
TVPDMSLPDL DSSLASIQEL LSPQEPPRPP EAENSSPDSG KQLVHYTAQP LFLLDPGSVD  660
TGSNDLPVLF ELGEGSYFSE GDGFAEDPTI SLLTGSEPPK AKDPTVSID             709

SEQ ID NO: 104           moltype = AA  length = 456
FEATURE                  Location/Qualifiers
REGION                   1..456
                         note = source = /note="Description of Artificial Sequence:
                         Syntheticpolypeptide"
source                   1..456
                         mol_type = protein
                         organism = synthetic construct
SEQUENCE: 104
MGSPKKKRKV EASMDAKSLT AWSRTLVTFK DVFVDFTREE WKLLDTAQQI VYRNVMLENY  60
KNLVSLGYQL TKPDVILRLE KGEEPWLVSR GSIVGILPPK KKRKVSRGRS RLLEDFRNNR  120
YPNLQLREIA GHIMEFSQDQ HGSRFIQLKL ERATPAERQL VFNEILQAAY QLMVDVFGNY  180
VIQKFFEFGS LEQKLALAER IRGHVLSLAL QMYGSRVIEK ALEFIPSDQQ NEMVRELDGH  240
VLKCVKDQNG NHVVQKCIEC VQPQSLQFII DAFKGQVFAL STHPYGCRVI QRILEHCLPD  300
QTLPILEELH QHTEQLVQDQ YGNYVIQHVL EHGRPEDKSK IVAEIRGNVL VLSQHKFASN  360
VVEKCVTHAS RTERAVLIDE VCTMNDGPHS ALYTMMKDQY ANYVVQKMID VAEPGQRKIV  420
MHKIRPHIAT LRKYTYGKHI LAKLEKYYMK NGVDLG                           456

SEQ ID NO: 105           moltype = AA  length = 727
FEATURE                  Location/Qualifiers
REGION                   1..727
                         note = source = /note="Description of Artificial Sequence:
                         Syntheticpolypeptide"
source                   1..727
                         mol_type = protein
                         organism = synthetic construct
SEQUENCE: 105
MAYPYDVPDY ASLGSGSPKK KRKVEDPKKK RKVDGIGSGS NGSSGSSELI KENMHMKLYM  60
EGTVDNHHFK CTSEGEGKPY EGTQTMRIKV VEGGPLPFAF DILATSFLYG SKTFINHTQG  120
IPDFFKQSFP EGFTWERVTT YEDGGVLTAT QDTSLQDGCL IYNVKIRGVN FTSNGPVMQK  180
KTLGWEAFTE TLYPADGGLE GRNDMALKLV GGSHLIANIK TTYRSKKPAK NLKMPGVYYV  240
DYRLERIKEA NNETYVEQHE VAVARYCDLP SKLGHKLNGG GGMDAKSLTA AWSRTLVTFK  300
```

```
DVFVDFTREE  WKLLDTAQQI  VYRNVMLENY  KNLVSLGYQL  TKPDVILRLE  KGEEPGGSGG   360
GSGPAGILPP  KKKRKVSRGR  SRLLEDFRNN  RYPNLQLREI  AGHIMEFSQD  QHGSRFIQLK   420
LERATPAERQ  LVFNEILQAA  YQLMVDVFGN  YVIQKFFEFG  SLEQKLALAE  RIRGHVLSLA   480
LQMYGSRVIE  KALEFIPSDQ  QNEMVRELDG  HVLKCVKDQN  GNHVVQKCIE  CVQPQSLQFI   540
IDAFKGQVFA  LSTHPYGCRV  IQRILEHCLP  DQTLPILEEL  HQHTEQLVQD  QYGNYVIQHV   600
LEHGRPEDKS  KIVAEIRGNV  LVLSQHKFAS  NVVEKCVTHA  SRTERAVLID  EVCTMNDGPH   660
SALYTMMKDQ  YANYVVQKMI  DVAEPGQRKI  VMHKIRPHIA  TLRKYTYGKH  ILAKLEKYYM   720
KNGVDLG                                                                  727

SEQ ID NO: 106          moltype =  AA   length = 1673
FEATURE                 Location/Qualifiers
REGION                  1..1673
                        note = source = /note="Description of Artificial Sequence:
                        Syntheticpolypeptide"
source                  1..1673
                        mol_type = protein
                        organism = synthetic construct
SEQUENCE: 106
MIDGGGGSGG  GGSGGGGSMY  PYDVPDYASP  KKKRKVEASD  KKYSIGLAIG  TNSVGWAVIT    60
DEYKVPSKKF  KVLGNTDRHS  IKKNLIGALL  FDSGETAEAT  RLKRTARRRY  TRRKNRICYL   120
QEIFSNEMAK  VDDSFFHRLE  ESFLVEEDKK  HERHPIFGNI  VDEVAYHEKY  PTIYHLRKKL   180
VDSTDKADLR  LIYLALAHMI  KFRGHFLIEG  DLNPDNSDVD  KLFIQLVQTY  NQLFEENPIN   240
ASGVDAKAIL  SARLSKSRRL  ENLIAQLPGE  KKNGLFGNLI  ALSLGLTPNF  KSNFDLAEDA   300
KLQLSKDTYD  DDLDNLLAQI  GDQYADLFLA  AKNLSDAILL  SDILRVNTEI  TKAPLSASMI   360
KRYDEHHQDL  TLLKALVRQQ  LPEKYKEIFF  DQSKNGYAGY  IDGGASQEEF  YKFIKPILEK   420
MDGTEELLVK  LNREDLLRKQ  RTFDNGSIPH  QIHLGELHAI  LRRQEDFYPF  LKDNREKIEK   480
ILTFRIPYYV  GPLARGNSRF  AWMTRKSEET  ITPWNFEEVV  DKGASAQSFI  ERMTNFDKNL   540
PNEKVLPKHS  LLYEYFTVYN  ELTKVKYVTE  GMRKPAFLSG  EQKKAIVDLL  FKTNRKVTVK   600
QLKEDYFKKI  ECFDSVEISG  VEDRFNASLG  TYHDLLKIIK  DKDFLDNEEN  EDILEDIVLT   660
LTLFEDREMI  EERLKTYAHL  FDDKVMKQLK  RRRYTGWGRL  SRKLINGIRD  KQSGKTILDF   720
LKSDGFANRN  FMQLIHDDSL  TFKEDIQKAQ  VSGQGDSLHE  HIANLAGSPA  IKKGILQTVK   780
VVDELVKVMG  RHKPENIVIE  MARENQTTQK  GQKNSRERMK  RIEEGIKELG  SQILKEHPVE   840
NTQLQNEKLY  LYYLQNGRDM  YVDQELDINR  LSDYDVDAIV  PQSFLKDDSI  DNKVLTRSDK   900
NRGKSDNVPS  EEVVKKMKNY  WRQLLNAKLI  TQRKFDNLTK  AERGGLSELD  KAGFIKRQLV   960
ETRQITKHVA  QILDSRMNTK  YDENDKLIRE  VKVITLKSKL  VSDFRKDFQF  YKVREINNYH  1020
HAHDAYLNAV  VGTALIKKYP  KLESEFVYGD  YKVYDVRKMI  AKSEQEIGKA  TAKYFFYSNI  1080
MNFFKTEITL  ANGEIRKRPL  IETNGETGEI  VWDKGRDFAT  VRKVLSMPQV  NIVKKTEVQT  1140
GGFSKESILP  KRNSDKLIAR  KKDWDPKKYG  GFDSPTVAYS  VLVVAKVEKG  KSKKLKSVKE  1200
LLGITIMERS  SFEKNPIDFL  EAKGYKEVKK  DLIIKLPKYS  LFELENGRKR  MLASAGELQK  1260
GNELALPSKY  VNFLYLASHY  EKLKGSPEDN  EQKQLFVEQH  KHYLDEIIEQ  ISEFSKRVIL  1320
ADANLDKVLS  AYNKHRDKPI  REQAENIIHL  FTLTNLGAPA  AFKYFDTTID  RKRYTSTKEV  1380
LDATLIHQSI  TGLYETRIDL  SQLGGDSPKK  KRKVEASGGG  GSGGGGSGGG  GSGPAMVSKG  1440
EEDNMAIIKE  FMRFKVHMEG  SVNGHEFEIE  GEGEGRPYEG  TQTAKLKVTK  GGPLPFAWDI  1500
LSPQFMYGSK  AYVKHPADIP  DYLKLSFPEG  FKWERVMNFE  DGGVVTVTQD  SSLQDGEFIY  1560
KVKLRGTNFP  SDGPVMQKKT  MGWEASSERM  YPEDGALKGE  IKQRLKLKDG  GHYDAEVKTT  1620
YKAKKPVQLP  GAYNVNIKLD  ITSHNEDYTI  VEQYERAEGR  HSTGGMDELY  KID         1673

SEQ ID NO: 107          moltype =  AA   length = 1220
FEATURE                 Location/Qualifiers
REGION                  1..1220
                        note = source = /note="Description of Artificial Sequence:
                        Syntheticpolypeptide"
source                  1..1220
                        mol_type = protein
                        organism = synthetic construct
SEQUENCE: 107
MIFKPEELRQ  ALMPTLEALY  RQDPESLPFR  QPVDPQLLGI  PDYFDIVKNP  MDLSTIKRKL    60
DTGQYQEPWQ  YVDDVWLMFN  NAWLYNRKTS  RVYKFCSKLA  EVFEQEIDPV  MQSLGYCCGR   120
KYEFSPQTLC  CYGKQLCTIP  RDAAYYSYQN  RYHFCEKCFT  EIQGENVTLG  DDPSQPQTTI   180
SKDQFEKKKN  DTLDPEPFVD  CKECGRKMHQ  ICVLHYDIIW  PSGFVCDNCL  KKTGRPRKEN   240
KFSAKRLQTT  RLGNHLEDRV  NKFLRRQNHP  EAGEVFVRVV  ASSDKTVEVK  PGMKSRFVDS   300
GEMSESFPYR  TKALFAFEEI  DGVDCFFGM  HVQEYGSDCP  PPNTRRVYIS  YLDSIHFFRP    360
RCLRTAVYHE  ILIGYLEYVK  KLGYVTGHIW  ACPPSEGDDY  IPHCHPPDQK  IPKPKRLQEN   420
YKKMLDKAFA  ERIINDYKDI  FKQANEDRLT  SAKELPYFEG  DFWPNVLEES  IKELEQEEEE   480
RKKEESTAAS  ETPEGSQGDS  KNAKKKNNKK  TNKNKSSISR  ANKKKPSMPN  VSNDLSQKLY   540
ATMEKHKEVF  FVIHLHAGPV  ISTQPPIVDP  DPLLSCDLMD  GRDAFLTLAR  DKHWEFSSLR   600
RSKWSTLCML  VELHTQGQDR  FVYTCNECKH  HVETRWHCTV  CEDYDLCINC  YNTKSHTHKM   660
VKWGLGLDDE  GSSQGEPQSK  SPQESRRLSI  QRCIQSLVHA  CQCRNANCSL  PSCQKMKRVV   720
QHTKGCKRKT  NGGCPVCKQL  IALCCYHAKH  CQENKCPVPF  CLNINDGGGG  SDPKKKRKVD   780
PKKKRKVDPK  KKRKVGSTGS  RNDGGGGSGG  GGSGGGGSGR  AGILPPKKKR  KVSRGRSRLL   840
EDFRNNRYPN  LQLREIAGHI  MEFSQDQHGS  RFIQLKLERA  TPAERQLVFN  EILQAAYQLM   900
VDVFGNYVIQ  KFFEFGSLEQ  KLALAERIRG  HVLSLALQMY  GSRVIEKALE  FIPSDQQNEM   960
VRELDGHVLK  CVKDQNGNHV  VQKCIECVQP  QSLQFIIDAF  KGQVFALSTH  PYGCRVIQRI  1020
LEHCLPDQTL  PILEELHQHT  EQLVQDQYGN  YVIQHVLEHG  RPEDKSKIVA  EIRGNVLVLS  1080
QHKFASNVVE  KCVTHASRTE  RAVLIDEVCT  MNDGPHSALY  TMMKDQYANY  VVQKMIDVAE  1140
PGQRKIVMHK  IRPHIATLRK  YTYGKHILAK  LEKYYMKNGV  DLGDPKKKRK  VDPKKKRKVG  1200
GRGGGGSGGG  GSGGGGSGPA                                                  1220

SEQ ID NO: 108          moltype =  AA   length = 1220
```

```
FEATURE                 Location/Qualifiers
REGION                  1..1220
                        note = source = /note="Description of Artificial Sequence:
                         Syntheticpolypeptide"
source                  1..1220
                        mol_type = protein
                        organism = synthetic construct
SEQUENCE: 108
MIDGGGGSDP KKKRKVDPKK KRKVDPKKKR KVGSTGSRND GGGGSGGGGS GGGGSGRAGI    60
LPPKKKRKVS RGRSRLLEDF RNNRYPNLQL REIAGHIMEF SQDQHGSRFI QLKLERATPA   120
ERQLVFNEIL QAAYQLMVDV FGNYVIQKFF EFGSLEQKLA LAERIRGHVL SLALQMYGSR   180
VIEKALEFIP SDQQNEMVRE LDGHVLKCVK DQNGNHVVQK CIECVQPQSL QFIIDAFKGQ   240
VFALSTHPYG CRVIQRILEH CLPDQTLPIL EELHQHTEQL VQDQYGNYVI QHVLEHGRPE   300
DKSKIVAEIR GNVLVLSQHK FASNVVEKCV THASRTERAV LIDEVCTMND GPHSALYTMM   360
KDQYANYVVQ KMIDVAEPGQ RKIVMHKIRP HIATLRKYTY GKHILAKLEK YYMKNGVDLG   420
DPKKKRKVDP KKKRKVGGRG GGGSGGGGSG GGGSGPAIFK PEELRQALMP TLEALYRQDP   480
ESLPFRQPVD PQLLGIPDYF DIVKNPMDLS TIKRKLDTGQ YQEPWQYVDD VWLMFNNAWL   540
YNRKTSRVYK FCSKLAEVFE QEIDPVMQSL GYCCGRKYEF SPQTLCCYGK QLCTIPRDAA   600
YYSYQNRYHF CEKCFTEIQG ENVTLGDDPS QPQTTISKDQ FEKKKNDTLD PEPFVDCKEC   660
GRKMHQICVL HYDIIWPSGF VCDNCLKKTG RPRKENKFSA KRLQTTRLGN HLEDRVNKFL   720
RRQNHPEAGE VFVRVVASSD KTVEVKPGMK SRFVDSGEMS ESFPYRTKAL FAFEEIDGVD   780
VCFFGMHVQE YGSDCPPPNT RRVYISYLDS IHFFRPRCLR TAVYHEILIG YLEYVKKLGY   840
VTGHIWACPP SEGDDYIFHC HPPDQKIPKP KRLQEWYKKM LDKAFAERII NDYKDIFKQA   900
NEDRLTSAKE LPYFEGDFWP NVLEESIKEL EQEEEERKKE ESTAASETPE GSQGDSKNAK   960
KKNNKKTNKN KSSISRANKK KPSMPNVSND LSQKLYATME KHKEVFFVIH LHAGPVISTQ  1020
PPIVDPDPLL SCDLMDGRDA FLTLARDKHW EFSSLRRSKW STLCMLVELH TQGQDRFVYT  1080
CNECKHHVET RWHCTVCEDY DLCINCYNTK SHTHKMVKWG LGLDDEGSSQ GEPQSKSPQE  1140
SRRLSIQRCI QSLVHACQCR NANCSLPSCQ KMKRVVQHTK GCKRKTNGGC PVCKQLIALC  1200
CYHAKHCQEN KCPVPFCLNI                                              1220

SEQ ID NO: 109          moltype = DNA  length = 454
FEATURE                 Location/Qualifiers
misc_difference         250..269
                        note = N may be a, c, t, g, unknown or other
misc_feature            1..454
                        note = source = /note="Description of Artificial Sequence:
                         Syntheticpolynucleotide"
source                  1..454
                        mol_type = other DNA
                        organism = synthetic construct
SEQUENCE: 109
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atcttttttt gttttagagc tagaaatagc aagttaaaat aaggctagtc   420
cgtagcgcgt gcgccaattc tgcagacaaa tggc                              454

SEQ ID NO: 110          moltype = DNA  length = 472
FEATURE                 Location/Qualifiers
misc_difference         250..269
                        note = N may be a, c, t, g, unknown or other
misc_feature            1..472
                        note = source = /note="Description of Artificial Sequence:
                         Syntheticpolynucleotide"
source                  1..472
                        mol_type = other DNA
                        organism = synthetic construct
SEQUENCE: 110
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atgcctgtat gtagccagat ctttttttgt tttagagcta gaaatagcaa   420
gttaaaataa ggctagtccg tagcgcgtgc gccaattctg cagacaaatg gc           472

SEQ ID NO: 111          moltype = DNA  length = 510
FEATURE                 Location/Qualifiers
misc_difference         250..269
                        note = N may be a, c, t, g, unknown or other
misc_feature            1..510
                        note = source = /note="Description of Artificial Sequence:
                         Syntheticpolynucleotide"
source                  1..510
                        mol_type = other DNA
```

```
                         organism = synthetic construct
SEQUENCE: 111
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gttgcagtt ttaaaattat gttttaaaat ggactatcat   180
atgcttaccg taacttgaaa gtatttcgat ttcttggctt tatatatctt gtggaaagga   240
cgaaacaccn nnnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag attgtatgta gcctgtatgt agcctgtatg tagcctgtat gtagcctgta   420
tgtaagatct ttttttgttt tagagctaga aatagcaagt taaaataagg ctagtccgta   480
gcgcgtgcgc caattctgca gacaaatggc                                    510

SEQ ID NO: 112         moltype = DNA    length = 621
FEATURE                Location/Qualifiers
misc_difference        250..269
                       note = N may be a, c, t, g, unknown or other
misc_feature           1..621
                       note = source = /note="Description of Artificial Sequence:
                         Syntheticpolynucleotide"
source                 1..621
                       mol_type = other DNA
                       organism = synthetic construct
SEQUENCE: 112
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gttgcagtt ttaaaattat gttttaaaat ggactatcat   180
atgcttaccg taacttgaaa gtatttcgat ttcttggctt tatatatctt gtggaaagga   240
cgaaacaccn nnnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag attgtatgta gcctgtatgt agcctgtatg tagcctgtat gtagcctgta   420
tgtaagattg tatgtagctg tatgtagcct gtatgtagcc tgtatgtagc ctgtatgtaa   480
gattgtatgt agcctgtatg tagcctgtat gtagcctgta tgtagcctgt atgtaagatc   540
ttttttgtt ttagagctag aaatagcaag taaaataag gctagtccgt agcgcgtgcg    600
ccaattctgc agacaaatgg c                                             621

SEQ ID NO: 113         moltype = DNA    length = 734
FEATURE                Location/Qualifiers
misc_difference        250..269
                       note = N may be a, c, t, g, unknown or other
misc_feature           1..734
                       note = source = /note="Description of Artificial Sequence:
                         Syntheticpolynucleotide"
source                 1..734
                       mol_type = other DNA
                       organism = synthetic construct
SEQUENCE: 113
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gttgcagtt ttaaaattat gttttaaaat ggactatcat   180
atgcttaccg taacttgaaa gtatttcgat ttcttggctt tatatatctt gtggaaagga   240
cgaaacaccn nnnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag attgtatgta gcctgtatgt agcctgtatg tagcctgtat gtagcctgta   420
tgtaagattg tatgtagcct gtatgtagcc tgtatgtagc ctgtatgtag cctgtatgta   480
agattgtatg tagcctgtat gtagcctgta tgtagcctgt atgtagcctg tatgtaagat   540
tgtatgtagc ctgtatgtag cctgtatgta gcctgtatgt agcctgtatg taagattgta   600
tgtagcctgt atgtagcctg tatgtagcct gtatgtagcc tgtatgtaag atcttttttt   660
gttttagagc tagaaatagc aagttaaaat aaggctagtc cgtagcgcgt gcgccaattc   720
tgcagacaaa tggc                                                     734

SEQ ID NO: 114         moltype = DNA    length = 472
FEATURE                Location/Qualifiers
misc_difference        250..269
                       note = N may be a, c, t, g, unknown or other
misc_feature           1..472
                       note = source = /note="Description of Artificial Sequence:
                         Syntheticpolynucleotide"
source                 1..472
                       mol_type = other DNA
                       organism = synthetic construct
SEQUENCE: 114
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gttgcagtt ttaaaattat gttttaaaat ggactatcat   180
atgcttaccg taacttgaaa gtatttcgat ttcttggctt tatatatctt gtggaaagga   240
cgaaacaccn nnnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atgccttgat atagccagat cttttttgt tttagagcta gaaatagcaa   420
gttaaaataa ggctagtccg tagcgcgtgc gccaattctg cagacaaatg gc           472
```

```
SEQ ID NO: 115            moltype = DNA  length = 477
FEATURE                   Location/Qualifiers
misc_difference           250..269
                          note = N may be a, c, t, g, unknown or other
misc_feature              1..477
                          note = source = /note="Description of Artificial Sequence:
                          Syntheticpolynucleotide"
source                    1..477
                          mol_type = other DNA
                          organism = synthetic construct
SEQUENCE: 115
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttccttggctt tatatatctt gtggaaagga   240
cgaaacaccn nnnnnnnnn nnnnnnnnng tttaagagct atgctggaaa cagcatagca    300
agtttaaata aggctagtcc gttatcaact tgaaaaagtg gcaccgagtc ggtgccaatt   360
gggtctccag atttgatata gccttgatat aagatctttt tttgttttag agctagaaat   420
agcaagttaa aataaggcta gtccgtagcg cgtgcgccaa ttctgcagac aaatggc     477

SEQ ID NO: 116            moltype = DNA  length = 510
FEATURE                   Location/Qualifiers
misc_difference           250..269
                          note = N may be a, c, t, g, unknown or other
misc_feature              1..510
                          note = source = /note="Description of Artificial Sequence:
                          Syntheticpolynucleotide"
source                    1..510
                          mol_type = other DNA
                          organism = synthetic construct
SEQUENCE: 116
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttccttggctt tatatatctt gtggaaagga   240
cgaaacaccn nnnnnnnnn nnnnnnnnng tttaagagct atgctggaaa cagcatagca    300
agtttaaata aggctagtcc gttatcaact tgaaaaagtg gcaccgagtc ggtgccaatt   360
gggtctccag atttgatata gccttgatat agccttgat atagccttga                420
tataagatct tttttttgttt tagagctaga aataagcaagt taaaataagg ctagtccgta   480
gcgcgtgcgc caattctgca gacaaatggc                                     510

SEQ ID NO: 117            moltype = DNA  length = 566
FEATURE                   Location/Qualifiers
misc_difference           250..269
                          note = N may be a, c, t, g, unknown or other
misc_feature              1..566
                          note = source = /note="Description of Artificial Sequence:
                          Syntheticpolynucleotide"
source                    1..566
                          mol_type = other DNA
                          organism = synthetic construct
SEQUENCE: 117
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttccttggctt tatatatctt gtggaaagga   240
cgaaacaccn nnnnnnnnn nnnnnnnnng tttaagagct atgctggaaa cagcatagca    300
agtttaaata aggctagtcc gttatcaact tgaaaaagtg gcaccgagtc ggtgccaatt   360
gggtctccag atttgatata gccttgatat agccttgat atagccttga                420
tataagatttt gatatagcct tgatatagcc ttgatatagc cttgatatag ccttgatata   480
agatcttttt tgttttagag ctagaaata gcaagttaaa ataaggctag tccgtagcgc   540
gtgcgccaat tctgcagaca aatggc                                          566

SEQ ID NO: 118            moltype = DNA  length = 622
FEATURE                   Location/Qualifiers
misc_difference           250..269
                          note = N may be a, c, t, g, unknown or other
misc_feature              1..622
                          note = source = /note="Description of Artificial Sequence:
                          Syntheticpolynucleotide"
source                    1..622
                          mol_type = other DNA
                          organism = synthetic construct
SEQUENCE: 118
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttccttggctt tatatatctt gtggaaagga   240
```

```
cgaaacaccn nnnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atttgatata gccttgatat agccttgata tagccttgat atagccttga   420
tataagattt gatatagcct tgatatagcc ttgatatagc cttgatatag ccttgatata   480
agatttgata tagccttgat atagccttga tatagccttg atatagcctt gatataagat   540
cttttttttgt tttagagcta gaaatagcaa gttaaaataa ggctagtccg tagcgcgtgc   600
gccaattctg cagacaaatg gc                                             622
```

| SEQ ID NO: 119 | moltype = DNA length = 678 |
|---|---|
| FEATURE | Location/Qualifiers |
| misc_difference | 250..269 |
|  | note = N may be a, c, t, g, unknown or other |
| misc_feature | 1..678 |
|  | note = source = /note="Description of Artificial Sequence: Syntheticpolynucleotide" |
| source | 1..678 |
|  | mol_type = other DNA |
|  | organism = synthetic construct |

```
SEQUENCE: 119
gagggcctat ttcccatgat tccttcatat ttgcatatac gatacaaggc tgttagagag   60
ataattggaa ttaatttgac tgtaaacaca aagatattag tacaaaatac gtgacgtaga   120
aagtaataat ttcttgggta gtttgcagtt ttaaaattat ggactatcat              180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atttgatata gccttgatat agccttgata tagccttgat atagccttga   420
tataagattt gatatagcct tgatatagcc ttgatatagc cttgatatag ccttgatata   480
agatttgata tagccttgat atagccttga tatagccttg atatagcctt gatataagat   540
ttgatatagc cttgatatag ccttgatata gccttgatat agccttgata taagatcttt   600
ttttgtttta gagctagaaa tagcaagtta aataaggct agtccgtagc gcgtgcgcca   660
attctgcaga caaatggc                                                 678
```

| SEQ ID NO: 120 | moltype = DNA length = 734 |
|---|---|
| FEATURE | Location/Qualifiers |
| misc_difference | 250..269 |
|  | note = N may be a, c, t, g, unknown or other |
| misc_feature | 1..734 |
|  | note = source = /note="Description of Artificial Sequence: Syntheticpolynucleotide" |
| source | 1..734 |
|  | mol_type = other DNA |
|  | organism = synthetic construct |

```
SEQUENCE: 120
gagggcctat ttcccatgat tccttcatat ttgcatatac gatacaaggc tgttagagag   60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atttgatata gccttgatat agccttgata tagccttgat atagccttga   420
tataagattt gatatagcct tgatatagcc ttgatatagc cttgatatag ccttgatata   480
agatttgata tagccttgat atagccttga tatagccttg atatagcctt gatataagat   540
ttgatatagc cttgatatag ccttgatata gccttgatat agccttgata taagatttga   600
tatagccttg atatagcctt gatatagcct tgatatagcc ttgatataag atctttttt   660
gttttagagc tagaaatagc aagttaaaat aaggctagtc cgtagcgcgt gcgccaattc   720
tgcagacaaa tggc                                                    734
```

| SEQ ID NO: 121 | moltype = DNA length = 979 |
|---|---|
| FEATURE | Location/Qualifiers |
| misc_difference | 250..269 |
|  | note = N may be a, c, t, g, unknown or other |
| misc_feature | 1..979 |
|  | note = source = /note="Description of Artificial Sequence: Syntheticpolynucleotide" |
| source | 1..979 |
|  | mol_type = other DNA |
|  | organism = synthetic construct |

```
SEQUENCE: 121
gagggcctat ttcccatgat tccttcatat ttgcatatac gatacaaggc tgttagagag   60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atttgatata gccttgatat agccttgata tagccttgat atagccttga   420
tataagattt gatatagcct tgatatagcc ttgatatagc cttgatatag ccttgatata   480
agatttgata taccttgata tagccttgat atagccttga tatagccttg atataagatt   540
tgatatagcc ttgatatagc cttgatatag ccttgatata gccttgatat agccttgata   600
tagccttgat ataagatttg atatagcctt gatatagcct tgatatagcc ttgatatagc   660
```

```
cttgatataa gatttgatat agccttgata tagccttgat atagccttga tatagccttg   720
atataagatt tgatatagcc ttgatatagc cttgatatag ccttgatata gccttgatat   780
aagatttgat atagccttga tatagccttg atatagcctt gatatagcct tgatataaga   840
tttgatatag ccttgatata gccttgatat agccttgata tagccttgat ataagatctt   900
tttttgtttt agagctagaa atagcaagtt aaaataaggc tagtccgtag cgcgtgcgcc   960
aattctgcag acaaatggc                                               979
```

| | | |
|---|---|---|
| SEQ ID NO: 122 | moltype = DNA length = 490 | |
| FEATURE | Location/Qualifiers | |
| misc_difference | 250..269 | |
| | note = N may be a, c, t, g, unknown or other | |
| misc_feature | 1..490 | |
| | note = source = /note="Description of Artificial Sequence: Syntheticpolynucleotide" | |
| source | 1..490 | |
| | mol_type = other DNA | |
| | organism = synthetic construct | |

```
SEQUENCE: 122
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atgccttgat atagccagat gccttgatat agccagatct ttttttgttt   420
tagagctaga aatagcaagt taaaataagg ctagtccgta gcgcgtgcgc caattctgca   480
gacaaatggc                                                          490
```

| | | |
|---|---|---|
| SEQ ID NO: 123 | moltype = DNA length = 562 | |
| FEATURE | Location/Qualifiers | |
| misc_difference | 250..269 | |
| | note = N may be a, c, t, g, unknown or other | |
| misc_feature | 1..562 | |
| | note = source = /note="Description of Artificial Sequence: Syntheticpolynucleotide" | |
| source | 1..562 | |
| | mol_type = other DNA | |
| | organism = synthetic construct | |

```
SEQUENCE: 123
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atgccttgat atagccagat gccttgatat agccagatgc cttgatatag   420
ccagatgcct tgatatagcc agatgccttg atatagccag atgccttgat atagccagat   480
cttttttgt tttagagcta gaaatagcaa gttaaaataa ggctagtccg tagcgcgtgc   540
gccaattctg cagacaaatg gc                                            562
```

| | | |
|---|---|---|
| SEQ ID NO: 124 | moltype = DNA length = 724 | |
| FEATURE | Location/Qualifiers | |
| misc_difference | 250..269 | |
| | note = N may be a, c, t, g, unknown or other | |
| misc_feature | 1..724 | |
| | note = source = /note="Description of Artificial Sequence: Syntheticpolynucleotide" | |
| source | 1..724 | |
| | mol_type = other DNA | |
| | organism = synthetic construct | |

```
SEQUENCE: 124
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atgccttgat atagccagat gccttgatat agccagatgc cttgatatag   420
ccagatgcct tgatatagcc agatgccttg atatagccag atgccttgat atagccagat   480
gccttgatat agccagatgc cttgatatag ccagatgcct tgatatagcc agatgccttg   540
atatagccag atgccttgat atagccagat gccttgatat agccagatgc cttgatatag   600
ccagatgcct tgatatagcc agatgccttg atatagccag atcttttttt gttttagagc   660
tagaaatagc aagttaaaat aaggctagtc cgtagcgcgt gcgccaattc tgcagacaaa   720
tggc                                                                724
```

| | | |
|---|---|---|
| SEQ ID NO: 125 | moltype = DNA length = 813 | |
| FEATURE | Location/Qualifiers | |
| misc_difference | 250..269 | |
| | note = N may be a, c, t, g, unknown or other | |

| misc_feature | 1..813 |
| | note = source = /note="Description of Artificial Sequence: |
| | Syntheticpolynucleotide" |
| source | 1..813 |
| | mol_type = other DNA |
| | organism = synthetic construct |

SEQUENCE: 125

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atgccttgat atagccagat gccttgatag cttgatatag               420
ccagatgcct tgatatagcc agatgccttg atatagccag atgccttgat atagccagat   480
gccttgatat agcagatgcc cttgatatag ccagatgcct tgatatagcc agatgccttg   540
atatagccag atgccttgat atagccagat gccttgatat agcagatgc cttgatatag    600
ccagatgcct tgatatagcc agatgccttg atatagccag atgccttgat atagccagat   660
gccttgatat agcagatgc cttgatatag ccagatccttg gatatagcca gatgccttga   720
tatagccaga tctttttttg ttttagagct agaaatagca agttaaaata aggctagtcc   780
gtagcgcgtg cgccaattct gcagacaaat ggc                                 813
```

| SEQ ID NO: 126 | moltype = DNA length = 515 |
| FEATURE | Location/Qualifiers |
| misc_difference | 330..349 |
| | note = N may be a, c, t, g, unknown or other |
| misc_feature | 1..515 |
| | note = source = /note="Description of Artificial Sequence: |
| | Syntheticpolynucleotide" |
| source | 1..515 |
| | mol_type = other DNA |
| | organism = synthetic construct |

SEQUENCE: 126

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccg caattgggtc tccagattgt atgtagcctg tatgtagcct gtatgtagcc   300
tgtatgtagc ctgtatgtaa gatctcaccn nnnnnnnnnn nnnnnnnnng tttaagagct   360
atgctggaaa cagcatagca agtttaaata aggctagtcc gttatcaact tgaaaaagtg   420
gcaccgagtc ggtgctttt tgttttagag ctagaaatag caagttaaaa taaggctagt   480
ccgtagcgcg tgcgccaatt ctgcagacaa atggc                              515
```

| SEQ ID NO: 127 | moltype = DNA length = 510 |
| FEATURE | Location/Qualifiers |
| misc_difference | 250..269 |
| | note = N may be a, c, t, g, unknown or other |
| misc_feature | 1..510 |
| | note = source = /note="Description of Artificial Sequence: |
| | Syntheticpolynucleotide" |
| source | 1..510 |
| | mol_type = other DNA |
| | organism = synthetic construct |

SEQUENCE: 127

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag attgtatgta gtctattgat atagtcttgt ctatgtatgt agtctattga   420
tataagatct tttttgtttt tagagctaga aatagcaagt taaataagg ctagtccgta    480
gcgcgtgcgc caattctgca gacaaatggc                                    510
```

| SEQ ID NO: 128 | moltype = DNA length = 678 |
| FEATURE | Location/Qualifiers |
| misc_difference | 250..269 |
| | note = N may be a, c, t, g, unknown or other |
| misc_feature | 1..678 |
| | note = source = /note="Description of Artificial Sequence: |
| | Syntheticpolynucleotide" |
| source | 1..678 |
| | mol_type = other DNA |
| | organism = synthetic construct |

SEQUENCE: 128

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
```

```
cgaaacaccn nnnnnnnnnn nnnnnnnnng tttaagagct atgctggaaa cagcatagca    300
agtttaaata aggctagtcc gttatcaact tgaaaaagtg gcaccgagtc ggtgccaatt    360
gggtctccag attgtatgta gtctattgat atagtcttgt ctatgtatgt agtctattga    420
tataagattg tatgtagtct attgatatag tcttgtctat gtatgtagtc tattgatata    480
agattgtatg tagtctattg atatagtctt gtctatgtat gtagtctatt gatataagat    540
tgtatgtagt ctattgatat agtcttgtct atgtatgtag tctattgata taagatcttt    600
ttttgtttta gagctagaaa tagcaagtta aaataaggct agtccgtagc gcgtgcgcca    660
attctgcaga caaatggc                                                  678

SEQ ID NO: 129          moltype = DNA   length = 566
FEATURE                 Location/Qualifiers
misc_difference         250..269
                        note = N may be a, c, t, g, unknown or other
misc_feature            1..566
                        note = source = /note="Description of Artificial Sequence:
                        Syntheticpolynucleotide"
source                  1..566
                        mol_type = other DNA
                        organism = synthetic construct
SEQUENCE: 129
gagggcctat ttcccatgat tccttcatat ttgcatatac gatacaaggc tgttagagag    60
ataattggaa ttaatttgac tgtaaacaca aagatattac acaaaatac gtgacgtaga    120
aagtaataat ttcttgggta gtttgcagtt ttaaaattat gttttaaaat ggactatcat    180
atgcttaccg taacttggaa gtatttcgat ttcttggctt tatatatctt gtggaaagga    240
cgaaacaccn nnnnnnnnn nnnnnnnnng tttaagagct atgctggaaa cagcatagca    300
agtttaaata aggctagtcc gttatcaact tgaaaaagtg gcaccgagtc ggtgccaatt    360
gggtctccag attgtatgta gtctattgat atagtcttgt ctatgtatgt agtctattga    420
tataagattg tatgtagtct attgatatag tcttgtctat gtatgtagtc tattgatata    480
agatcttttt ttgttttaga gctagaaata gcaagttaaa ataaggctag tccgtagcgc    540
gtgcgccaat tctgcagaca aatggc                                         566

SEQ ID NO: 130          moltype = DNA   length = 21
FEATURE                 Location/Qualifiers
misc_feature            1..21
                        note = source = /note="Description of Artificial Sequence:
                        Syntheticoligonucleotide"
source                  1..21
                        mol_type = other DNA
                        organism = synthetic construct
SEQUENCE: 130
gttctcttgc tgaaagctcg a                                              21

SEQ ID NO: 131          moltype = DNA   length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 131
gcttttctct atcactgata                                                20

SEQ ID NO: 132          moltype = DNA   length = 27
FEATURE                 Location/Qualifiers
misc_feature            1..27
                        note = source = /note="Description of Artificial Sequence:
                        Syntheticoligonucleotide"
source                  1..27
                        mol_type = other DNA
                        organism = synthetic construct
SEQUENCE: 132
gcatacttct gcctgctggg gagcctg                                        27

SEQ ID NO: 133          moltype = DNA   length = 22
FEATURE                 Location/Qualifiers
misc_feature            1..22
                        note = source = /note="Description of Artificial Sequence:
                        Syntheticoligonucleotide"
source                  1..22
                        mol_type = other DNA
                        organism = synthetic construct
SEQUENCE: 133
gaaagtcccc aggctcccca gc                                             22

SEQ ID NO: 134          moltype = DNA   length = 22
FEATURE                 Location/Qualifiers
misc_feature            1..22
                        note = source = /note="Description of Artificial Sequence:
```

```
                            Syntheticoligonucleotide"
source                      1..22
                            mol_type = other DNA
                            organism = synthetic construct
SEQUENCE: 134
gcatctcaat tagtcagcaa cc                                                    22

SEQ ID NO: 135              moltype = DNA  length = 22
FEATURE                     Location/Qualifiers
misc_feature                1..22
                            note = source = /note="Description of Artificial Sequence:
                            Syntheticoligonucleotide"
source                      1..22
                            mol_type = other DNA
                            organism = synthetic construct
SEQUENCE: 135
gttagggtta gggttagggt ta                                                    22

SEQ ID NO: 136              moltype = DNA  length = 21
FEATURE                     Location/Qualifiers
misc_feature                1..21
                            note = source = /note="Description of Artificial Sequence:
                            Syntheticoligonucleotide"
source                      1..21
                            mol_type = other DNA
                            organism = synthetic construct
SEQUENCE: 136
gttgaggcct tcgttggaaa c                                                     21

SEQ ID NO: 137              moltype = DNA  length = 22
FEATURE                     Location/Qualifiers
misc_feature                1..22
                            note = source = /note="Description of Artificial Sequence:
                            Syntheticoligonucleotide"
source                      1..22
                            mol_type = other DNA
                            organism = synthetic construct
SEQUENCE: 137
gaagagtgga ggccgtgcgc gg                                                    22

SEQ ID NO: 138              moltype = DNA  length = 22
FEATURE                     Location/Qualifiers
misc_feature                1..22
                            note = source = /note="Description of Artificial Sequence:
                            Syntheticoligonucleotide"
source                      1..22
                            mol_type = other DNA
                            organism = synthetic construct
SEQUENCE: 138
gcaagcaagg gaagcgacaa gg                                                    22

SEQ ID NO: 139              moltype = DNA  length = 21
FEATURE                     Location/Qualifiers
misc_feature                1..21
                            note = source = /note="Description of Artificial Sequence:
                            Syntheticoligonucleotide"
source                      1..21
                            mol_type = other DNA
                            organism = synthetic construct
SEQUENCE: 139
gatgtttcag gactaggctg a                                                     21

SEQ ID NO: 140              moltype = DNA  length = 21
FEATURE                     Location/Qualifiers
misc_feature                1..21
                            note = source = /note="Description of Artificial Sequence:
                            Syntheticoligonucleotide"
source                      1..21
                            mol_type = other DNA
                            organism = synthetic construct
SEQUENCE: 140
gagctgggcc aggagaggag a                                                     21

SEQ ID NO: 141              moltype = DNA  length = 20
FEATURE                     Location/Qualifiers
misc_feature                1..20
                            note = source = /note="Description of Artificial Sequence:
                            Syntheticoligonucleotide"
source                      1..20
```

```
                        mol_type = other DNA
                        organism = synthetic construct
SEQUENCE: 141
gagggtctg tggagagttt                                                  20

SEQ ID NO: 142          moltype = DNA  length = 20
FEATURE                 Location/Qualifiers
misc_feature            1..20
                        note = source = /note="Description of Artificial Sequence:
                         Syntheticoligonucleotide"
source                  1..20
                        mol_type = other DNA
                        organism = synthetic construct
SEQUENCE: 142
ggcttggtgt attcagaatg                                                 20

SEQ ID NO: 143          moltype = DNA  length = 20
FEATURE                 Location/Qualifiers
misc_feature            1..20
                        note = source = /note="Description of Artificial Sequence:
                         Syntheticoligonucleotide"
source                  1..20
                        mol_type = other DNA
                        organism = synthetic construct
SEQUENCE: 143
gtagagatgc cgccccgccc                                                 20

SEQ ID NO: 144          moltype = DNA  length = 20
FEATURE                 Location/Qualifiers
misc_feature            1..20
                        note = source = /note="Description of Artificial Sequence:
                         Syntheticoligonucleotide"
source                  1..20
                        mol_type = other DNA
                        organism = synthetic construct
SEQUENCE: 144
ggccccgccc cctggatggg                                                 20

SEQ ID NO: 145          moltype = DNA  length = 20
FEATURE                 Location/Qualifiers
misc_feature            1..20
                        note = source = /note="Description of Artificial Sequence:
                         Syntheticoligonucleotide"
source                  1..20
                        mol_type = other DNA
                        organism = synthetic construct
SEQUENCE: 145
gggggagaa actgaggcga                                                  20

SEQ ID NO: 146          moltype = DNA  length = 20
FEATURE                 Location/Qualifiers
misc_feature            1..20
                        note = source = /note="Description of Artificial Sequence:
                         Syntheticoligonucleotide"
source                  1..20
                        mol_type = other DNA
                        organism = synthetic construct
SEQUENCE: 146
ggtggtggca atggtgtctg                                                 20

SEQ ID NO: 147          moltype = DNA  length = 20
FEATURE                 Location/Qualifiers
misc_feature            1..20
                        note = source = /note="Description of Artificial Sequence:
                         Syntheticoligonucleotide"
source                  1..20
                        mol_type = other DNA
                        organism = synthetic construct
SEQUENCE: 147
gacacaactg gcgcccctcc                                                 20

SEQ ID NO: 148          moltype = DNA  length = 20
FEATURE                 Location/Qualifiers
misc_feature            1..20
                        note = source = /note="Description of Artificial Sequence:
                         Syntheticoligonucleotide"
source                  1..20
                        mol_type = other DNA
                        organism = synthetic construct
```

```
SEQUENCE: 148
ggcccctact tcccctttcaa                                              20

SEQ ID NO: 149          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 149
gagtgataag acacccgctt                                               20

SEQ ID NO: 150          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 150
gcctgggagg gactggggga                                               20

SEQ ID NO: 151          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 151
ggacaatccc ggtccccaga                                               20

SEQ ID NO: 152          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 152
ggtctgccgg aaggtctaca                                               20

SEQ ID NO: 153          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 153
ggcaggtaga ttatggggcc                                               20

SEQ ID NO: 154          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 154
gaagacggcc tctcagagga                                               20

SEQ ID NO: 155          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 155
gtatttctgg cctgggcaag                                               20
```

```
SEQ ID NO: 156          moltype = DNA   length = 20
FEATURE                 Location/Qualifiers
misc_feature            1..20
                        note = source = /note="Description of Artificial Sequence:
                          Syntheticoligonucleotide"
source                  1..20
                        mol_type = other DNA
                        organism = synthetic construct
SEQUENCE: 156
gcatgtgacg ggggctgtca                                              20

SEQ ID NO: 157          moltype = DNA   length = 20
FEATURE                 Location/Qualifiers
misc_feature            1..20
                        note = source = /note="Description of Artificial Sequence:
                          Syntheticoligonucleotide"
source                  1..20
                        mol_type = other DNA
                        organism = synthetic construct
SEQUENCE: 157
gctgccgggt tttgcatgaa                                              20

SEQ ID NO: 158          moltype = DNA   length = 20
FEATURE                 Location/Qualifiers
misc_feature            1..20
                        note = source = /note="Description of Artificial Sequence:
                          Syntheticoligonucleotide"
source                  1..20
                        mol_type = other DNA
                        organism = synthetic construct
SEQUENCE: 158
gccggccgcg cggggggaggc                                             20

SEQ ID NO: 159          moltype = DNA   length = 20
FEATURE                 Location/Qualifiers
misc_feature            1..20
                        note = source = /note="Description of Artificial Sequence:
                          Syntheticoligonucleotide"
source                  1..20
                        mol_type = other DNA
                        organism = synthetic construct
SEQUENCE: 159
ggcaggcgag gaggggggagg                                             20

SEQ ID NO: 160          moltype = DNA   length = 27
FEATURE                 Location/Qualifiers
misc_feature            1..27
                        note = source = /note="Description of Artificial Sequence:
                          Syntheticoligonucleotide"
source                  1..27
                        mol_type = other DNA
                        organism = synthetic construct
SEQUENCE: 160
gcatacttct gcctgctggg gagcctg                                      27

SEQ ID NO: 161          moltype = AA    length = 1399
FEATURE                 Location/Qualifiers
source                  1..1399
                        mol_type = protein
                        organism = Streptococcus pyogenes
SEQUENCE: 161
MYPYDVPDYA SPKKKRKVEA SDKKYSIGLA IGTNSVGWAV ITDEYKVPSK KFKVLGNTDR   60
HSIKKNLIGA LLFDSGETAE ATRLKRTARR RYTRRKNRIC YLQEIFSNEM AKVDDSFFHR  120
LEESFLVEED KKHERHPIFG NIVDEVAYHE KYPTIYHLRK KLVDSTDKAD LRLIYLALAH  180
MIKFRGHFLI EGDLNPDNSD VDKLFIQLVQ TYNQLFEENP INASGVDAKA ILSARLSKSR  240
RLENLIAQLP GEKKNGLFGN LIALSLGLTP NFKSNFDLAE DAKLQLSKDT YDDDLDNLLA  300
QIGDQYADLF LAAKNLSDAI LLSDILRVNT EITKAPLSAS MIKRYDEHHQ DLTLLKALVR  360
QQLPEKYKEI FFDQSKNGYA GYIDGGASQE EFYKFIKPIL EKMDGTEELL VKLNREDLLR  420
KQRTFDNGSI PHQIHLGELH AILRRQEDFY PFLKDNREKI EKILTFRIPY YVGPLARGNS  480
RFAWMTRKSE ETITPWNFEE VVDKGASAQS FIERMTNFDK NLPNEKVLPK HSLLYEYFTV  540
YNELTKVKYV TEGMRKPAFL SGEQKKAIVD LLFKTNRKVT VKQLKEDYFK KIECFDSVEI  600
SGVEDRFNAS LGTYHDLLKI IKDKDFLDNE ENEDILEDIV LTLTLFEDRE MIEERLKTYA  660
HLFDDKVMKQ LKRRRYTGWG RLSRKLINGI RDKQSGKTIL DFLKSDGFAN RNFMQLIHDD  720
SLTFKEDIQK AQVSGQGDSL HEHIANLAGS PAIKKGILQT VKVVDELVKV MGRHKPENIV  780
IEMARENQTT QKGQKNSRER MKRIEEGIKE LGSQILKEHP VENTQLQNEK LYLYYLQNGR  840
DMYVDQELDI NRLSDYDVDA IVPQSFLKDD SIDNKVLTRS DKNRGKSDNV PSEEVVKKMK  900
NYWRQLLNAK LITQRKFDNL TKAERGGLSE LDKAGFIKRQ LVETRQITKH VAQILDSRMN  960
TKYDENDKLI REVKVITLKS KLVSDFRKDF QFYKVREINN YHHAHDAYLN AVVGTALIKK 1020
```

```
YPKLESEFVY GDYKVYDVRK MIAKSEQEIG KATAKYFFYS NIMNFFKTEI TLANGEIRKR    1080
PLIETNGETG EIVWDKGRDF ATVRKVLSMP QVNIVKKTEV QTGGFSKESI LPKRNSDKLI    1140
ARKKDWDPKK YGGFDSPTVA YSVLVVAKVE KGKSKKLKSV KELLGITIME RSSFEKNPID    1200
FLEAKGYKEV KKDLIIKLPK YSLFELENGR KRMLASAGEL QKGNELALPS KYVNFLYLAS    1260
HYEKLKGSPE DNEQKQLFVE QHKHYLDEII EQISEFSKRV ILADANLDKV LSAYNKHRDK    1320
PIREQAENII HLFTLTNLGA PAAFKYFDTT IDRKRYTSTK EVLDATLIHQ SITGLYETRI    1380
DLSQLGGDSP KKKRKVEAS                                                 1399

SEQ ID NO: 162          moltype = AA   length = 1399
FEATURE                 Location/Qualifiers
source                  1..1399
                        mol_type = protein
                        organism = Streptococcus pyogenes
SEQUENCE: 162
MYPYDVPDYA SPKKKRKVEA SDKKYSIGLD IGTNSVGWAV ITDEYKVPSK KFKVLGNTDR    60
HSIKKNLIGA LLFDSGETAE ATRLKRTARR RYTRRKNRIC YLQEIFSNEM AKVDDSFFHR    120
LEESFLVEED KKHERHPIFG NIVDEVAYHE KYPTIYHLRK KLVDSTDKAD LRLIYLALAH    180
MIKFRGHFLI EGDLNPDNSD VDKLFIQLVQ TYNQLFEENP INASGVDAKA ILSARLSKSR    240
RLENLIAQLP GEKKNGLFGN LIALSLGLTP NFKSNFDLAE DAKLQLSKDT YDDDLDNLLA    300
QIGDQYADLF LAAKNLSDAI LLSDILRVNT EITKAPLSAS MIKRYDEHHQ DLTLLKALVR    360
QQLPEKYKEI FFDQSKNGYA GYIDGGASQE EFYKFIKPIL EKMDGTEELL VKLNREDLLR    420
KQRTFDNGSI PHQIHLGELH AILRRQEDFY PFLKDNREKI EKILTFRIPY YVGPLARGNS    480
RFAWMTRKSE ETITPWNFEE VVDKGASAQS FIERMTNFDK NLPNEKVLPK HSLLYEYFTV    540
YNELTKVKYV TEGMRKPAFL SGEQKKAIVD LLFKTNRKVT VKQLKEDYFK KIECFDSVEI    600
SGVEDRFNAS LGTYHDLLKI IKDKDFLDNE ENEDILEDIV LTLTLFEDRE MIEERLKTYA    660
HLFDDKVMKQ LKRRRYTGWG RLSRKLINGI RDKQSGKTIL DFLKSDGFAN RNFMQLIHDD    720
SLTFKEDIQK AQVSGQGDSL HEHIANLAGS PAIKKGILQT VKVVDELVKV MGRHKPENIV    780
IEMARENQTT QKGQKNSRER MKRIEEGIKE LGSQILKEHP VENTQLQNEK LYLYYLQNGR    840
DMYVDQELDI NRLSDYDVDH IVPQSFLKDD SIDNKVLTRS DKNRGKSDNV PSEEVVKKMK    900
NYWRQLLNAK LITQRKFDNL TKAERGGLSE LDKAGFIKRQ LVETRQITKH VAQILDSRMN    960
TKYDENDKLI REVKVITLKS KLVSDFRKDF QFYKVREINN YHHAHDAYLN AVVGTALIKK    1020
YPKLESEFVY GDYKVYDVRK MIAKSEQEIG KATAKYFFYS NIMNFFKTEI TLANGEIRKR    1080
PLIETNGETG EIVWDKGRDF ATVRKVLSMP QVNIVKKTEV QTGGFSKESI LPKRNSDKLI    1140
ARKKDWDPKK YGGFDSPTVA YSVLVVAKVE KGKSKKLKSV KELLGITIME RSSFEKNPID    1200
FLEAKGYKEV KKDLIIKLPK YSLFELENGR KRMLASAGEL QKGNELALPS KYVNFLYLAS    1260
HYEKLKGSPE DNEQKQLFVE QHKHYLDEII EQISEFSKRV ILADANLDKV LSAYNKHRDK    1320
PIREQAENII HLFTLTNLGA PAAFKYFDTT IDRKRYTSTK EVLDATLIHQ SITGLYETRI    1380
DLSQLGGDSP KKKRKVEAS                                                 1399

SEQ ID NO: 163          moltype = AA   length = 1399
FEATURE                 Location/Qualifiers
source                  1..1399
                        mol_type = protein
                        organism = Streptococcus pyogenes
SEQUENCE: 163
MYPYDVPDYA SPKKKRKVEA SDKKYSIGLA IGTNSVGWAV ITDEYKVPSK KFKVLGNTDR    60
HSIKKNLIGA LLFDSGETAE ATRLKRTARR RYTRRKNRIC YLQEIFSNEM AKVDDSFFHR    120
LEESFLVEED KKHERHPIFG NIVDEVAYHE KYPTIYHLRK KLVDSTDKAD LRLIYLALAH    180
MIKFRGHFLI EGDLNPDNSD VDKLFIQLVQ TYNQLFEENP INASGVDAKA ILSARLSKSR    240
RLENLIAQLP GEKKNGLFGN LIALSLGLTP NFKSNFDLAE DAKLQLSKDT YDDDLDNLLA    300
QIGDQYADLF LAAKNLSDAI LLSDILRVNT EITKAPLSAS MIKRYDEHHQ DLTLLKALVR    360
QQLPEKYKEI FFDQSKNGYA GYIDGGASQE EFYKFIKPIL EKMDGTEELL VKLNREDLLR    420
KQRTFDNGSI PHQIHLGELH AILRRQEDFY PFLKDNREKI EKILTFRIPY YVGPLARGNS    480
RFAWMTRKSE ETITPWNFEE VVDKGASAQS FIERMTNFDK NLPNEKVLPK HSLLYEYFTV    540
YNELTKVKYV TEGMRKPAFL SGEQKKAIVD LLFKTNRKVT VKQLKEDYFK KIECFDSVEI    600
SGVEDRFNAS LGTYHDLLKI IKDKDFLDNE ENEDILEDIV LTLTLFEDRE MIEERLKTYA    660
HLFDDKVMKQ LKRRRYTGWG RLSRKLINGI RDKQSGKTIL DFLKSDGFAN RNFMQLIHDD    720
SLTFKEDIQK AQVSGQGDSL HEHIANLAGS PAIKKGILQT VKVVDELVKV MGRHKPENIV    780
IEMARENQTT QKGQKNSRER MKRIEEGIKE LGSQILKEHP VENTQLQNEK LYLYYLQNGR    840
DMYVDQELDI NRLSDYDVDH IVPQSFLKDD SIDNKVLTRS DKNRGKSDNV PSEEVVKKMK    900
NYWRQLLNAK LITQRKFDNL TKAERGGLSE LDKAGFIKRQ LVETRQITKH VAQILDSRMN    960
TKYDENDKLI REVKVITLKS KLVSDFRKDF QFYKVREINN YHHAHDAYLN AVVGTALIKK    1020
YPKLESEFVY GDYKVYDVRK MIAKSEQEIG KATAKYFFYS NIMNFFKTEI TLANGEIRKR    1080
PLIETNGETG EIVWDKGRDF ATVRKVLSMP QVNIVKKTEV QTGGFSKESI LPKRNSDKLI    1140
ARKKDWDPKK YGGFDSPTVA YSVLVVAKVE KGKSKKLKSV KELLGITIME RSSFEKNPID    1200
FLEAKGYKEV KKDLIIKLPK YSLFELENGR KRMLASAGEL QKGNELALPS KYVNFLYLAS    1260
HYEKLKGSPE DNEQKQLFVE QHKHYLDEII EQISEFSKRV ILADANLDKV LSAYNKHRDK    1320
PIREQAENII HLFTLTNLGA PAAFKYFDTT IDRKRYTSTK EVLDATLIHQ SITGLYETRI    1380
DLSQLGGDSP KKKRKVEAS                                                 1399

SEQ ID NO: 164          moltype = AA   length = 1399
FEATURE                 Location/Qualifiers
source                  1..1399
                        mol_type = protein
                        organism = Streptococcus pyogenes
SEQUENCE: 164
MYPYDVPDYA SPKKKRKVEA SDKKYSIGLD IGTNSVGWAV ITDEYKVPSK KFKVLGNTDR    60
HSIKKNLIGA LLFDSGETAE ATRLKRTARR RYTRRKNRIC YLQEIFSNEM AKVDDSFFHR    120
LEESFLVEED KKHERHPIFG NIVDEVAYHE KYPTIYHLRK KLVDSTDKAD LRLIYLALAH    180
```

```
MIKFRGHFLI  EGDLNPDNSD  VDKLFIQLVQ  TYNQLFEENP  INASGVDAKA  ILSARLSKSR   240
RLENLIAQLP  GEKKNGLFGN  LIALSLGLTP  NFKSNFDLAE  DAKLQLSKDT  YDDDLDNLLA   300
QIGDQYADLF  LAAKNLSDAI  LLSDILRVNT  EITKAPLSAS  MIKRYDEHHQ  DLTLLKALVR   360
QQLPEKYKEI  FFDQSKNGYA  GYIDGGASQE  EFYKFIKPIL  EKMDGTEELL  VKLNREDLLR   420
KQRTFDNGSI  PHQIHLGELH  AILRRQEDFY  PFLKDNREKI  EKILTFRIPY  YVGPLARGNS   480
RFAWMTRKSE  ETITPWNFEE  VVDKGASAQS  FIERMTNFDK  NLPNEKVLPK  HSLLYEYFTV   540
YNELTKVKYV  TEGMRKPAFL  SGEQKKAIVD  LLFKTNRKVT  VKQLKEDYFK  KIECFDSVEI   600
SGVEDRFNAS  LGTYHDLLKI  IKDKDFLDNE  ENEDILEDIV  LTLTLFEDRE  MIEERLKTYA   660
HLFDDKVMKQ  LKRRRYTGWG  RLSRKLINGI  RDKQSGKTIL  DFLKSDGFAN  RNFMQLIHDD   720
SLTFKEDIQK  AQVSGQGDSL  HEHIANLAGS  PAIKKGILQT  VKVVDELVKV  MGRHKPENIV   780
IEMARENQTT  QKGQKNSRER  MKRIEEGIKE  LGSQILKEHP  VENTQLQNEK  LYLYYLQNGR   840
DMYVDQELDI  NRLSDYDVDA  IVPQSFLKDD  SIDNKVLTRS  DKNRGKSDNV  PSEEVVKKMK   900
NYWRQLLNAK  LITQRKFDNL  TKAERGGLSE  LDKAGFIKRQ  LVETRQITKH  VAQILDSRMN   960
TKYDENDKLI  REVKVITLKS  KLVSDFRKDF  QFYKVREINN  YHHAHDAYLN  AVVGTALIKK  1020
YPKLESEFVY  GDYKVYDVRK  MIAKSEQEIG  KATAKYFFYS  NIMNFFKTEI  TLANGEIRKR  1080
PLIETNGETG  EIVWDKGRDF  ATVRKVLSMP  QVNIVKKTEV  QTGGFSKESI  LPKRNSDKLI  1140
ARKKDWDPKK  YGGFDSPTVA  YSVLVVAKVE  KGKSKKLKSV  KELLGITIME  RSSFEKNPID  1200
FLEAKGYKEV  KKDLIIKLPK  YSLFELENGR  KRMLASAGEL  QKGNELALPS  KYVNFLYLAS  1260
HYEKLKGSPE  DNEQKQLFVE  QHKHYLDEII  EQISEFSKRV  ILADANLDKV  LSAYNKHRDK  1320
PIREQAENII  HLFTLTNLGA  PAAFKYFDTT  IDRKRYTSTK  EVLDATLIHQ  SITGLYETRI  1380
DLSQLGGDSP  KKKRKVEAS                                                   1399

SEQ ID NO: 165            moltype = AA   length = 641
FEATURE                   Location/Qualifiers
REGION                    1..641
                          note = source = /note="Description of Artificial Sequence:
                          Syntheticpolypeptide"
source                    1..641
                          mol_type = protein
                          organism = synthetic construct
SEQUENCE: 165
MVRGSHHHHH  HGMASMTGGQ  QMGRDLYDDD  DKDPMVSKGE  ELIKENMRMK  VVMEGSVNGH   60
QFKCTGEGEG  NPYMGTQTMR  IKVIEGGPLP  FAFDILATSF  MYGSRTFIKY  PKGIPDFFKQ  120
SFPEGFTWER  VTRYEDGGVV  TVMQDTSLED  GCLVYHVQVR  GVNFPSNGPV  MQKKTKGWEP  180
NTEMMYPADG  GLRGYTHMAL  KVDGGGHLSC  SFVTTYRSKK  TVGNIKMPGI  HAVDHRLERL  240
EESDNEMFVV  QREHAVAKFA  GLGGGMDELY  KGGGGSGPAG  ILPPKKKRKV  SRGRSRLLED  300
FRNNRYPNLQ  LREIAGHIME  FSQDQHGSRF  IQLKLERATP  AERQLVFNEI  LQAAYQLMVD  360
VFGNYVIQKF  FEFGSLEQKL  ALAERIRGHV  LSLALQMYGS  RVIEKALEFI  PSDQQNEMVR  420
ELDGHVLKCV  KDQNGNHVVQ  KCIECVQPQS  LQFIIDAFKG  QVFALSTHPY  GCRVIQRILE  480
HCLPDQTLPI  LEELHQHTEQ  LVQDQYGNYV  IQHVLEHGRP  EDKSKIVAEI  RGNVLVLSQH  540
KFASNVVEKC  VTHASRTERA  VLIDEVCTMN  DGPHSALYTM  MKDQYANYVV  QKMIDVAEPG  600
QRKIVMHKIR  PHIATLRKYT  YGKHILAKLE  KYYMKNGVDL  G                      641

SEQ ID NO: 166            moltype = AA   length = 641
FEATURE                   Location/Qualifiers
REGION                    1..641
                          note = source = /note="Description of Artificial Sequence:
                          Syntheticpolypeptide"
source                    1..641
                          mol_type = protein
                          organism = synthetic construct
SEQUENCE: 166
MVRGSHHHHH  HGMASMTGGQ  QMGRDLYDDD  DKDPMVSKGE  ELIKENMRMK  VVMEGSVNGH   60
QFKCTGEGEG  NPYMGTQTMR  IKVIEGGPLP  FAFDILATSF  MYGSRTFIKY  PKGIPDFFKQ  120
SFPEGFTWER  VTRYEDGGVV  TVMQDTSLED  GCLVYHVQVR  GVNFPSNGPV  MQKKTKGWEP  180
NTEMMYPADG  GLRGYTHMAL  KVDGGGHLSC  SFVTTYRSKK  TVGNIKMPGI  HAVDHRLERL  240
EESDNEMFVV  QREHAVAKFA  GLGGGMDELY  KGGGGSGPAG  ILPPKKKRKV  SRGRSRLLED  300
FRNNRYPNLQ  LREIAGHIME  FSQDQHGSRF  IQLKLERATP  AERQLVFNEI  LQAAYQLMVD  360
VFGNYVIQKF  FEFGSLEQKL  ALAERIRGHV  LSLALQMYGS  RVIQKALEFI  PSDQQNEMVR  420
ELDGHVLKCV  KDQNGNHVVQ  KCIECVQPQS  LQFIIDAFKG  QVFALSTHPY  GCRVIQRILE  480
HCLPDQTLPI  LEELHQHTEQ  LVQDQYGSYV  IEHVLEHGRP  EDKSKIVAEI  RGNVLVLSQH  540
KFANNVVQKC  VTHASRTERA  VLIDEVCTMN  DGPHSALYTM  MKDQYANYVV  QKMIDVAEPG  600
QRKIVMHKIR  PHIATLRKYT  YGKHILAKLE  KYYMKNGVDL  G                      641

SEQ ID NO: 167            moltype = AA   length = 621
FEATURE                   Location/Qualifiers
REGION                    1..621
                          note = source = /note="Description of Artificial Sequence:
                          Syntheticpolypeptide"
source                    1..621
                          mol_type = protein
                          organism = synthetic construct
SEQUENCE: 167
MVSKGEELFT  GVVPILVELD  GDVNGHKFSV  RGEGEGDATN  GKLTLKFICT  TGKLPVPWPT   60
LVTTFGYGVA  CFSRYPDHMK  QHDFFKSAMP  EGYVQERTIS  FKDDGTYKTR  AEVKFEGDTL  120
VNRIELKGID  FKEDGNILGH  KLEYNFNSHN  VYITADKQKN  GIKANFKIRH  NVEDGSVQLA  180
DHYQQNTPIG  DGPVLLPDNH  YLSHQSALSK  DPNEKRDHMV  LLEFVTAAGI  THGMDELYKS  240
RGPYSIVSPK  CGGGGSGPAG  ILPPKKKRKV  SRGRSRLLED  FRNNRYPNLQ  LREIAGHIME  300
FSQDQHGSRF  IQLKLERATP  AERQLVFNEI  LQAAYQLMVD  VFGNYVIQKF  FEFGSLEQKL  360
```

```
ALAERIRGHV LSLALQMYGS RVIEKALEFI PSDQQNEMVR ELDGHVLKCV KDQNGNHVVQ   420
KCIECVQPQS LQFIIDAFKG QVFALSTHPY GCRVIQRILE HCLPDQTLPI LEELHQHTEQ   480
LVQDQYGNYV IQHVLEHGRP EDKSKIVAEI RGNVLVLSQH KFASNVVEKC VTHASRTERA   540
VLIDEVCTMN DGPHSALYTM MKDQYANYVV QKMIDVAEPG QRKIVMHKIR PHIATLRKYT   600
YGKHILAKLE KYYMKNGVDL G                                            621

SEQ ID NO: 168          moltype = AA  length = 621
FEATURE                 Location/Qualifiers
REGION                  1..621
                        note = source = /note="Description of Artificial Sequence:
                           Syntheticpolypeptide"
source                  1..621
                        mol_type = protein
                        organism = synthetic construct
SEQUENCE: 168
MVSKGEELFT GVVPILVELD GDVNGHKFSV RGEGEGDATN GKLTLKFICT TGKLPVPWPT    60
LVTTFGYGVA CFSRYPDHMK QHDFFKSAMP EGYVQERTIS FKDDGTYKTR AEVKFEGDTL   120
VNRIELKGID FKEDGNILGH KLEYNFNSHN VYITADKQKN GIKANFKIRH NVEDGSVQLA   180
DHYQQNTPIG DGPVLLPDNH YLSHQSALSK DPNEKRDHMV LLEFVTAAGI THGMDELYKS   240
RGPYSIVSPK CGGGGSGPAG ILPPKKKRKV SRGRSRLLED FRNNRYPNLQ LREIAGHIME   300
FSQDQHGSRF IQLKLERATP AERQLVFNEI LQAAYQLMVD VFGNYVIQKF FEFGSLEQKL   360
ALAERIRGHV LSLALQMYGC RVIQKALEFI PSDQQNEMVR ELDGHVLKCV KDQNGNHVVQ   420
KCIECVQPQS LQFIIDAFKG QVFALSTHPY GCRVIQRILE HCLPDQTLPI LEELHQHTEQ   480
LVQDQYGSYV IEHVLEHGRP EDKSKIVAEI RGNVLVLSQH KFANNVVQKC VTHASRTERA   540
VLIDEVCTMN DGPHSALYTM MKDQYANYVV QKMIDVAEPG QRKIVMHKIR PHIATLRKYT   600
YGKHILAKLE KYYMKNGVDL G                                            621

SEQ ID NO: 169          moltype = AA  length = 424
FEATURE                 Location/Qualifiers
REGION                  1..424
                        note = source = /note="Description of Artificial Sequence:
                           Syntheticpolypeptide"
source                  1..424
                        mol_type = protein
                        organism = synthetic construct
SEQUENCE: 169
MGILPPKKKR KVSRGRSRLL EDFRNNRYPN LQLREIAGHI MEFSQDQHGS RFIQLKLERA    60
TPAERQLVFN EILQAAYQLM VDVFGNYVIQ KFFEFGSLEQ KLALAERIRG HVLSLALQMY   120
GSRVIEKALE FIPSDQQNEM VRELDGHVLK CVKDQNGNHV VQKCIECVQP QSLQFIIDAF   180
KGQVFALSTH PYGCRVIQRI LEHCLPDQTL PILEELHQT EQLVQDQYGN YVIQHVLEHG    240
RPEDKSKIVA EIRGNVLVLS QHKFASNVVE KCVTHASRTE RAVLIDEVCT MNDGPHSALY   300
TMMKDQYANY VVQKMIDVAE PGQRKIVMHK IRPHIATLRK YTYGKHILAK LEKYYMKNGV   360
DLGGPAGSGR ADALDDFDLD MLGSDALDDF DLDMLGSDAL DDFDLDMLGS DALDDFDLDM   420
LYID                                                               424

SEQ ID NO: 170          moltype = AA  length = 424
FEATURE                 Location/Qualifiers
REGION                  1..424
                        note = source = /note="Description of Artificial Sequence:
                           Syntheticpolypeptide"
source                  1..424
                        mol_type = protein
                        organism = synthetic construct
SEQUENCE: 170
MGILPPKKKR KVSRGRSRLL EDFRNNRYPN LQLREIAGHI MEFSQDQHGS RFIQLKLERA    60
TPAERQLVFN EILQAAYQLM VDVFGNYVIQ KFFEFGSLEQ KLALAERIRG HVLSLALQMY   120
GCRVIQKALE FIPSDQQNEM VRELDGHVLK CVKDQNGNHV VQKCIECVQP QSLQFIIDAF   180
KGQVFALSTH PYGCRVIQRI LEHCLPDQTL PILEELHQT EQLVQDQYGS YVIEHVLEHG    240
RPEDKSKIVA EIRGNVLVLS QHKFANNVVQ KCVTHASRTE RAVLIDEVCT MNDGPHSALY   300
TMMKDQYANY VVQKMIDVAE PGQRKIVMHK IRPHIATLRK YTYGKHILAK LEKYYMKNGV   360
DLGGPAGSGR ADALDDFDLD MLGSDALDDF DLDMLGSDAL DDFDLDMLGS DALDDFDLDM   420
LYID                                                               424

SEQ ID NO: 171          moltype = AA  length = 709
FEATURE                 Location/Qualifiers
REGION                  1..709
                        note = source = /note="Description of Artificial Sequence:
                           Syntheticpolypeptide"
source                  1..709
                        mol_type = protein
                        organism = synthetic construct
SEQUENCE: 171
MGILPPKKKR KVSRGRSRLL EDFRNNRYPN LQLREIAGHI MEFSQDQHGS RFIQLKLERA    60
TPAERQLVFN EILQAAYQLM VDVFGNYVIQ KFFEFGSLEQ KLALAERIRG HVLSLALQMY   120
GCRVIQKALE FIPSDQQNEM VRELDGHVLK CVKDQNGNHV VQKCIECVQP QSLQFIIDAF   180
KGQVFALSTH PYGCRVIQRI LEHCLPDQTL PILEELHQT EQLVQDQYGS YVIEHVLEHG    240
RPEDKSKIVA EIRGNVLVLS QHKFANNVVQ KCVTHASRTE RAVLIDEVCT MNDGPHSALY   300
TMMKDQYANY VVQKMIDVAE PGQRKIVMHK IRPHIATLRK YTYGKHILAK LEKYYMKNGV   360
DLGGPAGGGG SGGGGSGGGG SGPKKKRKVA AAGSPSGQIS NQALALAPSS APVLAQTMVP   420
```

```
SSAMVPLAQP PAPAPVLTPG PPQSLSAPVP KSTQAGEGTL SEALLHLQFD ADEDLGALLG  480
NSTDPGVFTD LASVDNSEFQ QLLNQGVSMS HSTAEPMLME YPEAITRLVT GSQRPPDPAP  540
TPLGTSGLPN GLSGDEDFSS IADMDFSALL SQISSSGQGG GGSGFSVDTS ALLDLFSPSV  600
TVPDMSLPDL DSSLASIQEL LSPQEPPRPP EAENSSPDSG KQLVHYTAQP LFLLDPGSVD  660
TGSNDLPVLF ELGEGSYFSE GDGFAEDPTI SLLTGSEPPK AKDPTVSID             709

SEQ ID NO: 172         moltype = AA  length = 456
FEATURE                Location/Qualifiers
REGION                 1..456
                       note = source = /note="Description of Artificial Sequence:
                         Syntheticpolypeptide"
source                 1..456
                       mol_type = protein
                       organism = synthetic construct
SEQUENCE: 172
MGSPKKKRKV EASMDAKSLT AWSRTLVTFK DVFVDFTREE WKLLDTAQQI VYRNVMLENY   60
KNLVSLGYQL TKPDVILRLE KGEEPWLVSR GSIVGILPPK KKRKVSRGRS RLLEDFRNNR  120
YPNLQLREIA GHIMEFSQDQ HGSRFIQLKL ERATPAERQL VFNEILQAAY QLMVDVFGNY  180
VIQKFFEFGS LEQKLALAER IRGHVLSLAL QMYGCRVIQK ALEFIPSDQQ NEMVRELDGH  240
VLKCVKDQNG NHVVQKCIEC VQPQSLQFII DAFKGQVFAL STHPYGCRVI QRILEHCLPD  300
QTLPILEELH QHTEQLVQDQ YGSYVIEHVL EHGRPEDKSK IVAEIRGNVL VLSQHKFANN  360
VVQKCVTHAS RTERAVLIDE VCTMNDGPHS ALYTMMKDQY ANYVVQKMID VAEPGQRKIV  420
MHKIRPHIAT LRKYTYGKHI LAKLEKYYMK NGVDLG                           456

SEQ ID NO: 173         moltype = DNA  length = 10
FEATURE                Location/Qualifiers
misc_feature           1..10
                       note = source = /note="Description of Artificial Sequence:
                         Syntheticoligonucleotide"
source                 1..10
                       mol_type = other DNA
                       organism = synthetic construct
SEQUENCE: 173
gccagatgcc                                                          10
```

THREE-COMPONENT CRISPR/Cas COMPLEX SYSTEM AND USES THEREOF

REFERENCE TO RELATED APPLICATIONS

This application is a divisional of co-pending U.S. application Ser. No. 15/702,944, filed on Sep. 13, 2017, which is a continuation application of International Patent Application No. PCT/US2016/021491, filed on Mar. 9, 2016 and published as WO2016/148994, which claims priority to U.S. Provisional Application No. 62/132,644, filed on Mar. 13, 2015, and 62/221,249, filed on Sep. 21, 2015, the entire contents of each of the applications (including sequence listing and drawings) are incorporated herein by reference in their entirety.

SEQUENCE LISTING

The contents of the electronic sequence listing (J022770035US03-SUBSEQ-EMB.xml; Size: 280,085 bytes; and Date of Creation: Aug. 25, 2022) is herein incorporated by reference in its entirety.

BACKGROUND OF THE INVENTION

In the CRISPR/Cas system, Cas9 protein and sgRNA (single guide RNA) constitute a sufficient two-component DNA endonuclease whose specificity is provided by target-matching sequence on sgRNA while endonuclease activity resides on the Cas9 protein.

Nuclease-defective or nuclease-deficient Cas9 protein (e.g., dCas9) with mutations on its nuclease domains retains DNA binding activity when complexed with sgRNA. dCas9 protein can tether and localize effector domains or protein tags by means of protein fusions to sites matched by sgRNA, thus constituting an RNA-guided DNA binding enzyme. dCas9 can be fused to transcriptional activation domain (e.g., VP64) or repressor domain (e.g., KRAB), and be guided by sgRNA to activate or repress target genes, respectively. dCas9 can also be fused with fluorescent proteins and achieve live-cell fluorescent labeling of chromosomal regions. However, in such systems, only one Cas9-effector fusion is possible because sgRNA:Cas9 pairing is exclusive. Also, in cases where multiple copies of protein tags or effector fusions are necessary to achieve some biological threshold or signal detection threshold, multimerization of effector or protein tags by direct fusion with dCas9 protein is technically limited, by constraints such as difficulty in delivering the large DNA encoding such fusions, or difficulty in translating or translocating such large proteins into the nucleus due to protein size.

SUMMARY OF THE INVENTION

The invention described herein enables multiplexity and polymerization of effector or protein tags, by providing a three-component CRISPR/Cas complex/system comprising a Cas9 protein (e.g., a wildtype (wt) Cas9, a Cas9 Nickase, or a dCas9 protein), a modified sgRNA as a subject polynucleotide (e.g., "sgRNA-PBS"), and one or more fusion proteins of PUF domain(s) with effector domains or protein tags ("PUF domain-fusion[s]"). sgRNA-PBS can be derived by inserting multiple copies of short PUF (e.g., 8-mer) recognition sequences downstream of the sgRNA stem loops or upstream of the target-matching region. PUF domains of each PUF domain-effector fusion can be programmed to recognize the 8-mer recognition sequence on the subject polynucleotide, thus bringing the one or more effector domains fused to the PUF domains to specific regions of a target DNA recognized by the target-matching sgRNA.

The three-component CRISPR/Cas complexes/systems of the invention are advantageous in terms of multiplicity, since different three-component CRISPR/Cas complexes/systems can be simultaneously delivered into a cell or animal, and each can operate at the defined target sites with orthogonality (i.e., without interference with other three-component CRISPR/Cas complexes/systems and their target sites). Since PUF domains can be easily programmed to recognize any 8-mer RNA recognition sequences, this system expands the multiplexibility to a theoretical maximum of $4^8$ (65536) when the RNA recognition sequence is only 8-mer (and potentially much more when the RNA recognition sequence is longer).

The three-component CRISPR/Cas complexes/systems of the invention are also advantageous in terms of polymerizability: the simplicity of the linear 8-mer sequence allows extensive polymerization without hindering Cas9:sgRNA DNA binding activity. Such feature allows multiple molecules of PUF-fusions to be assembled on the modified sgRNA, thus allowing local concentration of effector or protein tags. Such feature is particularly beneficial in applications such as fluorescent imaging or transcriptional regulation, where proximity synergism allows maximal effective regulation or signal-to-noise ratio.

A further advantage of the invention relates to stoichiometric complex formation. Different 8-mer sequences can be orderly inserted onto the sgRNA-PBS construct to allow complex formation with defined stoichiometry and ordering of the PUF-fusions on the sgRNA-PBS.

Thus one aspect of the invention provides a polynucleotide comprising: (1) a DNA-targeting sequence that is complementary to a target polynucleotide sequence; (2) a Cas9-binding sequence; and, (3) one or more copies of a PUF domain-Binding Sequence (PBS), wherein each of said one or more copies of the PBS binds to the same or a different PUF domain; wherein a Cas9 protein (e.g., a wildtype (wt) Cas9, a Cas9 Nickase, or a dCas9 protein) is capable of forming a complex with the polynucleotide by binding to the Cas9-binding sequence.

As used herein, "Cas9 protein" include a wildtype Cas9 protein, a Cas9 nickase in which one of the two catalytic sites for endonuclease activity (RuvC and HNH) is defective or lacks activity, and a dCas9 protein in which both catalytic sites for endonuclease activity are defective or lack activity. In certain embodiments, the Cas9 protein is a wt Cas9. In certain embodiments, the Cas9 protein lacks nuclease activity or is nuclease deficient. In certain embodiments, the Cas9 protein is a nickase (e.g., for example, the nickase can be a Cas9 Nickase with a mutation at a position corresponding to D10A of *S. pyogenes* Cas9; or the nickase can be a Cas9 Nickase with a mutation at a position corresponding to H840A of *S. pyogenes* Cas9). In certain embodiments, the Cas9 protein is a dCas9 (e.g., a dCas9 with mutations at positions corresponding to D10A and H840A of *S. pyogenes* Cas9). In certain embodiments, the Cas9 protein is not wt Cas9. In certain embodiments, the Cas9 protein is not nickase. In certain embodiments, the Cas9 protein is not dCas9.

In certain embodiments, a "modified Cas9 protein" refers to a Cas9 that is not a wt Cas9 protein, such as a dCas9 or Cas9 nickase.

In certain embodiments, the dCas9 protein is nuclease-deficient but retains DNA-binding ability when complexed with the polynucleotide.

In certain embodiments, the DNA-targeting sequence base-pairs with the target polynucleotide sequence when the Cas9 protein (e.g., wt, nickase, or dCas9 protein) is complexed with the polynucleotide.

In certain embodiments, the target polynucleotide sequence comprises or is adjacent to a transcription regulatory element. For example, the transcription regulatory element may comprise one or more of: core promoter, proximal promoter element, enhancer, silencer, insulator, and locus control region.

In certain embodiments, the target polynucleotide sequence comprises or is adjacent to a telomere sequence, a centromere, or a repetitive genomic sequence.

In certain embodiments, the target polynucleotide sequence comprises or is adjacent to a genomic marker sequence (or a genomic locus of interest).

In certain embodiments, the target polynucleotide sequence is immediately 3' to a PAM (protospacer adjacent motif) sequence of the complementary strand, which can be 5'-CCN-3' wherein N is any DNA nucleotide.

In certain embodiments, the DNA-targeting sequence is complementary to the target polynucleotide sequence over about 12-22 nucleotides (nts), about 14-20 nts, about 16-20 nts, about 18-20 nts, or about 12, 14, 16, 18, or 20 nts (preferably, the complementary region comprises a continuous stretch of 12-22 nts, preferably at the 3' end of the DNA-binding sequence). For example, the DNA-binding sequence can be 50, 60, 70, 80, 90, or 95-100% complementary to the target polynucleotide sequence.

In certain embodiments, the DNA-binding sequence has a 5' end nucleotide G.

In certain embodiments, the polynucleotide further comprises a linker sequence linking the DNA-targeting sequence to the Cas9-binding sequence.

In certain embodiments, the Cas9-binding sequence forms a hairpin structure.

In certain embodiments, the Cas9-binding sequence is about 37-47 nt, or about 42 nt.

In certain embodiments, the Cas9 nickase protein lacks endonuclease activity due to point mutations at one endonuclease catalytic sites (RuvC and HNH) of wild type Cas9. The point mutations can be D10A or H840A.

In certain embodiments, the dCas9 protein lacks endonuclease activity due to point mutations at both endonuclease catalytic sites (RuvC and HNH) of wild type Cas9. The point mutations can be D10A and H840A.

In certain embodiments, each of the one or more copies of the PBS has about 8 nucleotides.

In certain embodiments, the polynucleotide comprises 1, 2, 3, 4, 5, 10, 15, 20, 25, 30, 35, 40, 45, 46, 47, 48, 49, or 50 copies, or 1-50, 2-45, 3-40, 5-35, 5-10, 10-20 copies of identical or different PBS.

In certain embodiments, the polynucleotide comprises a PBS of the sequence 5'-UGUAUGUA-3' that can be bound by the PUF domain PUF(3-2).

In certain embodiments, the polynucleotide comprises a PBS of the sequence 5'-UUGAUAUA-3' that can be bound by the PUF domain PUF(6-2/7-2).

Another aspect of the invention provides a vector encoding any one of the subject polynucleotide.

In certain embodiments, transcription of the polynucleotide is under the control of a constitutive promoter, or an inducible promoter.

In certain embodiments, the vector is active in a cell from a mammal (a human; a non-human primate; a non-human mammal; a rodent such as a mouse, a rat, a hamster, a Guinea pig; a livestock mammal such as a pig, a sheep, a goat, a horse, a camel, cattle; or a pet mammal such as a cat or a dog); a bird, a fish, an insect, a worm, a yeast, or a bacterium.

In a related aspect, the invention provides a plurality of any one of the subject vectors, wherein two of the vectors differ in the encoded polynucleotides in their respective DNA-targeting sequences, Cas9-binding sequences, and/or the copy number, identity, or relative order of the PBS.

Another aspect of the invention provides a complex comprising any one of the subject polynucleotide, and the Cas9 protein (e.g., wt, nickase, or dCas9 protein).

In certain embodiments, the complex further comprises one or more PUF domain(s) bound to said one or more PBS(s).

In certain embodiments, each of the PUF domains is fused to an effector domain.

In certain embodiments, the effector domain is independently a transcription repressor, a transcription activator, a fluorescent protein, an enzyme, or a chromatin remodeling protein (HDAC/HAT).

In certain embodiments, at least two of the PUF domains are fused to different effector domains.

In certain embodiments, the Cas9 protein (e.g., wt, nickase, or dCas9 protein), the PUF domain, and/or the effector domain further comprises a nuclear localization sequence (NLS).

In certain embodiments, the complex is bound to the target polynucleotide sequence through the DNA-targeting sequence.

Another aspect of the invention provides a host cell comprising any one of the subject vector, or the plurality of the subject vectors.

In certain embodiments, the host cell further comprises a second vector encoding the Cas9 protein (e.g., wt, nickase, or dCas9 protein).

In certain embodiments, the second vector further encodes an effector domain fused to the Cas9 protein (e.g., wt, nickase, or dCas9 protein).

In certain embodiments, expression of the Cas9 protein (e.g., wt, nickase, or dCas9 protein) is under the control of a constitutive promoter or an inducible promoter.

In certain embodiments, the host cell further comprises a third vector encoding said one or more PUF domains, each fused to an effector domain.

In certain embodiments, expression of the one or more PUF domains is independently under the control of a constitutive promoter or an inducible promoter.

In certain embodiments, the effector domain is a transcription repressor, a transcription activator, a fluorescent protein, an enzyme, or a chromatin remodeling protein (HDAC/HAT).

In certain embodiments, the second vector further encodes a nuclear localization signal fused to the Cas9 protein (e.g., wt, nickase, or dCas9 protein) or the effector domain, and/or the third vector further encodes a nuclear localization signal fused to the PUF domain or the effector domain.

In certain embodiments, the second vector is the same as the vector, and/or wherein the third vector is the same as the vector or the second vector.

In certain embodiments, the host cell is in a live animal.

In certain embodiments, the host cell is a cultured cell.

Another aspect of the invention provides a method of assembling the complex of the invention at the target polynucleotide sequence, the method comprising contacting or bringing to the vicinity of the target polynucleotide sequence: (1) any one of the subject polynucleotide, or any one of the subject vector, or the subject plurality of vectors; (2) the Cas9 protein (e.g., wt, nickase, or dCas9 protein), or any one of the subject second vector; and, (3) one or more of the PUF domains, each fused to an effector domain, or any one of the subject third vector.

In certain embodiments, the complex is assembled inside a cell, the target polynucleotide sequence is a part of the genomic DNA of the cell, and wherein the subject vector, the subject second vector, and the subject third vector are introduced into the cell.

In certain embodiments, the target polynucleotide sequence is at or near a genomic locus rich in heterochromatin, and wherein the effector domain is a detectable marker (e.g., a fluorescent protein).

In certain embodiments, the target polynucleotide sequence is at or near a transcription regulatory element of a target gene, and wherein the effector domain is a transcription modulator (e.g., activator, suppressor).

In certain embodiments, transcription of the target gene affects cell fate determination, cell differentiation, metabolic flux, or a biologically or biochemically determinable outcome.

Another aspect of the invention provides a method of modulating transcription of a plurality of target genes in a cell, the method comprising: introducing into the cell the subject plurality of the vectors, a coding sequence for a Cas9 protein (e.g., wt, nickase, or dCas9 protein), and a coding sequence for one or more PUF domains, wherein each of said target genes comprises a target polynucleotide sequence that permits (1) the assembly, at the target polynucleotide sequence, of a tripartite complex of a polynucleotide encoded by one of said plurality of the vector, the Cas9 protein (e.g., wt, nickase, or dCas9 protein), and a PUF domain; and (2) transcription modulation of the target gene comprising the target polynucleotide sequence. In certain embodiments, the Cas9 protein is a dCas9 protein.

In certain embodiments, the transcription of at least one target gene is enhanced/stimulated, while the transcription of at least another target gene is inhibited.

In a related aspect, the invention also provides a method of epigenotic modulation (e.g., modulating the epigenetic states of chromatin not directly related to transcriptional activity), at a plurality of target genes in a cell, the method comprising: introducing into the cell the subject plurality of the vectors, a coding sequence for a wt Cas9 protein or a Cas9 nickase, and a coding sequence for one or more PUF domain fusions, wherein each of the target genes comprises a target polynucleotide sequence that permits (1) the assembly, at the target polynucleotide sequence, of a tripartite complex of a polynucleotide encoded by one of the plurality of the vector, the wt/nickase Cas9 protein, and a PUF domain fusion; and (2) epigenotic modulation of the target gene comprising the target polynucleotide sequence. The method can be useful, for example, to change epigenetic state (e.g., opening up the chromatin) at the same time to gain access/stability of Cas9 binding to closed chromatin sites (e.g., to increase cut and genome editing at those sites).

Another aspect of the invention provides a kit comprising: (1) a subject polynucleotide, or a subject vector; (2) a subject second vector encoding the Cas9 protein (e.g., wt, nickase, or dCas9 protein); and (3) a subject third vector encoding one or more PUF domains, each fused to an effector domain.

In certain embodiments, the kit further comprises transformation, transfection, or infection reagents to facilitate the introduction of said vectors into a cell.

It should be understood that any embodiments described herein, including those only described in the Example section or only under one aspect of the invention, can be combined with any one or more other embodiments, unless specifically disclaimed or otherwise improper.

BRIEF DESCRIPTION OF THE DRAWINGS

FIG. 1A is a schematic drawing showing the subject 3-component CRISPR/Cas complex/system, which improves the conventional two-hybrid dCas9 fusion design by splitting it into a three-hybrid system, in which sgRNA-PBS bridges the DNA binding activity of dCas9/sgRNA with the effector function provided by a PUF fusion. The middle panels represent the structure of a representative PUF domain, showing the 8 repeats in the C to N direction and the corresponding interaction with the 8-mer target RNA in the 5' to 3' direction. PUF RNA recognition code table shows exemplary di-residues and the corresponding RNA base recognized. In the lower panel, a table of notation adopted for simplicity to describe the 4 PUF isotypes and the corresponding pumilio binding sites (PBS) and their sequences. FIG. 1B, upper panel, is a schematic for the experiment to test the ability of dCas9-VP64 to bind and activate a tdTomato transgene after inserting varying number of PBSat the 3' end of the sgRNA, e.g., experimental set up for testing the effect of sgRNA-PBS (with 0, 5, 15, 25, or 47 PBS) on the ability of the dCas9::VP64 construct to activate a TetO::tdTomato transgene. The lower panel is column plot showing the mean fold changes (±S.E.M.) in tdTomato fluorescence (relative to the dCas9-VP64/sgCtl-0×PBSa control), as measured by fluorescence activated cell sorting (FACS), of cells transfected with the different constructs indicated in the legend below the plot. The legend describes the sgRNA used in three parameters: sgRNA match refers to the DNA target recognized by the sgRNA; #PBS and PBS Type indicate the number and the types of PBS, respectively, appended to the end of the sgRNA. In FIG. 1C, upper panel, is a schematic describing the experiment to test activation of a TetO::tdTomato transgene by the subject activator with different numbers of appended PBS. The lower panel is a column plot showing the fold changes (±S.E.M.) of tdTomato fluorescence (relative to control dCas9/PUFb-VP64/sgCtl-0×PBSb) of cells transfected with the different constructs indicated in the legend blow the plot. The legend describes the PUF isotype (PUF-VP64) used and the sgRNA-PBS used in terms of the number and type of PBS as well as the DNA target recognized by sgRNA indicated by shaded boxes. In FIG. 1D, upper panel, is a schematic illustrating the experiment to test the independency of the subject activator isotypes in activating a TetO::tdTomato transgene. The lower panel is a column plot showing the mean fold changes (±S.E.M.) of tdTomato fluorescence (relative to the respective controls dCas9/PUFx-VP64/sgCtl-5×PBSx for PUF/PBS isotype x) of cells transfected with the different constructs indicated in the legend below the plot. The legends indicate the PUF isotype used (PUF-VP64), the PBS isotype (5×PBS; "–" indicates sgRNA without PBS) and DNA target indicated by shaded boxes (sgRNA Match). All plots show results of three replicate measurements.

FIG. 2A is a schematic of the experiment testing the assembly of PUF(3-2)::VP64 and PUF(6-2/7-2)::P65-HSF1 via recruitment by sgRNA containing both PBS32 and PBS6272. The activity was measured by the tdTomato fluorescent reporter activity. FIG. 2B is a column chart showing the relative mean tdTomato fluorescence resulting from transfecting the activator protein(s) with non-targeting (sgControl) and Tet-targeting (sgTetO) sgRNAs with 4×[PBS32-PBS6272] heterodimer sites.

FIG. 3A, upper panel: a gene model showing the relative match positions (Strokes labeled 1~4) of sgRNA-PBS used to activate OCT4 gene. Lower panel: Mean fold changes (with 95% C.I.) measured by qRT-PCR (compared to the Control sample) for activation of OCT4 expression using dCas9/PUFa-p65HSF1 3-component system activator module, or dCas9-p65HSF1 activator with the indicated cocktail of OCT4 targeting sgRNA-5×PBSa or control sgRNAs-5×PBSa. The shaded boxes in the legend indicate the use of single sgRNA-5×PBSa with a control (Ctl) sequence, the individual OCT4-targeting sgRNA-5×PBSa corresponding to numbered strokes in the gene model, or a cocktail of the 4 OCT4-targeting sgRNA-5×PBSa. FIG. 3B, upper panel: a gene model showing the relative match positions (Strokes labeled 1~4) of sgRNA-PBS used to activate SOX2 gene. Mean fold changes (with 95% C.I.) measured by qRT-PCR (compared to the Ctl sample) for activation of SOX2 expression using dCas9/PUFa-p65HSF1 activator or dCas9-p65HSF1 activator with the indicated cocktail of SOX2 targeting sgRNA-5×PBSa or control sgRNA-5×PBSa. The shaded boxes in the legend indicate the use of single sgRNA-5×PBSa with a control (Ctl) sequence, the individual SOX2-targeting sgRNA-5×PBSa corresponding to the numbered strokes in the gene model, or a cocktail of 4 SOX2-targeting sgRNA-5×PBSa. FIG. 3C shows Mean fold changes (with 95% C.I.) of OCT4 expression with the indicated single or cocktails of OCT4-targeting sgRNA-PBSa with 1, 5, 15, or 25 copies of PBSa. FIG. 3D shows Mean fold changes (with 95% C.I.) of SOX2 expression with the indicated single or cocktails of SOX2-targeting sgRNA-PBSa with 1, 5, 15, or 25 copies of PBSa.

FIG. 4A is a schematic showing an experiment to simultaneously activate a TetO::tdTomato transgene with dCas9/sgTetO-PBS32/PUF(3-2)::VP64 and repress a SV40::EGFP transgene with dCas9/sgSV40-PBS6272/KRAB::PUF(6-2/7-2). FIG. 4B is a column chart showing relative mean EGFP and tdTomato fluorescence for the samples transfected with the constructs indicated in the table.

FIG. 4C, left panel: schematic diagram illustrating the experiment to achieve simultaneous activation and repression of TetO::tdTomato and SV40::EGFP by PUFc-p65HSF1 and KRAB-PUFa, respectively. Right panel: Top column plot shows mean fold changes (with S.E.M.) of tdTomato fluorescence; Bottom column plot shows mean fold changes (with S.E.M.) of EGFP fluorescence of cells transfected with constructs indicated in the central legend. The central legend indicates the inclusion by shading the transfection of PUFc-p65HSF1 and KRAB-PUFa, as well as the DNA match to either Ctl, TetO or SV40P1 of the sgRNA-PBSc and sgRNA-PBSa by the black shaded boxes. FIG. 4D, left panel: schematic diagram illustrating the experiment to simultaneously activate and repress OCT4 and SOX2, respectively by PUFb-p65HSF1 and BFPKRAB-PUFa. Right panel: Top column plot shows mean fold changes (with 95% C.I.) of gene expression of OCT4; Bottom column plot shows mean fold changes (with 95% C.I.) of gene expression of SOX2 of cells transfected with constructed indicated in the central legend. The central legend indicates the DNA match for the sgRNA-5×PBSb and sgRNA-5×PBSa to control (Ctl), OCT4 promoters (OCT4pp) or SOX2 promoters (SOX2pp) by the black shaded boxes. The PUFb-p65HSF1+BFPKRAB-PUFa row indicates the inclusion of the activator-repressor models in samples with the yellow-highlighted boxes. These experiments used cocktails of 4 sgRNA-5×PBS for both OCT4 and SOX2 genes.

FIG. 5A is a schematics of enhancer activation experiment using dCas9-CBPHAT direct fusion or 3-component module dCas9/CBPHAT-PUFa or dCas9/PUFa-CBPHAT to target Proximal Promoter (PP), Proximal Enhancer (PE) or Distal Enhancer (DE) of OCT4. The 4 guides targeting each of these regions are shown with the number above the red strokes indicating the locations of match. FIG. 5B shows Mean fold changes (with 95% C.I.) of OCT4 expression (relative to the corresponding sgCtl targeting experiments) of cells transfected with plasmids expressing dCas9-CBPHAT, dCas9/CBPHAT-PUFa or dCas9/PUFa-CBPHAT and cocktail of 4 sgRNA-5×PBSa targeting each of PP, PE or Distal Enhancer DE. FIG. 5C shows Mean fold changes (with 95% C.I.) of OCT4 expression (relative to the sgCtl experiment) after transfection of dCas9/CBPHAT-PUFa and single or cocktails of sgRNAs targeting PP, PE, DE of OCT4. The legend indicates the inclusion of the individual guides targeting each of the region or a cocktail of guides with the shaded boxes.

FIG. 6A is a schematic showing the use of dCas9/sgTelomere-PBS32/Clover::PUF(3-2) (or PUFa) to label telomeric repeats with green fluorescence. FIG. 6B shows confocal fluorescent microscopy images showing labeling of telomeres by Clover-PUFa and sgTelomere equipped with, from left to right, increasing number (0, 5, 15, 25) of PBSa. FIG. 6C shows anti-TRF2 immunostaining confirmation of labeling of telomeres by dCas9/Clover-PUFa/sgTelomere-25×PBSa. FIG. 6D shows quantification of the number of fluorescent foci in HEK293T cells transfected with dCas9/PUFa::Clover and a telomere-targeting sgRNA with 0, 5, 15 or 25 PBSa sites. (n=20; Mann-Whitney statistics: *=p<0.0005, =p<0.0001). FIG. 6E shows quantification of signal-to-noise ratio as a proportion of total signal at foci over the total nuclear signal by the subject 3-component system with 5, 15, or 25×PBSa on the sgRNA targeting telomeres. (n=20; Mann-Whitney statistics: **=p<0.0001). FIG. 6F shows anti-CREST confirmation of labeling of centromeres by Clover-PUFc/sgCentromere-20×PBSc. FIG. 6G is a representative confocal fluorescent microscopy image showing the co-labeling of centromeres and telomeres by Clover-PUFc/sgCentromere-20×PBSc and mRuby2-PUFa/sgTelomere-25×PBSa, respectively.

FIG. 8A illustrates multiplexing: sgRNA with different PBS isotypes can recruit the effectors tethered by the cognate PUF isotypes, providing the mechanism for multiplexing dCas9 for localizing different effector functions or proteins tags at separate chromosomal loci. FIG. 8B illustrates multimerization: the short and linear feature of PBS allow sgRNA to be equipped with many copies of PBS, thus allowing recruitment of many molecules of PUF-fusions at target loci. FIG. 8C illustrates complex formation: sgRNA equipped with different combinations, orders and numbers of PBS can potentially act as a scaffold to direct assembly of protein complexes with desired stoichiometry and configurations.

DETAILED DESCRIPTION OF THE INVENTION

1. Overview

Figure 1A:
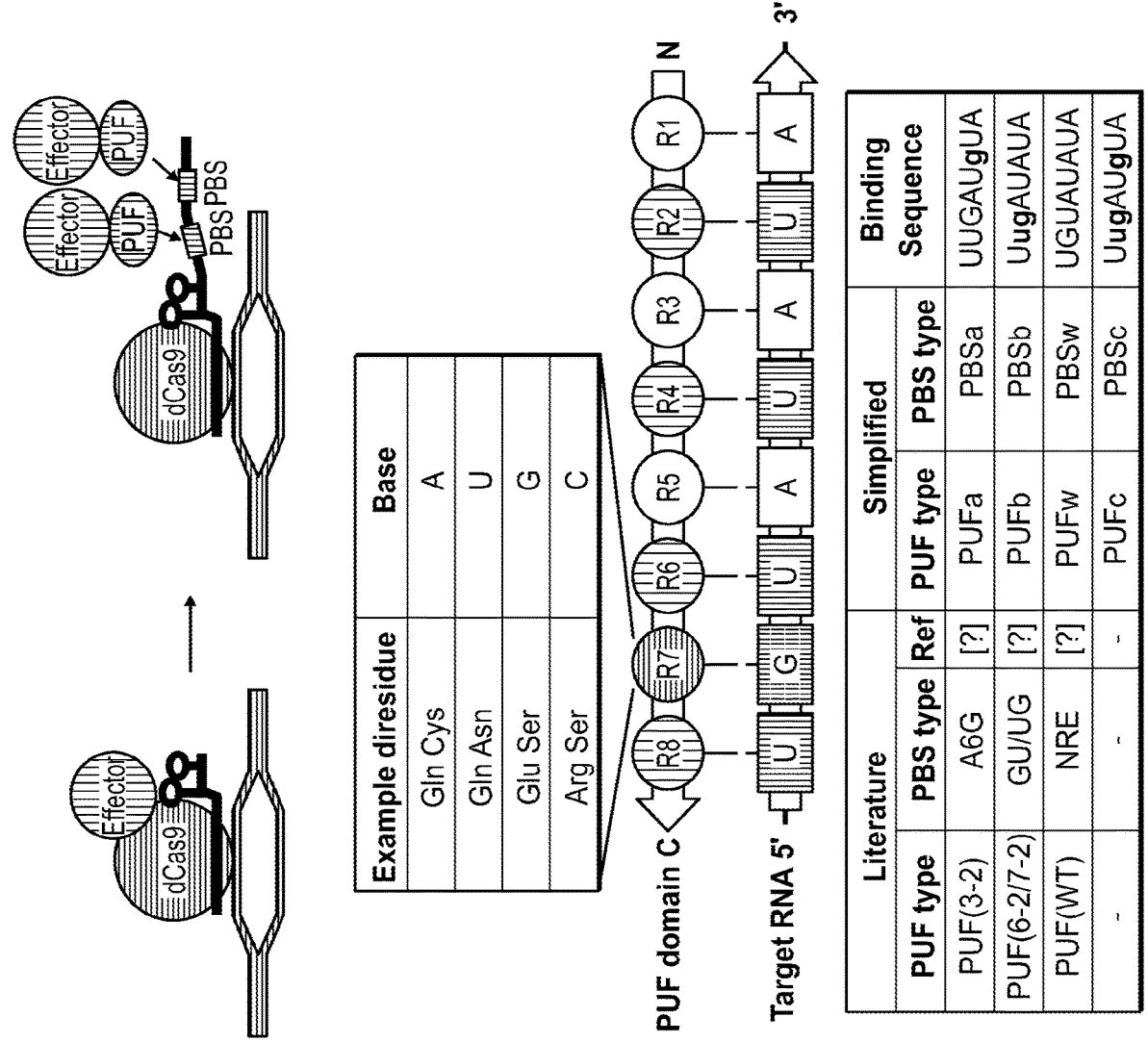
FIGS. 1A-1D show that insertion of PUF domain-binding sequences (PBS) to sgRNA 3'-end did not substantially impact dCas9/sgRNA function, and that independent recruitment and multimerization of activators can be achieved using the subject 3-component CRISPR/Cas complex/system.

The invention described herein provides a polynucleotide comprising three functional sequences, for binding to a target polynucleotide sequence (e.g., the DNA-targeting sequence); for binding to either a wildtype (wt) Cas9 protein, or a modified Cas9 protein (e.g., Cas9 nickase or dCas9) with reduced or deficient nuclease activity (e.g., Cas9-binding sequence); and for binding to one or more PUF domain(s), each fused to a functional or effector domain. The polynucleotide of the invention, together with the wt or modified Cas9 protein and the one or more PUF domain fusion proteins, may form a 3-component complex (the subject 3-component CRISPR/Cas complex/system) at a specific target DNA sequence to effect one or more biological effects at the specific target DNA sequence.

The invention also provides a vector encoding such a polynucleotide, and a complex formed by the polynucleotide, the Cas9 protein (e.g., wt, nickase, or dCas9 protein), and at least one of the PUF domain fusion proteins. The invention further provides host cells comprising the vector or the polynucleotide.

The subject 3-component CRISPR/Cas complex/system can bring about a variety of biological functions at the target DNA sequence, including but are not limited to: enhanced homologous recombination to increase efficiency of knock-in, simultaneous transcription activation and/or repression at multiple genomic loci; detection of specific sequences at genomic loci by fluorescent imaging or other detectable signal; and affecting cell fate determination, cell differentiation, metabolic flux, or a biologically or biochemically determinable outcome, etc.

The invention further provides kits and reagents for carrying out the methods of the invention.

Thus in one aspect, the invention provides a polynucleotide comprising: (1) a DNA-targeting sequence that is complementary to a target polynucleotide sequence; (2) a Cas9-binding sequence; and, (3) one or more copies of a PUF domain-Binding Sequence (PBS), wherein each of the one or more copies of the PBS binds to the same or a different PUF domain; wherein a Cas9 protein (e.g., wt, nickase, or dCas9 protein) is capable of forming a complex with the polynucleotide by binding to the Cas9-binding sequence. In certain embodiments, the dCas9 protein has reduced nuclease activity, or lacks nuclease activity (e.g., is nuclease-deficient), but retains DNA-binding ability when complexed with the subject polynucleotide. In certain embodiments, (1)-(3) are arranged from 5' to 3', in that order. In other embodiments, one or more of the PBS may be 5' to the DNA-targeting sequence, and/or 5' to the Cas9-binding sequence.

The target polynucleotide sequence can be any DNA sequence. In certain embodiments, the target polynucleotide sequence comprises, or is adjacent to, one or more transcription regulatory element(s). In certain embodiments, the transcription regulatory element(s) comprises one or more of: a core promoter, a proximal promoter element, an enhancer, a silencer, an insulator, and a locus control region. In another embodiment, the target polynucleotide sequence comprises, or is adjacent to, a centromere sequence, a telomere sequence, or a repetitive genomic sequence. The telomere sequence may be characterized by having 5-15 kb tracks of TTAGGG repeats. In yet another embodiment, the target polynucleotide sequence comprises, or is adjacent to, a genomic marker sequence or any genomic locus of interest.

In certain embodiments, the target polynucleotide sequence is immediately 3' to a PAM (protospacer adjacent motif) sequence of the complementary strand. For example, in certain embodiments, the PAM sequence of the complementary strand is 5'-CCN-3', wherein N is any DNA nucleotide.

In other embodiments, the PAM sequence of the complementary strand matches the specific Cas9 protein or homologs or orthologs to be used.

As is known in the art, for Cas9 to successfully bind to DNA, the target sequence in the genomic DNA must be complementary to the guide RNA sequence and must be immediately followed by the correct protospacer adjacent motif or PAM sequence. The PAM sequence is present in the DNA target sequence but not in the guide RNA sequence. Any DNA sequence with the correct target sequence followed by the PAM sequence will be bound by Cas9.

The PAM sequence varies by the species of the bacteria from which the Cas9 was derived. The most widely used Type II CRISPR system is derived from *S. pyogenes* and the PAM sequence is 5'-NGG-3' located on the immediate 3' end of the guide RNA recognition sequence (or 5'-CCN-3' on the complementary strand). The PAM sequences of other Type II CRISPR systems from different bacterial species are listed in the Table below.

| *Streptococcus pyogenes* (SP) | NGG |
| *Neisseria meningitidis* (NM) | NNNNGATT |
| *Streptococcus thermophilus* (ST) | NNAGAA |
| *Treponema denticola* (TD) | NAAAAC |

In certain embodiments, the DNA-targeting sequence base-pairs with the target polynucleotide sequence when the Cas9 protein (e.g., wt, nickase, or dCas9 protein) is complexed with the polynucleotide.

It should be noted that the DNA-targeting sequence may or may not be 100% complementary to the target polynucleotide sequence. In certain embodiments, the DNA-targeting sequence is complementary to the target polynucleotide sequence over about 8-25 nucleotides (nts), about 12-22 nucleotides, about 14-20 nts, about 16-20 nts, about 18-20 nts, or about 8, 9, 10, 11, 12, 13, 14, 15, 16, 17, 18, 19, 20, 21, 22, 23, 24, or 25 nts. In certain embodiments, the complementary region comprises a continuous stretch of about 12-22 nts, preferably at the 3' end of the DNA-targeting sequence. In certain embodiments, the 5' end of the DNA-targeting sequence has up to 8 nucleotide mismatches with the target polynucleotide sequence. In certain embodiments, the DNA-binding sequence is about 50, 55, 60, 65, 70, 75, 80, 85, 90, 95, or 100% complementary to the target polynucleotide sequence.

In a related embodiment, there is no more than 15-nucleotide match at the 3' end of the DNA-targeting sequence compared to the complementary target polynucleotide sequence, and the Cas9 protein in the complex is a wt Cas9 protein which, under the circumstance, binds but does not cut a target DNA.

In certain embodiments, the DNA-binding sequence has a 5' end nucleotide G.

In certain embodiments, the polynucleotide further comprises a linker sequence linking the DNA-targeting sequence to the Cas9-binding sequence.

In certain embodiments, the Cas9-binding sequence forms a hairpin structure. In certain embodiments, the Cas9-binding sequence is about 30-100 nt, about 35-50 nt, about 37-47 nt, or about 42 nt in length.

An exemplary Cas9-binding sequence is GTTT-TAGAGCTAGAAATAGCAAGTTAA AATAAGGCTA (SEQ ID NO: 1). Another exemplary Cas9-binding sequence is GTTTAAGAGCTATGC TG GAAACAGCAT-AGCAAGTTTAAATAAGGCTA (SEQ ID NO: 2).

The modified Cas9 protein (nickase or dCas9) may have reduced nuclease activity, or lacks nuclease activity at one or both endonuclease catalytic sites. In certain embodiments, the dCas9 protein lacks endonuclease activity due to point mutations at both endonuclease catalytic sites (RuvC and HNH) of wild type Cas9. For example, the point mutations may be D10A and H840A, respectively, in the S. pyogenes Cas9, or in the corresponding residues in species other than S. pyogenes. In certain embodiments, the modified Cas9 protein lacks endonuclease catalytic activity at one but not both sites of wt Cas9, and is able to create a nick on a dsDNA target (Cas9 nickase).

In certain embodiments, each of the one or more copies of the PBS has about 8 nucleotides. One exemplary PBS may have a sequence of 5'-UGUAUGUA-3', which can be bound by the PUF domain PUF(3-2). Another exemplary PBS may have a sequence of 5'-UUGAUAUA-3', which can be bound by the PUF domain PUF(6-2/7-2). Additional PBS and the corresponding PUF domains are described below.

The polynucleotide of the invention may have more than one copies of the PBS. In certain embodiments, the polynucleotide comprises 1, 2, 3, 4, 5, 10, 15, 20, 25, 30, 35, 40, 45, 46, 47, 48, 49, or 50 copies of PBS, such as 5, 6, 7, 8, 9, 10, 11, 12, 13, 14, or 15 copies of PBS.

In certain embodiments, the range of the PBS copy number is L to H, wherein L is any one of 1, 2, 3, 4, 5, 6, 7, 8, 9, 10, 11, 12, 13, 14, 15, 20, 25, 30, 35, or 40, and wherein H is any one of 2, 3, 4, 5, 6, 7, 8, 9, 10, 11, 12, 13, 14, 15, 20, 25, 30, 35, 40, 45, 50, 55, 60, 65, 70, 80, 90, or 100, so long as H is greater than L. Each PBS may be the same or different.

In certain embodiments, the polynucleotide comprises about 5-15 copies of PBS, or about 5-14 copies, about 5-13 copies, about 5-12 copies, about 5-11 copies, about 5-10 copies, or about 5-9 copies of PBS.

In certain embodiments, the amount of the sgRNA-PBS and/or the amount of the PUF fusions transfected or expressed is adjusted to maximize PBS/PUF binding. For example, this can be achieved by increasing the expression of PUF-activator by a stronger promoter or using an inducible promoter, such as a Dox-inducible promoter.

In certain embodiments, the spacing between PBS sites and/or spacer sequences are optimized to improve system efficiency. For example, spacing optimization can be subject to particular PUF fusions, and can be different between PUF fusions that work as individual proteins and those PUF fusions that may need to be positioned close enough to function (e.g., protein complexes).

Another aspect of the invention provides a vector encoding any one of the subject polynucleotide. In certain embodiments, transcription of the polynucleotide is under the control of a constitutive promoter, or an inducible promoter. In certain embodiments, the vector is active in a cell from a mammal (a human; a non-human primate; a non-human mammal; a rodent such as a mouse, a rat, a hamster, a Guinea pig; a livestock mammal such as a pig, a sheep, a goat, a horse, a camel, cattle; or a pet mammal such as a cat or a dog); a bird, a fish, an insect, a worm, a yeast, or a bacterium.

In certain embodiments, the vector is a plasmid, a viral vector (such as adenoviral, retroviral, or lentiviral vector, or AAV vector), or a transposon (such as piggyBac transposon). The vector can be transiently transfected into a host cell, or be integrated into a host genome by infection or transposition.

A related aspect of the invention provides a plurality or a library of any one of the vectors of the invention, wherein two of the vectors differ in the encoded polynucleotides in their respective DNA-targeting sequences, Cas9-binding sequences, and/or the copy number, identity (sequence, binding specificity, etc.), or relative order of the PBS.

Another aspect of the invention provides a complex comprising any one of the polynucleotide of the invention, and the Cas9 protein (e.g., wt, nickase, or dCas9 protein). In certain embodiments, the complex comprises any one of the polynucleotide of the invention, and the Cas9 protein (e.g., wt, nickase, or dCas9 protein). In certain embodiments, the complex does not comprise the wt Cas9 protein. In certain embodiments, the complex comprises the wt Cas9.

In certain embodiments, the complex may further comprise one or more PUF domain or fusion thereof bound to the one or more PBS(s). In certain embodiments, each of the PUF domain is fused to an effector domain. Each effector domain can be independently (but is not limited to): a transcription repressor, a transcription activator, a fluorescent protein, an enzyme, or a chromatin remodeling protein (HDAC/HAT). In certain embodiments, at least two of the PUF domains are fused to different effector domains.

In certain embodiments, the Cas9 protein (e.g., wt, nickase, or dCas9 protein), the PUF domain, and/or the effector domain further comprises a nuclear localization signal (NLS).

In certain embodiments, the complex is bound to the target polynucleotide sequence through the DNA-targeting sequence of the polynucleotide.

Another aspect of the invention provides a host cell comprising any one of the subject vector, or the plurality of vectors.

In certain embodiments, the host cell further comprises a second vector encoding the Cas9 protein (e.g., wt, nickase, or dCas9 protein). In certain embodiments, the second vector further encodes an effector domain fused to the Cas9 protein (e.g., wt, nickase, or dCas9 protein). The expression of the Cas9 protein (e.g., wt, nickase, or dCas9 protein) can be under the control of a constitutive promoter or an inducible promoter.

In certain embodiments, the host cell may further comprise a third vector encoding the one or more PUF domains, each fused to an effector domain. The expression of the one or more PUF domains can be independently under the control of a constitutive promoter or an inducible promoter.

The effector domain can have any of many functions or biological effects. Merely to illustrate, the effector domain can be a protein involved in homologous recombination, a transcription repressor, a transcription activator, a fluorescent protein, an enzyme, or a chromatin remodeling protein (HDAC/HAT), etc.

In certain embodiments, the second vector may further encode a nuclear localization signal (NLS) fused to the Cas9 protein (e.g., wt, nickase, or dCas9 protein) or the effector domain, and/or the third vector may further encode a nuclear localization signal (NLS) fused to the PUF domain or the effector domain.

In certain embodiments, sequences that can be encoded by different vectors may be on the same vector. For example, in certain embodiments, the second vector may be the same as the vector, and/or the third vector may be the same as the vector or the second vector.

The host cell may be in a live animal, or may be a cultured cell.

In certain embodiments, the host cell may constitutively or inducibly express one or more components of the subject 3-component system (e.g., dCas9, PUF fusions).

Yet another aspect of the invention provides a method of assembling the complex of the invention at the target polynucleotide sequence, the method comprising contacting or bringing to the vicinity of the target polynucleotide sequence: (1) any one of the subject polynucleotide, or any one of the subject vector, or the plurality of vectors; (2) the Cas9 protein (e.g., wt, nickase, or dCas9 protein), or any one of the subject second vector encoding the Cas9 protein (e.g., wt, nickase, or dCas9 protein); and, (3) one or more of the PUF domains, each fused to an effector domain, or any one of the third vector encoding the PUF domain fusions.

In certain embodiments, the complex is assembled inside a cell, the target polynucleotide sequence is a part of the genomic DNA of the cell, and wherein the subject vector, second vector, and third vector are introduced into the cell.

In certain embodiments, the target polynucleotide sequence is at or near a genomic locus rich in heterochromatin, and wherein the effector domain is a detectable marker (e.g., a fluorescent protein). In another embodiment, the target polynucleotide sequence is at or near a transcription regulatory element of a target gene, and wherein the effector domain is a transcription modulator (e.g., activator, suppressor). The transcription of the target gene, for example, may affect cell fate determination, cell differentiation, metabolic flux, or a biologically or biochemically determinable outcome.

A related aspect of the invention provides a method of modulating transcription of a plurality of target genes in a cell, the method comprising: introducing into the cell the subject plurality of the vectors, a coding sequence for a dCas9 protein, and a coding sequence for one or more PUF domain fusions, wherein each of the target genes comprises a target polynucleotide sequence that permits (1) the assembly, at the target polynucleotide sequence, of a tripartite complex of a polynucleotide encoded by one of the plurality of the vector, the dCas9 protein, and a PUF domain fusion; and (2) transcription modulation of the target gene comprising the target polynucleotide sequence.

In a related aspect, the invention also provides a method of epigenetic modulation (e.g., modulating the epigenetic states of chromatin not directly related to transcriptional activity), at a plurality of target genes in a cell, the method comprising: introducing into the cell the subject plurality of the vectors, a coding sequence for a wt Cas9 protein or Cas9 nickase, and a coding sequence for one or more PUF domain fusions, wherein each of the target genes comprises a target polynucleotide sequence that permits (1) the assembly, at the target polynucleotide sequence, of a tripartite complex of a polynucleotide encoded by one of the plurality of the vector, the wt Cas9 protein or the Cas9 nickase, and a PUF domain fusion; and (2) epigenetic modulation of the target gene comprising the target polynucleotide sequence. The method can be useful, for example, to change epigenetic state (e.g., opening up the chromatin) at the same time to gain access/stability of Cas9 binding to closed chromatin sites (e.g., to increase cut and genome editing at those sites).

In certain embodiments, the transcription of at least one target gene is enhanced/stimulated, while the transcription of at least another target gene is inhibited.

The invention further provides a kit comprising: (1) a subject polynucleotide, or a vector encoding the same; (2) a second vector encoding the Cas9 protein (e.g., wt, nickase, or dCas9 protein); and (3) a third vector encoding one or more PUF domain(s), each fused to an effector domain. The kit may further comprise transformation, transfection, or infection reagents to facilitate the introduction of the vectors into a cell.

With the invention generally described above, various features of the invention will be further elaborated below. It should be understood that features of the invention, even when described in the context of separate embodiments, or even separate embodiments under different aspects of the invention, may be provided in combination in a single embodiment. Conversely, various features of the invention described in the context of a single embodiment, may also be provided separately or in any suitable subcombination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

2. The Polynucleotide of the Invention

The polynucleotide of the invention comprises three sequence segments: i) a first segment comprising a nucleotide sequence that is complementary to a target sequence; ii) a second segment that interacts with a Cas9 protein (e.g., wt, nickase, or dCas9 protein with reduced nuclease activity or lacks nuclease activity) (e.g., the Cas9-binding sequence); and iii) one or more copies of a PUF domain-Binding Sequence (PBS).

In certain embodiments, the target sequence is an RNA. In certain embodiments, the target sequence is a DNA. In the description herein, the first segment is generally referred to as the "DNA-targeting sequence" when the target sequence is a DNA (such as a genomic DNA).

In related embodiments in which the target sequence is an RNA, the description herein below applies generally as well except that the reference to "DNA-targeting sequence" is replaced with "RNA-targeting sequence," in order to avoid redundancy. That is, the first segment comprises a nucleotide sequence complementary to the target polynucleotide sequence (DNA or RNA).

In certain embodiments, the three segments i)-iii) are arranged, in that order, from 5' to 3'.

In certain embodiments, the polynucleotide of the invention can be a single RNA molecule (single RNA polynucleotide), which may include a "single-guide RNA," or "sgRNA." In another embodiment, the polynucleotide of the invention can comprise two RNA molecules (e.g., joined together via hybridization at the Cas9-binding sequence, see below). Thus the subject polynucleotide is inclusive, referring both to two-molecule polynucleotide and to single-molecule polynucleotide (e.g., sgRNAs).

a. DNA-Targeting Sequence

The DNA-targeting sequence is functionally similar or equivalent to the crRNA or guide RNA or gRNA of the CRISPR/Cas complex/system. However, in the context of the instant invention, the DNA-targeting sequence may not originate from any particular crRNA or gRNA, but can be arbitrarily designed based on the sequence of the target polynucleotide sequence.

The DNA-targeting sequence comprises a nucleotide sequence that is complementary to a specific sequence within a target DNA (or the complementary strand of the target DNA). In other words, the DNA-targeting sequence interacts with a target polynucleotide sequence of the target DNA in a sequence-specific manner via hybridization (i.e., base pairing). As such, the nucleotide sequence of the DNA-targeting sequence may vary, and it determines the location within the target DNA that the subject polynucleotide and the target DNA will interact. The DNA-targeting sequence can be modified or designed (e.g., by genetic engineering) to hybridize to any desired sequence within the target DNA. In certain embodiments, the target polynucleotide sequence is immediately 3' to a PAM (protospacer adjacent motif) sequence of the complementary strand, which can be 5'-CCN-3', wherein N is any DNA nucleotide. That is, in this embodiment, the complementary strand of the target polynucleotide sequence is immediately 5' to a PAM sequence that is 5'-NGG-3', wherein N is any DNA nucleotide. In related embodiments, the PAM sequence of the complementary strand matches the wt or dCas9. See above for the PAM sequences from species other than S. pyogenes.

The DNA-targeting sequence can have a length of from about 12 nucleotides to about 100 nucleotides. For example, the DNA-targeting sequence can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. For example, the DNA-targeting sequence can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting sequence that is complementary to a target polynucleotide sequence of the target DNA can have a length of at least about 12 nt. For example, the DNA-targeting sequence that is complementary to a target polynucleotide sequence of the target DNA can have a length at least about 12 nt, at least about 15 nt, at least about 18 nt, at least about 19 nt, at least about 20 nt, at least about 25 nt, at least about 30 nt, at least about 35 nt or at least about 40 nt. For example, the DNA-targeting sequence that is complementary to a target polynucleotide sequence of a target DNA can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. The nucleotide sequence of the DNA-targeting sequence that is complementary to the target polynucleotide sequence of the target DNA can have a length of at least about 12 nt.

In some cases, the DNA-targeting sequence that is complementary to a target polynucleotide sequence of the target DNA is 20 nucleotides in length. In some cases, the DNA-targeting sequence that is complementary to a target polynucleotide sequence of the target DNA is 19 nucleotides in length.

The percent complementarity between the DNA-targeting sequence and the target polynucleotide sequence of the target DNA can be at least 50% (e.g., at least 55%, at least 60%, at least 65%, at least 70%, at least 75%, at least 80%, at least 85%, at least 90%, at least 95%, at least 97%, at least 98%, at least 99%, or 100%). In some cases, the percent complementarity between the DNA-targeting sequence and the target polynucleotide sequence is 100% over the seven or eight contiguous 5'-most nucleotides of the target polynucleotide sequence. In some cases, the percent complementarity between the DNA-targeting sequence and the target polynucleotide sequence is at least 60% over about 20 contiguous nucleotides. In some cases, the percent complementarity between the DNA-targeting sequence and the target polynucleotide sequence is 100% over the 7, 8, 9, 10, 11, 12, 13, or 14 contiguous 5'-most nucleotides of the target polynucleotide sequence (i.e., the 7, 8, 9, 10, 11, 12, 13, or 14 contiguous 3'-most nucleotides of the DNA-targeting sequence), and as low as 0% over the remainder. In such a case, the DNA-targeting sequence can be considered to be 7, 8, 9, 10, 11, 12, 13, or 14 nucleotides in length, respectively.

b. Cas9-Binding Sequence

The protein-binding segment or protein-binding sequence of the subject polynucleotide binds to a wt Cas9, or a modified dCas9 protein (e.g., nickase or dCas9) with reduced endonuclease activity, or lacks endonuclease activity. For simplicity, the protein-binding sequence of the subject polynucleotide, which may bind to wt and/or modified Cas9 proteins, may simply be referred to as "Cas9-binding sequence" herein. However, it should be understood that when the Cas9-binding sequence of the invention binds to a dCas9, it is not prevented from binding to a wt Cas9 or a Cas9 nickase. In certain embodiments, the Cas9-binding sequence of the invention binds to dCas9 as well as wt Cas9 and/or Cas9 nickase.

The Cas9-binding sequence interacts with or bind to a Cas9 protein (e.g., wt, nickase, or dCas9 protein), and together they bind to the target polynucleotide sequence recognized by the DNA-targeting sequence. The Cas9-binding sequence comprises two complementary stretches of nucleotides that hybridize to one another to form a double stranded RNA duplex (a dsRNA duplex). These two complementary stretches of nucleotides may be covalently linked by intervening nucleotides known as linkers or linker nucleotides (e.g., in the case of a single-molecule polynucleotide), and hybridize to form the double stranded RNA duplex (dsRNA duplex, or "Cas9-binding hairpin") of the Cas9-binding sequence, thus resulting in a stem-loop structure. Alternatively, in some embodiment, the two complementary stretches of nucleotides may not be covalently linked, but instead are held together by hybridization between complementary sequences (e.g., in the case of a two-molecule polynucleotide of the invention).

The Cas9-binding sequence can have a length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the Cas9-binding sequence can have a length of from about 15 nucleotides (nt) to about 80 nt, from about 15 nt to about 50 nt, from about 15 nt to about 40 nt, from about 15 nt to about 30 nt, from about 37 nt to about 47 nt (e.g., 42 nt), or from about 15 nt to about 25 nt.

The dsRNA duplex of the Cas9-binding sequence can have a length from about 6 base pairs (bp) to about 50 bp. For example, the dsRNA duplex of the Cas9-binding sequence can have a length from about 6 bp to about 40 bp, from about 6 bp to about 30 bp, from about 6 bp to about 25 bp, from about 6 bp to about 20 bp, from about 6 bp to about 15 bp, from about 8 bp to about 40 bp, from about 8 bp to about 30 bp, from about 8 bp to about 25 bp, from about 8 bp to about 20 bp or from about 8 bp to about 15 bp. For example, the dsRNA duplex of the Cas9-binding sequence can have a length from about from about 8 bp to about 10 bp, from about 10 bp to about 15 bp, from about 15 bp to about 18 bp, from about 18 bp to about 20 bp, from about 20 bp to about 25 bp, from about 25 bp to about 30 bp, from about 30 bp to about 35 bp, from about 35 bp to about 40 bp, or from about 40 bp to about 50 bp. In some embodiments, the dsRNA duplex of the Cas9-binding sequence has a length of 36 base pairs. The percent complementarity between the nucleotide sequences that hybridize to form the dsRNA duplex of the Cas9-binding sequence can be at least about 60%. For example, the percent complementarity between the nucleotide sequences that hybridize to form the dsRNA duplex of the Cas9-binding sequence can be at least about 65%, at least about 70%, at least about 75%, at least about 80%, at least about 85%, at least about 90%, at least about 95%, at least about 98%, or at least about 99%. In some cases, the percent complementarity between the nucleotide sequences that hybridize to form the dsRNA duplex of the Cas9-binding sequence is 100%.

The linker can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker is 4 nt.

Figure 8A:
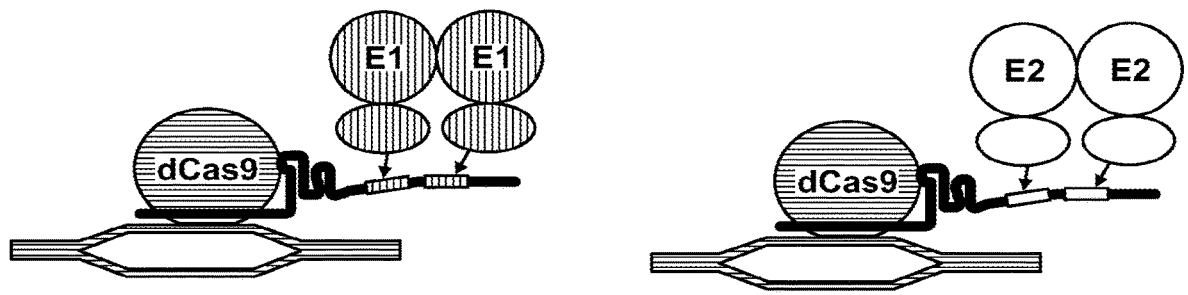
FIGS. 8A-8C is a cartoon illustration highlighting some features of the subject 3-component CRISPR/Cas complex/system.
Figure 8B:
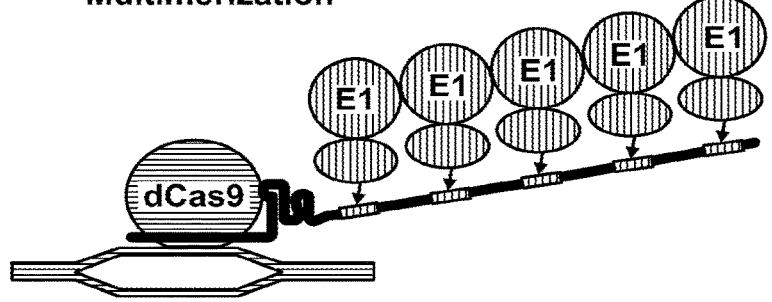
Figure 8C:
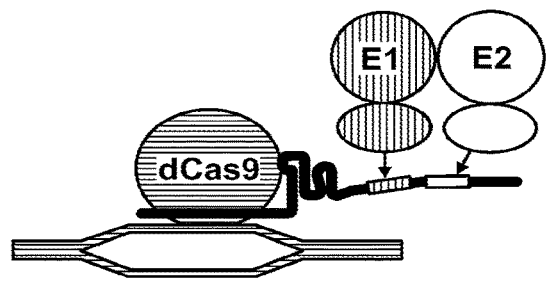

Non-limiting examples of nucleotide sequences that can be included in a suitable Cas9-binding sequence (i.e., Cas9 handle) are set forth in SEQ ID NOs: 563-682 of WO 2013/176772 (see, for examples, FIGS. 8 and 9 of WO 2013/176772), incorporated herein by reference.

In some cases, a suitable Cas9-binding sequence comprises a nucleotide sequence that differs by 1, 2, 3, 4, or 5 nucleotides from any one of the above-listed sequences.

c. PUF Domain-Binding Sequence (PBS)

The subject polynucleotide comprises one or more tandem sequences, each of which can be specifically recognized and bound by a specific PUF domain (infra). Since a PUF domain can be engineered to bind virtually any PBS based on the nucleotide-specific interaction between the individual PUF motifs of PUF domain and the single RNA nucleotide they recognize, the PBS sequences can be any designed sequence that bind their corresponding PUF domain.

In certain embodiments, a PBS of the invention has 8-mer. In other embodiments, a PBS of the invention has 5, 6, 7, 8, 9, 10, 11, 12, 13, 14, 15, 16 or more RNA nucleotides.

In certain embodiments, the PBS of the invention has the sequence 5'-UGUAUAUA-3', and binds the wt human Pumilio 1 PUF domain.

In certain embodiments, the PBS of the invention has the sequence 5'-UGUAUGUA-3', and binds the PUF domain PUF(3-2).

In certain embodiments, the PBS of the invention has the sequence 5'-UUGAUAUA-3', and binds the PUF domain PUF(6-2/7-2).

In certain embodiments, the PBS of the invention has the sequence 5'-UGGAUAUA-3', and binds the PUF domain PUF(6-2).

In certain embodiments, the PBS of the invention has the sequence 5'-UUUAUAUA-3', and binds the PUF domain PUF(7-2).

In certain embodiments, the PBS of the invention has the sequence 5'-UGUGUGUG-3', and binds the PUF domain $PUF^{531}$.

In certain embodiments, the PBS of the invention has the sequence 5'-UGUAUAUG-3', and binds the PUF domain PUF(1-1).

In certain embodiments, the PBS of the invention has the sequence 5'-UUUAUAUA-3' or 5'-UAUAUAUA-3', and binds the PUF domain PUF(7-1).

In certain embodiments, the PBS of the invention has the sequence 5'-UGUAUUUA-3', and binds the PUF domain PUF(3-1).

In certain embodiments, the PBS of the invention has the sequence 5'-UUUAUUUA-3', and binds the PUF domain PUF(7-2/3-1).

Applicant has created 65,536 8-mer PBS and their corresponding PUF domain sequences (see below) that can bind the specific PBS. Applicant has also created a python script to retrieve any of the 65,536 individual PUF domain sequences that binds a given 8-mer PBS. For example, for the 8-mer UUGAUGUA, one possible PUF domain sequence can be:

(SEQ ID NO: 3)
GRSRLLEDFRNNRYPNLQLREIAGHIMEFSQDQHGCRFIQLKLERATPAE

RQLVFNEILQAAYQLMVDVFGNYVIQKFFEFGSLEQKLALAERIRGHVLS

LALQMYGSRVIEKALEFIPSDQQNEMVRELDGHVLKCVKDQNGNHVVQKC

IECVQPQSLQFIIDAFKGQVFALSTHPYGCRVIQRILEHCLPDQTLPILE

ELHQHTEQLVQDQYGSYVIEHVLEHGRPEDKSKIVAEIRGNVLVLSQHKF

ANNVVQKCVTHASRTERAVLIDEVCTMNDGPHSALYTMMKDQYANYVVQK

MIDVAEPGQRKIVMHKIRPHIATLRKYTYGKHILAKLEKYYMKNGVDLG

In certain embodiments, one or more spacer region(s) separates two adjacent PBS sequences. The spacer regions may have a length of from about 3 nucleotides to about 100 nucleotides. For example, the spacer can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the spacer can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the spacer is 4 nt.

d. Optional Other Sequences

A stability control sequence (e.g., transcriptional terminator segment) influences the stability of an RNA (e.g., a subject polynucleotide). One example of a suitable stability control sequence is a transcriptional terminator segment (i.e., a transcription termination sequence). A transcriptional terminator segment of a subject polynucleotide can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell.

Non-limiting examples of nucleotide sequences that can be included in a stability control sequence (e.g., transcriptional termination segment, or in any segment of the DNA-targeting RNA to provide for increased stability) include sequences set forth in SEQ ID NO: 683-696 of WO 2013/176772 (incorporated herein by reference), see, for example, SEQ ID NO: 795 of WO 2013/176772, a Rho-independent transcription termination site.

The stability control sequence may be situated after the Cas9-binding sequence, for example, between the Cas9-binding sequence and the first PBS, between two adjacent PBS, or after the last PBS.

In some embodiments, the polynucleotide of the invention or parts thereof (e.g., the DNA-targeting sequence, the Cas9-binding sequence, and/or the one or more of the PBS), or a polynucleotide encoding the Cas9 protein (e.g., wt, nickase, or dCas9 protein), or a polynucleotide encoding one of the PUF domain fusions (infra), may comprise a modification or sequence that provides for an additional desirable feature, e.g., modified or regulated stability; subcellular targeting; tracking, e.g., a fluorescent label; a binding site for a protein or protein complex; etc.).

Non-limiting examples include: a 5' cap (e.g., a 7-methylguanylate cap ($m^7G$)); a 3' polyadenylated tail (i.e., a 3' poly(A) tail); a riboswitch sequence or an aptamer sequence (e.g., to allow for regulated stability and/or regulated accessibility by proteins and protein complexes); a terminator sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); a modification or sequence that provides for increased, decreased, and/or controllable stability; and combinations thereof.

3. The Cas9 Protein (Wt, Nickase, or dCas9)

The Cas9 protein (e.g., wt, nickase, or dCas9 protein) of the invention comprises: i) an RNA-binding portion that interacts with the Cas9-binding sequence of the subject polynucleotide, and ii) an activity portion that exhibits wt, reduced endonuclease (e.g., endodeoxyribonuclease) activity, or lacks endonuclease (e.g., endodeoxyribonuclease) activity, depending on the identity of the Cas9 protein.

The Cas9-binding sequence of the polynucleotide and the Cas9 protein (e.g., wt, nickase, or dCas9 protein) can form a complex that binds to a specific target polynucleotide sequence, based on the sequence complementarity between the DNA-targeting sequence and the target polynucleotide sequence. The DNA-targeting sequence of the subject polynucleotide provides target specificity to the complex via its sequence complementarity to the target polynucleotide sequence of a target DNA. If the target polynucleotide sequence is at or adjacent to a transcription regulatory element or an epigenetic modification site of a target gene, the complex, together with transcription regulators or effectors that modulate epigenetic modification fused to PBS-binding PUF domain, can selectively modulate transcription or epigenetic modulation of the target gene.

In certain embodiments, the modified Cas9 protein has reduced or lacks endonuclease (e.g., endodeoxyribonuclease) activity. For example, a modified Cas9 suitable for use in a method of the present invention may be a Cas9 nickase, or exhibits less than about 20%, less than about 15%, less than about 10%, less than about 5%, less than about 1%, or less than about 0.1%, of the endonuclease (e.g., endodeoxyribonuclease) activity of a wild-type Cas9 polypeptide, e.g., a wild-type Cas9 polypeptide comprising an amino acid sequence as depicted in FIG. 3 and SEQ ID NO: 8 of WO 2013/176772 (incorporated herein by reference). In some embodiments, the dCas9 has substantially no detectable endonuclease (e.g., endodeoxyribonuclease) activity. In some embodiments when a dCas9 has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the polypeptide can still bind to target DNA in a site-specific manner, because it is still guided to a target polynucleotide sequence by a DNA-targeting sequence of the subject polynucleotide, as long as it retains the ability to interact with the Cas9-binding sequence of the subject polynucleotide.

In some cases, a suitable Cas9 protein (e.g., wt, nickase, or dCas9 protein) comprises an amino acid sequence having at least about 75%, at least about 80%, at least about 85%, at least about 90%, at least about 95%, at least about 99% or 100% amino acid sequence identity to amino acids 7-166 or 731-1003 of the Cas9/Csn1 amino acid sequence (of *Streptococcus pyogenes*), as depicted in FIG. 3 and SEQ ID NO: 8 of WO 2013/176772 (incorporated by reference), or to the corresponding portions in any one of the amino acid sequences SEQ ID NOs: 1-256 and 795-1346 of WO 2013/176772 (incorporated by reference), preferably to the corresponding portions in any one of the amino acid sequences of the orthogonal Cas9 sequences from *S. pyogenes, N. meningitidis, S. thermophilus* and *T. denticola* (see, Esvelt et al., *Nature Methods,* 10(11): 1116-1121, 2013, incorporated by reference).

In some cases, the Cas9 nickase can cleave the complementary strand of the target DNA but has reduced ability to cleave the non-complementary strand of the target DNA. For example, the Cas9 nickase can have a mutation (amino acid substitution) that reduces the function of the RuvC domain. As a non-limiting example, in some cases, the Cas9 nickase is a D10A (aspartate to alanine) mutation of the amino acid sequence depicted in FIG. 3 of WO 2013/176772, or the corresponding mutation of any of the amino acid sequences set forth in SEQ ID NOs: 1-256 and 795-1346 of WO 2013/176772 (all such sequences incorporated by reference).

In some cases, the Cas9 nickase can cleave the non-complementary strand of the target DNA but has reduced ability to cleave the complementary strand of the target DNA. For example, the Cas9 nickase can have a mutation (amino acid substitution) that reduces the function of the HNH domain (RuvC/HNH/RuvC domain motifs). As a non-limiting example, in some cases, the Cas9 nickase is a H840A (histidine to alanine at amino acid position 840 of SEQ ID NO: 8 of WO 2013/176772, incorporated by reference) or the corresponding mutation of any of the amino acid sequences set forth in SEQ ID NOs: 1-256 and 795-1346 of WO 2013/176772 (all such sequences incorporated by reference).

In some cases, the dCas9 has a reduced ability to cleave both the complementary and the non-complementary strands of the target DNA. As a non-limiting example, in some cases, the dCas9 harbors both D10A and H840A mutations of the amino acid sequence depicted in FIG. 3 of WO 2013/176772 or the corresponding mutations of any of the amino acid sequences set forth in SEQ ID NOs: 1-256 and 795-1346 of WO 2013/176772 (all such sequences incorporated by reference).

Other residues can be mutated to achieve the same effect (i.e. inactivate one or the other nuclease portions). As non-limiting examples, residues D10, G12, G17, E762, H840, N854, N863, H982, H983, A984, D986, and/or A987 (or the corresponding mutations of any of the proteins set forth as SEQ ID NOs: 1-256 and 795-1346) can be altered (i.e., substituted) (see FIGS. 3, 5, 11A, and Table 1 of WO 2013/176772 (all incorporated by reference) for more information regarding the conservation of Cas9 amino acid residues). Also, mutations other than alanine substitutions are suitable.

In some cases, the Cas9 protein (e.g., wt, nickase, or dCas9 protein) is optionally a fusion polypeptide comprising: i) a Cas9 protein (e.g., wt, nickase, or dCas9 protein); and b) a covalently linked heterologous polypeptide (also referred to as a "fusion partner"), which can be the same or different from the fusion partner fused to the PUF domains (infra).

4. PUF Domain (and the optional Cas9) Fusion Proteins

PUF proteins (named after *Drosophila Pumilio* and *C. elegans* fem-3 binding factor) are known to be involve in mediating mRNA stability and translation. These protein contain a unique RNA-binding domain known as the PUF domain. The RNA-binding PUF domain, such as that of the human Pumilio 1 protein (referred here also as PUM), contains 8 repeats (each repeat called a PUF motif or a PUF repeat) that bind consecutive bases in an anti-parallel fashion, with each repeat recognizing a single base—i.e., PUF repeats R1 to R8 recognize nucleotides N8 to N1, respectively. For example, PUM is composed of eight tandem repeats, each repeat consisting of 34 amino acids that folds into tightly packed domains composed of alpha helices.

Each PUF repeat uses two conserved amino acids from the center of each repeat to specifically recognize the edge of one individual base within the RNA recognition sequence, and a third amino acid (Tyr, His or Arg) to stack between adjacent bases, causing a very specific binding between a PUF domain and an 8-mer RNA. For example, the code to recognize base U is the amino acid sequence "NYxxQ", whereas "(C/S)RxxQ" recognizes A and "SNxxE" recognizes G. These amino acids correspond to positions 12, 13, and 16 in the human Pumilio 1 PUF motif. The two recognition amino acid side chains at positions 12 and 16 in each PUF α-α-α repeat recognize the Watson-Crick edge of the corresponding base and largely determine the specificity of that repeat.

Therefore, the sequence specificity of the PUF domains can be altered precisely by changing the conserved amino acid (e.g., by site-directed mutagenesis) involved in base recognition within the RNA recognition sequence. By changing two amino acids in each repeat, a PUF domain can be modified to bind almost any 8-nt RNA sequence. This unique binding mode makes PUF and its derivatives a programmable RNA-binding domain that can be used in the instant invention, as part of a PUF domain-fusion that brings any effector domain to a specific PBS on the subject polynucleotide.

As used herein, "PUF domain" refers to a wildtype or naturally existing PUF domain, as well as a PUF homologue domain that is based on/derived from a natural or existing PUF domain, such as the prototype human Pumilio 1 PUF domain. The PUF domain of the invention specifically binds to an RNA sequence (e.g., an 8-mer RNA sequence), wherein the overall binding specificity between the PUF domain and the RNA sequence is defined by sequence specific binding between each PUF motif/PUF repeat within the PUF domain and the corresponding single RNA nucleotide.

In certain embodiments, the PUF domain comprises or consists essentially of 8 PUF motifs, each specifically recognizes and binds to one RNA nucleotide (e.g., A, U, G, or C).

Applicant has created 65,536 8-mer PBS and their corresponding PUF domain sequences (each about 350 amino acids long) that can bind the specific PBS. Applicant has also created a python script to retrieve any of the 65,536 individual PUF domain sequences that binds a given 8-mer PBS.

In certain embodiments, the PUF domain has more or less than 8 PUF motifs/repeats, e.g., the PUF domain comprises or consists essentially of 5, 6, 7, 8, 9, 10, 11, 12, 13, 14, 15, 16, or more PUF repeats/motifs, each specifically recognizes and binds to one RNA nucleotide (e.g., A, U, G, or C), so long as the PUF domain binds the RNA of 5, 6, 7, 8, 9, 10, 11, 12, 13, 14, 15, 16 or more nucleotides. By increasing or decreasing the number of PUF motifs, the length of the recognized RNA will be correspondingly increased or decreased. Since each PUF motif recognizes one RNA base, decreasing the domain by one motif decreases the length of the RNA recognized by one base; while increasing the domain by one motif increases the length of the RNA recognized by one base. Any number of motifs may be present. Therefore, in such embodiments, the specificity of the PUF domain-fusions of the invention may be altered due to changes in PUF domain length. In certain embodiments, the additional PUF motifs are inserted between two of the original PUF motifs, e.g., before the $1^{st}$, between the $1^{st}$ and the $2^{nd}$, the $2^{nd}$ and the $3^{rd}$, the $3^{rd}$, and the $4^{th}$, the $4^{th}$ and the $5^{th}$, the $5^{th}$ and the $6^{th}$, the $6^{th}$ and the $7^{th}$, the $7^{th}$ and the $8^{th}$, or after the $8^{th}$. In certain embodiments, there are 1, 2, 3, 4, 5, 6, 7, 8, or more inserted PUF motifs between any of the insertion points above. For example, in certain embodiments, there are 1, 2, 3, 4, 5, 6, 7, 8, or more inserted PUF motifs between the $5^{th}$ and the $6^{th}$ original PUF motif. Filipovska et al. (Nature Chemical Biology doi: 10.1038/NChemBio.577, published online: 15 may 2011) have reported an engineered PUF domain with 16 PUF motifs, including 8 additional PUF motifs inserted between the $5^{th}$ and $6^{th}$ original PUF motifs.

In certain embodiments, the PUF domain comprises PUF motifs from different PUF domains from different proteins. For example, a PUF domain of the invention may be constructed with PUF motifs from the human Pumilio 1 protein and one or more other PUF motifs from one or more other PUF proteins, such as PuDp or FBF. The RNA binding pockets of PUF domains have natural concave curvatures. Since different PUF proteins may have different curvatures, different PUF motifs in a PUF domain may be used to alter the curvature of the PUF domain. Altering the curvature is another method for altering the specificity and/or binding affinity of the PUF domain since flatter curvatures may allow for the recognition of more RNA bases.

Also included in the scope of the invention are functional variants of the subject PUF domains or fusions thereof. The term "functional variant" as used herein refers to a PUF domain having substantial or significant sequence identity or similarity to a parent PUF domain, which functional variant retains the biological activity of the PUF domain of which it is a variant—e.g., one that retains the ability to recognize target RNA to a similar extent, the same extent, or to a higher extent in terms of binding affinity, and/or with substantially the same or identical binding specificity, as the parent PUF domain. The functional variant PUF domain can, for instance, be at least about 30%, 50%, 75%, 80%, 90%, 98% or more identical in amino acid sequence to the parent PUF domain. The functional variant can, for example, comprise the amino acid sequence of the parent PUF domain with at least one conservative amino acid substitution, for example, conservative amino acid substitutions in the scaffold of the PUF domain (i.e., amino acids that do not interact with the RNA). Alternatively or additionally, the functional variants can comprise the amino acid sequence of the parent PUF domain with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent PUF domain, or may alter the stability of the PUF domain to a desired level (e.g., due to substitution of amino acids in the scaffold). The PUF domain can consist essentially of the specified amino acid sequence or sequences described herein, such that other components, e.g., other amino acids, do not materially change the biological activity of the functional variant.

In certain embodiments, the PUF domain is a Pumilio homology domain (PU-HUD). In a particular embodiment, the PU-HUD is a human Pumilio 1 domain. The sequence of the human PUM is known in the art and is reproduced below:

```
                                        (SEQ ID NO: 4)
Gly Arg Ser Arg Leu Leu Glu Asp Phe Arg Asn Asn

Arg Tyr Pro Asn Leu Gln Leu Arg Glu Ile Ala Gly

His Ile Met Glu Phe Ser Gln Asp Gln His Gly Ser

Arg Phe Ile Gln Leu Lys Leu Glu Arg Ala Thr Pro

Ala Glu Arg Gln Leu Val Phe Asn Glu Ile Leu Gln

Ala Ala Tyr Gln Leu Met Val Asp Val Phe Gly Asn

Tyr Val Ile Gln Lys Phe Phe Glu Phe Gly Ser Leu

Glu Gln Lys Leu Ala Leu Ala Glu Arg Ile Arg Gly

His Val Leu Ser Leu Ala Leu Gln Met Tyr Gly Cys

Arg Val Ile Gln Lys Ala Leu Glu Phe Ile Pro Ser

Asp Gln Gln Asn Glu Met Val Arg Glu Leu Asp Gly

His Val Leu Lys Cys Val Lys Asp Gln Asn Gly Asn

His Val Val Gln Lys Cys Ile Glu Cys Val Gln Pro

Gln Ser Leu Gln Phe Ile Ile Asp Ala Phe Lys Gly

Gln Val Phe Ala Leu Ser Thr His Pro Tyr Gly Cys

Arg Val Ile Gln Arg Ile Leu Glu His Cys Leu Pro

Asp Gln Thr Leu Pro Ile Leu Glu Glu Leu His Gln

His Thr Glu Gln Leu Val Gln Asp Gln Tyr Gly Asn

Tyr Val Ile Gln His Val Leu Glu His Gly Arg Pro

Glu Asp Lys Ser Lys Ile Val Ala Glu Ile Arg Gly

Asn Val Leu Val Leu Ser Gln His Lys Phe Ala Ser

Asn Val Val Glu Lys Cys Val Thr His Ala Ser Arg
```

-continued

```
Thr Glu Arg Ala Val Leu Ile Asp Glu Val Cys Thr

Met Asn Asp Gly Pro His Ser Ala Leu Tyr Thr Met

Met Lys Asp Gln Tyr Ala Asn Tyr Val Val Gln Lys

Met Ile Asp Val Ala Glu Pro Gly Gln Arg Lys Ile

Val Met His Lys Ile Arg Pro His Ile Ala Thr Leu

Arg Lys Tyr Thr Tyr Gly Lys His Ile Leu Ala Lys

Leu Glu Lys Tyr Tyr Met Lys Asn Gly Val Asp Leu

Gly
```

The wt human PUM specifically binds the Nanos Response Element (NRE) RNA, bearing a core 8-nt sequence 5'-UGUAUAUA-3'.

In certain embodiments, the PUF domain of the invention is any PUF protein family member with a Pum-HD domain. Non-limiting examples of a PUF family member include FBF in *C. elegans*, Ds pum in *Drosophila*, and PUF proteins in plants such as *Arabidopsis* and rice. A phylogenetic tree of the PUM-HDs of *Arabidopsis*, rice and other plant and non-plant species is provided in Tam et al. ("The Puf family of RNA-binding proteins in plants: phylogeny, structural modeling, activity and subcellular localization." *BMC Plant Biol.* 10:44, 2010, the entire contents of which are incorporated by reference herein).

PUF family members are highly conserved from yeast to human, and all members of the family bind to RNA in a sequence specific manner with a predictable code. The accession number for the domain is PS50302 in the Prosite database (Swiss Institute of Bioinformatics) and a sequence alignment of some of the members of this family is shown in FIGS. 5 & 6 of WO 2011-160052 A2 (ClustalW multiple sequence alignment of human, mouse, rat Pumilio 1 (hpum1, Mpum1, Ratpum1) and human and mouse Pumilio 2 (hpum2, Mpum2), respectively.

The *Drosophila Pumilio* (PumDr) is very different in length from other mammalian Pumilio 1 homologues, thus only the C-terminal PUF HUD domain is shown in the sequence alignment with human PUM1 and PUM2 in FIG. 6 of WO 2011/160052A2. The N-terminal part of human and fly Pum proteins shows weak homology (40% similarity) and differs significantly in size and protein sequence. The C-terminal part shows a very high degree of homology and evolutionary conservation (78% identity, 86% similarity for PUM1 and 79% identity, 88% similarity for PUM2), with highly conserved protein sequence and structure of the Pum RNA-binding domain. In all three proteins PUM-HD is composed of the N-terminal conserved part of 20 amino acids, eight Pum repeats of 36 amino acids each, and the C-terminal conserved region. In human Pumilio proteins, the C-conserved part is 44 amino acids long, whereas *Drosophila* protein has an insert of additional 85 amino acids in the C-conserved region. The nucleotide and amino acid sequences can be found in the DDBJ/EMBL/GENBANK® databases under accession nos. AF315592 (PUM1) and AF315591 (PUM2) (Spassov & Jurecic, "Cloning and comparative sequence analysis of PUM1 and PUM2 genes, human members of the Pumilio family of RNA-binding proteins," *Gene*, 299:195-204, October 2002, the entire contents of each of which (publication and sequences) are incorporated by reference herein).

In addition, all aligned sequences, i.e., SEQ ID NOs:55-60 of WO 2011/160052A2, are incorporated herein by reference.

In some embodiments, the PUF domain of the invention can be made up of eight 36 mers, in which 33 of the amino acids are conserved and the $34^{th}$, $35^{th}$ and $36^{th}$ amino acids can vary, imparting specificity for a particular base in an RNA sequence. In particular embodiments, the RNA binding domain is about 300 (e.g., 310, 309, 308, 307, 306, 305, 304, 303, 302, 301, 300, 299, 298, 297, 296, 295, 294, 293, 292, 291, 290, etc.) amino acids in length. In some embodiments, the PUF domain of this invention is designed to bind to a specific RNA sequence of about 8 nucleotides (e.g., 8-16 contiguous RNA bases). In particular embodiments, the fifth nucleotide of the 8-nt sequence is a U or C, while the other 7 nucleotides can vary.

In some embodiments, the PUF domain is modified from a wt PUF domain to bind an RNA sequence that is different from the RNA sequence bound by the unmodified (i.e., wild type) RNA binding PUF domain. The RNA sequence can be about an 8mer (e.g., an 8mer, 9 mer, 10 mer, 11 mer, 12mer, 13mer, 14mer, 15mer, 16mer, etc.). The ability to introduce modifications into the amino acid sequence of the RNA binding domain to alter its specificity for a target RNA sequence is based on the known interactions of bases with the different amino acid side chains of the RNA binding domain (e.g., PUF proteins). The RNA recognition code of the PUF domain is shown below, which can be generally written as:

SerXXXGlu for G (guanine), such as SNxxE;
CysXXXGln, such as CysArgXXGln or SerArgXXGln (i.e., (C/S)RxxQ) for A (adenine);
AsnXXXGln for U (uracil), such as NYxxQ, and,
SnXXXArg for C (cytosine), such as SerTyrXXArg.
where X is any amino acid, and Sn represents a small or nucleophilic residue such as Gly, Ala, Ser, Thr, or Cys.

Based on the guidelines above, at least one PUF domain can be constructed based on any given 8-mer sequences. Specifically, a PUF domain binding to an 8-mer RNA sequence of 5'-$N_1N_2N_3N_4N_5N_6N_7N_8$-3' can have the following sequence formula, in which R1-R8 each represents a PUF motif peptide sequence listed in the tables below, depending on the specific identity of the ribonucleotide (i.e., A, U, C, or G) at any of the $N_1$-$N_8$ locations. Note that R1 binds $N_8$, R2 binds $N_7$, etc.

(SEQ ID NO: 5)
GlyArgSerArgLeuLeuGluAspPheArgAsnAsnArgTyrProAsn

LeuGlnLeuArgGluIleAlaGlyHisIleMetGluPheSerGlnAsp

[R1]ThrProAlaGluArgGlnLeuValPheAsnGluIleLeuGlnAla

AlaTyrGlnLeuMetValAsp[R2]SerLeuGluGlnLysLeuAlaLeu

AlaGluArgIleArgGlyHisValLeuSerLeuAlaLeuGln[R3]Pro

SerAspGlnGlnAsnGluMetValArgGluLeuAspGlyHisValLeu

LysCysValLysAsp[R4]GlnProGlnSerLeuGlnPheIleIleAsp

AlaPheLysGlyGlnValPheAlaLeuSerThrHis[R5]LeuProAsp

GlnThrLeuProIleLeuGluGluLeuHisGlnHisThrGluGlnLeu

ValGlnAsp[R6]ArgProGluAspLysSerLysIleValAlaGluIle

ArgGlyAsnValLeuValLeuSerGlnHis[R7]SerArgThrGluArg

AlaValLeuIleAspGluValCysThrMetAsnAspGlyProHisSer

AlaLeuTyrThrMetMetLysAsp[R8]GluProGlyGlnArgLysIle

-continued
ValMetHisLysIleArgProHisIleAlaThrLeuArgLysTyrThr

TyrGlyLysHisIleLeuAlaLysLeuGluLysTyrTyrMetLysAsn

GlyValAspLeuGly

| N8 nucleotide | R1 peptide sequence(s) |
|---|---|
| A | GlnHisGlyCysArgPheIleGlnLeuLysLeuGluArgAla (SEQ ID NO: 6) |
|  | GlnHisGlySerArgPheIleGlnLeuLysLeuGluArgAla (SEQ ID NO: 7) |
| C | GlnHisGlySerArgPheIleArgLeuLysLeuGluArgAla (SEQ ID NO: 8) |
|  | GlnHisGlyGlyArgPheIleArgLeuLysLeuGluArgAla (SEQ ID NO: 9) |
|  | GlnHisGlyAlaArgPheIleArgLeuLysLeuGluArgAla (SEQ ID NO: 10) |
|  | GlnHisGlyThrArgPheIleArgLeuLysLeuGluArgAla (SEQ ID NO: 11) |
|  | GlnHisGlyCysArgPheIleArgLeuLysLeuGluArgAla (SEQ ID NO: 12) |
| G | GlnHisGlySerArgPheIleGluLeuLysLeuGluArgAla (SEQ ID NO: 13) |
| U | GlnHisGlyAsnArgPheIleGlnLeuLysLeuGluArgAla (SEQ ID NO: 14) |

| N7 nucleotide | R2 peptide sequence(s) |
|---|---|
| A | ValPheGlyCysArgValIleGlnLysPhePheGluPheGly (SEQ ID NO: 15) |
|  | ValPheGlySerArgValIleGlnLysPhePheGluPheGly (SEQ ID NO: 16) |
|  | ValPheGlyCysTyrValIleGlnLysPhePheGluPheGly (SEQ ID NO: 17) |
|  | ValPheGlySerTyrValIleGlnLysPhePheGluPheGly (SEQ ID NO: 18) |
| C | ValPheGlySerTyrValIleArgLysPhePheGluPheGly (SEQ ID NO: 19) |
|  | ValPheGlyGlyTyrValIleArgLysPhePheGluPheGly (SEQ ID NO: 20) |
|  | ValPheGlyAlaTyrValIleArgLysPhePheGluPheGly (SEQ ID NO: 21) |
|  | ValPheGlyThrTyrValIleArgLysPhePheGluPheGly (SEQ ID NO: 22) |
|  | ValPheGlyCysTyrValIleArgLysPhePheGluPheGly (SEQ ID NO: 23) |
| G | ValPheGlySerTyrValIleGluLysPhePheGluPheGly (SEQ ID NO: 24) |
| U | ValPheGlyAsnTyrValIleGlnLysPhePheGluPheGly (SEQ ID NO: 25) |

| N6 nucleotide | R3 peptide sequence(s) |
|---|---|
| A | MetTyrGlyCysArgValIleGlnLysAlaLeuGluPheIle (SEQ ID NO: 26) |
|  | MetTyrGlySerArgValIleGlnLysAlaLeuGluPheIle (SEQ ID NO: 27) |
| C | MetTyrGlySerArgValIleArgLysAlaLeuGluPheIle (SEQ ID NO: 28) |
|  | MetTyrGlyGlyArgValIleArgLysAlaLeuGluPheIle (SEQ ID NO: 29) |
|  | MetTyrGlyAlaArgValIleArgLysAlaLeuGluPheIle (SEQ ID NO: 30) |
|  | MetTyrGlyThrArgValIleArgLysAlaLeuGluPheIle (SEQ ID NO: 31) |
|  | MetTyrGlyCysArgValIleArgLysAlaLeuGluPheIle (SEQ ID NO: 32) |
| G | MetTyrGlySerArgValIleGluLysAlaLeuGluPheIle (SEQ ID NO: 33) |
| U | MetTyrGlyAsnArgValIleGlnLysAlaLeuGluPheIle (SEQ ID NO: 34) |

| N5 nucleotide | R4 peptide sequence(s) |
|---|---|
| A | GlnAsnGlyCysArgValValGlnLysCysIleGluCysVal (SEQ ID NO: 35) |
|  | GlnAsnGlySerArgValValGlnLysCysIleGluCysVal (SEQ ID NO: 36) |
|  | GlnAsnGlyCysHisValValGlnLysCysIleGluCysVal (SEQ ID NO: 37) |
|  | GlnAsnGlySerHisValValGlnLysCysIleGluCysVal (SEQ ID NO: 38) |
| C | GlnAsnGlySerHisValValArgLysCysIleGluCysVal (SEQ ID NO: 39) |
|  | GlnAsnGlyGlyHisValValArgLysCysIleGluCysVal (SEQ ID NO: 40) |
|  | GlnAsnGlyAlaHisValValArgLysCysIleGluCysVal (SEQ ID NO: 41) |
|  | GlnAsnGlyThrHisValValArgLysCysIleGluCysVal (SEQ ID NO: 42) |
|  | GlnAsnGlyCysHisValValArgLysCysIleGluCysVal (SEQ ID NO: 43) |
| G | GlnAsnGlySerHisValValGluLysCysIleGluCysVal (SEQ ID NO: 44) |
| U | GlnAsnGlyAsnHisValValGlnLysCysIleGluCysVal (SEQ ID NO: 45) |

| $N_4$ nucleotide | R5 peptide sequence(s) |
|---|---|
| A | ProTyrGlyCysArgValIleGlnArgIleLeuGluHisCys (SEQ ID NO: 46) |
| | ProTyrGlySerArgValIleGlnArgIleLeuGluHisCys (SEQ ID NO: 47) |
| C | ProTyrGlySerArgValIleArgArgIleLeuGluHisCys (SEQ ID NO: 48) |
| | ProTyrGlyGlyArgValIleArgArgIleLeuGluHisCys (SEQ ID NO: 49) |
| | ProTyrGlyAlaArgValIleArgArgIleLeuGluHisCys (SEQ ID NO: 50) |
| | ProTyrGlyThrArgValIleArgArgIleLeuGluHisCys (SEQ ID NO: 51) |
| | ProTyrGlyCysArgValIleArgArgIleLeuGluHisCys (SEQ ID NO: 52) |
| G | ProTyrGlySerArgValIleGluArgIleLeuGluHisCys (SEQ ID NO: 53) |
| U | ProTyrGlyAsnArgValIleGlnArgIleLeuGluHisCys (SEQ ID NO: 54) |

| $N_3$ nucleotide | R6 peptide sequence(s) |
|---|---|
| A | GlnTyrGlyCysArgValIleGlnHisValLeuGluHisGly (SEQ ID NO: 55) |
| | GlnTyrGlySerArgValIleGlnHisValLeuGluHisGly (SEQ ID NO: 56) |
| | GlnTyrGlyCysTyrValIleGlnHisValLeuGluHisGly (SEQ ID NO: 57) |
| | GlnTyrGlySerTyrValIleGlnHisValLeuGluHisGly (SEQ ID NO: 58) |
| C | GlnTyrGlySerTyrValIleArgHisValLeuGluHisGly (SEQ ID NO: 59) |
| | GlnTyrGlyGlyTyrValIleArgHisValLeuGluHisGly (SEQ ID NO: 60) |
| | GlnTyrGlyAlaTyrValIleArgHisValLeuGluHisGly (SEQ ID NO: 61) |
| | GlnTyrGlyThrTyrValIleArgHisValLeuGluHisGly (SEQ ID NO: 62) |
| | GlnTyrGlyCysTyrValIleArgHisValLeuGluHisGly (SEQ ID NO: 63) |
| G | GlnTyrGlySerTyrValIleGluHisValLeuGluHisGly (SEQ ID NO: 64) |
| U | GlnTyrGlyAsnTyrValIleGlnHisValLeuGluHisGly (SEQ ID NO: 65) |

| $N_2$ nucleotide | R7 peptide sequence(s) |
|---|---|
| A | LysPheAlaCysArgValValGlnLysCysValThrHisAla (SEQ ID NO: 66) |
| | LysPheAlaSerArgValValGlnLysCysValThrHisAla (SEQ ID NO: 67) |
| | LysPheAlaCysAsnValValGlnLysCysValThrHisAla (SEQ ID NO: 68) |
| | LysPheAlaSerAsnValValGlnLysCysValThrHisAla (SEQ ID NO: 69) |
| C | LysPheAlaSerAsnValValArgLysCysValThrHisAla (SEQ ID NO: 70) |
| | LysPheAlaGlyAsnValValArgLysCysValThrHisAla (SEQ ID NO: 71) |
| | LysPheAlaAlaAsnValValArgLysCysValThrHisAla (SEQ ID NO: 72) |
| | LysPheAlaThrAsnValValArgLysCysValThrHisAla (SEQ ID NO: 73) |
| | LysPheAlaCysAsnValValArgLysCysValThrHisAla (SEQ ID NO: 74) |
| G | LysPheAlaSerAsnValValGluLysCysValThrHisAla (SEQ ID NO: 75) |
| U | LysPheAlaAsnAsnValValGlnLysCysValThrHisAla (SEQ ID NO: 76) |

| $N_1$ nucleotide | R8 peptide sequence(s) |
|---|---|
| A | GlnTyrAlaCysArgValValGlnLysMetIleAspValAla (SEQ ID NO: 77) |
| | GlnTyrAlaSerArgValValGlnLysMetIleAspValAla (SEQ ID NO: 78) |
| | GlnTyrAlaCysTyrValValGlnLysMetIleAspValAla (SEQ ID NO: 79) |
| | GlnTyrAlaSerTyrValValGlnLysMetIleAspValAla (SEQ ID NO: 80) |
| C | GlnTyrAlaSerTyrValValArgLysMetIleAspValAla (SEQ ID NO: 81) |
| | GlnTyrAlaGlyTyrValValArgLysMetIleAspValAla (SEQ ID NO: 82) |
| | GlnTyrAlaAlaTyrValValArgLysMetIleAspValAla (SEQ ID NO: 83) |
| | GlnTyrAlaThrTyrValValArgLysMetIleAspValAla (SEQ ID NO: 84) |
| | GlnTyrAlaCysTyrValValArgLysMetIleAspValAla (SEQ ID NO: 85) |
| G | GlnTyrAlaSerTyrValValGluLysMetIleAspValAla (SEQ ID NO: 86) |
| U | GlnTyrAlaAsnTyrValValGlnLysMetIleAspValAla (SEQ ID NO: 87) |

Several exemplary PUF domains with modified RNA binding specificity, constructed based on the above RNA recognition code, are provided below, each can be used to construct PUF domain-fusions of the invention.

PUF (3-2)

(SEQ ID NO: 88)

Gly Arg Ser Arg Leu Leu Glu Asp Phe Arg Asn Asn

Arg Tyr Pro Asn Leu Gln Leu Arg Glu Ile Ala Gly

His Ile Met Glu Phe Ser Gln Asp Gln His Gly Ser

Arg Phe Ile Gln Leu Lys Leu Glu Arg Ala Thr Pro

Ala Glu Arg Gln Leu Val Phe Asn Glu Ile Leu Gln

Ala Ala Tyr Gln Leu Met Val Asp Val Phe Gly Asn

Tyr Val Ile Gln Lys Phe Phe Glu Phe Gly Ser Leu

Glu Gln Lys Leu Ala Leu Ala Glu Arg Ile Arg Gly

His Val Leu Ser Leu Ala Leu Gln Met Tyr Gly Ser

Arg Val Ile Glu Lys Ala Leu Glu Phe Ile Pro Ser

Asp Gln Gln Asn Glu Met Val Arg Glu Leu Asp Gly

His Val Leu Lys Cys Val Lys Asp Gln Asn Gly Asn

His Val Val Gln Lys Cys Ile Glu Cys Val Gln Pro

Gln Ser Leu Gln Phe Ile Ile Asp Ala Phe Lys Gly

Gln Val Phe Ala Leu Ser Thr His Pro Tyr Gly Cys

Arg Val Ile Gln Arg Ile Leu Glu His Cys Leu Pro

Asp Gln Thr Leu Pro Ile Leu Glu Glu Leu His Gln

His Thr Glu Gln Leu Val Gln Asp Gln Tyr Gly Asn

Tyr Val Ile Gln His Val Leu Glu His Gly Arg Pro

Glu Asp Lys Ser Lys Ile Val Ala Glu Ile Arg Gly

Asn Val Leu Val Leu Ser Gln His Lys Phe Ala Ser

Asn Val Val Glu Lys Cys Val Thr His Ala Ser Arg

Thr Glu Arg Ala Val Leu Ile Asp Glu Val Cys Thr

Met Asn Asp Gly Pro His Ser Ala Leu Tyr Thr Met

Met Lys Asp Gln Tyr Ala Asn Tyr Val Val Gln Lys

Met Ile Asp Val Ala Glu Pro Gly Gln Arg Lys Ile

Val Met His Lys Ile Arg Pro His Ile Ala Thr Leu

Arg Lys Tyr Thr Tyr Gly Lys His Ile Leu Ala Lys

Leu Glu Lys Tyr Tyr Met Lys Asn Gly Val Asp Leu

Gly

PUF(3-2) has two point mutations (C935S/Q939E) in the PUF repeat 3, and recognizes a cognate RNA with a mutation at position 6 of the NRE (A6G; 5'-UGUAUGUA-3').

PUF (6-2/7-2)

(SEQ ID NO: 89)

Gly Arg Ser Arg Leu Leu Glu Asp Phe Arg Asn Asn

Arg Tyr Pro Asn Leu Gln Leu Arg Glu Ile Ala Gly

His Ile Met Glu Phe Ser Gln Asp Gln His Gly Ser

Arg Phe Ile Gln Leu Lys Leu Glu Arg Ala Thr Pro

Ala Glu Arg Gln Leu Val Phe Asn Glu Ile Leu Gln

Ala Ala Tyr Gln Leu Met Val Asp Val Phe Gly Asn

Tyr Val Ile Gln Lys Phe Phe Glu Phe Gly Ser Leu

Glu Gln Lys Leu Ala Leu Ala Glu Arg Ile Arg Gly

His Val Leu Ser Leu Ala Leu Gln Met Tyr Gly Cys

Arg Val Ile Gln Lys Ala Leu Glu Phe Ile Pro Ser

Asp Gln Gln Asn Glu Met Val Arg Glu Leu Asp Gly

His Val Leu Lys Cys Val Lys Asp Gln Asn Gly Asn

His Val Val Gln Lys Cys Ile Glu Cys Val Gln Pro

Gln Ser Leu Gln Phe Ile Ile Asp Ala Phe Lys Gly

Gln Val Phe Ala Leu Ser Thr His Pro Tyr Gly Cys

Arg Val Ile Gln Arg Ile Leu Glu His Cys Leu Pro

Asp Gln Thr Leu Pro Ile Leu Glu Glu Leu His Gln

His Thr Glu Gln Leu Val Gln Asp Gln Tyr Gly Ser

Tyr Val Ile Glu His Val Leu Glu His Gly Arg Pro

Glu Asp Lys Ser Lys Ile Val Ala Glu Ile Arg Gly

Asn Val Leu Val Leu Ser Gln His Lys Phe Ala Asn

Asn Val Val Gln Lys Cys Val Thr His Ala Ser Arg

Thr Glu Arg Ala Val Leu Ile Asp Glu Val Cys Thr

Met Asn Asp Gly Pro His Ser Ala Leu Tyr Thr Met

Met Lys Asp Gln Tyr Ala Asn Tyr Val Val Gln Lys

Met Ile Asp Val Ala Glu Pro Gly Gln Arg Lys Ile

Val Met His Lys Ile Arg Pro His Ile Ala Thr Leu

Arg Lys Tyr Thr Tyr Gly Lys His Ile Leu Ala Lys

Leu Glu Lys Tyr Tyr Met Lys Asn Gly Val Asp Leu

Gly

PUF (6-2/7-2) has double point mutations (N1043S/Q1047E and S1079N/E1083Q) in repeats 6 and 7, respectively, and recognizes a cognate RNA sequence with two mutations at positions 2 and 3 of the NRE (GU/UG; 5'-UUGAUAUA-3').

A related PUF (6-2) has point mutations (N1043S/Q1047E) in repeats 6, and recognizes a cognate RNA sequence with a mutation at position 3 of the NRE (5'-UGGAUAUA-3').

Another related PUF (7-2) has point mutations (S1079N/E1083Q) in repeats 7, and recognizes a cognate RNA sequence with a mutation at position 2 of the NRE (5'-UUUAUAUA-3').

PUF[531]

(SEQ ID NO: 90)

Gly Arg Ser Arg Leu Leu Glu Asp Phe Arg Asn Asn

Arg Tyr Pro Asn Leu Gln Leu Arg Glu Ile Ala Gly

His Ile Met Glu Phe Ser Gln Asp Gln His Gly Ser

Arg Phe Ile Glu Leu Lys Leu Glu Arg Ala Thr Pro

Ala Glu Arg Gln Leu Val Phe Asn Glu Ile Leu Gln

Ala Ala Tyr Gln Leu Met Val Asp Val Phe Gly Asn

Tyr Val Ile Gln Lys Phe Phe Glu Phe Gly Ser Leu

Glu Gln Lys Leu Ala Leu Ala Glu Arg Ile Arg Gly

His Val Leu Ser Leu Ala Leu Gln Met Tyr Gly Ser

Arg Val Ile Glu Lys Ala Leu Glu Phe Ile Pro Ser

Asp Gln Gln Asn Glu Met Val Arg Glu Leu Asp Gly

His Val Leu Lys Cys Val Lys Asp Gln Asn Gly Asn

His Val Val Gln Lys Cys Ile Glu Cys Val Gln Pro

Gln Ser Leu Gln Phe Ile Ile Asp Ala Phe Lys Gly

Gln Val Phe Ala Leu Ser Thr His Pro Tyr Gly Ser

Arg Val Ile Glu Arg Ile Leu Glu His Cys Leu Pro

Asp Gln Thr Leu Pro Ile Leu Glu Glu Leu His Gln

His Thr Glu Gln Leu Val Gln Asp Gln Tyr Gly Asn

Tyr Val Ile Gln His Val Leu Glu His Gly Arg Pro

Glu Asp Lys Ser Lys Ile Val Ala Glu Ile Arg Gly

Asn Val Leu Val Leu Ser Gln His Lys Phe Ala Ser

Asn Val Val Glu Lys Cys Val Thr His Ala Ser Arg

Thr Glu Arg Ala Val Leu Ile Asp Glu Val Cys Thr

Met Asn Asp Gly Pro His Ser Ala Leu Tyr Thr Met

Met Lys Asp Gln Tyr Ala Asn Tyr Val Val Gln Lys

Met Ile Asp Val Ala Glu Pro Gly Gln Arg Lys Ile

Val Met His Lys Ile Arg Pro His Ile Ala Thr Leu

Arg Lys Tyr Thr Tyr Gly Lys His Ile Leu Ala Lys

Leu Glu Lys Tyr Tyr Met Lys Asn Gly Val Asp Leu

Gly

The PUF domain PUF[531] has mutations (Q867E/Q939E/C935S/Q1011E/C1007S) in wild type PUF rep -continued Arg Val Ile Glu Lys Ala Leu Glu Phe Ile Pro Ser Asp Gln Gln Asn Glu Met Val Arg Glu Leu Asp Gly His Val Leu Lys Cys Val Lys Asp Gln Asn Gly Asn His Val Val Gln Lys Cys Ile Glu Cys Val Gln Pro Gln Ser Leu Gln Phe Ile Ile Asp Ala Phe Lys Gly Gln Val Phe Ala Leu Ser Thr His Pro Tyr Gly Ser Arg Val Ile Glu Arg Ile Leu Glu His Cys Leu Pro Asp Gln Thr Leu Pro Ile Leu Glu Glu Leu His Gln His Thr Glu Gln Leu Val Gln Asp Gln Tyr Gly Ser Tyr Val Ile Glu His Val Leu Glu His Gly Arg Pro Glu Asp Lys Ser Lys Ile Val Ala Glu Ile Arg Gly Asn Val Leu Val Leu Ser Gln His Lys Phe Ala Cys Asn Val Val Gln Lys Cys Val Thr His Ala Ser Arg Thr Glu Arg Ala Val Leu Ile Asp Glu Cys Val Thr Met Asn Asp Gly Pro His Ser Ala Leu Tyr Thr Met Met Lys Asp Gln Tyr Ala Ser Tyr Val Val Glu Lys Met Ile Asp Val Ala Glu Pro Gly Gln Arg Lys Ile Val Met His Lys Ile Arg Pro His Ile Ala Thr Leu Arg Lys Tyr Thr Tyr Gly Lys His Ile Leu Ala Lys Leu Glu Lys Tyr Tyr (SEQ ID NO: 93)
Gly Arg Ser Arg Leu Leu Glu Asp Phe Arg Asn Asn Arg Tyr Pro Asn Leu Gln Leu Arg Glu Ile Ala Gly His Ile Met Glu Phe Ser Gln Asp Gln His Gly Cys Arg Phe Ile Gln Leu Lys Leu Glu Arg Ala Thr Pro Ala Glu Arg Gln Leu Val Phe Asn Glu Ile Leu Gln Ala Ala Tyr Gln Leu Met Val Asp Val Phe Gly Ser Tyr Val Ile Glu Lys Phe Phe Glu Phe Gly Ser Leu Glu Gln Lys Leu Ala Leu Ala Glu Arg Ile Arg Gly His Val Leu Ser Leu Ala Leu Gln Met Tyr Gly Asn Arg Val Ile Gln Lys Ala Leu Glu Phe Ile Pro Ser Asp Gln Gln Asn Glu Met Val Arg Glu Leu Asp Gly His Val Leu Lys Cys Val Lys Asp Gln Asn Gly Asn His Val Val Gln Lys Cys Ile Glu Cys Val Gln Pro Gln Ser Leu Gln Phe Ile Ile Asp Ala Phe Lys Gly Gln Val Phe Ala Leu Ser Thr His Pro Tyr Gly Cys Arg Val Ile Gln Arg Ile Leu Glu His Cys Leu Pro Asp Gln Thr Leu Pro Ile Leu Glu Glu Leu His Gln His Thr Glu Gln Leu Val Gln Asp Gln Tyr Gly Ser Tyr Val Ile Glu His Val Leu Glu His Gly Arg Pro Glu Asp Lys Ser Lys Ile Val Ala Glu Ile Arg Gly Asn Val Leu Val Leu Ser Gln His Lys Phe Ala Cys Asn Val Val Gln Lys Cys Val Thr His Ala Ser Arg Thr Glu Arg Ala Val Leu Ile Asp Glu Cys Val Thr Met Asn Asp Gly Pro His Ser Ala Leu Tyr Thr Met Met Lys Asp Gln Tyr Ala Cys Tyr Val Val Gln Lys Met Ile Asp Val Ala Glu Pro Gly Gln Arg Lys Ile Val Met His Lys Ile Arg Pro His Ile Ala Thr Leu Arg Lys Tyr Thr Tyr Gly Lys His Ile Leu Ala Lys Leu Glu Lys Tyr Tyr According to the invention, heterologous polypeptide (also referred to as a "fusion partner") can be fused to the PUF domain of the invention that binds to at least one of the PBS on the subject polynucleotide. In addition, if desired, the same or different fusion partner can also optionally be fused to the Cas9 protein (e.g., wt, nickase, or dCas9 protein). Thus as described herein, unless specifically disclaimed, any of the fusion partners are intended to be fused to PUF domain, and optionally also fused to the Cas9 protein (e.g., wt, nickase, or dCas9 protein). The fusion partner fused to the PUF domain can be the same or different from the optional fusion partner fused to the Cas9 protein (e.g., wt, nickase, or dCas9 protein) (infra).

The fusion partner may exhibit an activity (e.g., enzymatic activity). Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying the DNA directly (e.g., methylation of DNA) or at modifying a DNA-associated polypeptide (e.g., a histone or DNA binding protein).

| Protein name | Function |
|---|---|
| Transcriptional Activators | |
| GAL4 | Transcription activation |
| VP16 | Transcription activation |
| VP64 | Transcription activation |
| p65 subdomain (NFkB) | Transcription activation |

-continued

| Protein name | Function |
|---|---|
| Transcriptional repressers | |
| KRAB | Transcription repression |
| Mad mSIN3 interaction domain (SID) | Transcription repression |
| the ERF repressor domain (ERD) | Transcription repression |
| Histone lysine methyltransferases (KMT) | |
| KMT1 family: SUV39H1, SUV39H2, G9A, ESET/SETDB1, and homologs (Clr4, Su(var)3-9) | Heterochromatin formation/ transcription repression |
| KMT2 family: hSET1A, hSET1B, MLL1 to 5, ASH1, and homologs (Trx, Trr, Ash1) | Transcription activation |
| KMT3 family: SYMD2, NSD1 | Transcription activation |
| KMT4: DOT1L and homologs | Transcription activation |
| KMT5 family: Pr-SET7/8, SUV4-20H1, and homologs (PR-set7, Suv4-20, Set9) | DNA damage response, transcription repression |
| KMT6: EZH2 | Polycomb silencing |
| KMT8: RIZ1 | Transcription repression |
| Histone lysine demethylates (KDM) | |
| KDM1: LSD1/BHC110 and homologs (SpLsd1/Swm1/Saf110, Su(var)3-3) | Transcription activation and repression, heterochromatin formation |
| KDM3 family: JHDM2a/b | Androgen receptor gene activation, spermatogenesis |
| KDM4 family: JMJD2A/JHDM3A, JMJD2B, JMJD2C/GASC1, JMJD2D, and homologs (Rph1) | Transcription elongation, transcription repression, heterochromatin formation, genome integrity |
| KDM5 family: JARID1A/RBP2, JARID1B/PLU-1, JARID1C/SMCX, JARID1D/SMCY, and homologs (Lid, Jhn2, Jmj2) | Transcription repression |
| KDM6 family: UTX, JMJD3 | Transcription activation |
| Histone lysine acetyltransferases (KAT) | |
| KAT2 family: hGCN5, PCAF, and homologs (dGCN5/PCAF, Gcn5) | Transcription activation, DNA repair |
| KAT3 family: CBP, p300, and homologs (dCBP/NEJ) | Transcription activation, DNA repair |
| KAT4: TAF1 and homologs (dTAF1) | Transcription activation |
| KAT5: TIP60/PLIP, and homologs | Transcription activation, DNA repair |
| KAT6: MOZ/MYST3, MORF/MYST4, and homologs (Mst2, Sas3, CG1894) | Transcription activation and elongation, DNA replication |
| KAT7: HBO1/MYST2, and homologs (CHM, Mst2) | Transcription, DNA replication |
| KAT8: HMOF/MYST1, and homologs (dMOF, CG1894, Sas2, Mst2) | Chromatin boundaries, dosage compensation, DNA repair |
| KAT13 family: SRC1, ACTR, P160, CLOCK, and homologs | Transcription activation |
| Histone lysine deacetylases | |
| Class I: HDAC1, HDAC2, HDAC3, HDAC8, and its homologs (Rpd3, Hos1, Cir6) | Transcription repression, heterochromatin formation |
| Class IIa: HDAC4, HDAC5, HDAC7, HDAC9, and its homologs (Hda1, Cir3 etc.) | Transcription repression, heterochromatin formation |
| Class III: SIRT1, SIRT2, and its homologs (Sir2, Hst1, Hst2, Hst3, Hst4) | Transcription repression, heterochromatin formation |
| Class IV: HDAC11 | Transcription repression |
| DNA methylases (adenosine or cytosine modification) | |
| Dam (*E. coli*) | Restriction system |
| Dcm (*E. coli*) | Restriction system |
| M. SssI (*Spiroplasma* sp) | Restriction system |
| DNMT1 | Transcription repression. imprinting, heterochromatin formation |
| DNMT3a/DNMT3b, MET1, DRM3 (plants), and homologs | Transcription repression. imprinting, heterochromatin formation |
| Chromomethylases e.g. ZMET2, CMT1, CMT2 (plants) | Transcription repression. imprinting, heterochromatin formation |
| DNA demethylases | |
| AID/Apobec deaminase family: AID | Transcription activation, genome integrity |
| TET dioxygenase family: TET1 | Transcription activation, genome integrity |
| DEMETER glycosylase family: DME, DML1, DML2, ROS1 | Transcription activation, genome integrity |
| Boundary elements | |
| CTCF | Chromatin insulation, heterochromatin spreading suppression |

-continued

| Protein name | Function |
| --- | --- |
| Periphery recruitment elements | |
| Lamin A | Transcription repression |
| Lamin B | Transcription repression |
| Protein docking elements | |
| FKBP/FRB (*S. pombe*) | rapamycin dependent recruitment |
| Pil1/Aby1 (*E. coli*) | ABA dependent recruitment |

Additional fusion partners may include the various fluorescent protein, polypeptides, variants, or functional domains thereof, such as GFP, Superfolder GFP, EGFP, BFP, EBFP, EBFP2, Azurite, mKalama1, CFP, ECFP, Cerulean, CyPet, mTurquoise2, YFP, Citrine, Venus, Ypet, BFPms1, roGFP, and bilirubin-inducible fluorescent proteins such as UnaG, dsRed, eqFP611, Dronpa, TagRFPs, KFP, EosFP, Dendra, IrisFP, etc.

Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Abyl, etc.).

Additional non-limiting examples of fusion partners to accomplish increased or decreased transcription are listed below, and include transcription activator and transcription repressor domains (e.g., the Kruppel associated box (KRAB or SKD); the Mad mSIN3 interaction domain (SID); the ERF repressor domain (ERD), etc.).

In some embodiments, the heterologous sequence can be fused to the C-terminus of the PUF domain or Cas9 protein (e.g., wt, nickase, or dCas9 protein). In some embodiments, the heterologous sequence can be fused to the N-terminus of the PUF domain or Cas9 protein (e.g., wt, nickase, or dCas9 protein). In some embodiments, the heterologous sequence can be fused to an internal portion (i.e., a portion other than the N- or C-terminus) of the PUF domain or Cas9 protein (e.g., wt, nickase, or dCas9 protein).

In some embodiments, a PUF domain fusion is generated by fusing a PUF domain with a heterologous sequence that provides for subcellular localization (i.e., the heterologous sequence is a subcellular localization sequence, e.g., a nuclear localization signal (NLS, such as PPKKKRKV (SEQ ID NO: 94)) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6xHis tag (SEQ ID NO: 95); a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some cases is controllable (e.g., a temperature sensitive or drug controllable degron sequence, see below). In some embodiments, the heterologous sequence can provide for increased or decreased transcription from the target DNA (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a chimeric PUF domain or Cas9 protein (e.g., wt, nickase, or dCas9 protein) to bind to another protein of interest, e.g., a DNA or histone modifying protein, a transcription factor or transcription repressor, a recruiting protein, etc.).

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled at least in part by the degron sequence. In some cases, a suitable degron is constitutive such that the degron exerts its influence on protein stability independent of experimental control (i.e., the degron is not drug inducible, temperature inducible, etc.). In some cases, the degron provides the PUF domain or Cas9 protein (e.g., wt, nickase, or dCas9 protein) with controllable stability such that the PUF domain or Cas9 protein (e.g., wt, nickase, or dCas9 protein) can be turned "on" (i.e., stable) or "off" (i.e., unstable, degraded) depending on the desired conditions. For example, if the degron is a temperature sensitive degron, the PUF domain or Cas9 protein (e.g., wt, nickase, or dCas9 protein) may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non- functional (i.e., "off, degraded) above the threshold temperature. As another example, if the degron is a drug inducible degron, the presence or absence of drug can switch the protein from an "off (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., *Science*, 263(5151): 1273-1276, 1994: "Heat-inducible degron: a method for constructing temperature-sensitive mutants"; Schoeber et al., *Am. J. Physiol. Renal. Physiol.*, 296(1): F204-211, 2009: "Conditional fast expression and function of multimeric TRPV5 channels using Shield-1"; Chu et al., *Bioorg. Med. Chem. Lett.*, 18(22): 5941-4, 2008: "Recent progress with FKBP-derived destabilizing domains"; Kanemaki, *Pflugers Arch.*, 2012: "Frontiers of protein expression control with conditional degrons"; Yang et al., *Mol. Cell.*, 48(4):487-8, 2012: "Titivated for destruction: the methyl degron"; Barbour et al., *Biosci. Rep.,* 33(1), 2013: "Characterization of the bipartite degron that regulates ubiquitin-independent degradation of thymidylate synthase"; and Greussing et al., *J. Vis. Exp.,* (69), 2012: "Monitoring of ubiquitin-proteasome activity in living cells using a Degron (dgn)-destabilized green fluorescent protein (GFP)-based reporter protein"; all of which are incorporated in their entirety by reference).

Exemplary degron sequences have been well-characterized and tested in both cells and animals. Thus, fusing Cas9 protein (e.g., wt, nickase, or dCas9 protein) to a degron sequence produces a "tunable" and "inducible" PUF domain or Cas9 (e.g., wt, nickase, or dCas9 protein). Any of the fusion partners described herein can be used in any desirable combination.

As one non-limiting example to illustrate, each PUF domain can be independently fused to the same or different fusion partners, and they may bind in any order on the series of PBS of the subject polynucleotide. For example, one PUF domain can be fused to a YFP sequence for detection, a second PUF domain fused to a degron sequence for stability, and a third PUF domain fused to a transcription activator sequence to increase transcription of the target DNA. Any of these types of PUF domain fusions can have more than 1 binding sites or PBS on the subject polynucleotide, in any desired order. The number of fusion partners that can be used in the PUF domain fusions is largely unlimited (e.g., at least 2, 5, 10, 20, 30, 40, 50 or more).

In some embodiments, any PUF domain or Cas9 protein (e.g., wt, nickase, or dCas9 protein) fusion protein may comprises one or more (e.g. two or more, three or more, four or more, or five or more) heterologous sequences or fusion partners.

In some embodiments, any of the subject Cas9 protein (e.g., wt, nickase, or dCas9 protein) or PUF domain fusions can be codon-optimized. This type of optimization is known in the art and entails the mutation of foreign-derived DNA to mimic the codon preferences of the intended host organism or cell while encoding the same protein. Thus, the codons are changed, but the encoded protein remains unchanged. For example, if the intended target cell was a human cell, a human codon-optimized PUF domain or Cas9 protein (e.g., wt, nickase, or dCas9 protein) fusion would be a better suited PUF domain or Cas9 protein (e.g., wt, nickase, or dCas9 protein) fusion. As another non-limiting example, if the intended host cell were a mouse cell, than a mouse codon-optimized PUF domain fusion or Cas9 protein (e.g., wt, nickase, or dCas9 protein) would be a suitable PUF domain fusion or Cas9 protein (e.g., wt, nickase, or dCas9 protein). While codon optimization is not required, it is acceptable and may be preferable in certain cases.

Any of the subject PUF domain can be made using, for example, a Golden Gate Assembly kit (see Abil et al., *Journal of Biological Engineering* 8:7, 2014), which is available at Addgene (Kit #1000000051).

5. Modulation of Transcription

The PUF domain and/or Cas9 protein (e.g., wt, nickase, or dCas9 protein) fusion protein of the invention is targeted by the DNA-targeting sequence of the subject polynucleotide to a specific location (i.e., target polynucleotide sequence) in the target DNA, and exerts locus-specific regulation, such as blocking RNA polymerase binding to a promoter (which selectively inhibits transcription activator function), and/or modifying the local chromatin status (e.g., when a fusion sequence is used that modifies the target DNA or modifies a polypeptide associated with the target DNA). In some cases, the changes are transient (e.g., transcription repression or activation). In some cases, the changes are inheritable (e.g., when epigenetic modifications are made to the target DNA or to proteins associated with the target DNA, e.g., nucleosomal histones).

The biological effects of a method using a subject PUF domain or Cas9 protein (e.g., wt, nickase, or dCas9 protein) fusion protein can be detected by any convenient method (e.g., gene expression assays; chromatin-based assays, e.g., Chromatin immunoPrecipitation (ChiP), Chromatin in vivo Assay (CiA), etc.; and the like).

In some cases, a subject method involves using two or more different DNA-targeting sequences. For example, two different DNA-targeting sequences can be used in a single host cell, where the two different DNA-targeting sequences target two different target polynucleotide sequences in the same target nucleic acid. Thus, for example, a subject transcriptional modulation method can further comprise introducing into the host cell a second DNA-targeting sequence, or a nucleic acid comprising a nucleotide sequence encoding the second DNA-targeting sequence. In some cases, use of two different DNA-targeting sequences targeting two different targeting sequences in the same target nucleic acid provides for increased modulation (e.g., reduction or increase) in transcription of the target nucleic acid.

As another example, two different DNA-targeting sequences can be used in a single host cell, where the two different DNA-targeting sequences target two different target nucleic acids.

Thus, in certain embodiments, a transcription modulation method of the present invention provides for selective modulation (e.g., reduction or increase) of a target nucleic acid in a host cell. For example, "selective" reduction of transcription of a target nucleic acid reduces transcription of the target nucleic acid by at least about 10%, at least about 20%, at least about 30%, at least about 40%, at least about 50%, at least about 60%, at least about 70%, at least about 80%, at least about 90%, or greater than 90%, compared to the level of transcription of the target nucleic acid in the absence of a DNA-targeting sequence/modified Cas9 polypeptide/PUF domain-fusion complex. Selective reduction of transcription of a target nucleic acid reduces transcription of the target nucleic acid, but does not substantially reduce transcription of a non-target nucleic acid, e.g., transcription of a non-target nucleic acid is reduced, if at all, by less than 10% compared to the level of transcription of the non-target nucleic acid in the absence of the DNA-targeting sequence/modified Cas9 polypeptide/PUF domain-fusion complex.

On the other hand, "selective" increased transcription of a target DNA can increase transcription of the target DNA by at least about 1.1 fold (e.g., at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 12 fold, at least about 15 fold, or at least about 20-fold) compared to the level of transcription of the target DNA in the absence of the DNA-targeting sequence/modified Cas9 polypeptide/PUF domain-fusion complex. Selective increase of transcription of a target DNA increases transcription of the target DNA, but does not substantially increase transcription of a non-target DNA, e.g., transcription of a non-target DNA is increased, if at all, by less than about 5-fold (e.g., less than about 4-fold, less than about 3-fold, less than about 2-fold, less than about 1.8-fold, less than about 1.6-fold, less than about 1.4-fold, less than about 1.2-fold, or less than about 1.1-fold) compared to the level of transcription of the non-targeted DNA in the absence of the DNA-targeting sequence/modified Cas9 polypeptide/PUF domain-fusion complex.

As a non-limiting example, increased transcription can be achieved by fusing dCas9 to a heterologous sequence, and/or by fusing the heterologous sequence to one of the PUF domains that binds to a PBS of the subject polynucleotide. Suitable fusion partners include, but are not limited to, a polypeptide that provides an activity that indirectly increases transcription by acting directly on the target DNA or on a polypeptide (e.g., a histone or other DNA-binding protein) associated with the target DNA. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). See section entitled "PUF domain (and the optional dCas9) Fusion Proteins."

A non-limiting example of a subject method using a dCas9 fusion protein and/or a PUF domain-fusion protein to increase transcription in a prokaryote includes a modification of the bacterial one-hybrid (B1H) or two-hybrid (B2H) system. In the B1H system, a DNA binding domain (BD) is fused to a bacterial transcription activation domain (AD, e.g., the alpha subunit of the *E. coli* RNA polymerase (RNAPα)). Thus, a subject dCas9 or PUF domain can be fused to a heterologous sequence comprising an AD. When the subject dCas9 or PUF domain fusion protein arrives at the upstream region of a promoter (targeted there by the DNA-targeting sequence) the AD (e.g., RNAPα) of the dCas9 or PUF domain fusion protein recruits the RAP holoenzyme, leading to transcription activation. In the B2H system, the BD is not directly fused to the AD; instead, their interaction is mediated by a protein-protein interaction (e.g., GAL11P-GAL4 interaction). To modify such a system for use in the subject methods, dCas9 or PUF domain can be fused to a first protein sequence that provides for protein-protein interaction (e.g., the yeast GAL11P and/or GAL4 protein) and RNAPα can be fused to a second protein sequence that completes the protein-protein interaction (e.g., GAL4 if GAL11P is fused to dCas9 or PUF domain, GAL11P if GAL4 is fused to dCas9 or PUF domain, etc.). The binding affinity between GAL11P and GAL4 increases the efficiency of binding and transcription rate.

A non-limiting example of a subject method using a dCas9 and/or PUF domain fusion protein to increase transcription in a eukaryotes includes fusion of dCas9 and/or PUF domain to an activation domain (AD) (e.g., GAL4, herpesvirus activation protein VP16 or VP64, human nuclear factor NF-κB p65 subunit, etc.). To render the system inducible, expression of the dCas9/PUF domain fusion protein can be controlled by an inducible promoter (e.g., Tet-ON, Tet-OFF, etc.). The DNA-targeting sequence can be designed to target known transcription response elements (e.g., promoters, enhancers, etc.), known upstream activating sequences (UAS), sequences of unknown or known function that are suspected of being able to control expression of the target DNA, etc.

In some embodiments, multiple subject polynucleotides are used simultaneously in the same cell to simultaneously modulate transcription at different locations on the same target DNA or on different target DNAs. In some embodiments, two or more subject polynucleotides target the same gene or transcript or locus. In some embodiments, two or more subject polynucleotides target different unrelated loci. In some embodiments, two or more subject polynucleotides target different, but related loci.

Because the subject polynucleotides are small and robust, they can be simultaneously present on the same expression vector and can even be under the same transcriptional control if so desired. In some embodiments, two or more (e.g., 3 or more, 4 or more, 5 or more, 10 or more, 15 or more, 20 or more, 25 or more, 30 or more, 35 or more, 40 or more, 45 or more, or 50 or more) subject polynucleotides are simultaneously expressed in a target cell, from the same or different vectors. The expressed subject polynucleotides can be differently recognized by orthogonal dCas9 proteins from different bacteria, such as *S. pyogenes, S. thermophilus, L. innocua*, and *N. meningitidis*.

To express multiple subject polynucleotides, an artificial RNA processing system mediated by the Csy4 endoribonuclease can be used. Multiple subject polynucleotides can be concatenated into a tandem array on a precursor transcript (e.g., expressed from a U6 promoter), and separated by Csy4-specific RNA sequence. Co-expressed Csy4 protein cleaves the precursor transcript into multiple subject polynucleotides. Advantages for using an RNA processing system include: first, there is no need to use multiple promoters or vectors; second, since all subject polynucleotides are processed from a precursor transcript, their concentrations are normalized for similar wt Cas9/Cas9 nickase/dCas9-binding.

Csy4 is a small endoribonuclease (RNase) protein derived from bacteria *Pseudomonas aeruginosa*. Csy4 specifically recognizes a minimal 17-bp RNA hairpin, and exhibits rapid (<1 min) and highly efficient (>99.9) RNA cleavage. Unlike most RNases, the cleaved RNA fragment remains stable and functionally active. The Csy4-based RNA cleavage can be repurposed into an artificial RNA processing system. In this system, the 17-bp RNA hairpins are inserted between multiple RNA fragments that are transcribed as a precursor transcript from a single promoter. Co-expression of Csy4 is effective in generating individual RNA fragments.

6. Host Cells

A method of the present invention to modulate transcription may be employed to induce transcriptional modulation in mitotic or post-mitotic cells in vivo and/or ex vivo and/or in vitro. Because the subject polynucleotide provides specificity by hybridizing to target polynucleotide sequence of a target DNA, a mitotic and/or post-mitotic cell can be any of a variety of host cell, where suitable host cells include, but are not limited to, a bacterial cell; an archaeal cell; a single-celled eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell; an animal cell; a cell from an invertebrate animal (e.g., an insect, a cnidarian, an echinoderm, a nematode, etc.); a eukaryotic parasite (e.g., a malarial parasite, e.g., *Plasmodium falciparum*, a helminth; etc.); a cell from a vertebrate animal (e.g., fish, amphibian, reptile, bird, mammal); a mammalian cell, e.g., a rodent cell, a human cell, a non-human primate cell, etc. Suitable host cells include naturally-occurring cells; genetically modified cells (e.g., cells genetically modified in a laboratory, e.g., by the "hand of man"); and cells manipulated in vitro in any way. In some cases, a host cell is isolated or cultured.

Any type of cell may be of interest (e.g., a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells," "primary cell lines," and "primary cultures" are used interchangeably herein to refer to cells and cells cultures that have been derived from a subject and allowed to grow in vitro for a limited number of passages, i.e. splittings, of the culture. For example, primary cultures include cultures that may have been passaged 0 times, 1 time, 2 times, 4 times, 5 times, 10 times, or 15 times, but not enough times go through the crisis stage. Primary cell lines can be are maintained for fewer than 10 passages in vitro. Target cells are in many embodiments unicellular organisms, or are grown in culture.

If the cells are primary cells, such cells may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, e.g., from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% dimethyl sulfoxide (DMSO), 50% serum, 40% buffered medium, or other solutions commonly used in the art to preserve cells at such freezing temperatures, and thawed in a manner as commonly known in the art for thawing frozen cultured cells.

7. Introducing Nucleic Acid into a Host Cell

A subject polynucleotide, a nucleic acid comprising a nucleotide sequence encoding same, or a nucleic acid comprising a nucleotide sequence encoding the subject Cas9 protein (e.g., wt, nickase, or dCas9 protein) or PUF domain fusion, can be introduced into a host cell by any of a variety of well-known methods.

Methods of introducing a nucleic acid into a host cell are known in the art, and any known method can be used to introduce a nucleic acid (e.g., vector or expression construct) into a stem cell or progenitor cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., *Adv. Drug Deliv. Rev.*, pii: S0169-409X(12) 00283-9.doi:10.1016/j.addr.2012.09.023), and the like.

Thus the present invention also provides an isolated nucleic acid comprising a nucleotide sequence encoding a subject polynucleotide. In some cases, a subject nucleic acid also comprises a nucleotide sequence encoding a subject Cas9 protein (e.g., wt, nickase, or dCas9 protein) and/or a subject PUF domain fusion.

In some embodiments, a subject method involves introducing into a host cell (or a population of host cells) one or more nucleic acids (e.g., vectors) comprising nucleotide sequences encoding a subject polynucleotide and/or a subject Cas9 protein (e.g., wt, nickase, or dCas9 protein) and/or a subject PUF domain fusion. In some embodiments a host cell comprising a target DNA is in vitro. In some embodiments a host cell comprising a target DNA is in vivo. Suitable nucleic acids comprising nucleotide sequences encoding a subject polynucleotide and/or a subject Cas9 protein (e.g., wt, nickase, or dCas9 protein) and/or a subject PUF domain fusion include expression vectors, where the expression vectors may be recombinant expression vector.

In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see, e.g., Li et al., *Invest Opthalmol. Vis. Sci.*, 35:2543-2549, 1994; Borras et al., *Gene Ther.*, 6:515-524, 1999; Li and Davidson, *Proc. Natl. Acad. Sci. USA*, 92:7700-7704, 1995; Sakamoto et al., *Hum. Gene Ther.*, 5:1088-1097, 1999; WO 94/12649, WO 93/03769; WO 93/19191; WO 94/28938; WO 95/11984 and WO 95/00655); adeno-associated virus (see, e.g., Ali et al., *Hum. Gene Ther.*, 9:81-86, 1998, Flannery et al., *Proc. Natl. Acad. Sci. USA*, 94:6916-6921, 1997; Bennett et al., *Invest Opthalmol Vis Sci* 38:2857-2863, 1997; Jomary et al., *Gene Ther.*, 4:683-690, 1997, Rolling et al., *Hum. Gene Ther.*, 10:641-648, 1999; Ali et al., *Hum. Mol. Genet.*, 5:591-594, 1996; Srivastava in WO 93/09239, Samulski et al., *J. Vir.*, 63:3822-3828, 1989; Mendelson et al., *Virol.*, 166: 154-165, 1988; and Flotte et al., *Proc. Natl. Acad. Sci. USA*, 90: 10613-10617, 1993); SV40; herpes simplex virus; human immunodeficiency virus (see, e.g., Miyoshi et al., *Proc. Natl. Acad. Sci. USA*, 94: 10319-23, 1997; Takahashi et al., *J. Virol.*, 73:7812-7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, HIV virus, myeloproliferative sarcoma virus, and mammary tumor virus); and the like.

Numerous suitable expression vectors are known to those skilled in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al., *Methods in Enzymology*, 153:516-544, 1987).

In some embodiments, a nucleotide sequence encoding a subject polynucleotide and/or a subject Cas9 protein (e.g., wt, nickase, or dCas9 protein) and/or a subject PUF domain fusion is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a subject polynucleotide and/or a subject Cas9 protein (e.g., wt, nickase, or dCas9 protein) and/or a subject PUF domain fusion is operably linked to multiple control elements that allow expression of the nucleotide sequence encoding the subject polynucleotide and/or a subject Cas9 protein (e.g., wt, nickase, or dCas9 protein) and/or a subject PUF domain fusion in both prokaryotic and eukaryotic cells.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.) (e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., *Nature Biotech.*, 20:497-500, 2002), an enhanced U6 promoter (e.g., Xia et al., *Nucleic Acids Res.*, 31(17):e100, 2003), a human HI promoter (HI), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter (e.g., Tet-ON, Tet-OFF, etc.), Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a subject Cas9 protein (e.g., wt, nickase, or dCas9 protein) or PUF domain fusion in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g., EMBL HSEN02, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al., *Cell*, 51:7-19, 1987; and Llewellyn et al., *Nat. Med.*, 16(10): 1161-1166, 2010); a serotonin receptor promoter (see, e.g., GenBank S62283); a tyrosine hydroxylase promoter (TH) (see, e.g., Oh et al., *Gene Ther.*, 16:437, 2009; Sasaoka et al., *Mol. Brain Res.*, 16:274, 1992; Boundy et al., *Neurosci.*, 18:9989, 1998; and Kaneda et al., *Neuron*, 6:583-594, 1991); a GnRH promoter (see, e.g., Radovick et al., *Proc. Natl. Acad. Sci. USA*, 88:3402-3406, 1991); an L7 promoter (see, e.g., Oberdick et al., *Science*, 248:223-226, 1990); a DNMT promoter (see, e.g., Bartge et al., *Proc. Natl. Acad. Sci. USA*, 85:3648-3652, 1988); an enkephalin promoter (see, e.g., Comb et al., *EMBO J.*, 17:3793-3805, 1988); a myelin basic protein (MBP) promoter; a $Ca^{2+}$-calmodulin-dependent protein kinase II-alpha (CamKIIa) promoter (see, e.g., Mayford et al., *Proc. Natl. Acad. Sci. USA*, 93: 13250, 1996; and Casanova et al., *Genesis*, 31:37, 2001); a CMV enhancer/platelet-derived growth factor-β promoter (see, e.g., Liu et al., *Gene Therapy*, 11:52-60, 2004); and the like.

Adipocyte-specific spatially restricted promoters include, but are not limited to aP2 gene promoter/enhancer, e.g., a region from −5.4 kb to +21 bp of a human aP2 gene (see, e.g., Tozzo et al., *Endocrinol.* 138: 1604, 1997; Ross et al., *Proc. Natl. Acad. Sci. USA*, 87:9590, 1990; and Pavjani et al., *Nat. Med.*, 11:797, 2005); a glucose transporter-4 (GLUT4) promoter (see, e.g., Knight et al., *Proc. Natl. Acad. Sci. USA*, 100: 14725, 2003); a fatty acid translocase (FAT/CD36) promoter (see, e.g., Kuriki et al., *Biol. Pharm. Bull.*, 25: 1476, 2002; and Sato et al., *Biol. Chem.* 277: 15703, 2002); a stearoyl-CoA desaturase-1 (SCD1) promoter (Tabor et al., *Biol. Chem.* 274:20603, 1999); a leptin promoter (see, e.g., Mason et al., *Endocrinol.* 139: 1013, 1998; and Chen et al., *Biochem. Biophys. Res. Comm.*, 262: 187, 1999); an adiponectin promoter (see, e.g., Kita et al., *Biochem. Biophys. Res. Comm.*, 331:484, 2005; and Chakrabarti, *Endocrinol.* 151:2408, 2010); an adipsin promoter (see, e.g., Piatt et al., *Proc. Natl. Acad. Sci. USA*, 86:7490, 1989); a resistin promoter (see, e.g., Seo et al., *Molec. Endocrinol.*, 17: 1522, 2003); and the like.

Cardiomyocyte-specific spatially restricted promoters include, but are not limited to control sequences derived from the following genes: myosin light chain-2, a-myosin heavy chain, AE3, cardiac troponin C, cardiac actin, and the like. Franz et al., *Cardiovasc. Res.*, 35:560-566, 1997; Robbins et al., *Ann. N.Y. Acad. Sci.*, 752:492-505, 1995; Linn et al., *Circ. Res.*, 76:584-591, 1995; Parmacek et al., *Mol. Cell. Biol.*, 14:1870-1885, 1994; Hunter et al., *Hyper-*

*tension*, 22:608-617, 1993; and Sartorelli et al., *Proc. Natl. Acad. Sci.*, 89:4047-4051, 1992.

Smooth muscle-specific spatially restricted promoters include, but are not limited to an SM22a promoter (see, e.g., Akyurek et al., *Mol. Med.*, 6:983, 2000; and U.S. Pat. No. 7,169,874); a smoothelin promoter (see, e.g., WO 2001/018048); an a-smooth muscle actin promoter; and the like. For example, a 0.4 kb region of the SM22a promoter, within which lie two CArG elements, has been shown to mediate vascular smooth muscle cell-specific expression (see, e.g., Kim et al., *Mol. Cell. Biol.*, 17:2266-2278, 1997; Li et al., *J. Cell Biol.*, 132:849-859, 1996; and Moessler et al., *Development*, 122:2415-2425, 1996).

Photoreceptor-specific spatially restricted promoters include, but are not limited to, a rhodopsin promoter; a rhodopsin kinase promoter (Young et al., *Ophthalmol. Vis. Sci.*, 44:4076, 2003); a beta phosphodiesterase gene promoter (Nicoud et al., *Gene Med.*, 9: 1015, 2007); a retinitis pigmentosa gene promoter (Nicoud et al., 2007, supra); an interphotoreceptor retinoid-binding protein (IRBP) gene enhancer (Nicoud et al. (2007) supra); an IRBP gene promoter (Yokoyama et al., *Exp. Eye Res.*, 55:225, 1992); and the like.

8. Libraries

The present invention also provides a plurality or library of the subject polynucleotide sequences, or a plurality or library of the vectors encoding the same. The latter may comprise a library of recombinant expression vectors comprising nucleotides encoding the subject polynucleotides.

A subject library can comprise from about 10 individual members to about $10^{12}$ individual members; e.g., a subject library can comprise from about 10 individual members to about $10^2$ individual members, from about $10^2$ individual members to about $10^3$ individual members, from about $10^3$ individual members to about $10^5$ individual members, from about $10^5$ individual members to about $10^7$ individual members, from about $10^7$ individual members to about $10^9$ individual members, or from about $10^9$ individual members to about $10^{12}$ individual members.

In certain embodiments, two of the vectors differ in the encoded polynucleotides in their respective DNA-targeting sequences, Cas9-binding sequences, and/or the copy number, identity (e.g., sequence, or binding specificity), or relative order of the PBS.

For example, in certain embodiments, an "individual member" of a subject library differs from other members of the library in the nucleotide sequence of the DNA-targeting sequence of the subject polynucleotide. Thus, e.g., each individual member of a subject library can comprise the same or substantially the same nucleotide sequence of the Cas9-binding sequence as all other members of the library; and can comprise the same or substantially the same nucleotide sequence of the PBS as all other members of the library; but differs from other members of the library in the nucleotide sequence of the DNA-targeting sequence of the subject polynucleotide. In this way, the library can comprise members that bind to different target polynucleotide sequences that are either on the same target gene or on different target genes.

In a related embodiment, members of the library may differ such that different DNA-targeting sequences are associated with different PBS, such that different target DNA can be independently regulated—e.g., some target genes are transcriptionally activated (and optionally labeled by a first fluorescent color), while others are transcriptionally repressed (and optionally labeled by a second fluorescent color).

In certain other embodiments, an individual member of a subject library differs from other members of the library in the nucleotide sequence of the Cas9-binding sequence of the subject polynucleotide. Thus, e.g., each individual member of a subject library can comprise the same or substantially the same nucleotide sequence of the DNA-targeting sequence as all other members of the library; and can comprise the same or substantially the same nucleotide sequence of the PBS as all other members of the library; but differs from other members of the library in the nucleotide sequence of the Cas9-binding sequence of the subject polynucleotide. In this way, the library can comprise members that bind to different orthogonal Cas9 protein (e.g., wt, nickase, or dCas9 protein) from different species, allowing separately and parallelly regulatable systems in the same host cell.

In certain other embodiments, an individual member of a subject library differs from other members of the library in the nucleotide sequence of the PBS of the subject polynucleotide. Thus, e.g., each individual member of a subject library can comprise the same or substantially the same nucleotide sequence of the DNA-targeting sequence as all other members of the library; and can comprise the same or substantially the same nucleotide sequence of the Cas9-binding sequence as all other members of the library; but differs from other members of the library in the nucleotide sequence of the PBS of the subject polynucleotide.

9. Exemplary Utilities

A method for modulating transcription according to the present invention finds use in a variety of applications, including research applications; diagnostic applications; industrial applications; and treatment applications.

Research applications may include, e.g., determining the effect of reducing or increasing transcription of a target nucleic acid on, e.g., development, metabolism, expression of a downstream gene, and the like.

High through-put genomic analysis can be carried out using a subject transcription modulation method, in which only the DNA-targeting sequence of the subject polynucleotide needs to be varied, while the Cas9-binding sequence and the PBS can (in some cases) be held constant. A library (e.g., a subject library) comprising a plurality of nucleic acids used in the genomic analysis would include: a promoter operably linked to a subject polynucleotide-encoding nucleotide sequence, where each nucleic acid would include a different DNA-targeting sequence, a common Cas9-binding sequence, and a common PBS. A chip could contain over $5 \times 10^4$ unique polynucleotide of the invention.

Applications would include large-scale phenotyping, gene-to-function mapping, and meta-genomic analysis.

The subject methods disclosed herein can also find use in the field of metabolic engineering. Because transcription levels can be efficiently and predictably controlled by designing an appropriate DNA-targeting RNA, as disclosed herein, the activity of metabolic pathways (e.g., biosynthetic pathways) can be precisely controlled and tuned by controlling the level of specific enzymes (e.g., via increased or decreased transcription) within a metabolic pathway of interest. Metabolic pathways of interest include those used for chemical (fine chemicals, fuel, antibiotics, toxins, agonists, antagonists, etc.) and/or drug production.

Biosynthetic pathways of interest include but are not limited to (1) the mevalonate pathway (e.g., HMG-CoA reductase pathway) (converts acetyl-CoA to dimethylallyl pyrophosphate (DMAPP) and isopentenyl pyrophosphate (IPP), which are used for the biosynthesis of a wide variety of biomolecules including terpenoids/isoprenoids), (2) the non-mevalonate pathway (i.e., the "2-C-methyl-D-erythritol 4-phosphate/1-deoxy-D-xylulose 5-phosphate pathway" or "MEP/DOXP pathway" or "DXP pathway") (also produces DMAPP and IPP, instead by converting pyruvate and glyceraldehyde 3-phosphate into DMAPP and IPP via an alternative pathway to the mevalonate pathway), (3) the polyketide synthesis pathway (produces a variety of polyketides via a variety of polyketide synthase enzymes. Polyketides include naturally occurring small molecules used for chemotherapy (e. g., tetracyclin, and macrolides) and industrially important polyketides include rapamycin (immunosuppressant), erythromycin (antibiotic), lovastatin (anticholesterol drug), and epothilone B (anticancer drug)), (4) fatty acid synthesis pathways, (5) the DAHP (3-deoxy-D-arabino-heptulosonate 7-phosphate) synthesis pathway, (6) pathways that produce potential biofuels (such as short-chain alcohols and alkane, fatty acid methyl esters and fatty alcohols, isoprenoids, etc.), etc.

The methods disclosed herein can also be used to design integrated networks (i.e., a cascade or cascades) of control. For example, a subject polynucleotide/Cas9 protein (e.g., wt, nickase, or dCas9 protein)/PUF domain fusion may be used to control (i.e., modulate, e.g., increase, decrease) the expression of another polynucleotide/Cas9 protein (e.g., wt, nickase, or dCas9 protein)/PUF domain fusion. For example, a first subject polynucleotide may be designed to target the modulation of transcription of a second Cas9 protein (e.g., wt, nickase, or dCas9 protein) or PUF domain fusion with a function that is different than the first PUF domain fusion (e.g., methyltransferase activity, demethylase activity, acetyltansferase activity, deacetylase activity, etc.). In addition, because different Cas9 proteins (e.g., wt, nickase, or dCas9 protein) (e.g., derived from different species) may require a different Cas9 handle (i.e., Cas9-binding sequence), the second Cas9 protein (e.g., wt, nickase, or dCas9 protein) can be derived from a different species than the first Cas9 protein (e.g., wt, nickase, or dCas9 protein) above. Thus, in some cases, the second Cas9 protein (e.g., wt, nickase, or dCas9 protein) can be selected such that it may not interact with the first subject polynucleotide. In other cases, the second Cas9 protein (e.g., wt, nickase, or dCas9 protein) can be selected such that it does interact with the first subject polynucleotide. In some such cases, the activities of the two (or more) Cas9 proteins (e.g., wt, nickase, or dCas9 protein)/PUF domain fusions may compete (e.g., if the polypeptides have opposing activities) or may synergize (e.g., if the polypeptides have similar or synergistic activities). Likewise, as noted above, any of the complexes (i.e., polynucleotide/Cas9 protein (e.g., wt, nickase, or dCas9 protein)/PUF domain fusion) in the network can be designed to control other polynucleotide/Cas9 protein (e.g., wt, nickase, or dCas9 protein)/PUF domain fusion. Because a subject polynucleotide/Cas9 protein (e.g., wt, nickase, or dCas9 protein)/PUF domain fusion can be targeted to any desired DNA sequence, the methods described herein can be used to control and regulate the expression of any desired target. The integrated networks (i.e., cascades of interactions) that can be designed range from very simple to very complex, and are without limit.

In a network wherein two or more components (e.g., polynucleotide/Cas9 protein (e.g., wt, nickase, or dCas9 protein)/PUF domain fusion) are each under regulatory control of another polynucleotide/Cas9 protein (e.g., wt, nickase, or dCas9 protein)/PUF domain fusion complex, the level of expression of one component of the network may affect the level of expression (e.g., may increase or decrease the expression) of another component of the network. Through this mechanism, the expression of one component may affect the expression of a different component in the same network, and the network may include a mix of components that increase the expression of other components, as well as components that decrease the expression of other components. As would be readily understood by one of skill in the art, the above examples whereby the level of expression of one component may affect the level of expression of one or more different component(s) are for illustrative purposes, and are not limiting. An additional layer of complexity may be optionally introduced into a network when one or more components are modified (as described above) to be manipulatable (i.e., under experimental control, e.g., temperature control; drug control, i.e., drug inducible control; light control; etc.).

As one non-limiting example, a first subject polynucleotide can bind to the promoter of a second subject polynucleotide, which controls the expression of a target therapeutic/metabolic gene. In such a case, conditional expression of the first subject polynucleotide indirectly activates the therapeutic/metabolic gene. RNA cascades of this type are useful, for example, for easily converting a repressor into an activator, and can be used to control the logics or dynamics of expression of a target gene.

A subject transcription modulation method can also be used for drug discovery and target validation.

10. Kits

The present invention also provides a kit for carrying out a subject method. A subject kit may comprise: a) a polynucleotide of the present invention, or a nucleic acid (e.g., vector) comprising a nucleotide sequence encoding the same; optionally, b) a subject Cas9 protein (e.g., wt, nickase, or dCas9 protein), or a vector encoding the same (including an expressible mRNA encoding the same); and optionally, c) one or more subject PUF domain fusion each comprising a PUF domain fused to an effector domain that may be the same or different among the different PUF domain fusions, or a vector encoding the same (including an expressible mRNA encoding the same).

In certain embodiments, one or more of a)-c) may be encoded by the same vector.

In certain embodiments, the kit also comprises one or more buffers or reagents that facilitate the introduction of any one of a)-c) into a host cell, such as reagents for transformation, transfection, or infection.

For example, a subject kit can further include one or more additional reagents, where such additional reagents can be selected from: a buffer; a wash buffer; a control reagent; a control expression vector or RNA polynucleotide; a reagent for in vitro production of the wt or dCas9 or PUF domain fusion from DNA; and the like.

Components of a subject kit can be in separate containers; or can be combined in a single container.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example 1 sgRNA Scaffold Remains Functional with Insertion of 47 Copies of Engineered Pumilio Binding Sites This example demonstrates that the subject 3-component CRISPR/Cas complex/system can have at least 47 copies of the engineered 8-mer Pumilio homologue domain-binding sequences (PBSs) at the 3' end of sgRNA, without substantially affecting the function of the dCas9/sgRNA complex.

In particular, to test whether appending PBS to the 3' end of sgRNA affects sgRNA function, a series of modified Tet-targeting (sgTetO) or non-targeting control (sgControl) sgRNA were generated, with 0 copy, 5 copies, 15 copies, 25 copies, and 47 copies of the 8-mer Pumilio homologue domain-binding sequence (PBS) for PUF (3-2) (also simply referred to as PUFa) [PBS32 or PBSa: 5'-UGUAUgUA-3'], PUF(6-2/7-2) (also simply referred to as PUFb) [PBS6272 or PBSb: 5'-UugAUAUA-3']. See FIG. 1A. The ability of these constructs to direct the dCas9-VP64 transcriptional activator to activate tdTomato expression in a HEK293T/TetO::tdTomato cell line was tested.

Figure 1B:
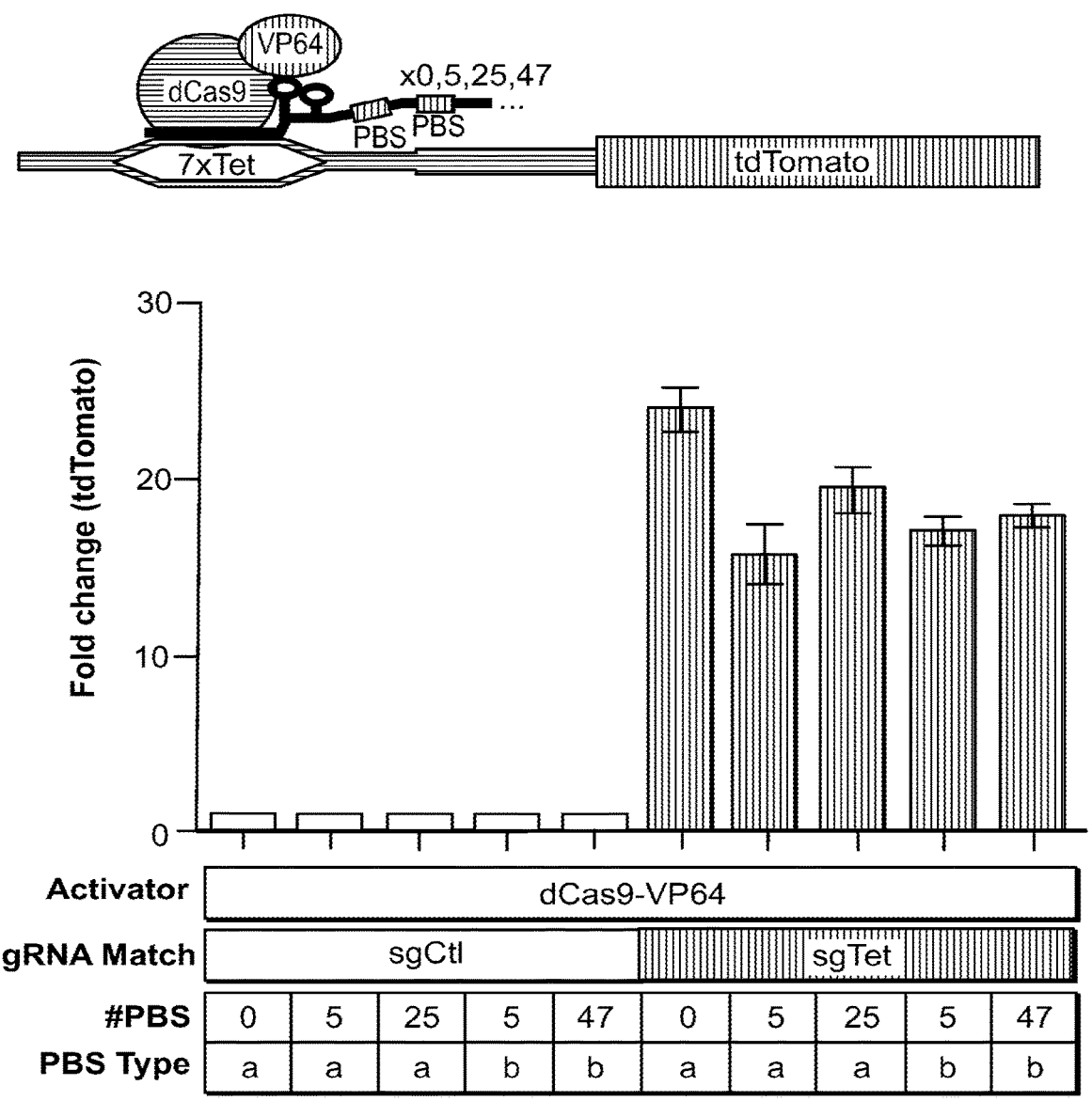
Figure 1C:
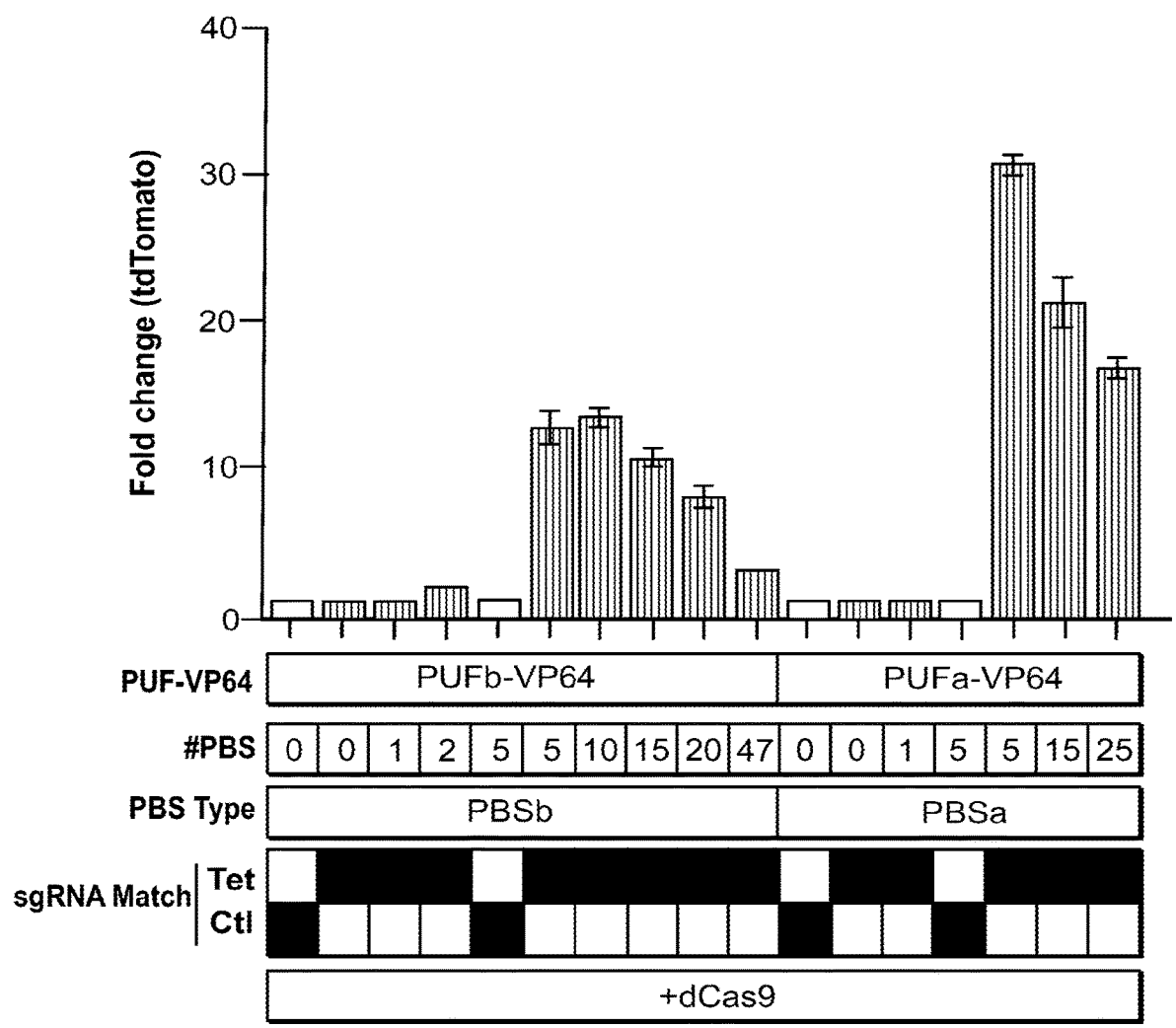

Cells were transfected with dCas9-VP64 with the different sgRNA scaffolds, and were analyzed by fluorescent-activated cell sorting (FACS) two days after transfection (FIG. 1B). All the control non-targeting sgRNAs did not activate tdTomato expression. Meanwhile, all the Tet-targeting sgRNAs with different number of PBS could direct dCas9-VP64 to activate tdTomato expression, showing that insertion of at least 47 copies of 8-mer sites do not substantially impact the activity of sgRNA in directing dCas9-VP64 to its targets (FIG. 1C).

Under the test condition, and for both PUFa-VP64/PBSa and PUFb-VP64/PBSb, 5-10 copies of PBS appended to the sgRNA were best able to activate the target transgene. Meanwhile, 15, 20, and 47 copies of PBS led to slightly lower, albeit still substantial transgene activation (FIG. 1C).

Example 2 the Subject 3-Component CRISPR/Cas Complexes/Systems are Orthogonal to Each Other Due to the Specificity of the Engineered Pumilio with the Cognate 8-Mer Binding Sites This example demonstrates that specificity between the differently programmed PUF domains and their corresponding sgRNA with their cognate 8-mer motifs provide independence or orthogonality between each of the subject 3-component CRISPR/Cas complex/system.

Fusions of PUF(3-2)::VP64 and PUF(6-2/7-2)::VP64, which interacts with sgRNA (sgRNA-PBS32) with 5'-UGUAUgUA-3' binding sites and sgRNA-PBS6272 with 5'-UugAUAUA-3' binding sites, respectively, were created, and their activity to turn on tdTomato expression in conjunction with dCas9 was tested. In addition, two additional pairs, PUFw-VP64 recognizing PBSw (5'-UGUAUAUA-3') and PUFc-VP64 recognizing PBSc (5'-UugAUgUA-3'), were also constructed to test their ability to activate the same TetO::tdTomato expression in conjunction with dCas9 (FIG. 1D).

Figure 1D:
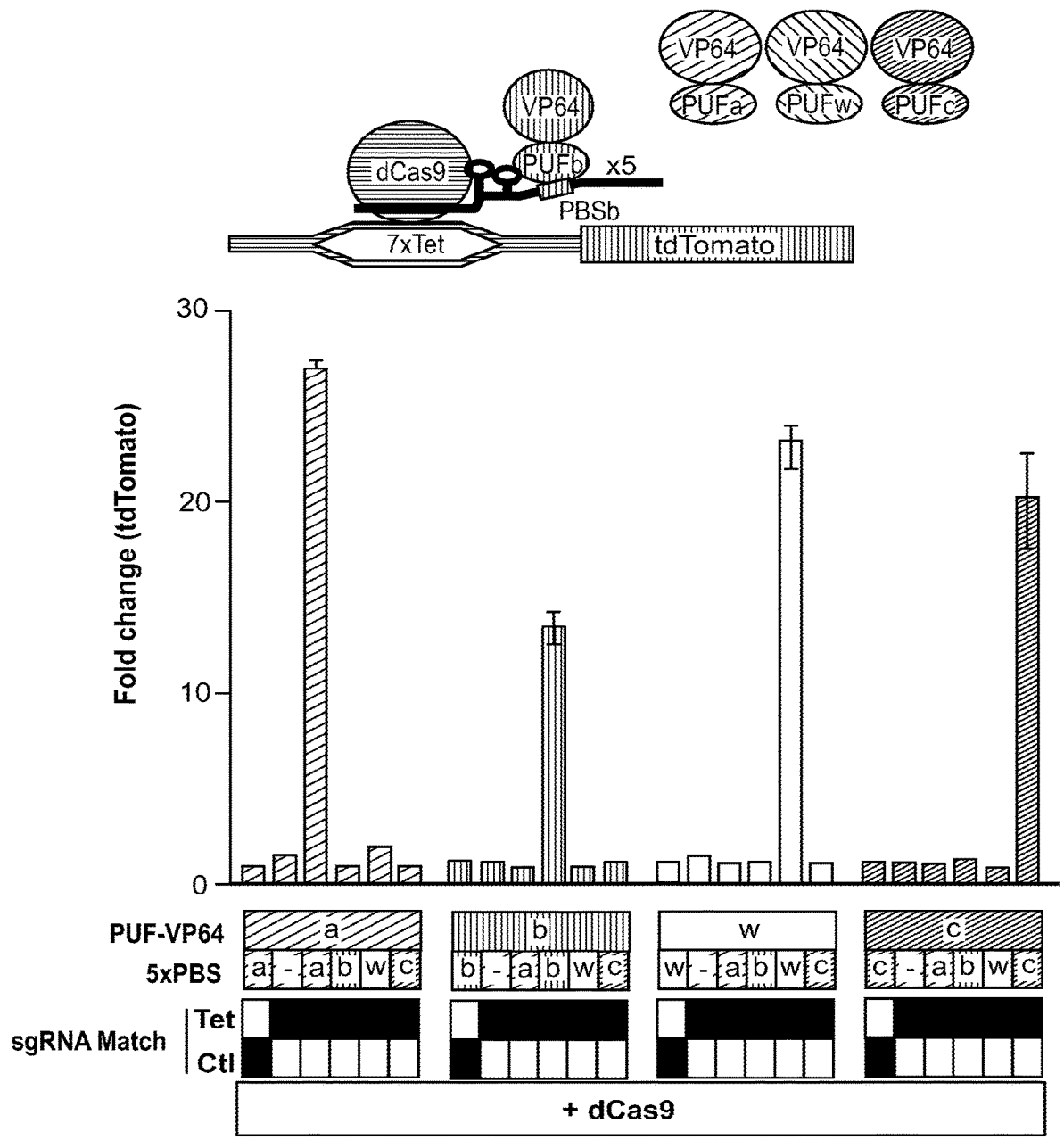

As shown in FIG. 1D, PUF::VP64 can activate tdTomato expression only when the sgRNA with the cognate binding sites were provided. This demonstrates that the subject 3-component CRISPR/Cas complex/system provides independence or orthogonality of effector function based on the pairing of PUF domains and their 8-mer binding sites on the sgRNA-PBS. Impressively, although PBSa and PBSw binding sites only differ by one nucleotide, their gene activation remains target-specific, demonstrating the high specificity of the subject 3-component CRISPR/Cas complex/system.

Example 3 the Subject 3-Component CRISPR/Cas Complex/System Allows Assembly of Protein Complex at Target Loci This example demonstrates that protein complexes with two or more different protein components can be assembled on sgRNA and operate at defined loci using the subject system.

Figure 2A:
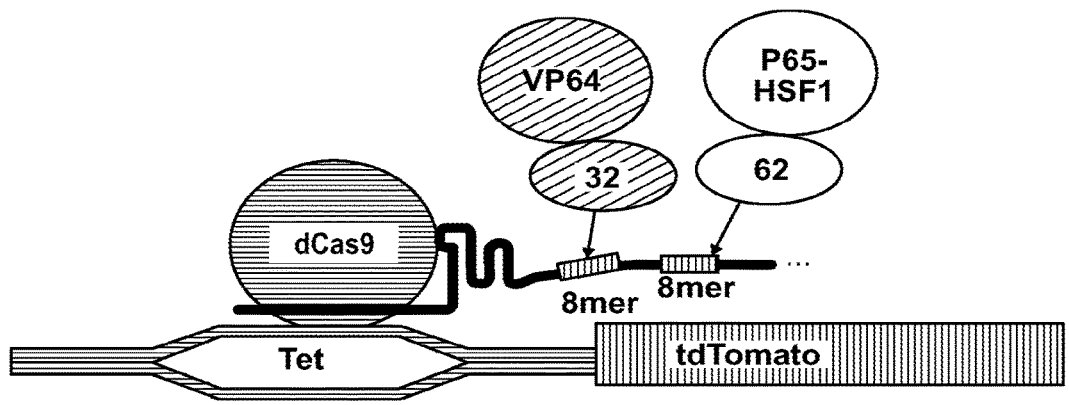
FIGS. 2A and 2B relate to the assembly of the subject 3-component CRISPR/Cas complex/system comprising VP64 and P65-HSF1.
Figure 2B:
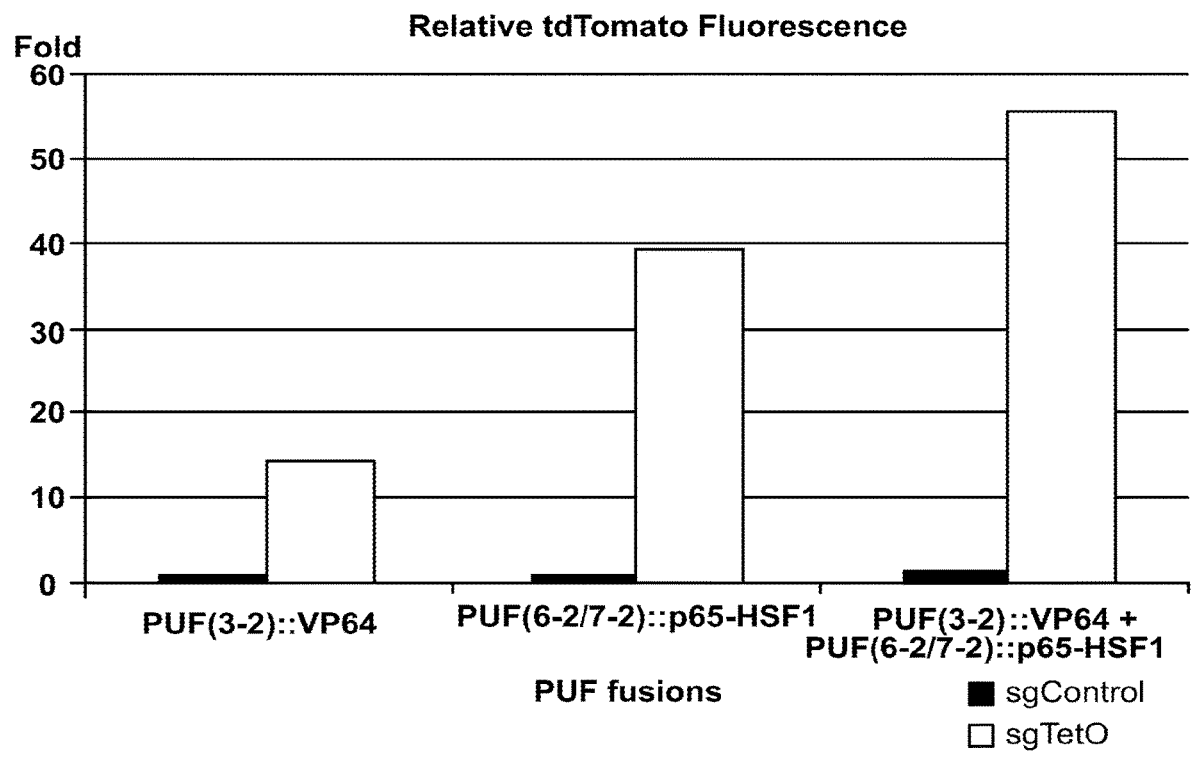

Specifically, p65-HSF1 has recently been shown to be a potent activator domain. An sgRNA with both PBS32 and PBS6272 positioned next to each other, and PUF(3-2)::VP64 and PUF(6-2/7-2)::p65-HSF1 fusions that would occupy the two different sites, were generated (FIG. 2A). Co-transfection of both PUF(3-2)::VP64 and PUF(6-2/7-2)::p65-HSF1 induced a tdTomato fluorescence, with an intensity about the sum of the fluorescent intensity resulting from transfecting the single activators alone. This indicates that sgRNA with binding sites for both PUF(3-2) and PUF(6-2/7-2) allows both fusion proteins of both types to assemble on the targeted genomic locus.

Figure 2C:
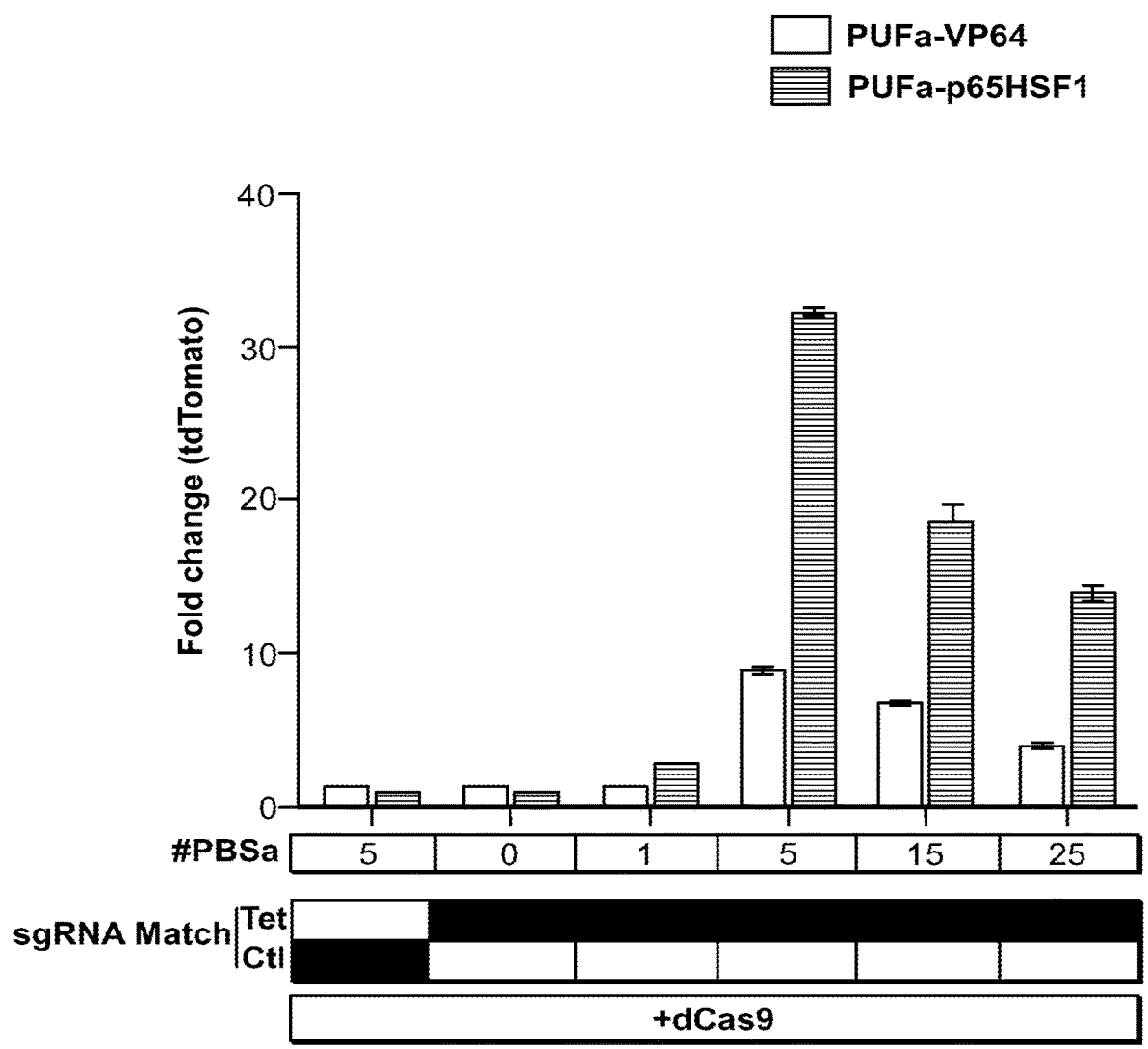
FIG. 2C shows comparison of the subject 3-component system activator using VP64 (PUFa::VP64; red columns) versus p65HSF1 (PUFa::p65HSF1; blue columns) as the activation domain in conjunction with Control sgRNA with 5×PBSa or TetO-targeting sgRNA with 0, 1, 5, 15, or 25 copies of PBSa. Columns show mean fold change (with S.E.M.; n=3) of tdTomato fluorescence relative to experiments using control sgRNA (sgCtl). The legend indicates the number of PBSa (#PBSa) on the sgRNA-PBS as well as the DNA match indicated by the shaded boxes.

A recent paper has tested both VP64 and p65HSF1 as transcriptional activation domains, and found p65HSF1 to be a more potent activator. To directly compare these two transcriptional activation domains, p65HSF1 PUF fusion (PUFa-p65HSF1) and VP64 PUF fusion (PUFa-VP64) were used to activate the TetO::tdTomato transgene using sgRNA with different number of PBSa (FIG. 2C). PUFa-p65HSF1 provided up to 3 times more activation as did PUFa-VP64. Activation was observed even with only one PBSa (previously not observed with PUFa-VP64 module). Thus p65HSF1 is confirmed to be a more potent transcriptional activation domain than VP64.

Example 4 the Subject 3-Component CRISPR/Cas Complex/System can Activate Endogenous Genes More Efficiently than dCas9 Direct Fusion with Activator We previously used a cocktail of 3-4 sgRNAs per gene to achieve robust endogenous gene activation of OCT4 and SOX2 using a dCas9-VP160 direct fusion while single sgRNAs failed to induce much activation (data not shown).

This example demonstrates that recruitment of multiple molecules of activator domains via multiple PBS on the sgRNA-PBS in the subject system increases transactivation activity, thus allowing the use of fewer sgRNAs to achieve endogenous gene activation.

Figure 3A:
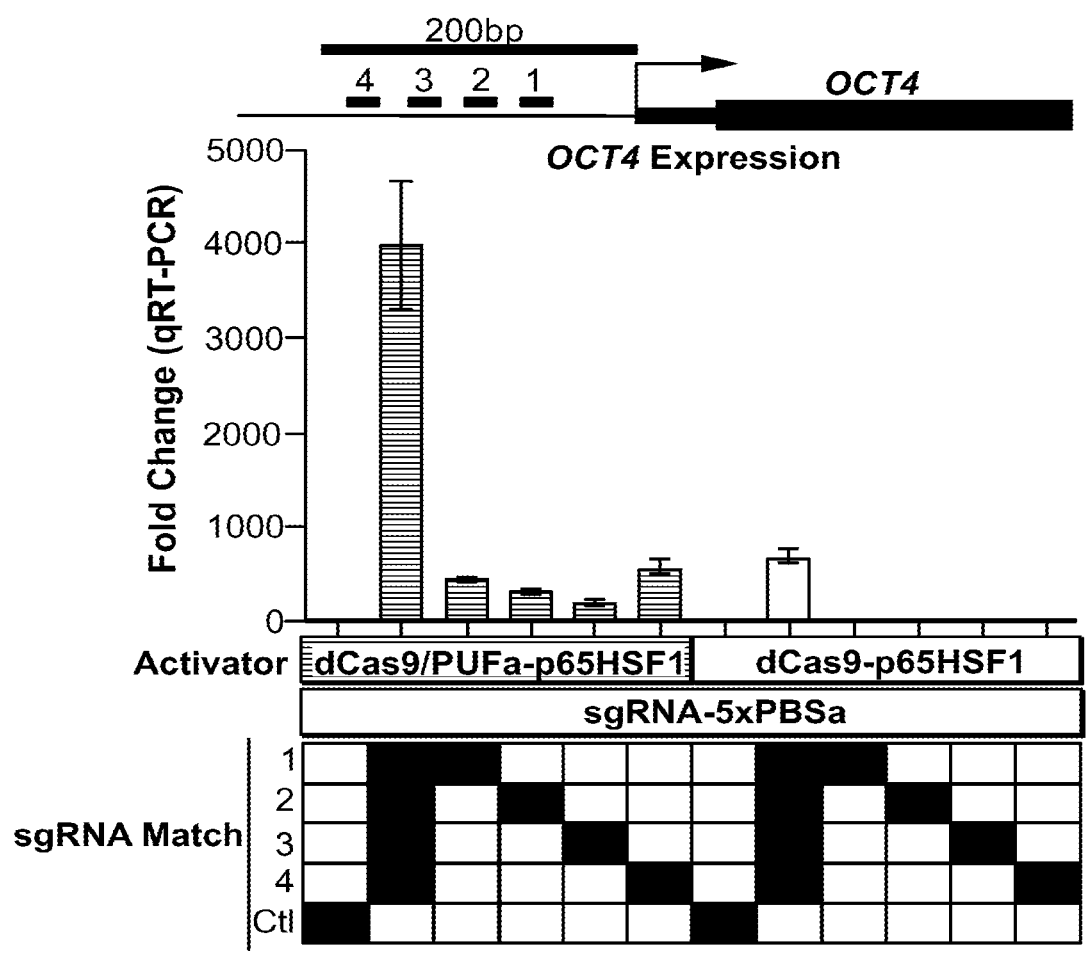
FIGS. 3A-3D show that the subject system allows for multimerization of activator to achieve robust endogenous gene activation.
Figure 3B:
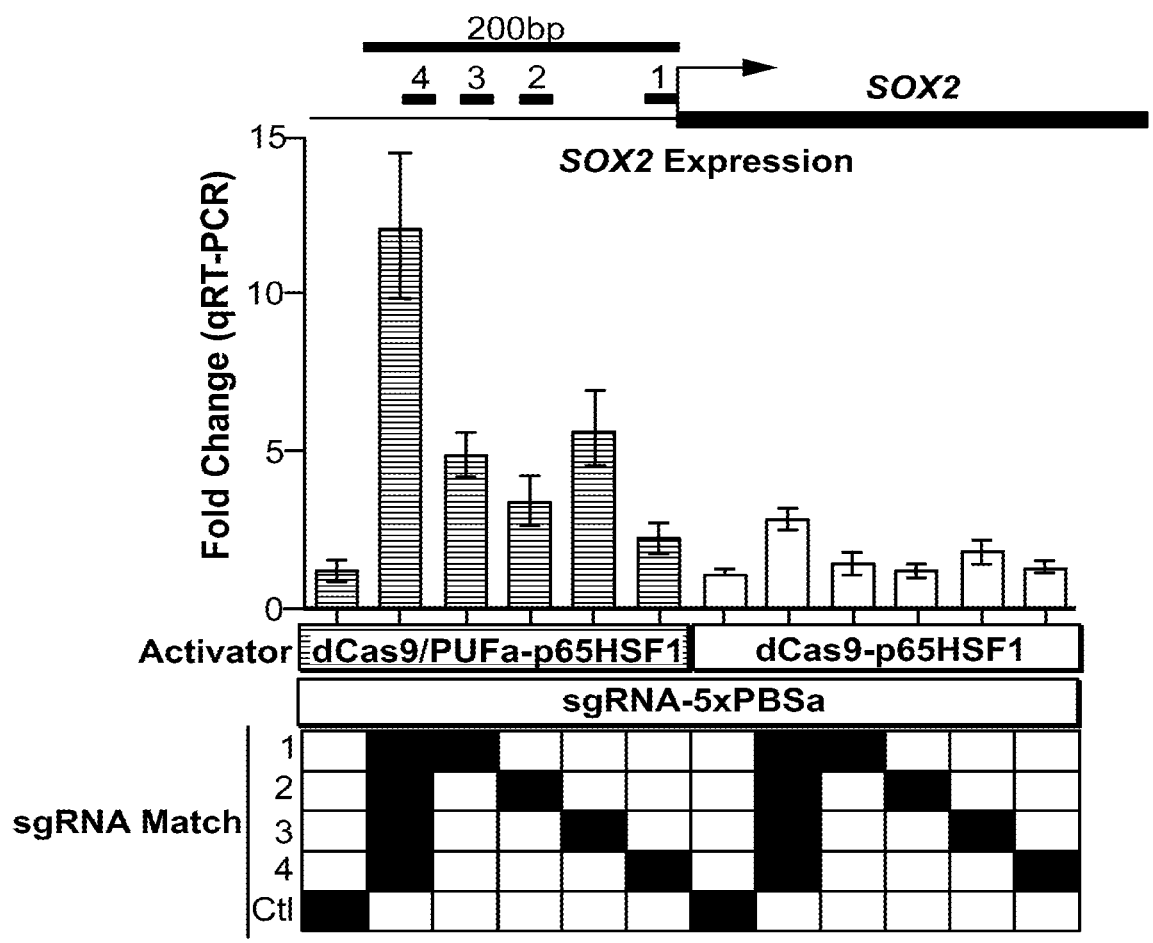
Figure 3C:
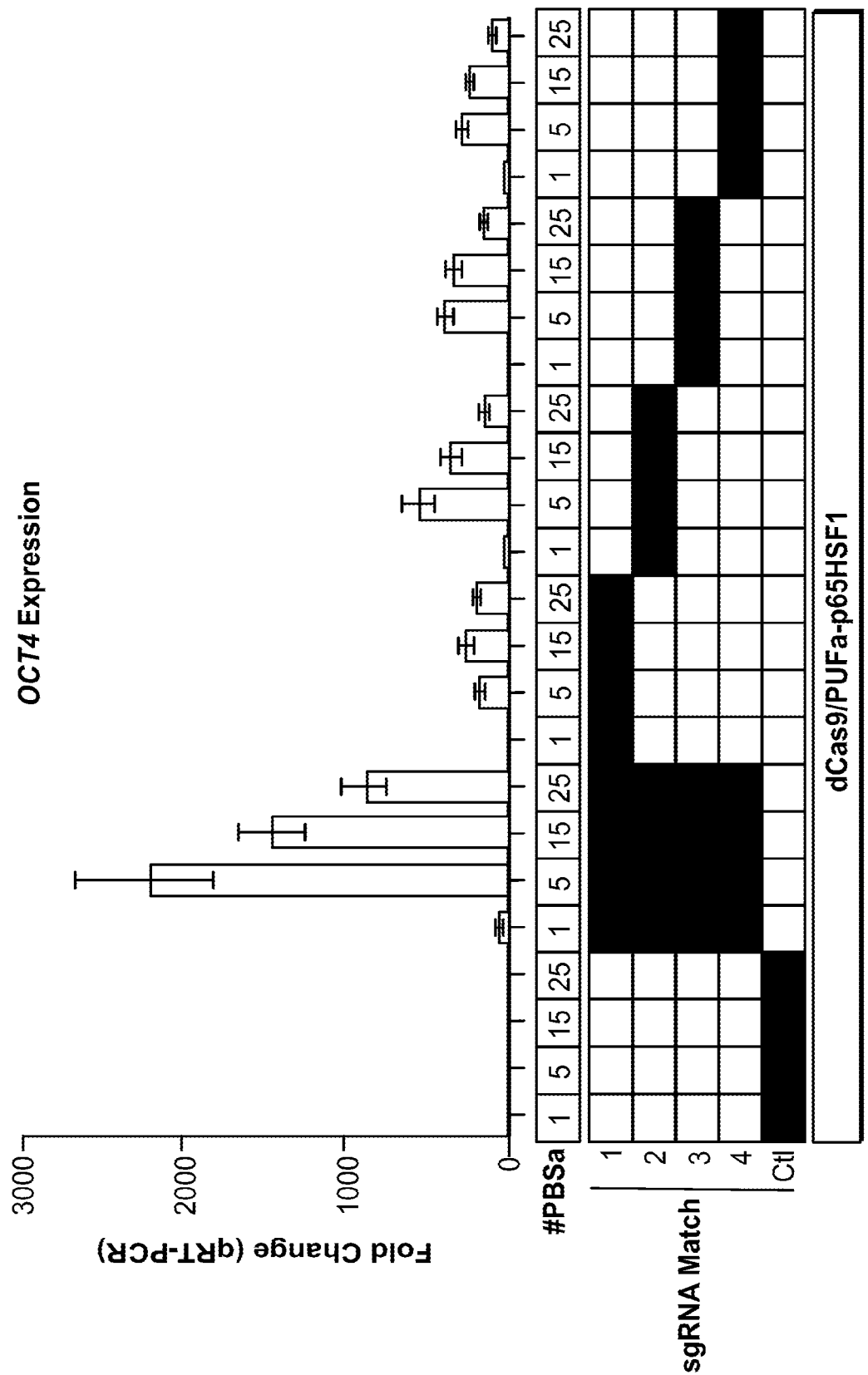

Specifically, activation of endogenous genes OCT4 and SOX2 in HEK293T were compared using the subject system with a direct dCas9-p65HSF1 activator using either a cocktail of four sgRNA-PBS per gene, or individual sgRNA-PBS (FIGS. 3A and 3B). Higher activation was observed using the subject 3-Component CRISPR/Cas Complex/System compared to direct fusion in the mixed sgRNA-PBS cocktail, as well as in single guide experiments in both OCT4 and SOX2 activation experiments (FIGS. 3A and 3B). Little to no activation by single guide targeting of direct fusion dCas9-p65HSF1 to OCT4 and SOX2 was observed, while robust activation was observed in the corresponding 3-component system experiments, showing the superior activity of the subject 3-Component CRISPR/Cas Complex/System activator over the direct fusion.

Figure 3D:
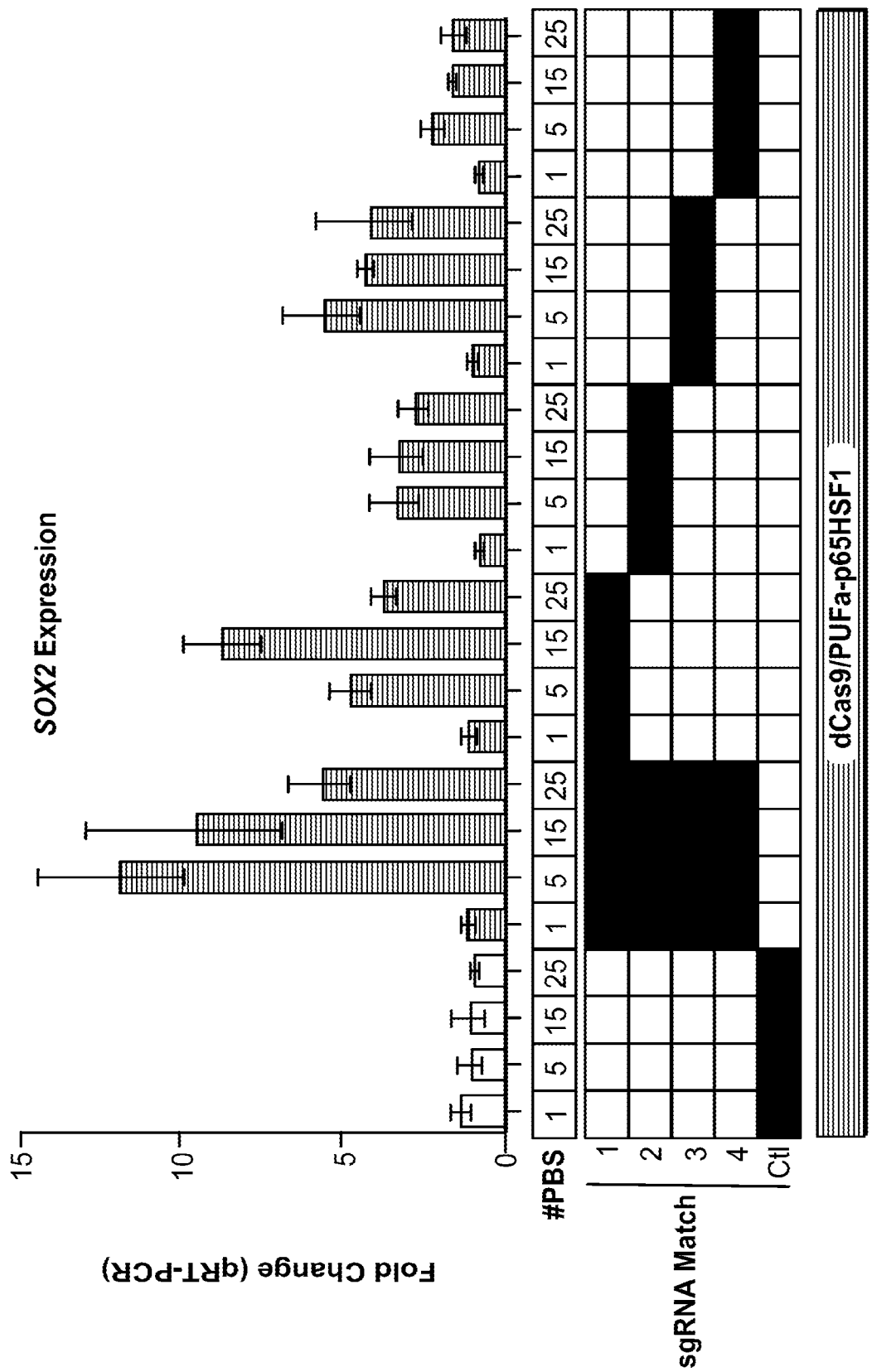

To determine the optimal number of PBSa sites on the sgRNA for OCT4 and SOX2 activation, sgRNA-PBS targeting either OCT4 or SOX2 proximal promoter with 1, 5, 15 or 25 copies of PBSa were constructed. In both OCT4 and SOX2 experiments, we observed highest activation using 5×PBSa, in either sgRNA-5×PBSa cocktail experiments and single sgRNA-5×PBSa experiments, recapitulating the finding in the TetO::tdTomato reporter experiments (FIGS. 3D and 3E).

Example 5 the Subject 3-Component CRISPR/Cas Complex/System Allows Simultaneous Activation and Repression of Target Genes This example demonstrates that different effector functions can be assigned to each of the subject 3-component CRISPR/Cas complex/system.

Figure 4A:
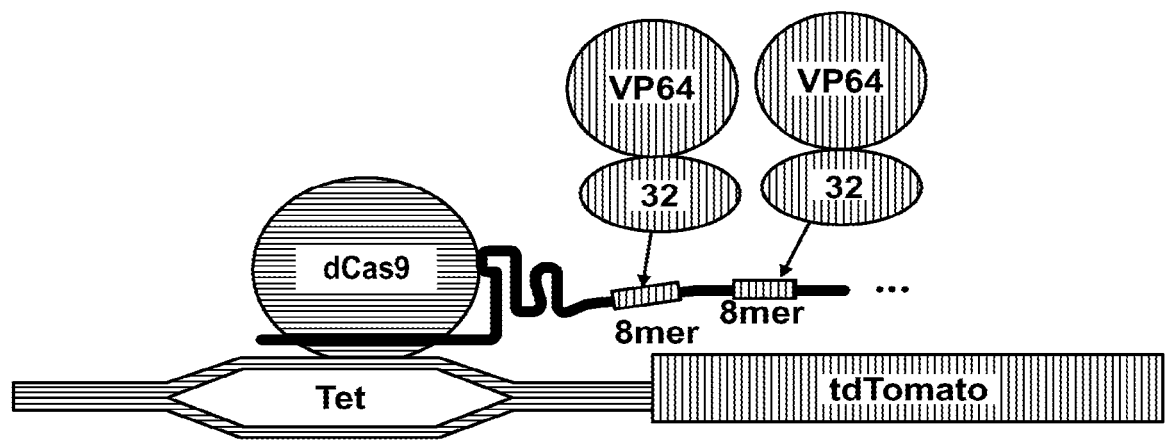
FIGS. 4A and 4B show that the subject 3-component CRISPR/Cas complex/system allows simultaneous activation and repression of two different target reporter genes.
Figure 4A:
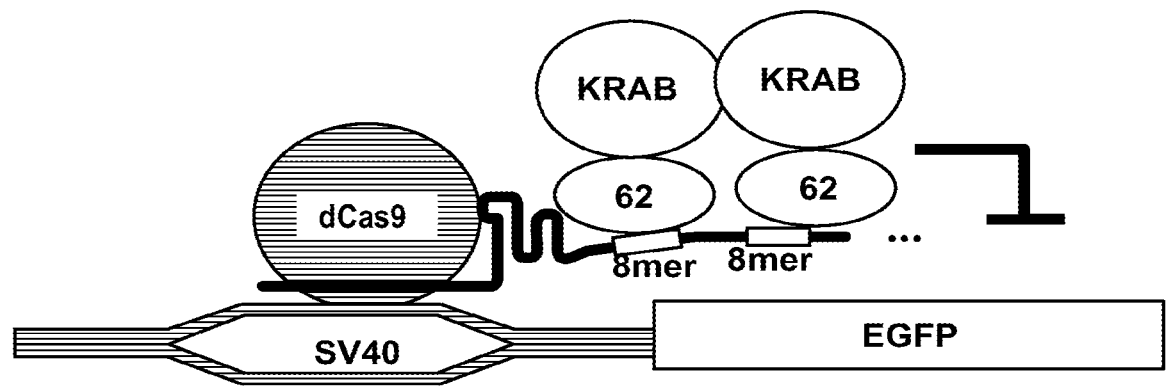
Figure 4B:
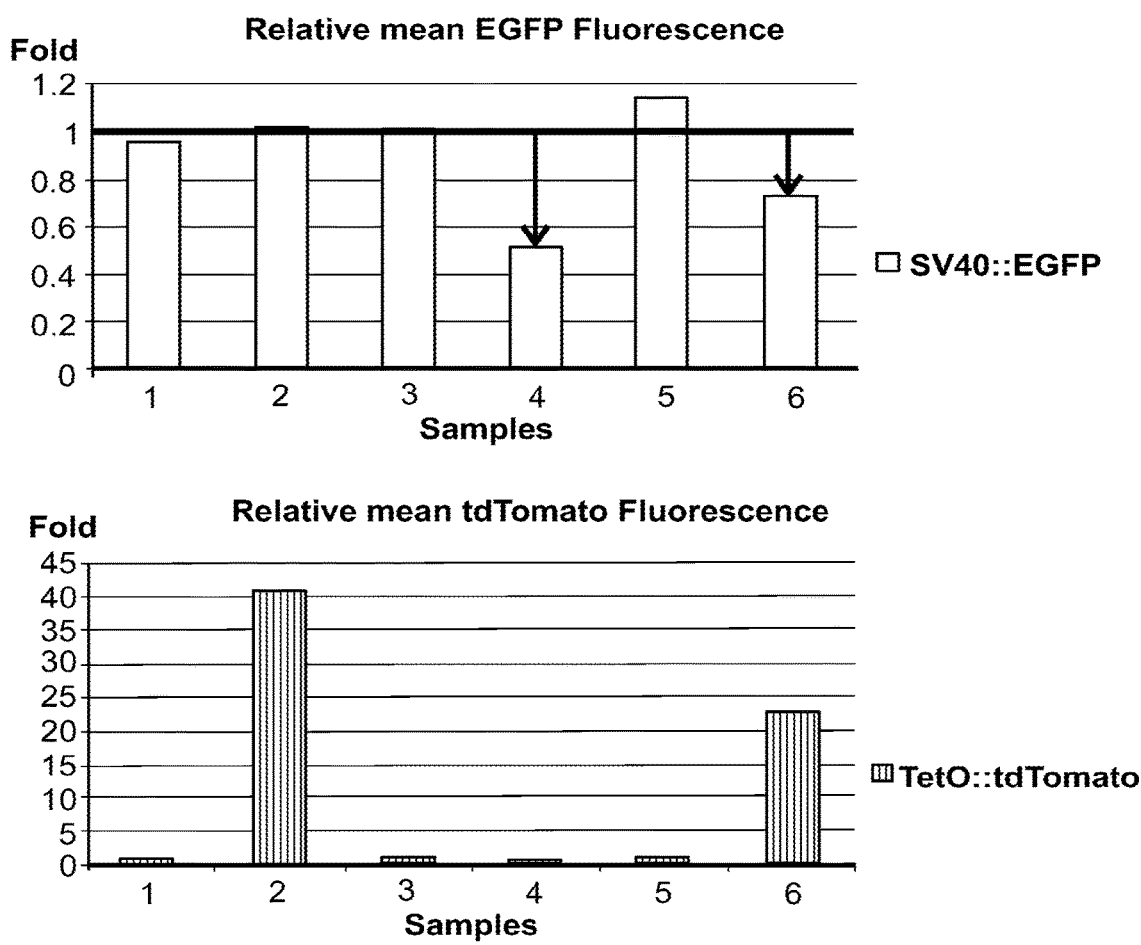

The KRAB::PUF(6-2/7-2) repression fusion and the sgRNA targeting SV40 promoter were first generated. A HEK293T reporter cell line having a tdTomato reporter under the control of the TetO promoter, and an EGFP reporter under the control of the SV40 promoter (HEK293T/TetO::tdTomato/SV40::EGFP) was then used to test simultaneous (1) activation of tdTomato via dCas9/sgTetO-PBS32/PUF(3-2)::VP64 binding to TetO promoter, and (2) repression of EGFP expression via binding of dCas9/sgSV40-PBS6272/KRAB::PUF(6-2/7-2) at the SV40 promoter (FIG. 4A). Expression of the 3-component CRISPR/Cas activator complex consisting of dCas9, sgTetO-5×PBS32 and PUF(3-2)::VP64 activated tdTomato fluorescence (FIG. 4B; sample 2) while expression of the 3-component CRISPR/Cas repressor complex consisting of dCas9, sgSV40-5×PBS6272 reduced EGFP fluorescence (FIG. 4B; sample 4). Co-expression of both activator and repressor complexes induced simultaneous activation of the tdTomato and repression of the EGFP transgene, respectively (FIG. 4B, sample 6), demonstrating that the subject 3-component CRISPR/Cas complexes with different effector functions can operate within the same cell and produce different output at their targets.

Figure 4C:
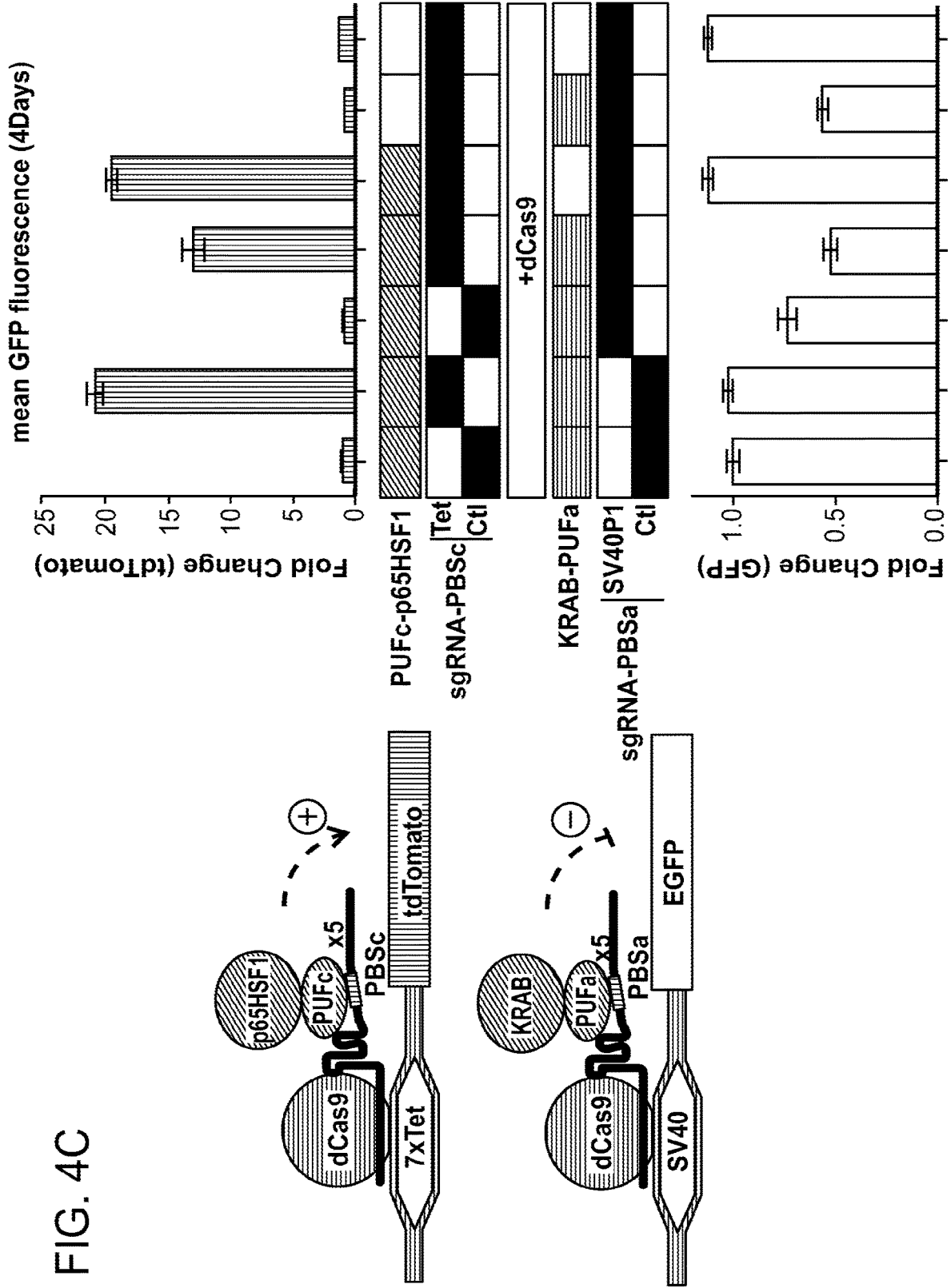
FIGS. 4C and 4D further demonstrate that the subject 3-component CRISPR/Cas complex/system can activate and repress different genes simultaneously.

To further confirm the versatility of the subject system in recruiting various effectors, a KRAB-PUFa repressor fusion and as well as a PUFc-p65HSF1 activator fusion were constructed. In a reporter cell line HEK293T/TetO::tdTomato/SV40::EGFP, the TetO::tdTomato reporter gene can be efficiently activated by dCas9/PUFc-p65HSF1/sgTetO-PBSc, while SV40::EGFP expression is significantly repressed by dCas9/KRAB-PUFa/sgSV40-PBSa (FIG. 4C). When both systems were applied, simultaneous activation of TetO::tdTomato and repression of SV40::EGFP expression were achieved (FIG. 4C). When non-targeting (sgCtl) sgRNA were used, or when the PUF fusions were omitted, the fluorescent levels of the respective reporters were not affected, showing that the effects on the reporters are specific and are due to the action of the effectors recruited by the cognate dCas9/sgRNA-PBSat the targets.

Figure 4D:
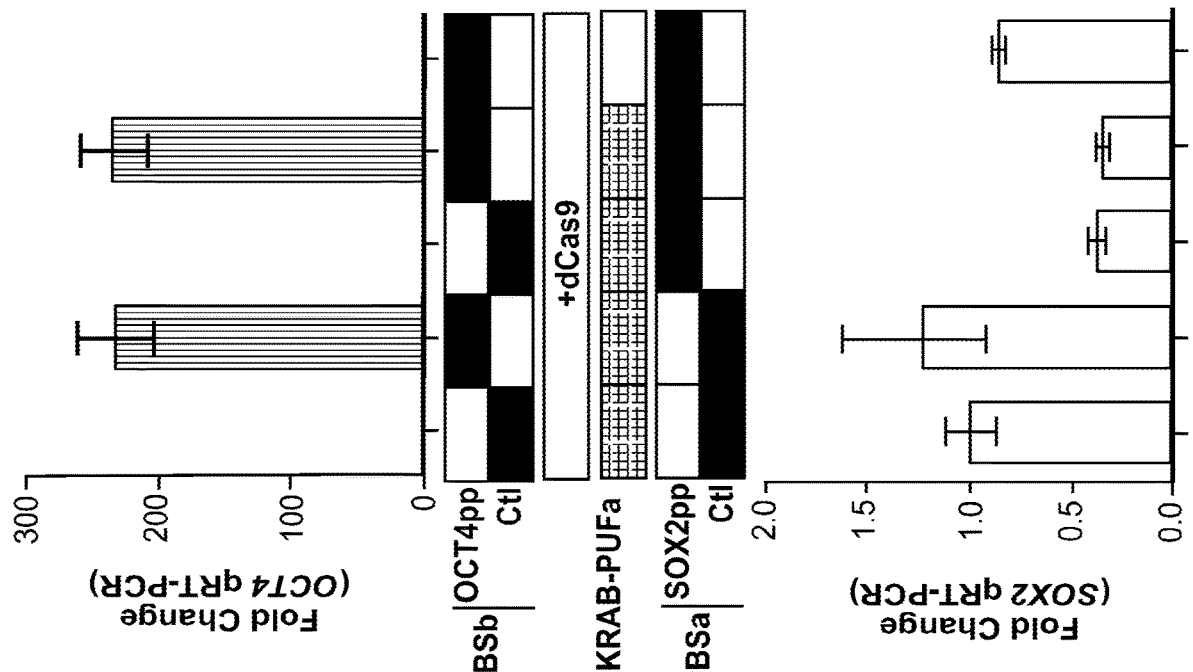
Figure 4D:
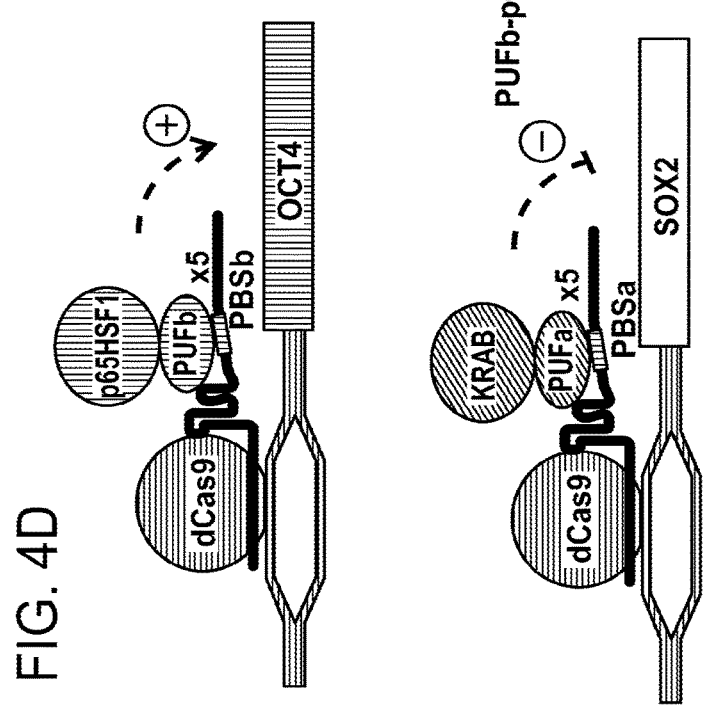

Next, it was tested whether the expression of multiple endogenous genes can be independently regulated using this strategy. The subject 3-component modules were directed to endogenous target genes by changing the targeting sequence of sgRNA-PBSb and sgRNA-PBSa so that PUFb-p65HSF1 was recruited to the OCT4 promoter and BFPKRAB-PUFa to the SOX2 promoter. Similar to the results from reporter gene experiments, effector-mediated simultaneous as well as independent activation of OCT4 and repression of SOX2 were achieved (FIG. 4D).

Example 6 Recruitment of Histone Acetyltransferase (HAT) Domain by the Subject 3-Component CRISPR/Cas Complex/System Achieves Enhancer Activation Artificial transcription factor systems can be used to recruit epigenetic modifiers to activate or repress genes. Recent experiments have used histone acetyltransferase (HAT) to activate enhancers. To demonstrate that the subject 3-component system can recruit multiple molecules of HAT domain to increase the efficiency of epigenetic editing, OCT4 was used as a model gene since its enhancers and the promoter are well defined, and the choice of enhancer usage is of biological significance corresponding to the embryonic stem cell states.

Figure 5A:
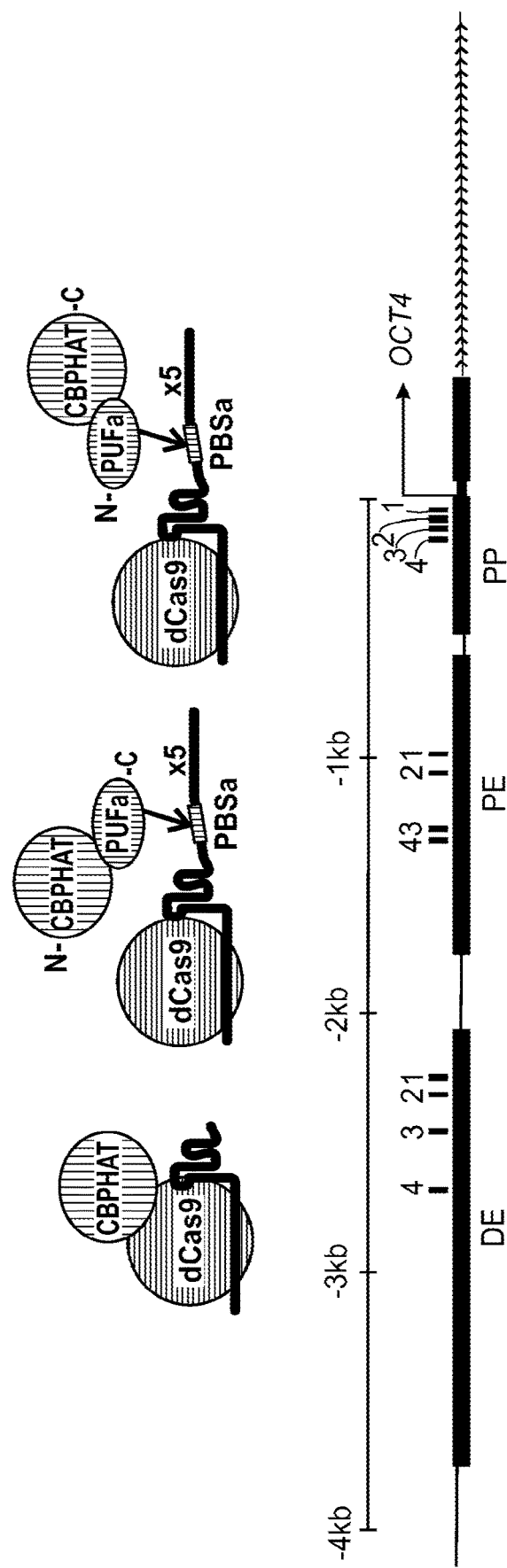
FIG. 5A-5C show that the subject 3-Component CRISPR/Cas Complex/System can be used to recruit histone acetyltransferase (HAT) domain of CREB-binding protein (CBP) at enhancers to activate target gene expression.

In this experiment, the Proximal Promoter (PP), Proximal Enhancer (PE) and Distal Enhancer (DE) were targeted, each with four different sgRNA-PBS (FIG. 5A). Direct fusion between HAT from CREB-binding protein (CBP) and the C-terminus of dCas9 (dCas9::CBPHAT) was constructed, so were an N-terminal fusion module CBPHAT::PUFa, and a C-terminal fusion module PUFa::CBPHAT. Their activity in activating OCT4 expression via binding to PP, PE and DE were then tested.

Figure 5B:
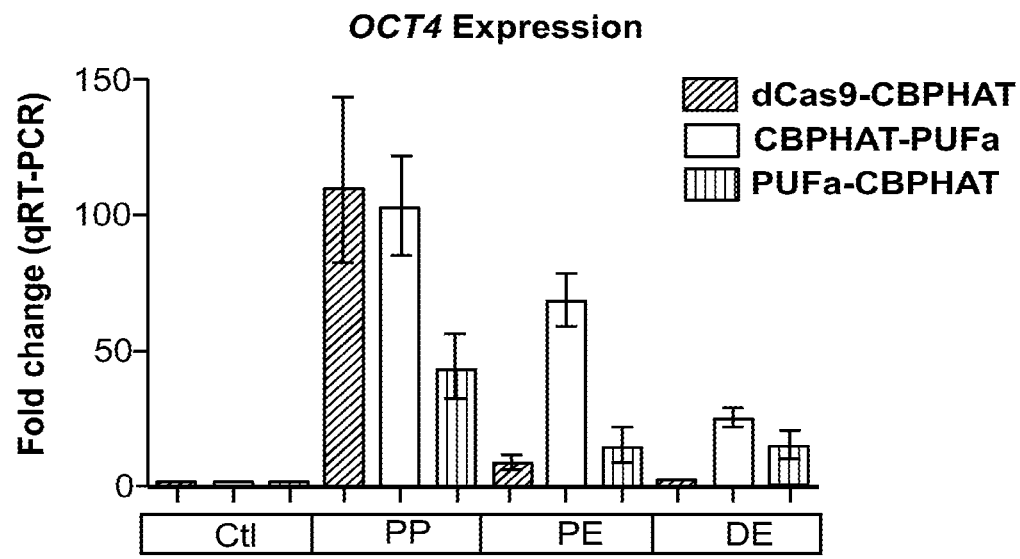
Figure 5C:
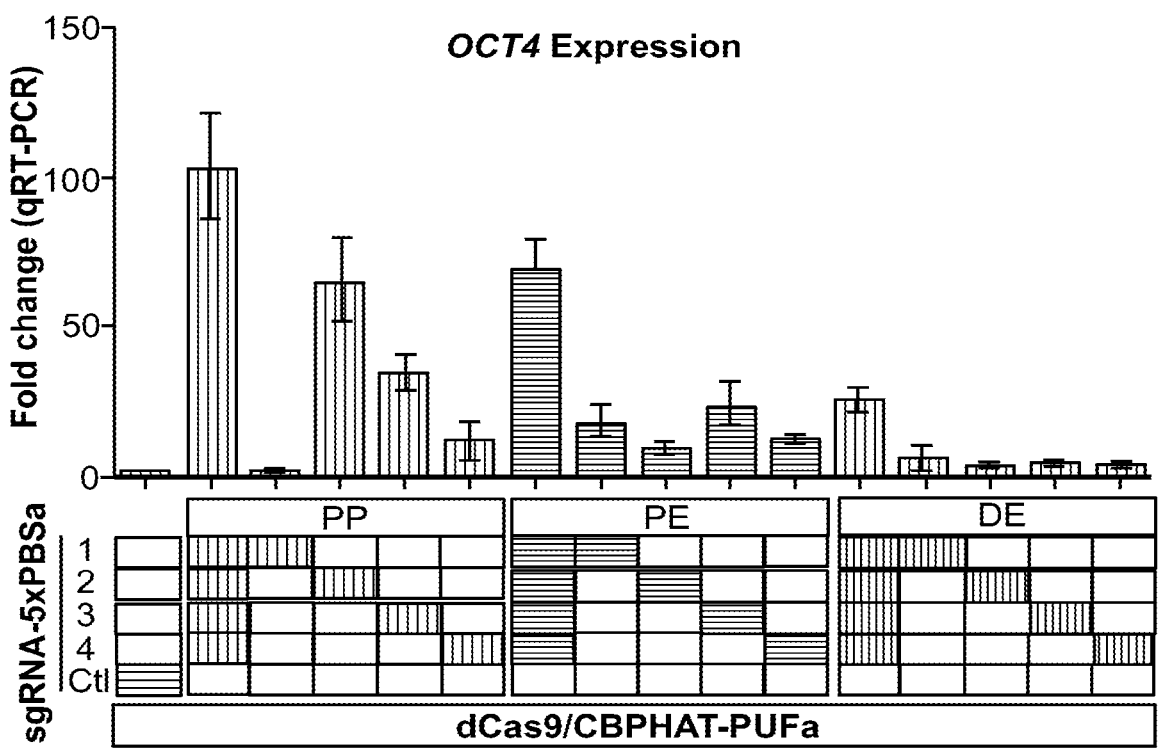

As shown in FIG. 5B, dCas9::CBPHAT and CBPHAT::PUFa have similar activity at proximal promoter (PP). Interestingly, when coupled with sgRNA with 5×PBSa, the subject 3-component modules have higher efficiency activating OCT4 gene via both enhancers PE and DE, with N-terminal fusion CBPHAT::PUFa giving the highest activation. Next, it was analyzed the activity of CBPHAT::PUFa directed by single sgRNA-5×PBSa to PP, PE and DE by sgRNA-5×PBSa (FIG. 5C). Although with smaller fold changes than using cocktails of 4 sgRNA-5×PBSa, single sgRNA-5×PBSa were able to activate the expression of OCT4 gene through targeting of these elements (FIG. 5C).

Example 7 the Subject 3-Component CRISPR/Cas Complex/System Allows Fluorescent Tagging of Telomeres In addition to transcriptional regulation, another important application of dCas9-effector is to label genomic loci for live cell imaging. This example demonstrates that the subject 3-component CRISPR/Cas complex/system can be used for fluorescent tagging of chromosomal loci, such as labeling of telomeres.

Figure 6A:
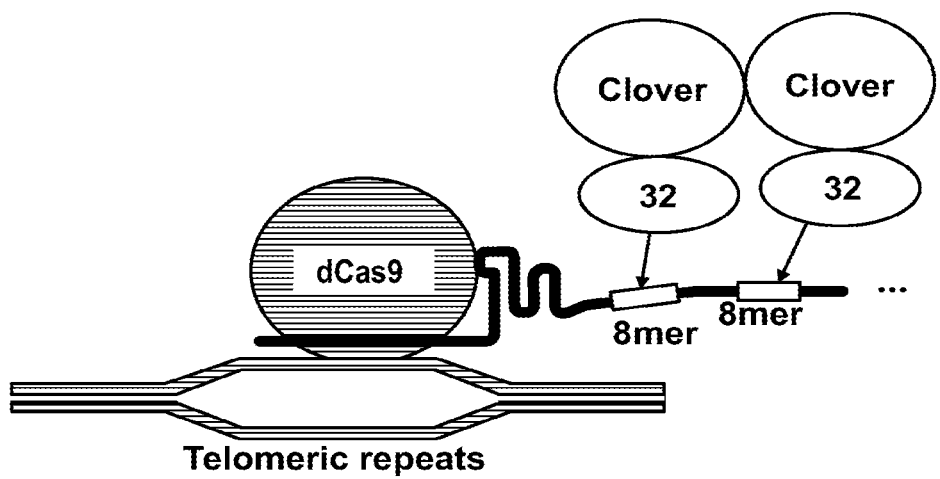
FIGS. 6A-6G show that the subject 3-component CRISPR/Cas complex/system allows multimerization of fluorescent proteins and simultaneous labeling of telomeres and centromeres (Scale bars: 5 µm).
Figure 6B:
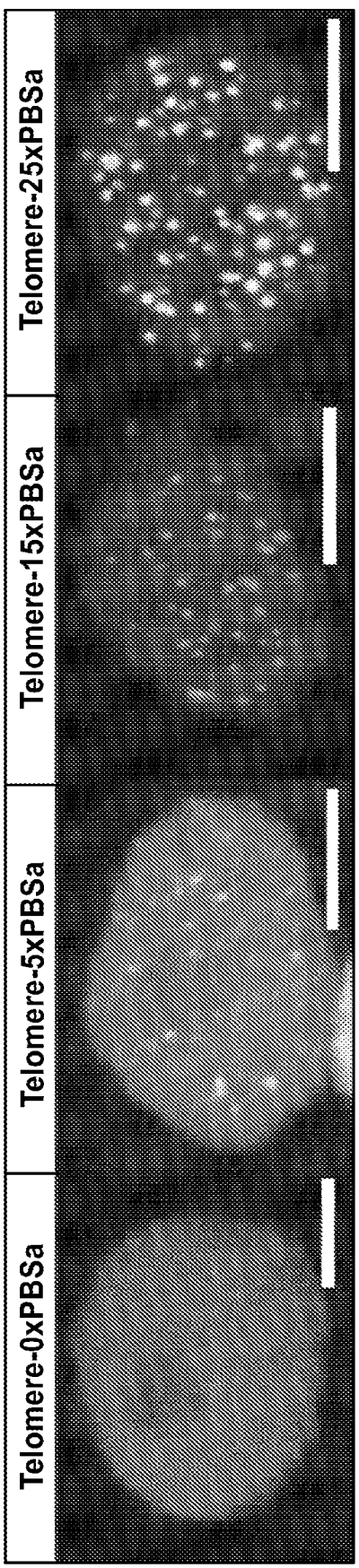
Figure 6C:
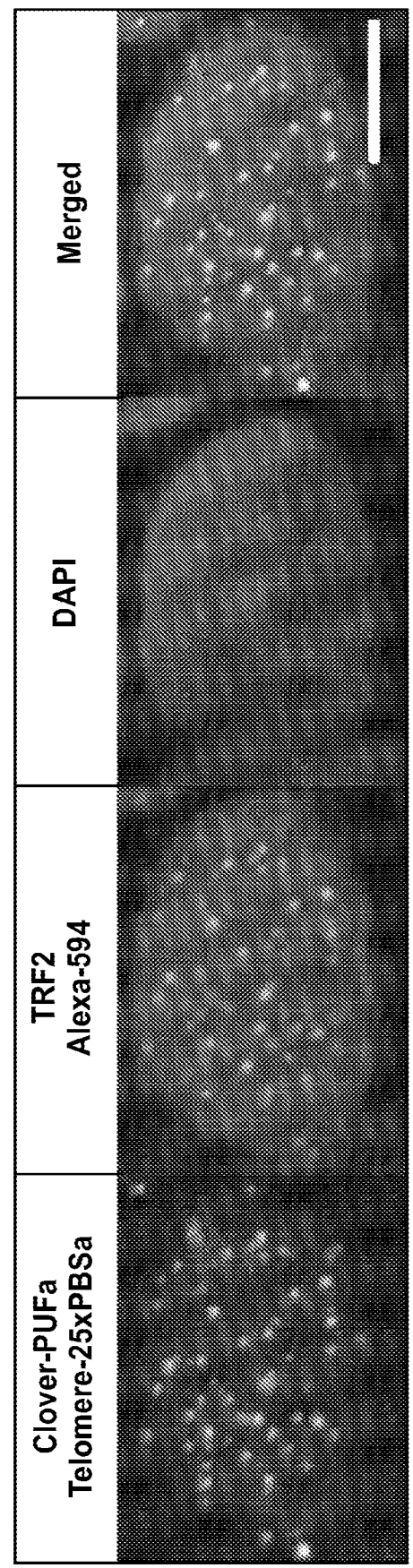
Figure 6D:
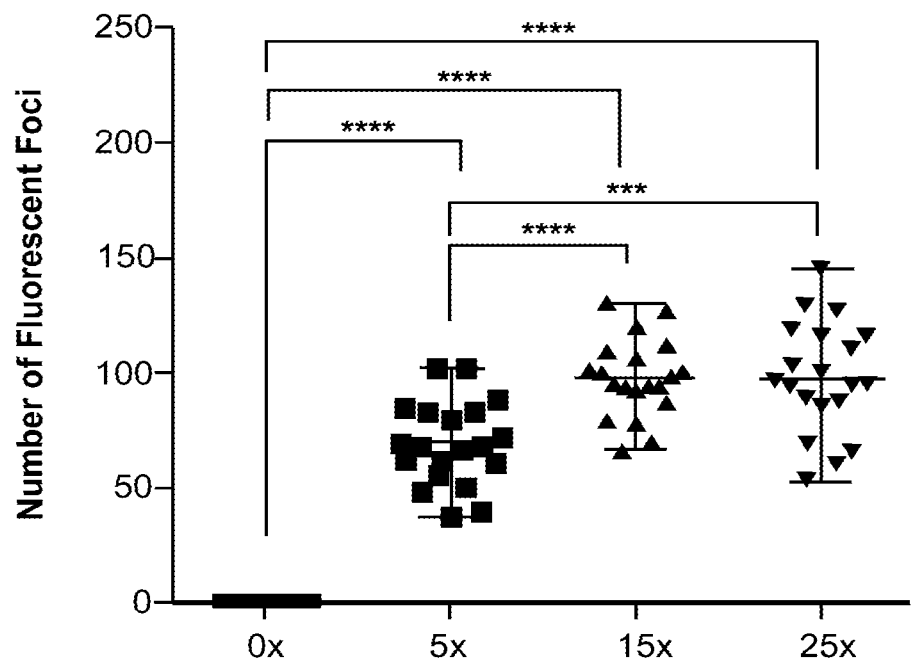
Figure 6E:
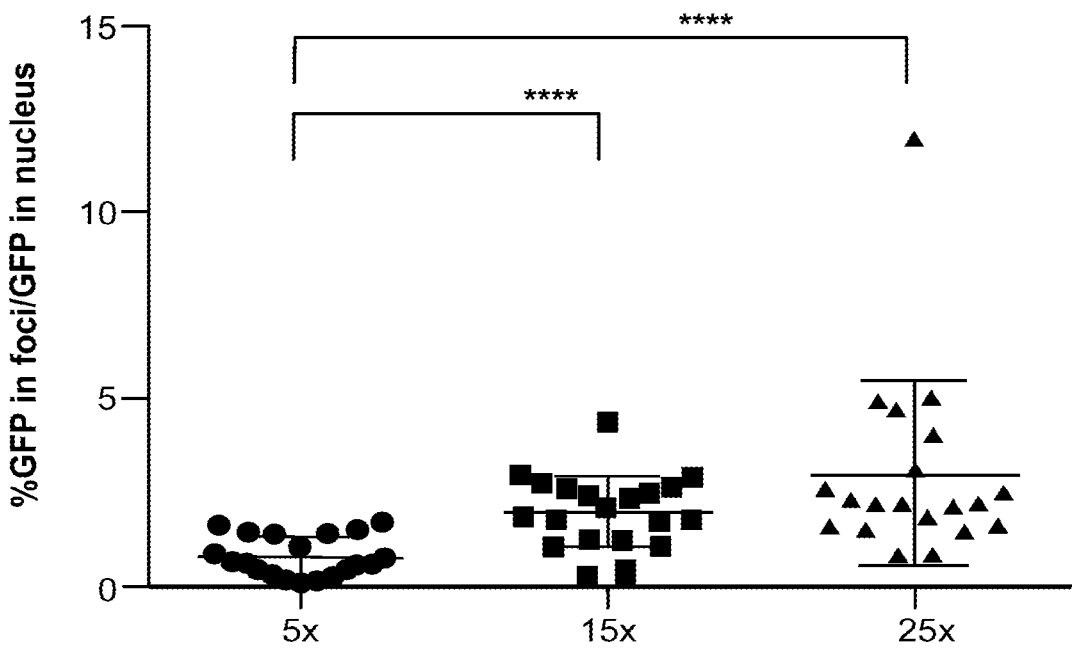

We appended sgRNA designed to target telomeres (sgTelomere) with 0, 5, 15, or 25 copies of PBSa to recruit fluorescent proteins fused to a PUFa domain (FIG. 6A). While expression of sgTelomere-5×PBSa, 15×PBSa and 25×PBSa with dCas9 and Clover::PUFa produced green fluorescent foci consistent with telomere labeling, expression of sgRNA harboring no PBSa site did not produce any foci (FIG. 6B). To confirm that subject 3-component system-directed fluorescent signal is indeed localized at telomeres, co-labeling experiment with antibody against telomeric repeat binding factor TRF2 was performed. The 3-component system telomere signals largely overlapped with the TRF labeling (FIG. 6C), indicating highly specific labeling of telomeres by sgRNA appended with PBSa sites that recruit Clover-PUFa.

Interestingly, the strength of telomere labeling increased as more copies of PBS were appended to the Telomere-sgRNAs (FIG. 6B). Quantification of foci number and signal-to-noise (% GFP in foci/total GFP in nucleus) showed progressive increase from experiment using sgRNA with 5, 15 to 25×PBSa (FIGS. 6D and 6E), indicating the multimerization feature of the subject 3-component system allows for titration of labeling intensity at target loci.

Example 8 The Subject 3-Component CRISPR/Cas Complex/System Allows Simultaneous Fluorescent Tagging of Telomeres and Centromeres This example demonstrates that the subject 3-component CRISPR/Cas complex/system can label more than one (e.g., two) genomic loci simultaneously in the same cells by using the multiplexing feature.

Figure 6F:
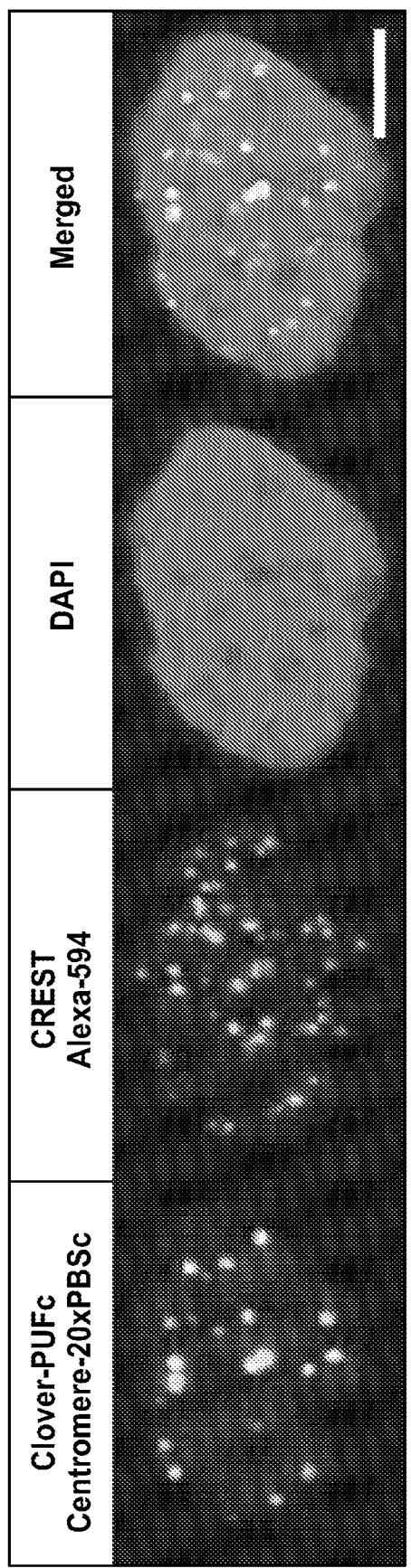
Figure 6G:
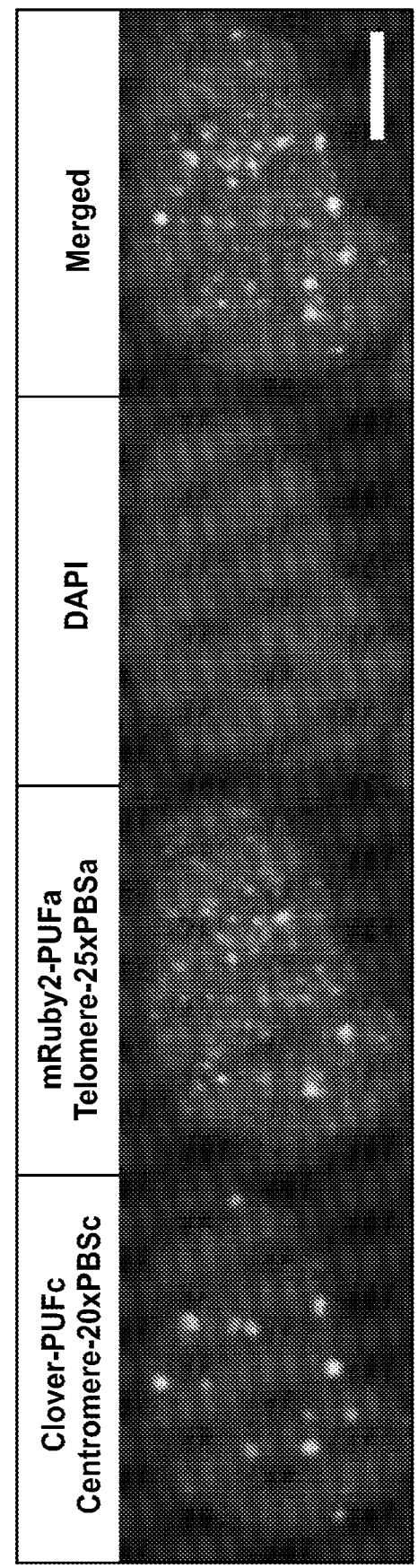

To further demonstrate the ability of the subject 3-component system to label two genomic loci simultaneously, an sgRNA was designed to target centromeres with appended binding sites for PUFc (sgCentromere-20×PBSc). Labeling of centromeres by the subject 3-component system and immunostaining using anti-CREST antibody were observed and confirmed (FIG. 6F). When Clover-PUFb/sgCentromere-20×PBSc, Ruby-PUFa/sgTelomere-25×PBSa and dCas9 were co-introduced into HEK293T cells, independent labeling of both centromeres and telomeres in the same cells were observed (FIG. 6G), demonstrating that the subject 3-component system can be used to independently label multiple genomic loci.

Example 9 The Subject 3-Component CRISPR/Cas Complex/System Allows Fluorescent Tagging of Non-repeat Chromosomal Loci A previous study using dCas9::GFP to label non-repetitive DNA reported the requirement of >32 targeting events to concentrate enough signal to label such non-repeat regions. This example demonstrates that, by incorporating multiple binding sites for PUF-fluorescent protein fusions, fluorescent signals can be concentrated at a target site, thus reducing the amount of targeting sites needed for detection of non-repeat DNA.

Figure 7:
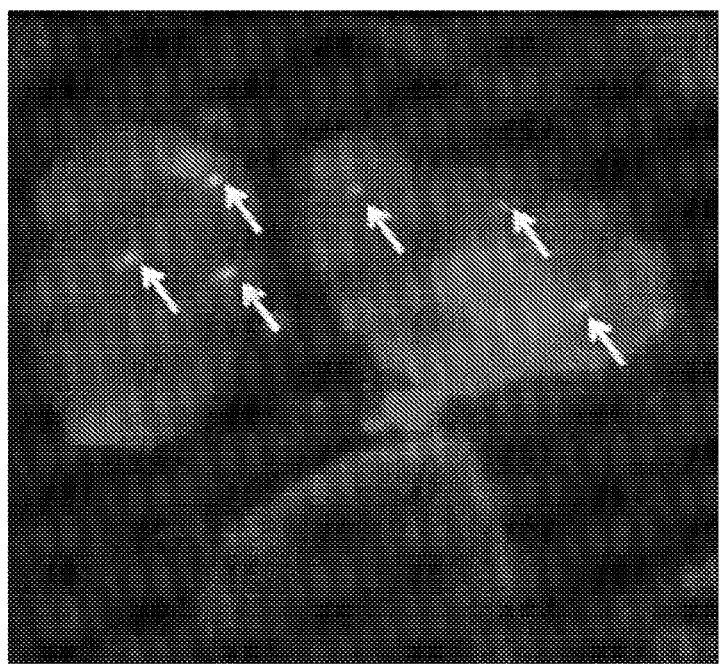
FIG. 7 is a representative confocal microscopy image of the MUC4 labeling, showing that the subject 3-component CRISPR/Cas complex/system allows labeling of non-repeat region with 7 sgRNA-15×PBS32 targeting MUC4 locus.

The non-repeat region at the MUC4 locus was tested in this example. Seven (7) sgRNAs each harboring 15×PBS32, Clover::PUF(3-2) and dCas9, labeling pattern reminiscent of that of MUC4 labeling was successfully detected (FIG. 7). This demonstrates that the subject 3-component CRISPR/Cas complex/system can be used to "polymerize" proteins at defined genomic loci, which enables and greatly expands the application of the subject 3-component CRISPR/Cas complex/system in the field of imaging.

The above examples demonstrate the ability of the subject 3-component CRISPR/Cas complex/system to achieve multiplexing (FIG. 8A), complex formation (FIG. 8C), and polymerization of proteins (FIG. 8B), including transcriptional regulators, epigenetic modifiers, and fluorescent proteins, and the system can independently direct them to defined genomic loci. This enables construction of complex molecular behavior at multiple loci, and allows studying and reconstitution of protein complexes with defined stoichiometry. The polymerization feature of the subject 3-component CRISPR/Cas complex/system allows concentration of enzymatic activity or other proteins to defined genomic loci, to increase the effect of the enzymatic activity or to concentrate signal enrichment for applications like chromosomal imaging.

More specifically, some main advantages of the subject 3-component system include: (A) Multiplexing. Different modules of the subject 3-component system can be simultaneously delivered into a cell and each can operate at their defined target sites with independence (i.e., without interference with other modules and their target sites). Since PUF domains can be easily programmed to recognize any 8-mer RNA motifs, this expands the potential number of independent modules to a theoretical maximum of $4^8$ (65536). By inserting a PUF array within another, the recognition site can be programmed to a 16-mer RNA motif, with a sequence space of $4^{16}$ (4.29 billion). (B) Multimerization: Simplicity of the linear 8-mer PBS motif allows extensive multimerization of PUF fusions on sgRNA-PBS without hindering sgRNA transcription or Cas9/sgRNA DNA binding activity. This feature allows multiple molecules of PUF fusions to be assembled on the sgRNA, allowing for localized concentration of effectors or protein tags. This is particularly beneficial for fluorescent imaging or transcriptional regulation. As shown with the above experiments labeling repeat sequences such as telomeres, sgRNA-PBS with more PBS increases signal at the telomeric foci. This feature may facilitate labeling of non-repeat sequences where usually tiling of more than 30 sgRNAs were required. Higher efficiency of HAT-mediated enhancer activation using the subject system versus direct dCas9-HAT fusion was observed. It is contemplated that multimerization can facilitate spreading of the epigenetic modification directed by the artificial epigenetic factors useful for reprogramming of large epigenetic domains such as super-enhancers or imprinted loci. (C) Stoichiometrically defined Complex formation: although not directly tested here, it is contemplated that the sgRNA-PBS can act as RNA scaffold for PUF-directed assembly of Stoichiometrically defined protein complexes. Specifically, Varying numbers of PBS copies with varying specificities can be appended to the sgRNA to allow for multiprotein complex formation with defined stoichiometry, as well as with defined ordering along the sgRNA-PBS.

The materials and methods used in the examples above are compiled below.

Cloning

A list of vectors, links to their Addgene entries are provided in Table 51 below. Detailed description of cloning strategies and sequences are given below.

PUFa [PUF(3-2)] and PUFb [PUF(6-2/7-2)] with N-terminal NLS were amplified from constructs containing these coding sequences with primers containing SgrAI and PacI sites and were used to replace SgrAI-dCas9-FseI from pAC164:pmax-dCas9Master_VP64 to create pAC1355: pmax-NLSPUFa_VP64 and pAC1356:pmax-NLSPUFb_VP64. A fusion PCR with 5' fragment up to repeat 4 of NLSPUFb and 3' fragment from repeat 5 to the end of NLSPUFa was used to create pAC1357:pmax-NLSPUFw_VP64. A fusion PCR of 5' fragment of NLSPUFa with 3' fragment of NLSPUb was used to create pAC1358:pmax-NLSPUFc_VP64.

p65HSF1 activator ORF was amplified from MS2-P65-HSF1_GFP (Addgene: 61423) with FseI PacI sites to replace VP64 fragment in pAC164 to create pAC1410:pmax-dCas9_p65HSF1, and replace VP64 in pAC1355 and pAC1358 to create pAC1393: pmax-NLSPUFa_p65HSF1 and pAC1411:pmax-NLSPUFc_p65HSF1, respectively.

Clover and mRuby2 were amplified from pcDNA3-Clover (Addgene #40259) and pcDNA3-mRuby2 (Addgene

40260) respectively with primers containing SgrAI and FseI cloning site, ligated with various FseI-PUF-PacI amplified from the above pAC1356~1358 and vector digested from pAC149:pCR8-dCas9VP160 (Addgene #48221) to create gateway donor vectors pAC1402, pAC1403 and pAC1404 containing ORFs of Clover_PUFa and Clover_PUFc, mRuby2_PUFa, respectively. These ORFs are then transferred to PB3-neo vector by recombining with pAC1119:PB3-neo(−)-pmaxDEST(+) by LR Clonase (Invitrogen) to create expression vectors pAC1360 (Clover_PUFa), pAC1381 (Clover_PUFc) and pAC1362 (mRuby2_PUFa).

NLSKRAB repressor domain was amplified from SOX2 TALE Repressor (KRAB 1-75) (Addgene #42945) with primers containing AgeI-ClaI sites and ligated with NLSPUFa amplified with primers containing AclI PacI and with pAC1360 digested with SgrAI-PacI as vector to create pAC1412: PB3-neo(−)-pmax-NLSKRAB_NLSPUFa.

The FseI-p65HSF1-PacI fragment was released from pAC1393 and ligated with SgrAI-NLSPUMb fragment released from pAC1356 and pAC1360 digested with SgrAI-PacI as vector to create pAC1413: PB3-neo(−)-pmax-NLSPUFb_p65HSF1. The BFPKRAB fragment was amplified from pHR-SFFV-dCas9-BFP-KRAB (Addgene #46911) and was used to replace Clover fragment from pAC1360 to create pAC1414: PB3-neo(−)-pmax-BFPKRAB_NLSPUFa. Then, an NheI-CAGGS-NLSPUFb_p65HSF1-NheI fragment was amplified from pAC1413 and inserted into pAC1414 digested with NheI to create a dual expression vector for BFPKRAB-NLSPUFa and NLSPUFb-p65HSF1 (pAC1414: PB3-NLSPUFb_p65HSF1(−)neo(−)-BFPKRAB2_NLSPUFa).

Four gateway donor vectors with improved linker sequences and three extra NLS on the N-terminal and one additional NLS on the C-terminal of PUF as well as cloning sites for N-terminal (SgrAI,ClaI) and C-terminal (FseI-PacI) insertions were created (pAC1404~1408). HAT sequence was amplified from mouse Crebbp gene using mouse cDNA with primers containing FseI-PacI site and inserted into pAC164 to create pAC1364: pmax-dCas9Master_CBPHAT and into pAC1405 to create pAC1415: pCR8-4×NLSPUFa_2×NLS_CBPHAT. HAT sequence was amplified with another pair of primers containing SgrAI-AclI site and cloned into SgrAI-ClaI site of pAC1405 to create pAC1416: pCR8-CBPHAT_4×NLSPUFa_2×NLS. pAC1415 and pAC1416 were recombined into pAC90:pmax-DEST (Addgene #48222) to create expression vectors pAC1417: pmax-4×NLSPUFa_2×NLS_CBPHAT and pAC1418: pmax-CBPHAT_4×NLSPUFa_2×NLS, respectively. FseI-mCherry-PacI fragment was amplified from a plasmid containing mCherry sequence and ligated with SgrAI-dCas9-FseI to PB3-neo(−)-pmax to generate pAC1419: PB3-neo(−)-pmax-dCas9Master_mCherry.

Expression vectors for sgRNA-PBS were constructed as follows: First, a sgRNA scaffold based on sgF+E with BbsI for oligo cloning of guide sequence and with 3′ BsaI (right upstream of the terminator) for insertion of PBS were ordered as a gBlock (IDT), and were cloned into pX330 (Addgene #42230) replacing the AflIII-NotI region to create vector pAC1394: pX-sgFE-BsaI(AGAT). Then, oligos encoding 5×PBSa sites each separated by ggc-spacer flanked by 5′-AGAT-3′ overhangs on one side and 5′-ATCT-3′ on the other side were treated with T4PNK and annealed and ligated into pAC1394 digested with BsaI (to create compatible overhangs). Clones were then screened for 1 copy (5×PBS), 2 copies (10×PBS), etc of the oligo insertions for the different number of PBS. For 1×PBS and 2×PBS vectors, they were constructed using oligo containing one PBS site. Guide sequence for each target were then cloned onto the sgRNA-PBS expression vectors via BbsI site as previously described. For sgRNA expression vectors with GFP expression markers, they were constructed by transferring the sgRNA-PBS expression cassette from the pX vectors onto a PB-GFP vector via AscI site. The different sgRNA expression constructs are listed in Table 51.

Cell Culture for Experiments

HEK293T cells were cultivated in Dulbecco's modified Eagle's medium (DMEM)(Sigma) with 10% fetal bovine serum (FBS)(Lonza), 4% Glutamax (Gibco), 1% Sodium Pyruvate (Gibco) and penicillin-streptomycin (Gibco). Incubator conditions were 37° C. and 5% $CO_2$. For activation experiments, cells were seeded into 12-well plates at 100,000 cells per well the day before being transfected with 200 ng of dCas9 construct, 100 ng of modified sgRNA and 100 ng of PUF-fusion with Attractene transfection reagent (Qiagen). After transfection, cells were grown for 48 hrs and harvested for either RNA extraction or fluorescent-activated cell sorting (FACS). For dual activation-repression experiments, transfection remained the same, however cells were seeded into 12-well plates at 150,000 cells per well and were grown for 72 hrs before being harvested for FACS. For experiments with OCT4 and SOX2 dual activation-repression, cells were triple-sorted by BFP (for the activator-repressor module PUFb-p65HSF1/BFPKRAB-PUFa), mCherry (for dCas9mCherry) and GFP (for the sgRNA-PBS on vectors co-expressing EGFP) before RNA extraction. For imaging experiments, cells were seeded into 6-well plates with 22×22×1 microscope cover glass at 300,000 cells per well the day before being transfected with 50 ng of dCas9 construct, 500 ng of modified sgRNA, and 50 ng of a PUF-fluorescent fusion with Attractene transfection reagent. After transfection, cells were grown for 48 hrs then immunostained.

Quantitative RT-PCR Analysis

Cells were harvested with trypsin, washed with Dulbecco's phosphate-buffered saline (dPBS), centrifuged at 125 g for 5 mins and then RNA was extracted using RNeasy Plus Mini Kit (Qiagen). A cDNA library was made using Applied Biosystems High Capacity RNA-to-cDNA kit with 1 µg of RNA. TaqMan Gene expression assays (Applied Biosystems) were designed using GAPDH (Hs03929097, VIC) as endogenous control and OCT4 (Hs00999632, FAM) and SOX2 (Hs01053049, FAM) as targets. TaqMan Universal Master Mix II, with UNG (Applied Biosystems) was used for Quantitative PCR (qPCR), with 2 µl of 1:10 diluted cDNA used for each reaction. Activation was analyzed with the Applied Biosystems ViiA7 instrument. Gene expression levels were calculated by "delta delta Ct" algorithm and normalized to control samples.

Fluorescent-Activated Cell Sorting

Cells were trypisinized and fixed for 10 min with 2% paraformaldehyde. Afterwards, the cells were centrifuged at 125 g for 5 min and resuspended in dPBS. Samples were analyzed on a FACScalibur flow cytometer using CellQuest Pro software (BD Bioscience). thousands events were collected in each run.

Immunostaining and Microscopy

While adherent to a cover glass, cells were fixed in 2% paraformaldehyde, washed with 0.1% Triton X-100 in dPBS, permeabilized with 0.4% Triton X-100 in dPBS for 5 min at 4° C., blocked in 5% Blotting-grade blocking buffer (BIO-RAD) for 30 min, incubated with the primary antibody in blocking buffer at 4° C. overnight, washed three times with dPBS, then incubated in the dark with a respective Alexa Fluor-conjugated secondary antibody at room temperature for 3 hours, washed again, and stained with DAPI. The cover glass was mounted on a slide with glycerol before imaging. Immunostaining of telomeres was performed with a 1:100 dilution of an anti-TRF2 primary antibody (Novus Biologicals: NB110-57130) and a 1:500 dilution of an Alexa fluor 594-conjugated anti-Rabbit IgG secondary antibody (Invitrogen, A11037). A 1:100 dilution of CREST antibody (Antibodies Incorporated: 15-235-0001) was used in conjunction with a 1:500 dilution of an Alexa fluor 594-conjugated anti-Human IgG secondary antibody (Invitrogen, A11014) to detect centromeres.

Sequences of some of the constructs used in the examples above and the related sequences are listed herein below.

```
>NLSPUFa_VP64 Key: NLS PUFa VP64
                                      (SEQ ID NO: 96)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGSRVIEKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGNYVIQHVLEHGRPEDKSKIVA

EIRGNVLVLSQHKFASNVVEKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID
```

In the above sequence, the NLS sequence is residues 6-12, PUFa is residues 15-363, and VP64 is residues 371-421.

```
>NLSPUFb_VP64 Key: NLS PUFb VP64
                                      (SEQ ID NO: 97)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGCRVIQKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGSYVIEHVLEHGRPEDKSKIVA

EIRGNVLVLSQHKFANNVVQKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID
```

In the above sequence, the NLS sequence is residues 6-12, PUFb is residues 15-363, and VP64 is residues 371-421.

```
>NLSPUFw_VP64 Key: NLS PUFw VP64
                                      (SEQ ID NO: 98)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGCRVIQKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGNYVIQHVLEHGRPEDKSKIVA

EIRGNVLVLSQHKFASNVVEKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID
```

In the above sequence, the NLS sequence is residues 6-12, PUFw is residues 15-363, and VP64 is residues 371-421.

```
>NLSPUFc_VP64 Key: NLS PUFc VP64
                                      (SEQ ID NO: 99)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGSRVIEKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGSYVIEHVLEHGRPEDKSKIVA

EIRGNVLVLSQHKFANNVVQKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID
```

In the above sequence, the NLS sequence is residues 6-12, PUFc is residues 15-363, and VP64 is residues 371-421.

```
>Clover_NLSPUFa Key: Clover NLS PUFa
                                      (SEQ ID NO: 100)
MVSKGEELFTGVVPILVELDGDVNGHKFSVRGEGEGDATNGKLTLKFICT

TGKLPVPWPTLVTTFGYGVACFSRYPDHMKQHDFFKSAMPEGYVQERTIS

FKDDGTYKTRAEVKFEGDTLVNRIELKGIDFKEDGNILGHKLEYNFNSHN

VYITADKQKNGIKANFKIRHNVEDGSVQLADHYQQNTPIGDGPVLLPDNH

YLSHQSALSKDPNEKRDHMVLLEFVTAAGITHGMDELYKSRGPYSIVSPK

CGGGGSGPAGILPPKKKRKVSRGRSRLLEDFRNNRYPNLQLREIAGHIME

FSQDQHGSRFIQLKLERATPAERQLVFNEILQAAYQLMVDVFGNYVIQKF

FEFGSLEQKLALAERIRGHVLSLALQMYGSRVIEKALEFIPSDQQNEMVR

ELDGHVLKCVKDQNGNHVVQKCIECVQPQSLQFIIDAFKGQVFALSTHPY

GCRVIQRILEHCLPDQTLPILEELHQHTEQLVQDQYGNYVIQHVLEHGRP

EDKSKIVAEIRGNVLVLSQHKFASNVVEKCVTHASRTERAVLIDEVCTMN

DGPHSALYTMMKDQYANYVVQKMIDVAEPGQRKIVMHKIRPHIATLRKYT

YGKHILAKLEKYYMKNGVDLG
```

In the above sequence, the NLS sequence is residues 264-270, PUFa is residues 273-621, and Clover is residues 1-251.

```
>Clover_NLSPUFc Key: Clover NLS PUFc
                                      (SEQ ID NO: 101)
MVSKGEELFTGVVPILVELDGDVNGHKFSVRGEGEGDATNGKLTLKFICT

TGKLPVPWPTLVTTFGYGVACFSRYPDHMKQHDFFKSAMPEGYVQERTIS

FKDDGTYKTRAEVKFEGDTLVNRIELKGIDFKEDGNILGHKLEYNFNSHN

VYITADKQKNGIKANFKIRHNVEDGSVQLADHYQQNTPIGDGPVLLPDNH

YLSHQSALSKDPNEKRDHMVLLEFVTAAGITHGMDELYKSRGPYSIVSPK
```

-continued

CGGGGSGPAGILPPKKKRKVSRGRSRLLEDFRNNRYPNLQLREIAGHIME

FSQDQHGSRFIQLKLERATPAERQLVFNEILQAAYQLMVDVFGNYVIQKF

FEFGSLEQKLALAERIRGHVLSLALQMYGSRVIEKALEFIPSDQQNEMVR

ELDGHVLKCVKDQNGNHVVQKCIECVQPQSLQFIIDAFKGQVFALSTHPY

GCRVIQRILEHCLPDQTLPILEELHQHTEQLVQDQYGSYVIEHVLEHGRP

EDKSKIVAEIRGNVLVLSQHKFANNVVQKCVTHASRTERAVLIDEVCTMN

DGPHSALYTMMKDQYANYVVQKMIDVAEPGQRKIVMHKIRPHIATLRKYT

YGKHILAKLEKYYMKNGVDLG

In the above sequence, the NLS sequence is residues 264-270, PUFc is residues 273-621, and Clover is residues 1-251.

>mRuby2_NLSPUFa Key: 6xHis-mRuby2
("6xHis" disclosed as SEQ ID NO: 95) NLS PUFa
(SEQ ID NO: 102)
MVRGSHHHHHHGMASMTGGQQMGRDLYDDDDKDPMVSKGEELIKENMRMK

VVMEGSVNGHQFKCTGEGEGNPYMGTQTMRIKVIEGGPLPFAFDILATSF

MYGSRTFIKYPKGIPDFFKQSFPEGFTWERVTRYEDGGVVTVMQDTSLED

GCLVYHVQVRGVNFPSNGPVMQKKTKGWEPNTEMMYPADGGLRGYTHMAL

KVDGGGHLSCSFVTTYRSKKTVGNIKMPGIHAVDHRLERLEESDNEMFVV

QREHAVAKFAGLGGGMDELYKGGGGSGPAGILPPKKKRKVSRGRSRLLED

FRNNRYPNLQLREIAGHIMEFSQDQHGSRFIQLKLERATPAERQLVFNEI

LQAAYQLMVDVFGNYVIQKFFEFGSLEQKLALAERIRGHVLSLALQMYGS

RVIEKALEFIPSDQQNEMVRELDGHVLKCVKDQNGNHVVQKCIECVQPQS

LQFIIDAFKGQVFALSTHPYGCRVIQRILEHCLPDQTLPILEELHQHTEQ

LVQDQYGNYVIQHVLEHGRPEDKSKIVAEIRGNVLVLSQHKFASNWEKCV

THASRTERAVLIDEVCTMNDGPHSALYTMMKDQYANYVVQKMIDVAEPGQ

RKIVMHKIRPHIATLRKYTYGKHILAKLEKYYMKNGVDLG

In the above sequence, the NLS sequence is residues 284-290, PUFa is residues 293-641, and 6×His-mRuby2 ("6xHis" disclosed as SEQ ID NO: 95) is residues 1-271, including the 6×His tag ("6xHis" disclosed as SEQ ID NO: 95) at residues 6-11.

>NLSPUFa_p5HSF1 Key: PUFa NLS p65HSF1
(SEQ ID NO: 103)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGSRVIEKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGNYVIQHVLEHGRPEDKSKIVA

EIRGNVLVLSQHKFASNVVEKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGGGGSGGGGSGGGGSGPKKKRKVAAAGSPSGQIS

NQALALAPSSAPVLAQTMVPSSAMVPLAQPPAPAPVLTPGPPQSLSAPVP

KSTQAGEGTLSEALLHLQFDADEDLGALLGNSTDPGVFTDLASVDNSEFQ

QLLNQGVSMSHSTAEPMLMEYPEAITRLVTGSQRPPDPAPTPLGTSGLPN

GLSGDEDFSSIADMDFSALLSQISSSGQGGGGSGFSVDTSALLDLFSPSV

TVPDMSLPDLDSSLASIQELLSPQEPPRPPEAENSSPDSGKQLVHYTAQP

LFLLDPGSVDTGSNDLPVLFELGEGSYFSEGDGFAEDPTISLLTGSEPPK

AKDPTVSID

In the above sequence, the NLS sequence is residues 6-12, PUFa is residues 15-363, p65 is residues 427-575, and HSF1 is residues 584-707.

>NLSKRAB_NLSPUFa Key: NLSKRAB PUFa
(SEQ ID NO: 104)
MGSPKKKRKVEASMDAKSLTAWSRTLVTFKDVFVDFTREEWKLLDTAQQI

VYRNVMLENYKNLVSLGYQLTKPDVILRLEKGEEPWLVSRGSIVGILPPK

KKRKVSRGRSRLLEDFRNNRYPNLQLREIAGHIMEFSQDQHGSRFIQLKL

ERATPAERQLVFNEILQAAYQLMVDVFGNYVIQKFFEFGSLEQKLALAER

IRGHVLSLALQMYGSRVIEKALEFIPSDQQNEMVRELDGHVLKCVKDQNG

NHVVQKCIECVQPQSLQFIIDAFKGQVFALSTHPYGCRVIQRILEHCLPD

QTLPILEELHQHTEQLVQDQYGNYVIQHVLEHGRPEDKSKIVAEIRGNVL

VLSQHKFASNVVEKCVTHASRTERAVLIDEVCTMNDGPHSALYTMMKDQY

ANYVVQKMIDVAEPGQRKIVMHKIRPHIATLRKYTYGKHILAKLEKYYMK

NGVDLG

In the above sequence, the two NLS sequences are residues 4-10 and residues 99-105, PUFa is residues 108-456, and KRAB is residues 11-92.

>BFPKRAB_NLSPUFa Key: HA-2xNLS-BFPKRAB NLS PUFa
(SEQ ID NO: 105)
MAYPYDVPDYASLGSGSPKKKRKVEDPKKKRKVDGIGSGSNGSSGSSE

LIKENMHMKLYMEGTVDNHHFKCTSEGEGKPYEGTQTMRIKVVEGGPLP

FAFDILATSFLYGSKTFINHTQGIPDFFKQSFPEGFTWERVTTYEDGGV

LTATQDTSLQDGCLIYNVKIRGVNFTSNGPVMQKKTLGWEAFTETLYPA

DGGLEGRNDMALKLVGGSHLIANIKTTYRSKKPAKNLKMPGVYYVDYRL

ERIKEANNETYVEQHEVAVARYCDLPSKLGHKLNGGGGGMDAKSLTAWS

RTLVTFKDVFVDFTREEWKLLDTAQQIVYRNVMLENYKNLVSLGYQLTK

PDVILRLEKGEEPGGSGGGSGPAGILPPKKKRKVSRGRSRLLEDFRNNR

YPNLQLREIAGHIMEFSQDQHGSRFIQLKLERATPAERQLVFNEILQAA

YQLMVDVFGNYVIQKFFEFGSLEQKLALAERIRGHVLSLALQMYGSRVI

EKALEFIPSDQQNEMVRELDGHVLKCVKDQNGNHVVQKCIECVQPQSLQ

FIIDAFKGQVFALSTHPYGCRVIQRILEHCLPDQTLPILEELHQHTEQL

VQDQYGNYVIQHVLEHGRPEDKSKIVAEIRGNVLVLSQHKFASNVVEKC

VTHASRTERAVLIDEVCTMNDGPHSALYTMMKDQYANYVVQKMIDVAEP

GQRKIVMHKIRPHIATLRKYTYGKHILAKLEKYYMKNGVDLG

In the above sequence, the NLS sequence is residues 370-376, PUFa is residues 379-727, and HA-2×NLS-BFPKRAB is residues 1-355, including the HA tag at residues 3-11.

```
>dCas9Master_mCherry HATag NLS dCas9 mCherry
                                       (SEQ ID NO: 106)
MIDGGGGSGGGGSGGGGSMYPYDVPDYASPKKKRKVEASDKKYSIGLAIG
TNSVGWAVITDEYKVPSKKFKVLGNTDRHSIKKNLIGALLFDSGETAEAT
RLKRTARRRYTRRKNRICYLQEIFSNEMAKVDDSFFHRLEESFLVEEDKK
HERHPIFGNIVDEVAYHEKYPTIYHLRKKLVDSTDKADLRLIYLALAHMI
KFRGHFLIEGDLNPDNSDVDKLFIQLVQTYNQLFEENPINASGVDAKAIL
SARLSKSRRLENLIAQLPGEKKNGLFGNLIALSLGLTPNFKSNFDLAEDA
KLQLSKDTYDDDLDNLLAQIGDQYADLFLAAKNLSDAILLSDILRVNTEI
TKAPLSASMIKRYDEHHQDLTLLKALVRQQLPEKYKEIFFDQSKNGYAGY
IDGGASQEEFYKFIKPILEKMDGTEELLVKLNREDLLRKQRTFDNGSIPH
QIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVK
QLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRL
SRKLINGIRDKQSGKTILDFLKSDGFANRNFMQLIHDDSLTFKEDIQKAQ
VSGQGDSLHEHIANLAGSPAIKKGILQTVKVVDELVKVMGRHKPENIVIE
MARENQTTQKGQKNSRERMKRIEEGIKELGSQILKEHPVENTQLQNEKLY
LYYLQNGRDMYVDQELDINRLSDYDVDAIVPQSFLKDDSIDNKVLTRSDK
NRGKSDNVPSEEVVKKMKNYWRQLLNAKLITQRKFDNLTKAERGGLSELD
KAGFIKRQLVETRQITKHVAQILDSRMNTKYDENDKLIREVKVITLKSKL
VSDFRKDFQFYKVREINNYHHAHDAYLNAVVGTALIKKYPKLESEFVYGD
YKVYDVRKMIAKSEQEIGKATAKYFFYSNIMNFFKTEITLANGEIRKRPL
IETNGETGEIVWDKGRDFATVRKVLSMPQVNIVKKTEVQTGGFSKESILP
KRNSDKLIARKKDWDPKKYGGFDSPTVAYSVLVVAKVEKGKSKKLKSVKE
LLGITIMERSSFEKNPIDFLEAKGYKEVKKDLIIKLPKYSLFELENGRKR
MLASAGELQKGNELALPSKYVNFLYLASHYEKLKGSPEDNEQKQLFVEQH
KHYLDEIIEQISEFSKRVILADANLDKVLSAYNKHRDKPIREQAENIIHL
FTLTNLGAPAAFKYFDTTIDRKRYTSTKEVLDATLIHQSITGLYETRIDL
SQLGGDSPKKKRKVEASGGGGSGGGGSGGGGSGPAMVSKGEEDNMAIIKE
FMRFKVHMEGSVNGHEFEIEGEGEGRPYEGTQTAKLKVTKGGPLPFAWDI
LSPQFMYGSKAYVKHPADIPDYLKLSFPEGFKWERVMNFEDGGVVTVTQD
SSLQDGEFIYKVKLRGTNFPSDGPVMQKKTMGWEASSERMYPEDGALKGE
IKQRLKLKDGGHYDAEVKTTYKAKKPVQLPGAYNVNIKLDITSHNEDYTI
VEQYERAEGRHSTGGMDELYKID
```

In the above sequence, the two NLS sequences are residues 30-36 and 1408-1414, dCas9 is residues 40-1406, mCherry is residues 1436-1671, and the HA tag is at residues 20-28.

```
>CBPHAT_4xNLS_PUFa_2xNLS Key: CBPHATNLS PUFa
                                       (SEQ ID NO: 107)
MIFKPEELRQALMPTLEALYRQDPESLPFRQPVDPQLLGIPDYFDIVKNP
MDLSTIKRKLDTGQYQEPWQYVDDVWLMFNNAWLYNRKTSRVYKFCSKLA
EVFEQEIDPVMQSLGYCCGRKYEFSPQTLCCYGKQLCTIPRDAAYYSYQN
RYHFCEKCFTEIQGENVTLGDDPSQPQTTISKDQFEKKKNDTLDPEPFVD
CKECGRKMHQICVLHYDIIWPSGFVCDNCLKKTGRPRKENKFSAKRLQTT
RLGNHLEDRVNKFLRRQNHPEAGEVFVRVVASSDKTVEVKPGMKSRFVDS
GEMSESFPYRTKALFAFEEIDGVDVCFFGMHVQEYGSDCPPPNTRRVYIS
YLDSIHFFRPRCLRTAVYHEILIGYLEYVKKLGYVTGHIWACPPSEGDDY
IFHCHPPDQKIPKPKRLQEWYKKMLDKAFAERIINDYKDIFKQANEDRLT
SAKELPYFEGDFWPNVLEESIKELEQEEEERKKEESTAASETPEGSQGDS
KNAKKKNNKKTNKNKSSISRANKKKPSMPNVSNDLSQKLYATMEKHKEVF
FVIHLHAGPVISTQPPIVDPDPLLSCDLMDGRDAFLTLARDKHWEFSSLR
RSKWSTLCMLVELHTQGQDRFVYTCNECKHHVETRWHCTVCEDYDLCINC
YNTKSHTHKMVKWGLGLDDEGSSQGEPQSKSPQESRRLSIQRCIQSLVHA
CQCRNANCSLPSCQKMKRVVQHTKGCKRKTNGGCPVCKQLIALCCYHAKH
CQENKCPVPFCLNINDGGGGSDPKKKRKVDPKKKRKVDPKKKRKVGSTGS
RNDGGGGSGGGGSGGGGSGRAGILPPKKKRKVSRGRSRLLEDFRNNRYPN
LQLREIAGHIMEFSQDQHGSRFIQLKLERATPAERQLVFNEILQAAYQLM
VDVFGNYVIQKFFEFGSLEQKLALAERIRGHVLSLALQMYGSRVIEKALE
FIPSDQQNEMVRELDGHVLKCVKDQNGNHVVQKCIECVQPQSLQFIIDAF
KGQVFALSTHPYGCRVIQRILEHCLPDQTLPILEELHQHTEQLVQDQYGN
YVIQHVLEHGRPEDKSKIVAEIRGNVLVLSQHKFASNVVEKCVTHASRTE
RAVLIDEVCTMNDGPHSALYTMMKDQYANYVVQKMIDVAEPGQRKIVMHK
IRPHIATLRKYTYGKHILAKLEKYYMKNGVDLGDPKKKRKVDPKKKRKVG
GRGGGGSGGGGSGGGGSGPA
```

In the above sequence, the six 7-residue NLS sequences begin at residues 773, 781, 789, 826, 1185, and 1193, PUFa is residues 835-1183, and CBPHAT is residues 2-764.

```
>4xNLS_PUFa_2xNLS_CBPHATKey: NLS PUFa CBPHAT
                                       (SEQ ID NO: 108)
MIDGGGGSDPKKKRKVDPKKKRKVDPKKKRKVGSTGSRNDGGGGSGGGGS
GGGGSGRAGILPPKKKRKVSRGRSRLLEDFRNNRYPNLQLREIAGHIMEF
SQDQHGSRFIQLKLERATPAERQLVFNEILQAAYQLMVDVFGNYVIQKFF
EFGSLEQKLALAERIRGHVLSLALQMYGSRVIEKALEFIPSDQQNEMVRE
LDGHVLKCVKDQNGNHVVQKCIECVQPQSLQFIIDAFKGQVFALSTHPYG
CRVIQRILEHCLPDQTLPILEELHQHTEQLVQDQYGNYVIQHVLEHGRPE
DKSKIVAEIRGNVLVLSQHKFASNVVEKCVTHASRTERAVLIDEVCTMND
GPHSALYTMMKDQYANYVVQKMIDVAEPGQRKIVMHKIRPHIATLRKYTY
GKHILAKLEKYYMKNGVDLGDPKKKRKVDPKKKRKVGGRGGGGSGGGGSG
GGGSGPAIFKPEELRQALMPTLEALYRQDPESLPFRQPVDPQLLGIPDYF
DIVKNPMDLSTIKRKLDTGQYQEPWQYVDDVWLMFNNAWLYNRKTSRVYK
```

-continued

FCSKLAEVFEQEIDPVMQSLGYCCGRKYEFSPQTLCCYGKQLCTIPRDAA

YYSYQNRYHFCEKCFTEIQGENVTLGDDPSQPQTTISKDQFEKKKNDTLD

PEPFVDCKECGRKMHQICVLHYDIIWPSGFVCDNCLKKTGRPRKENKFSA

KRLQTTRLGNHLEDRVNKFLRRQNHPEAGEVFVRVVASSDKTVEVKPGMK

SRFVDSGEMSESFPYRTKALFAFEEIDGVDVCFFGMHVQEYGSDCPPPNT

RRVYISYLDSIHFFRPRCLRTAVYHEILIGYLEYVKKLGYVTGHIWACPP

SEGDDYIFHCHPPDQKIPKPKRLQEWYKKMLDKAFAERIINDYKDIFKQA

NEDRLTSAKELPYFEGDFWPNVLEESIKELEQEEEERKKEESTAASETPE

-continued

GSQGDSKNAKKKNNKKTNKNKSSISRANKKKPSMPNVSNDLSQKLYATME

KHKEVFFVIHLHAGPVISTQPPIVDPDPLLSCDLMDGRDAFLTLARDKHW

EFSSLRRSKWSTLCMLVELHTQGQDRFVYTCNECKHHVETRWHCTVCEDY

DLCINCYNTKSHTHKMVKWGLGLDDEGSSQGEPQSKSPQESRRLSIQRCI

QSLVHACQCRNANCSLPSCQKMKRVVQHTKGCKRKTNGGCPVCKQLIALC

CYHAKHCQENKCPVPFCLNI

In the above sequence, the six 7-residue NLS sequences begin at residues 10, 18, 26, 63, 422, and 430, PUFa is residues 72-420, and CBPHAT is residues 458-1220.

| Name and Description | DNA sequence |
|---|---|
| sgRNA-PBS expression cassettes: | |
| U6::sgRNA-0xPBS expression cassette containing the target sequences as Ns without PBS sequences | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccAGATCTTTTTTTgttttagagctagaaatagcaagttaaaataaggct agtccgtagcgcgtgcgccaattctgcagacaaatggc (SEQ ID NO: 109) |
| U6::sgRNA-1xPBS32 expression cassette containing the target sequences as Ns and 1 copy of PBS32 (UGUAUGUA) | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccagatGCCTGTATGTAGCCagatCTTTTTTTgttttagagctagaaata gcaagttaaaataaggctagtccgtagcgcgtgcgccaattctgcagacaaa tggc (SEQ ID NO: 110) |
| U6::sgRNA-5xPBS32 expression cassette containing the target sequences as Ns and 5 copies of PBS32 (UGUAUGUA) separated by GCC spacer sequence attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt CtCCagatTGTATGTAGCCTGTATGTAGCCTGTATGTAGCCTGTATGTAGCC TGTATGTAagatCTTTTTTTgttttagagctagaaatagcaagttaaaataa ggctagtccgtagcgcgtgcgccaattctgcagacaaatggc (SEQ ID NO: 111) |
| U6::sgRNA-15xPBS32 expression and cloning cassette containing the target sequences as Ns and 15 copies of PBS32 (UGUAUGUA) separated by GCC spacer sequence attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt CtCCagatTGTATGTAGCCTGTATGTAGCCTGTATGTAGCCTGTATGTAGCC TGTATGTAAGATTGTATGTAGCCTGTATGTAGCCTGTATGTAGCCTGTATGTA GCCTGTATGTAAGATTGTATGTAGCCTGTATGTAGCCTGTATGTAGCCTGTA TGTAGCCTGTATGTAagatCTTTTTTTgttttagagctagaaatagcaagtt aaaataaggctagtccgtagcgcgtgcgccaattctgcagacaaatggc (SEQ ID NO: 112) |
| U6::sgRNA-25xPBS32 expression and cloning cassette containing the target sequences as Ns and 25 copies of PBS32 (UGUAUGUA) separated by GCC spacer sequence attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt CtCCagatTGTATGTAGCCTGTATGTAGCCTGTATGTAGCCTGTATGTAGCC TGTATGTAAGATTGTATGTAGCCTGTATGTAGCCTGTATGTAGCCTGTATGT AGCCTGTATGTAAGATTGTATGTAGCCTGTATGTAGCCTGTATGTAGCCTGT ATGTAGCCTGTATGTAAGATTGTATGTAGCCTGTATGTAGCCTGTATGTAGC CTGTATGTAGCCTGTATGTAAGATTGTATGTAGCCTGTATGTAGCCTGTATG |

| | |
|---|---|
| | TAGCCTGTATGTAGCCTGTATGTAagatCTTTTTTTgttttagagctagaaa<br>tagcaagttaaaataaggctagtccgtagcgcgtgcgccaattctgcagaca<br>aatggc (SEQ ID NO: 113) |
| U6::sgRNA-1xPBS6272<br>expression cassette<br>containing the target<br>sequences as Ns and 1 copy<br>ofPBS6272<br>(UUGAUAUA) | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatgccTtgATATAgccagatCTTTTTTTgttttagagctagaaata<br>gcaagttaaaataaggctagtccgtagcgcgtgcgccaattctgcagacaaa<br>tggc (SEQ ID NO: 114) |
| U6::sgRNA-2xPBS6272<br>expression cassette<br>containing the target<br>sequences as Ns and 2<br>copies of PBS6272<br>(UUGAUAUA) separated<br>by GCC spacer sequence<br>attached at 3' region of the<br>sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatTTGATATAGCCTTGATATAagatCTTTTTTTgttttagagctag<br>aaatagcaagttaaaataaggctagtccgtagcgcgtgcgccaattctgcag<br>acaaatggc (SEQ ID NO: 115) |
| U6::sgRNA-5xPBS6272<br>expression cassette<br>containing the target<br>sequences as Ns and 5<br>copies of PBS6272<br>(UUGAUAUA) separated<br>by GCC spacer sequence<br>attached at 3' region of the<br>sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>CtCCagatTTGATATAGCCTTGATATAGCCTTGATATAGCCTTGATATAGCC<br>TTGATATAagatCTTTTTTTgttttagagctagaaatagcaagttaaaataa<br>ggctagtccgtagcgcgtgcgccaattctgcagacaaatggc<br>(SEQ ID NO: 116) |
| U6::sgRNA-10xPBS6272<br>expression cassette<br>containing the target<br>sequences as Ns and 10<br>copies of PBS6272<br>(UUGAUAUA) separated<br>by GCC spacer sequence<br>attached at 3' region of the<br>sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>CtCCagatTTGATATAGCCTTGATATAGCCTTGATATAGCCTTGATATAGCC<br>TTGATATAAGATTTGATATAGCCTTGATATAGCCTTGATATAGCCTTGATAT<br>AGCCTTGATATAagatCTTTTTTTgttttagagctagaaatagcaagttaaa<br>ataaggctagtccgtagcgcgtgcgccaattctgcagacaaatggc<br>(SEQ ID NO: 117) |
| U6::sgRNA-15xPBS6272<br>expression cassette<br>containing the target<br>sequences as Ns and 15<br>copies of PBS6272<br>(UUGAUAUA) separated<br>by GCC spacer sequence<br>attached at 3' region of the<br>sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>CtCCagatTTGATATAGCCTTGATATAGCCTTGATATAGCCTTGATATAGCC<br>TTGATATAAGATTTGATATAGCCTTGATATAGCCTTGATATAGCCTTGATAT<br>AGCCTTGATATAAGATTTGATATAGCCTTGATATAGCCTTGATATAGCCTTG<br>ATATAGCCTTGATATAagatCTTTTTTTgttttagagctagaaatagcaagt<br>taaaataaggctagtccgtagcgcgtgcgccaattctgcagacaaatggc<br>(SEQ ID NO: 118) |
| U6::sgRNA-20xPBS6272<br>expression cassette<br>containing the target<br>sequences as Ns and 20<br>copies of PBS6272<br>(UUGAUAUA) separated<br>by GCC spacer sequence<br>attached at 3' region of the<br>sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>CtCCagatTTGATATAGCCTTGATATAGCCTTGATATAGCCTTGATATAGCC<br>TTGATATAAGATTTGATATAGCCTTGATATAGCCTTGATATAGCCTTGATAT<br>AGCCTTGATATAAGATTTGATATAGCCTTGATATAGCCTTGATATAGCCTTG<br>ATATAGCCTTGATATAAGATTTGATATAGCCTTGATATAGCCTTGATATAGC<br>CTTGATATAGCCTTGATATAagatCTTTTTTTgttttagagctagaaatagc<br>aagttaaaataaggctagtccgtagcgcgtgcgccaattctgcagacaaatg<br>gc (SEQ ID NO: 119) |
| U6::sgRNA-25xPBS6272<br>expression cassette<br>containing the target<br>sequences as Ns and 25 | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg |

| | |
|---|---|
| copies of PBS6272 (UUGAUAUA) separated by GCC spacer sequence attached at 3' region of the sgRNA | atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt CtCCagatTTGATATAGCCTTGATATAGCCTTGATATAGCCTTGATATAGCC TTGATATAAGATTTGATATAGCCTTGATATAGCCTTGATATAGCCTTGATAT AGCCTTGATATAAGATTTGATATAGCCTTGATATAGCCTTGATATAGCCTTG ATATAGCCTTGATATAAGATTTGATATAGCCTTGATATAGCCTTGATATAGC CTTGATATAGCCTTGATATAAGATTTGATATAGCCTTGATATAGCCTTGATA TAGCCTTGATATAGCCTTGATATAagatCTTTTTTTgttttagagctagaaa tagcaagttaaaataaggctagtccgtagcgcgtgcgccaattctgcagaca aatggc (SEQ ID NO: 120) |
| U6::sgRNA-47xPBS6272 expression cassette containing the target sequences as Ns and 47 copies of PBS6272 (UUGAUAUA) separated by GCC spacer sequence attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt CtCCagatTTGATATAGCCTTGATATAGCCTTGATATAGCCTTGATATAGCC TTGATATAAGATTTGATATAGCCTTGATATAGCCTTGATATAGCCTTGATAT AGCCTTGATATAAGATTTGATATACCTTGATATAGCCTTGATATAGCCTTGA TATAGCCTTGATATAAGATTTGATATAGCCTTGATATAGCCTTGATATAGCC TTGATATAGCCTTGATATAGCCTTGATATAGCCTTGATATAAGATTTGATAT AGCCTTGATATAGCCTTGATATAGCCTTGATATAGCCTTGATATAAGATTTG ATATAGCCTTGATATAGCCTTGATATAGCCTTGATATAGCCTTGATATAAGA TTTGATATAGCCTTGATATAGCCTTGATATAGCCTTGATATAGCCTTGATAT AAGATTTGATATAGCCTTGATATAGCCTTGATATAGCCTTGATATAGCCTTG ATATAAGATTTGATATAGCCTTGATATAGCCTTGATATAGCCTTGATATAGC CTTGATATAagatCTTTTTTTgttttagagctagaaatagcaagttaaaata aggctagtccgtagcgcgtgcgccaattctgcagacaaatggc (SEQ ID NO: 121) |
| U6::sgRNA-2xPBS6272-10Spacer expression cassette containing the target sequences as Ns and 2 copies of PBS6272 (UUGAUAUA) separated by GCCAGATGCC spacer sequence (SEQ ID NO: 173) attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt CtCCagatGCCTTGATATAGCCAGATGCCTTGATATAGCCagatCTTTTTTT gttttagagctagaaatagcaagttaaaataaggctagtccgtagcgcgtgc gccaattctgcagacaaatggc (SEQ ID NO: 122) |
| U6::sgRNA-6xPBS6272-10Spacer expression cassette containing the target sequences as Ns and 6 copies of PBS6272 (UUGAUAUA) separated by GCCAGATGCC spacer sequence (SEQ ID NO: 173) attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt CtCCagatGCCTTGATATAGCCAGATGCCTTGATATAGCCAGATGCCTTGAT ATAGCCAGATGCCTTGATATAGCCAGATGCCTTGATATAGCCAGATGCCTTG ATATAGCCagatCTTTTTTTgttttagagctagaaatagcaagttaaaataa ggctagtccgtagcgcgtgcgccaattctgcagacaaatggc (SEQ ID NO: 123) |
| U6::sgRNA-15xPBS6272-10Spacer expression cassette containing the target sequences as Ns and 15 copies of PBS6272 (UUGAUAUA) separated by GCCAGATGCC spacer sequence (SEQ ID NO: 173) attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt CtCCagatGCCTTGATATAGCCAGATGCCTTGATATAGCCAGATGCCTTGAT ATAGCCAGATGCCTTGATATAGCCAGATGCCTTGATATAGCCAGATGCCT TGATATAGCCAGATGCCTTGATATAGCCAGATGCCTTGATATAGCCAGATGC CTTGATATAGCCAGATGCCTTGATATAGCCAGATGCCTTGATATAGCCAGAT GCCTTGATATAGCCagatCTTTTTTTgttttagagctagaaatagcaagtta aaataaggctagtccgtagcgcgtgcgccaattctgcagacaaatggc (SEQ ID NO: 124) |
| U6::sgRNA-20xPBS6272-10Spacer expression cassette containing the target sequences as Ns and 20 copies of PBS6272 (UUGAUAUA) separated by GCCAGATGCC spacer sequence (SEQ ID NO: 173) attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt CtCCagatGCCTTGATATAGCCAGATGCCTTGATATAGCCAGATGCCTTGAT ATAGCCAGATGCCTTGATATAGCCAGATGCCTTGATATAGCCAGATGCCTTG ATATAGCCAGATGCCTTGATATAGCCAGATGCCTTGATATAGCCAGATGCCT TGATATAGCCAGATGCCTTGATATAGCCAGATGCCTTGATATAGCCAGATGC |

| | |
|---|---|
| | CTTGATATAGCCAGATGCCTTGATATAGCCAGATGCCTTGATATAGCCAGAT<br>GCCTTGATATAGCCAGATGCCTTGATATAGCCAGATGCCTTGATATAGCCAG<br>ATGCCTTGATATAGCCAGATCCTTGATATAGCCAGATGCCTTGATATAGCCa<br>gatCTTTTTTgttttagagctagaaatagcaagttaaaataaggctagtcc<br>gtagcgcgtgcgccaattctgcagacaaatggc (SEQ ID NO: 125) |
| U6::5xPBS32-sgRNA expression cassette containing the target sequences as Ns and 5 copies of PBS32 (UGUAUGUA) separated by GCCAGATGCC spacer sequence (SEQ ID NO: 173) attached at 5' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCgCAATTGggtc<br>tCCAGATTGTATGTAGCCTGTATGTAGCCTGTATGTAGCCTGTATGTAGCCT<br>GTATGTAAGATCTCACCNNNNNNNNNNNNNNNNNNNNgtttAagagctaTGC<br>TGGAAACAGCAtagcaagttTaaataaggctagtccgttatcaacttgaaaa<br>agtggcaccgagtcggtgcTTTTTTgttttagagctagaaatagcaagttaa<br>aataaggctagtccgtagcgcgtgcgccaattctgcagacaaatggc<br>(SEQ ID NO: 126) |
| U6::sgRNA-2x[PBS32-PBS6272] expression cassette containing the target sequences as Ns and 2 copies of PBS32(UGUAUGUA)-PBS6272 (UUGAUAUA) clusters attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>CtCCagatTGTATGTAGTCTATTGATATAGTCTTGTCTATGTATGTAGTCTA<br>TTGATATAagatCTTTTTTTgttttagagctagaaatagcaagttaaaataa<br>ggctagtccgtagcgcgtgcgccaattctgcagacaaatggc<br>(SEQ ID NO: 127) |
| U6::sgRNA-8x[PBS32-PBS6272] expression cassette containing the target sequences as Ns and 8 copies of PBS32(UGUAUGUA)-PBS6272 (UUGAUAUA) clusters attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>CtCCagatTGTATGTAGTCTATTGATATAGTCTTGTCTATGTATGTAGTCTA<br>TTGATATAAGATTGTATGTAGTCTATTGATATAGTCTTGTCTATGTATGTAG<br>TCTATTGATATAAGATTGTATGTAGTCTATTGATATAGTCTTGTCTATGTAT<br>GTAGTCTATTGATATAAGATTGTATGTAGTCTATTGATATAGTCTTGTCTAT<br>GTATGTAGTCTATTGATATAagatCTTTTTTgttttagagctagaaatagc<br>aagttaaaataaggctagtccgtagcgcgtgcgccaattctgcagacaaatg<br>gc (SEQ ID NO: 128) |
| U6::sgRNA-4x[PBS32-PBS6272] expression cassette containing the target sequences as Ns and 4 copies of PBS32(UGUAUGUA)-PBS6272 (UUGAUAUA) clusters attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>CtCCagatTGTATGTAGTCTATTGATATAGTCTTGTCTATGTATGTAGTCTA<br>TTGATATAAGATTGTATGTAGTCTATTGATATAGTCTTGTCTATGTATGTAG<br>TCTATTGATATAagatCTTTTTTgttttagagctagaaatagcaagttaaa<br>ataaggctagtccgtagcgcgtgcgccaattctgcagacaaatggc<br>(SEQ ID NO: 129) |
| sgRNA target Sequences (sometimes an additional G is prepended to increase U6 transcriptional efficiency): | |
| Control Sequence | GTTCTCTTGCTGAAAGCTCGA (SEQ ID NO: 130)) |
| TetO promoter | GCTTTTCTCTATCACTGATA (SEQ ID NO: 131) |
| SV40P1 | GCATACTTCTGCCTGCTGGGGAGCCTG(SEQ ID NO: 132) |
| SV40P2 | GAAAGTCCCCAGGCTCCCCAGC(SEQ ID NO: 133) |
| SV40P3 | GCATCTCAATTAGTCAGCAACC(SEQ ID NO: 134) |
| Telomere | GTTAGGGTTAGGGTTAGGGTTA (SEQ ID NO: 135) |
| Centromere | GTTGAGGCCTTCGTTGGAAAC (SEQ ID NO: 136) |
| MUC4-Nonrepeat-1 | GAAGAGTGGAGGCCGTGCGCGG (SEQ ID NO: 137) |
| MUC4-Nonrepeat-2 | GCAAGCAAGGGAAGCGACAAGG(SEQ ID NO: 138) |
| MUC4-Nonrepeat-3 | GATGTTTCAGGACTAGGCTGA (SEQ ID NO: 139) |
| MUC4-Nonrepeat-4 | GAGCTGGGCCAGGAGAGGAGA (SEQ ID NO: 140) |
| MUC4-Nonrepeat-5 | |
| MUC4-Nonrepeat-6 | GGCTTGGTGTATTCAGAATG(SEQ ID NO: 142) |
| MUC4-Nonrepeat-7 | GTAGAGATGCCGCCCCGCCC (SEQ ID NO: 143) |
| OCT4-PP-1 | GGCCCCGCCCCTGGATGGG (SEQ ID NO: 144) |
| OCT4-PP-2 | GGGGGGAGAAACTGAGGCGA (SEQ ID NO: 145) |
| OCT4-PP-3 | GGTGGTGGCAATGGTGTCTG(SEQ ID NO: 146) |
| OCT4-PP-4 | GACACAACTGGCGCCCCTCC (SEQ ID NO: 147) |
| OCT4-PE-1 | GGCCCCTACTTCCCCTTCAA (SEQ ID NO: 148) |
| OCT4-PE-2 | GAGTGATAAGACACCCGCTT (SEQ ID NO: 149) |
| OCT4-PE-3 | GCCTGGGAGGGACTGGGGA (SEQ ID NO: 150) |
| OCT4-PE-4 | GGACAATCCCGGTCCCCAGA (SEQ ID NO: 151) |
| OCT4-DE-1 | GGTCTGCCGGAAGGTCTACA (SEQ ID NO: 152) |
| OCT4-DE-2 | GGCAGGTAGATTATGGGGCC(SEQ ID NO: 153) |

-continued

| | |
|---|---|
| OCT4-DE-3 | GAAGACGGCCTCTCAGAGGA (SEQ ID NO: 154) |
| OCT4-DE-4 | GTATTTCTGGCCTGGGCAAG (SEQ ID NO: 155) |
| SOX2-PP-1 | GCATGTGACGGGGGCTGTCA (SEQ ID NO: 156) |
| SOX2-PP-2 | GCTGCCGGGTTTTGCATGAA (SEQ ID NO: 157) |
| SOX2-PP-3 | GCCGGCCGCGCGGGGAGGC (SEQ ID NO: 158) |
| SOX2-PP-4 | GGCAGGCGAGGAGGGGGAGG (SEQ ID NO: 159) |
| SV40-P1 | GCATACTTCTGCCTGCTGGGGAGCCTG (SEQ ID NO: 160) |

| Name | Peptide sequence |
|---|---|
| S. pyrogene NLS-dCas9-NLS | MYPYDVPDYASPKKKRKVEASDKKYSIGLAIGTNSVGWAVITDEYKVPSKKFKVLGNT<br>DRHSIKKNLIGALLFDSGETAEATRLKRTARRRYTRRKNRICYLQEIFSNEMAKVDDS<br>FFHRLEESFLVEEDKKHERHPIFGNIVDEVAYHEKYPTIYHLRKKLVDSTDKADLRLI<br>YLALAHMIKFRGHFLIEGDLNPDNSDVDKLFIQLVQTYNQLFEENPINASGVDAKAIL<br>SARLSKSRRLENLIAQLPGEKKNGLFGNLIALSLGLTPNFKSNFDLAEDAKLQLSKDT<br>YDDDLDNLLAQIGDQYADLFLAAKNLSDAILLSDILRVNTEITKAPLSASMIKRYDEH<br>HQDLTLLKALVRQQLPEKYKEIFFDQSKNGYAGYIDGGASQEEFYKFIKPILEKMDGT<br>EELLVKLNREDLLRKQRTFDNGSIPHQIHLGELHAILRRQEDFYPFLKDNREKIEKIL<br>TFRIPYYVGPLARGNSRFAWMTRKSEETITPWNFEEVVDKGASAQSFIERMTNFDKNL<br>PNEKVLPKHSLLYEYFTVYNELTKVKYVTEGMRKPAFLSGEQKKAIVDLLFKTNRKVT<br>VKQLKEDYFKKIECFDSVEISGVEDRFNASLGTYHDLLKIIKDKDFLDNEENEDILED<br>IVLTLTLFEDREMIEERLKTYAHLFDDKVMKQLKRRRYTGWGRLSRKLINGIRDKQSG<br>KTILDFLKSDGFANRNFMQLIHDDSLTFKEDIQKAQVSGQGDSLHEHIANLAGSPAIK<br>KGILQTVKvvDELVKVMGRHKPENIVIEMARENQTTQKGQKNSRERMKRIEEGIKELG<br>SQILKEHPVENTQLQNEKLYLYYLQNGRDMYVDQELDINRLSDYDVDAIVPQSFLKDD<br>SIDNKVLTRSDKNRGKSDNVPSEEvvKKMKNYWRQLLNAKLITQRKFDNLTKAERGGL<br>SELDKAGFIKRQLVETRQITKHVAQILDSRMNTKYDENDKLIREVKVITLKSKLVSDF<br>RKDFQFYKVREINNYHHAHDAYLNAvvGTALIKKYPKLESEFVYGDYKVYDVRKMIAK<br>SEQEIGKATAKYFFYSNIMNFFKTEITLANGEIRKRPLIETNGETGEIVWDKGRDFAT<br>VRKVLSMPQVNIVKKTEVQTGGFSKESILPKRNSDKLIARKKDWDPKKYGGFDSPTVA<br>YSVLVvvAKVEKGKSKKLKSVKELLGITIMERSSFEKNPIDFLEAKGYKEVKKDLIIKL<br>PKYSLFELENGRKRMLASAGELQKGNELALPSKYVNFLYLASHYEKLKGSPEDNEQKQ<br>LFVEQHKYLDEIIEQISEFSKRVILADANLDKVLSAYNKHRDKPIREQAENIIHLFT<br>LTNLGAPAAFKYFDTTIDRKRYTSTKEVLDATLIHQSITGLYETRIDLSQLGGDSPKK<br>KRKVEAS (SEQ ID NO: 161) |
| S. pyogenes NLS-Cas9WT-NLS | MYPYDVPDYASPKKKRKVEASDKKYSIGLDIGTNSVGWAVITDEYKVPSKKFKVLGNT<br>DRHSIKKNLIGALLFDSGETAEATRLKRTARRRYTRRKNRICYLQEIFSNEMAKVDDS<br>FFHRLEESFLVEEDKKHERHPIFGNIVDEVAYHEKYPTIYHLRKKLVDSTDKADLRLI<br>YLALAHMIKFRGHFLIEGDLNPDNSDVDKLFIQLVQTYNQLFEENPINASGVDAKAIL<br>SARLSKSRRLENLIAQLPGEKKNGLFGNLIALSLGLTPNFKSNFDLAEDAKLQLSKDT<br>YDDDLDNLLAQIGDQYADLFLAAKNLSDAILLSDILRVNTEITKAPLSASMIKRYDEH<br>HQDLTLLKALVRQQLPEKYKEIFFDQSKNGYAGYIDGGASQEEFYKFIKPILEKMDGT<br>EELLVKLNREDLLRKQRTFDNGSIPHQIHLGELHAILRRQEDFYPFLKDNREKIEKIL<br>TFRIPYYVGPLARGNSRFAWMTRKSEETITPWNFEEVVDKGASAQSFIERMTNFDKNL<br>PNEKVLPKHSLLYEYFTVYNELTKVKYVTEGMRKPAFLSGEQKKAIVDLLFKTNRKVT<br>VKQLKEDYFKKIECFDSVEISGVEDRFNASLGTYHDLLKIIKDKDFLDNEENEDILED<br>IVLTLTLFEDREMIEERLKTYAHLFDDKVMKQLKRRRYTGWGRLSRKLINGIRDKQSG<br>KTILDFLKSDGFANRNFMQLIHDDSLTFKEDIQKAQVSGQGDSLHEHIANLAGSPAIK<br>KGILQTVKVVDELVKVMGRHKPENIVIEMARENQTTQKGQKNSRERMKRIEEGIKELG<br>SQILKEHPVENTQLQNEKLYLYYLQNGRDMYVDQELDINRLSDYDVDHIVPQSFLKDD<br>SIDNKVLTRSDKNRGKSDNVPSEEvvKKMKNYWRQLLNAKLITQRKFDNLTKAERGGL<br>SELDKAGFIKRQLVETRQITKHVAQILDSRMNTKYDENDKLIREVKVITLKSKLVSDF<br>RKDFQFYKVREINNYHHAHDAYLNAvvGTALIKKYPKLESEFVYGDYKVYDVRKMIAK<br>SEQEIGKATAKYFFYSNIMNFFKTEITLANGEIRKRPLIETNGETGEIVWDKGRDFAT<br>VRKVLSMPQVNIVKKTEVQTGGFSKESILPKRNSDKLIARKKDWDPKKYGGFDSPTVA<br>YSVLVVVAKVEKGKSKKLKSVKELLGITIMERSSFEKNPIDFLEAKGYKEVKKDLIIKL<br>PKYSLFELENGRKRMLASAGELQKGNELALPSKYVNFLYLASHYEKLKGSPEDNEQKQ<br>LFVEQHKYLDEIIEQISEFSKRVILADANLDKVLSAYNKHRDKPIREQAENIIHLFT<br>LTNLGAPAAFKYFDTTIDRKRYTSTKEVLDATLIHQSITGLYETRIDLSQLGGDSPKK<br>KRKVEAS (SEQ ID NO: 162) |
| S. pyogenes NLS-Cas9Nickase(D10A)-NLS | MYPYDVPDYASPKKKRKVEASDKKYSIGLAIGTNSVGWAVITDEYKVPSKKFKVLGNT<br>DRHSIKKNLIGALLFDSGETAEATRLKRTARRRYTRRKNRICYLQEIFSNEMAKVDDS<br>FFHRLEESFLVEEDKKHERHPIFGNIVDEVAYHEKYPTIYHLRKKLVDSTDKADLRLI<br>YLALAHMIKFRGHFLIEGDLNPDNSDVDKLFIQLVQTYNQLFEENPINASGVDAKAIL<br>SARLSKSRRLENLIAQLPGEKKNGLFGNLIALSLGLTPNFKSNFDLAEDAKLQLSKDT<br>YDDDLDNLLAQIGDQYADLFLAAKNLSDAILLSDILRVNTEITKAPLSASMIKRYDEH<br>HQDLTLLKALVRQQLPEKYKEIFFDQSKNGYAGYIDGGASQEEFYKFIKPILEKMDGT<br>EELLVKLNREDLLRKQRTFDNGSIPHQIHLGELHAILRRQEDFYPFLKDNREKIEKIL<br>TFRIPYYVGPLARGNSRFAWMTRKSEETITPWNFEEVVDKGASAQSFIERMTNFDKNL<br>PNEKVLPKHSLLYEYFTVYNELTKVKYVTEGMRKPAFLSGEQKKAIVDLLFKTNRKVT<br>VKQLKEDYFKKIECFDSVEISGVEDRFNASLGTYHDLLKIIKDKDFLDNEENEDILED<br>IVLTLTLFEDREMIEERLKTYAHLFDDKVMKQLKRRRYTGWGRLSRKLINGIRDKQSG<br>KTILDFLKSDGFANRNFMQLIHDDSLTFKEDIQKAQVSGQGDSLHEHIANLAGSPAIK<br>KGILQTVKvvDELVKVMGRHKPENIVIEMARENQTTQKGQKNSRERMKRIEEGIKELG<br>SQILKEHPVENTQLQNEKLYLYYLQNGRDMYVDQELDINRLSDYDVDHIVPQSFLKDD<br>SIDNKVLTRSDKNRGKSDNVPSEEvvKKMKNYWRQLLNAKLITQRKFDNLTKAERGGL<br>SELDKAGFIKRQLVETRQITKHVAQILDSRMNTKYDENDKLIREVKVITLKSKLVSDF<br>RKDFQFYKVREINNYHHAHDAYLNAvvGTALIKKYPKLESEFVYGDYKVYDVRKMIAK<br>SEQEIGKATAKYFFYSNIMNFFKTEITLANGEIRKRPLIETNGETGEIVWDKGRDFAT |

|                                    |                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                     |
|---|---|
|                                    | VRKVLSMPQVNIVKKTEVQTGGFSKESILPKRNSDKLIARKKDWDPKKYGGFDSPTVA<br>YSVLvvAKVEKGKSKKLKSVKELLGITIMERSSFEKNPIDFLEAKGYKEVKKDLIIKL<br>PKYSLFELENGRKRMLASAGELQKGNELALPSKYVNFLYLASHYEKLKGSPEDNEQKQ<br>LFVEQHKHYLDEIIEQISEFSKRVILADANLDKVLSAYNKHRDKPIREQAENIIHLFT<br>LTNLGAPAAFKYFDTTIDRKRYTSTKEVLDATLIHQSITGLYETRIDLSQLGGDSPKK<br>KRKVEAS (SEQ ID NO: 163) |
| S. pyogenes NLS-<br>Cas9Nickase(H840A)-NLS | MYPYDVPDYASPKKKRKVEASDKKYSIGLDIGTNSVGWAVITDEYKVPSKKFKVLGNT<br>DRHSIKKNLIGALLFDSGETAEATRLKRTARRRYTRRKNRICYLQEIFSNEMAKVDDS<br>FFHRLEESFLVEEDKKHERHPIFGNIVDEVAYHEKYPTIYHLRKKLVDSTDKADLRLI<br>YLALAHMIKFRGHFLIEGDLNPDNSDVDKLFIQLVQTYNQLFEENPINASGVDAKAIL<br>SARLSKSRRLENLIAQLPGEKKNGLFGNLIALSLGLTPNFKSNFDLAEDAKLQLSKDT<br>YDDDLDNLLAQIGDQYADLFLAAKNLSDAILLSDILRVNTEITKAPLSASMIKRYDEH<br>HQDLTLLKALVRQQLPEKYKEIFFDQSKNGYAGYIDGGASQEEFYKFIKPILEKMDGT<br>EELLVKLNREDLLRKQRTFDNGSIPHQIHLGELHAILRRQEDFYPFLKDNREKIEKIL<br>TFRIPYYVGPLARGNSRFAWMTRKSEETITPWNFEEVVDKGASAQSFIERMTNFDKNL<br>PNEKVLPKHSLLYEYFTVYNELTKVKYVTEGMRKPAFLSGEQKKAIVDLLFKTNRKVT<br>VKQLKEDYFKKIECFDSVEISGVEDRFNASLGTYHDLLKIIKDKDFLDNEENEDILED<br>IVLTLTLFEDREMIEERLKTYAHLFDDKVMKQLKRRRYTGWGRLSRKLINGIRDKQSG<br>KTILDFLKSDGFANRNFMQLIHDDSLTFKEDIQKAQVSGQGDSLHEHIANLAGSPAIK<br>KGILQTVKVVDELVKVMGRHKPENIVIEMARENQTTQKGQKNSRERMKRIEEGIKELG<br>SQILKEHPVENTQLQNEKLYLYYLQNGRDMYVDQELDINRLSDYDVDAIVPQSFLKDD<br>SIDNKVLTRSDKNRGKSDNVPSEEvvKKMKNYWRQLLNAKLITQRKFDNLTKAERGGL<br>SELDKAGFIKRQLVETRQITKHVAQILDSRMNTKYDENDKLIREVKVITLKSKLVSDF<br>RKDFQFYKVREINNYHHAHDAYLNAvvGTALIKKYPKLESEFVYGDYKVYDVRKMIAK<br>SEQEIGKATAKYFFYSNIMNFFKTEITLANGEIRKRPLIETNGETGEIVWDKGRDFAT<br>VRKVLSMPQVNIVKKTEVQTGGFSKESILPKRNSDKLIARKKDWDPKKYGGFDSPTVA<br>YSVLVVAKVEKGKSKKLKSVKELLGITIMERSSFEKNPIDFLEAKGYKEVKKDLIIKL<br>PKYSLFELENGRKRMLASAGELQKGNELALPSKYVNFLYLASHYEKLKGSPEDNEQKQ<br>LFVEQHKHYLDEIIEQISEFSKRVILADANLDKVLSAYNKHRDKPIREQAENIIHLFT<br>LTNLGAPAAFKYFDTTIDRKRYTSTKEVLDATLIHQSITGLYETRIDLSQLGGDSPKK<br>KRKVEAS (SEQ ID NO: 164) |
| Ruby::PUF(3-2)                     | MVRGSHHHHHGMASMTGGQQMGRDLYDDDDKDPMVSKGEELIKENMRMKVVMEGSVN<br>GHQFKCTGEGEGNPYMGTQTMRIKVIEGGPLPFAFDILATSFMYGSRTFIKYPKGIPD<br>FFKQSFPEGFTWERVTRYEDGGvvTVMQDTSLEDGCLVYHVQVRGVNFPSNGPVMQKK<br>TKGWEPNTEMMYPADGGLRGYTHMALKVDGGGHLSCSFVTTYRSKKTVGNIKMPGIHA<br>VDHRLERLEESDNEMFvvQREHAVAKFAGLGGGMDELYKGGGGSGPAGILPPKKKRKV<br>SRGRSRLLEDFRNNRYPNLQLREIAGHIMEFSQDQHGSRFIQLKLERATPAERQLVFN<br>EILQAAYQLMVDVFGNYVIQKFFEFGSLEQKLALAERIRGHVLSLALQMYGSRVIEKA<br>LEFIPSDQQNEMVRELDGHVLKCVKDQNGNHvvQKCIECVQPQSLQFIIDAFKGQVFA<br>LSTHPYGCRVIQRILEHCLPDQTLPILEELHQHTEQLVQDQYGNYVIQHVLEHGRPED<br>KSKIVAEIRGNVLVLSQHKFASNvvEKCVTHASRTERAVLIDEVCTMNDGPHSALYTM<br>MKDQYANYvvQKMIDVAEPGQRKIVMHKIRPHIATLRKYTYGKHILAKLEKYYMKNGV<br>DLG (SEQ ID NO: 165) |
| Ruby::PUF(6-2/7-2)                 | MVRGSHHHHHGMASMTGGQQMGRDLYDDDDKDPMVSKGEELIKENMRMKVVMEGSVN<br>GHQFKCTGEGEGNPYMGTQTMRIKVIEGGPLPFAFDILATSFMYGSRTFIKYPKGIPD<br>FFKQSFPEGFTWERVTRYEDGGvvTVMQDTSLEDGCLVYHVQVRGVNFPSNGPVMQKK<br>TKGWEPNTEMMYPADGGLRGYTHMALKVDGGGHLSCSFVTTYRSKKTVGNIKMPGIHA<br>VDHRLERLEESDNEMFvvQREHAVAKFAGLGGGMDELYKGGGGSGPAGILPPKKKRKV<br>SRGRSRLLEDFRNNRYPNLQLREIAGHIMEFSQDQHGSRFIQLKLERATPAERQLVFN<br>EILQAAYQLMVDVFGNYVIQKFFEFGSLEQKLALAERIRGHVLSLALQMYGCRVIQKA<br>LEFIPSDQQNEMVRELDGHVLKCVKDQNGNHvvQKCIECVQPQSLQFIIDAFKGQVFA<br>LSTHPYGCRVIQRILEHCLPDQTLPILEELHQHTEQLVQDQYGSYVIEHVLEHGRPED<br>KSKIVAEIRGNVLVLSQHKFANNVVQKCVTHASRTERAVLIDEVCTMNDGPHSALYTM<br>MKDQYANYvvQKMIDVAEPGQRKIVMHKIRPHIATLRKYTYGKHILAKLEKYYMKNGV<br>DLG (SEQ ID NO: 166) |
| Clover::PUF(3-2)                   | MVSKGEELFTGVVPILVELDGDVNGHKFSVRGEGEGDATNGKLTLKFICTTGKLPVPW<br>PTLVTTFGYGVACFSRYPDHMKQHDFFKSAMPEGYVQERTISFKDDGTYKTRAEVKFE<br>GDTLVNRIELKGIDFKEDGNILGHKLEYNFNSHNVYITADKQKNGIKANFKIRHNVED<br>GSVQLADHYQQNTPIGDGPVLLPDNHYLSHQSALSKDPNEKRDHMVLLEFVTAAGITH<br>GMDELYKSRGPYSIVSPKCGGGGSGPAGILPPKKKRKVSRGRSRLLEDFRNNRYPNLQ<br>LREIAGHIMEFSQDQHGSRFIQLKLERATPAERQLVFNEILQAAYQLMVDVFGNYVIQ<br>KFFEFGSLEQKLALAERIRGHVLSLALQMYGSRVIEKALEFIPSDQQNEMVRELDGHV<br>LKCVKDQNGNHvvQKCIECVQPQSLQFIIDAFKGQVFALSTHPYGCRVIQRILEHCLP<br>DQTLPILEELHQHTEQLVQDQYGNYVIQHVLEHGRPEDKSKIVAEIRGNVLVLSQHKF<br>ASNVVEKCVTHASRTERAVLIDEVCTMNDGPHSALYTMMKDQYANYVVQKMIDVAEPG<br>QRKIVMHKIRPHIATLRKYTYGKHILAKLEKYYMKNGVDLG (SEQ ID NO: 167) |
| Clover::PUF(6-2/7-2)               | MVSKGEELFTGVVPILVELDGDVNGHKFSVRGEGEGDATNGKLTLKFICTTGKLPVPW<br>PTLVTTFGYGVACFSRYPDHMKQHDFFKSAMPEGYVQERTISFKDDGTYKTRAEVKFE<br>GDTLVNRIELKGIDFKEDGNILGHKLEYNFNSHNVYITADKQKNGIKANFKIRHNVED<br>GSVQLADHYQQNTPIGDGPVLLPDNHYLSHQSALSKDPNEKRDHMVLLEFVTAAGITH<br>GMDELYKSRGPYSIVSPKCGGGGSGPAGILPPKKKRKVSRGRSRLLEDFRNNRYPNLQ<br>LREIAGHIMEFSQDQHGSRFIQLKLERATPAERQLVFNEILQAAYQLMVDVFGNYVIQ<br>KFFEFGSLEQKLALAERIRGHVLSLALQMYGCRVIQKALEFIPSDQQNEMVRELDGHV<br>LKCVKDQNGNHvvQKCIECVQPQSLQFIIDAFKGQVFALSTHPYGCRVIQRILEHCLP<br>DQTLPILEELHQHTEQLVQDQYGSYVIEHVLEHGRPEDKSKIVAEIRGNVLVLSQHKF<br>ANNVVQKCVTHASRTERAVLIDEVCTMNDGPHSALYTMMKDQYANYVVQKMIDVAEPG<br>QRKIVMHKIRPHIATLRKYTYGKHILAKLEKYYMKNGVDLG (SEQ ID NO: 168) |

-continued

| | |
|---|---|
| PUF(3-2)::VP64 | MGILPPKKKRKVSRGRSRLLEDFRNNRYPNLQLREIAGHIMEFSQDQHGSRFIQLKLE<br>RATPAERQLVFNEILQAAYQLMVDVFGNYVIQKFFEFGSLEQKLALAERIRGHVLSLA<br>LQMYGSRVIEKALEFIPSDQQNEMVRELDGHVLKCVKDQNGNHvvQKCIECVQPQSLQ<br>FIIDAFKGQVFALSTHPYGCRVIQRILEHCLPDQTLPILEELHQHTEQLVQDQYGNYV<br>IQHVLEHGRPEDKSKIVAEIRGNVLVLSQHKFASNVVEKCVTHASRTERAVLIDEVCT<br>MNDGPHSALYTMMKDQYANYVVQKMIDVAEPGQRKIVMHKIRPHIATLRKYTYGKHIL<br>AKLEKYYMKNGVDLGGPAGSGRADALDDFDLDMLGSDALDDFDLDMLGSDALDDFDLD<br>MLGSDALDDFDLDMLYID (SEQ ID NO: 169) |
| Name | Peptide sequence |
| PUF(6-2/7-2)::VP64 | MGILPPKKKRKVSRGRSRLLEDFRNNRYPNLQLREIAGHIMEFSQDQHGSRFIQLKLE<br>RATPAERQLVFNEILQAAYQLMVDVFGNYVIQKFFEFGSLEQKLALAERIRGHVLSLA<br>LQMYGCRVIQKALEFIPSDQQNEMVRELDGHVLKCVKDQNGNHvvQKCIECVQPQSLQ<br>FIIDAFKGQVFALSTHPYGCRVIQRILEHCLPDQTLPILEELHQHTEQLVQDQYGSYV<br>IEHVLEHGRPEDKSKIVAEIRGNVLVLSQHKFANNvvQKCVTHASRTERAVLIDEVCT<br>MNDGPHSALYTMMKDQYANYvvQKMIDVAEPGQRKIVMHKIRPHIATLRKYTYGKHIL<br>AKLEKYYMKNGVDLGGPAGSGRADALDDFDLDMLGSDALDDFDLDMLGSDALDDFDLD<br>MLGSDALDDFDLDMLYID (SEQ ID NO: 170) |
| PUF(6-2/7-2)::p65_HSF1 | MGILPPKKKRKVSRGRSRLLEDFRNNRYPNLQLREIAGHIMEFSQDQHGSRFIQLKLE<br>RATPAERQLVFNEILQAAYQLMVDVFGNYVIQKFFEFGSLEQKLALAERIRGHVLSLA<br>LQMYGCRVIQKALEFIPSDQQNEMVRELDGHVLKCVKDQNGNHvvQKCIECVQPQSLQ<br>FIIDAFKGQVFALSTHPYGCRVIQRILEHCLPDQTLPILEELHQHTEQLVQDQYGSYV<br>IEHVLEHGRPEDKSKIVAEIRGNVLVLSQHKFANNvvQKCVTHASRTERAVLIDEVCT<br>MNDGPHSALYTMMKDQYANYvvQKMIDVAEPGQRKIVMHKIRPHIATLRKYTYGKHIL<br>AKLEKYYMKNGVDLGGPAGGGGSGGGGSGGGGSGPKKKRKVAAAGSPSGQISNQALAL<br>APSSAPVLAQTMVPSSAMVPLAQPPAPAPVLTPGPPQSLSAPVPKSTQAGEGTLSEAL<br>LHLQFDADEDLGALLGNSTDPGVFTDLASVDNSEFQQLLNQGVSMSHSTAEPMLMEYP<br>EAITRLVTGSQRPPDPAPTPLGTSGLPNGLSGDEDFSSIADMDFSALLSQISSSGQGG<br>GGSGFSVDTSALLDLFSPSVTVPDMSLPDLDSSLASIQELLSPQEPPRPPEAENSSPD<br>SGKQLVHYTAQPLFLLDPGSVDTGSNDLPVLFELGEGSYFSEGDGFAEDPTISLLTGS<br>EPPKAKDPTVSID (SEQ ID NO: 171) |
| KRAB::PUF(6-2/7-2) | MGSPKKKRKVEASMDAKSLTAWSRTLVTFKDVFVDFTREEWKLLDTAQQIVYRNVMLE<br>NYKNLVSLGYQLTKPDVILRLEKGEEPWLVSRGSIVGILPPKKKRKVSRGRSRLLEDF<br>RNNRYPNLQLREIAGHIMEFSQDQHGSRFIQLKLERATPAERQLVFNEILQAAYQLMV<br>DVFGNYVIQKFFEFGSLEQKLALAERIRGHVLSLALQMYGCRVIQKALEFIPSDQQNE<br>MVRELDGHVLKCVKDQNGNHvvQKCIECVQPQSLQFIIDAFKGQVFALSTHPYGCRVI<br>QRILEHCLPDQTLPILEELHQHTEQLVQDQYGSYVIEHVLEHGRPEDKSKIVAEIRGN<br>VLVLSQHKFANNVVQKCVTHASRTERAVLIDEVCTMNDGPHSALYTMMKDQYANYVVQ<br>KMIDVAEPGQRKIVMHKIRPHIATLRKYTYGKHILAKLEKYYMKNGVDLG<br>(SEQ ID NO: 172) |

List of Vectors and their Addgene
Accession Numbers

| pAC number | Descriptive name | Description |
|---|---|---|
| pAC164 | pmax-dCas9Master_VP64 | dCas9-VP64 driven by CAGGS promoter in expression vector pmax (Clontech) |
| pAC1119 | PB3-neo(-)-pmaxDEST(+) | PB gateway destination vector with neo selectable marker and pmax cassette (Clonetech) |
| pAC1355 | pmax-NLSPUFa_VP64 | NLSPUFa_VP64 in transient expression vector pmax |
| pAC1356 | pmax-NLSPUFb_VP64 | NLSPUFb_VP64 in expression vector pmax |
| pAC1357 | pmax-NLSPUFw_VP64 | NLSPUFw_VP64 in expression vector pmax |
| pAC1358 | pmax-NLSPUFc_VP64 | NLSPUFc_VP64 in expression vector pmax |
| pAC1360 | PB3-neo(-)-pmax-Clover_NLSPUFa | Clover_NLSPUFa in pAC1119 |
| pAC1362 | PB3-neo(-)-pmax-mRuby2_NLSPUFa | mRuby2_NLSPUFa in pAC1119 |
| pAC1364 | pmax-dCas9Master_mCBPHAT | dCas9Master_mCBPHAT in pmax expression vector |
| pAC1371 | pX-sgRNA-5xPBSa | Cloning vector for expression of sgRNA-5xPBSa |
| pAC1372 | pX-sgRNA-15xPBSa | Cloning vector for expression of sgRNA-15xPBSa |
| pAC1373 | pX-sgRNA-25xPBSa | Cloning vector for expression of sgRNA-25xPBSa |
| pAC1374 | pX-sgRNA-5xPBSb | Cloning vector for transient expression of sgRNA-5xPBSb |
| pAC1375 | pX-sgRNA-15xPBSb | Cloning vector for expression of sgRNA-15xPBSb |
| pAC1376 | pX-sgRNA-25xPBSb | Cloning vector for expression of sgRNA-25xPBSb |
| pAC1379 | pX-sgRNA-5xPBSw | Cloning vector for expression of sgRNA-5xPBSw |
| pAC1380 | pX-sgRNA-5xPBSc | Cloning vector for expression of sgRNA-5xPBSc |
| pAC1381 | PB3-neo(-)-pmax-Clover_NLSPUFc | Clover_NLSPUFc in pAC1119 |
| pAC1393 | pmax-NLSPUFa_p65HSF1 | NLSPUFa_p65HSF1 in pmax expression vector |
| pAC1394 | pX-sgRNA-0xPBS | Cloning vector for expression of sgRNA without PBS. It contains extra sequences for BsaI digestion for insertion of PBS |

-continued

| pAC number | Descriptive name | Description |
|---|---|---|
| pAC1399 | pX-sgRNA-20xPBSc | Cloning vector for expression of sgRNA-20xPBSc |
| pAC1402 | pCR8-Clover_NLSPUFa | Clover_NLSPUFa in pCR8 gateway donor vector |
| pAC1403 | pCR8-Clover_NLSPUFc | Clover_NLSPUFc in pCR8 gateway donor vector |
| pAC1404 | pCR8-mRuby2_NLSPUFa | mRuby2_NLSPUFa in pCR8 gateway donor vector |
| pAC1405 | pCR8-4xNLS_PUFa_2xNLS | NLSPUFa pCR8 gateway donor vector for insertion of N-terminal domain (SgrAI or AgeI with ClaI) and C-terminal domain (FseI PacI). Grow in dcm- cells (e.g., NEB C3040) to prepare vector for ClaI digestion |
| pAC1406 | pCR8-4xNLS_PUFb_2xNLS | NLSPUFb pCR8 gateway donor vector for insertion of N-terminal domain (SgrAI or AgeI with ClaI) and C-terminal domain (FseI PacI). Grow in dcm- cells (e.g., NEB C3040) to prepare vector for ClaI digestion |
| pAC1407 | pCR8-4xNLS_PUFw_2xNLS | NLSPUFw pCR8 gateway donor vector for insertion of N-terminal domain (SgrAI or AgeI with ClaI) and C-terminal domain (FseI PacI). Grow in dcm- cells (e.g., NEB C3040) to prepare vector for ClaI digestion |
| pAC1408 | pCR8-4xNLS_PUFc_2xNLS | NLSPUFc pCR8 gateway donor vector for insertion of N-terminal domain (SgrAI or AgeI with ClaI) and C-terminal domain (FseI PacI). Grow in dcm- cells (e.g., NEB C3040) to prepare vector for ClaI digestion |
| pAC1410 | pmax-dCas9Master_p65HSF1 | dCas9Master_p65HSF1 in pmax expression vector |
| pAC1411 | pmax-NLSPUFc_p65HSF1 | NLSPUFc_p65HSF1 in pmax expression vector |
| pAC1412 | PB3-neo(−)-pmax-NLSKRAB_NLSPUFa | NLSKRAB_NLSPUFa in pAC1119 |
| pAC1413 | PB3-neo(−)-pmax-NLSPUFb_p65HSF1 | NLSPUFb_p65HSF1 in pAC1119 |
| pAC1414 | PB3-NLSPUFb_p65HSF1-neo(−)-BFPKRAB_NLSPUFa | Dual expression vector for NLSPUFb_p65HSF1 and BFPKRAB_NLSPUFa |
| pAC1415 | pCR8-4xNLS_PUFa_2xNLS_mCBPHAT | 4xNLS_PUFa_2xNLS_mCBPHAT in pCR8 Gateway donor vector |
| pAC1416 | pCR8-mCBPHAT_4xNLS_PUFa_2xNLS | mCBPHAT_4xNLS_PUFa_2xNLS in pCR8 Gateway donor vector |
| pAC1417 | pmax-4xNLS_PUFa_2xNLS_mCBPHAT | 4xNLS_PUFa_2xNLS_mCBPHAT in pmax expression vector |
| pAC1418 | pmax-mCBPHAT_4xNLS_PUFa_2xNLS | mCBPHAT_4xNLS_PUFa_2xNLS in pmax expression vector |
| pAC1419 | PB3-neo(−)-pmax-dCas9Master_mCherry | dCas9Master_mCherry in pAC1119 |
| pAC1420 | pX-sgRNA-1xPBSa | Cloning vector for expression of sgRNA-1xPBSa |
| pAC1421 | pX-sgRNA-2xPBSa | Cloning vector for expression of sgRNA-2xPBSa |
| pAC1422 | pX-sgRNA-1xPBSb | Cloning vector for expression of sgRNA-1xPBSb |
| pAC1423 | pX-sgRNA-2xPBSb | Cloning vector for expression of sgRNA-2xPBSb |
| pAC1424 | pX-sgRNA-10xPBSb | Cloning vector for expression of sgRNA-10xPBSb |
| pAC1425 | pX-sgRNA-20xPBSb | Cloning vector for expression of sgRNA-20xPBSb |
| pAC1426 | pX-sgRNA-47xPBSb | Cloning vector for expression of sgRNA-47xPBSb |
| pAC1427 | pX-sgRNA-10xPBSw | Cloning vector for expression of sgRNA-10xPBSw |
| pAC1428 | pX-sgRNA-15xPBSw | Cloning vector for expression of sgRNA-15xPBSw |
| pAC1429 | pX-sgRNA-10xPBSc | Cloning vector for expression of sgRNA-10xPBSc |
| pAC1430 | pX-sgRNA-15xPBSc | Cloning vector for expression of sgRNA-15xPBSc |
| pAC1431 | PB3-LGFPL(−)-sgSOX2PP1-5xPBSa | Vector for expression of sgSOX2PP1-5xPBSa with a GFP marker flanked by loxP sites |
| pAC1432 | PB3-LGFPL(−)-sgSOX2PP2-5xPBSa(−) | Vector for expression of sgSOX2PP2-5xPBSa with a GFP marker flanked by loxP sites |
| pAC1433 | PB3-LGFPL(−)-sgSOX2PP3-5xPBSa | Vector for expression of sgSOX2PP3-5xPBSa with a GFP marker flanked by loxP sites |
| pAC1434 | PB3-LGFPL(−)-sgSOX2PP4-5xPBSa | Vector for expression of sgSOX2PP4-5xPBSa with a GFP marker flanked by loxP sites |
| pAC1435 | PB3-LGFPL(−)-sgOCT4PP1-5xPBSb | Vector for expression of sgOCT4PP1-5xPBSb with a GFP marker flanked by loxP sites |
| pAC1436 | PB3-LGFPL(−)-sgOCT4PP4-5xPBSb | Vector for expression of sgOCT4PP4-5xPBSb with a GFP marker flanked by loxP sites |
| pAC1437 | PB3-LGFPL(−)-sgOCT4PP3-5xPBSb | Vector for expression of sgOCT4PP3-5xPBSb with a GFP marker flanked by loxP sites |
| pAC1438 | PB3-LGFPL(−)-sgOCT4PP2-5xPBSb | Vector for expression of sgOCT4PP2-5xPBSb with a GFP marker flanked by loxP sites |

List of sgRNA-PBS Expression Vectors by Number and Type of PBS

| #PBS | PBSType | | | |
|---|---|---|---|---|
| | PUFa | PUFb | PUFw | PUFc |
| 1x | pAC1420 | pAC1422 | | |
| 2x | pAC1421 | pAC1423 | | |
| 5x | pAC1371 | pAC1374 | pAC1379 | pAC1380 |

-continued

| #PBS | PBSType | | | |
|---|---|---|---|---|
| | PUFa | PUFb | PUFw | PUFc |
| 10x | | pAC1424 | pAC1427 | pAC1429 |
| 15x | pAC1372 | pAC1375 | pAC1428 | pAC1430 |
| 20x | | pAC1425 | | pAC1399 |
| 25x | pAC1373 | pAC1376 | | |
| 47x | | pAC1426 | | |

The invention claimed is:

1. A method comprising delivering to a cell a ribonucleic acid (RNA) or a deoxyribonucleic acid (DNA) encoding an RNA that comprises: (a) a DNA-targeting sequence that is complementary to a target polynucleotide sequence in the cell; (b) a Cas9-binding sequence; and (c) at least 5 tandem copies of a PUF domain-Binding Sequence (PBS).

2. The method of claim 1, wherein the DNA-targeting sequence is complementary to the target polynucleotide sequence over about 12-22 nucleotides.

3. The method of claim 1, wherein the RNA further comprises a linker sequence linking the DNA-targeting sequence to the Cas9-binding sequence.

4. The method of claim 1, wherein the Cas9-binding sequence forms a hairpin structure.

5. The method of claim 1, wherein the Cas9-binding sequence has a length of about 37-47 nucleotides.

6. The method of claim 1, wherein each of the at least 5 tandem copies of the PBS has a length of about 8 nucleotides.

7. The method of claim 1, wherein the RNA comprises a PBS of the sequence 5'-UGUAUGUA-3' that can be bound by the PUF domain PUF (3-2).

8. The method of claim 1, wherein the RNA comprises a PBS of the sequence 5'-UUGAUAUA-3' that can be bound by the PUF domain PUF (6-2/7-2).

9. The method of claim 1, wherein the RNA comprises 5-35 tandem copies of identical PUF domain-Binding Sequences.

10. The method of claim 1, wherein the RNA comprises 5-35 tandem copies of different PUF domain-Binding Sequences.

11. The method of claim 1, wherein the RNA comprises 5-10 tandem copies of identical PUF domain-Binding Sequences.

12. The method of claim 1, wherein the RNA comprises 5-10 tandem copies of different PUF domain-Binding Sequences.

13. The method of claim 1, wherein the tandem copies of the PBS are separated from each other by a spacer sequence.

14. The method of claim 1, further comprising delivering to the cell:
(a) a Cas9 protein or a polynucleotide encoding a Cas9 protein; and
(b) a polynucleotide encoding a PUF domain.

15. The method of claim 14, wherein the Cas9 protein is a wild-type Cas9 protein.

16. The method of claim 14, wherein the Cas9 protein is a nuclease-deficient dCas9 protein.

17. The method of claim 14, wherein the PUF domain is fused to an effector domain.

18. The method of claim 17, wherein the effector domain is a fluorescent protein.

19. The method of claim 18, wherein the method further comprises imaging the cell.

20. The method of claim 19, wherein the cell is a live cell.

* * * * *